United States Patent
Sumida et al.

(10) Patent No.: US 8,551,999 B2
(45) Date of Patent: Oct. 8, 2013

(54) HETEROCYCLIC COMPOUND AND PHARMACEUTICAL COMPOSITION THEREOF

(75) Inventors: Takumi Sumida, Osaka (JP); Fujio Tabusa, Osaka (JP); Kazuo Sekiguchi, Osaka (JP); Takeshi Kodama, Osaka (JP); Koichi Yasumura, Osaka (JP); Yutaka Kojima, Osaka (JP); Masaaki Motoyama, Osaka (JP); Keisuke Miyajima, Osaka (JP); Kenji Yoshida, Osaka (JP); Keizo Kan, Osaka (JP); Makoto Sakamoto, Osaka (JP); Hideki Takasu, Osaka (JP); Takashi Nakagawa, Osaka (JP); Naoto Ohi, Osaka (JP); Yasuo Harada, Osaka (JP); Norikazu Hashimoto, Osaka (JP); Hironori Matsuyama, Osaka (JP); Masatoshi Iida, Osaka (JP); Shigekazu Fujita, Osaka (JP); Tae Fukushima, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 310 days.

(21) Appl. No.: 12/740,684

(22) PCT Filed: Oct. 29, 2008

(86) PCT No.: PCT/JP2008/070153
§ 371 (c)(1), (2), (4) Date: Apr. 29, 2010

(87) PCT Pub. No.: WO2009/057811
PCT Pub. Date: May 7, 2009

(65) Prior Publication Data
US 2010/0261720 A1    Oct. 14, 2010

(30) Foreign Application Priority Data

Oct. 30, 2007 (JP) ................................ 2007-281601
Dec. 27, 2007 (JP) ................................ 2007-336157

(51) Int. Cl.
| | |
|---|---|
| *A61K 31/496* | (2006.01) |
| *A61K 31/454* | (2006.01) |
| *C07D 401/12* | (2006.01) |
| *C07D 401/14* | (2006.01) |
| *C07D 405/14* | (2006.01) |
| *C07D 417/14* | (2006.01) |
| *A61K 31/506* | (2006.01) |
| *C07D 403/12* | (2006.01) |

(52) U.S. Cl.
USPC ............ 514/253.06; 514/253.09; 514/253.1; 514/318; 514/252.19; 544/295; 544/363; 544/364; 546/194

(58) Field of Classification Search
None
See application file for complete search history.

(56) References Cited

U.S. PATENT DOCUMENTS

| | | | |
|---|---|---|---|
| 6,511,995 B1 | 1/2003 | Edamatsu et al. | |
| 7,253,286 B2 * | 8/2007 | Funahashi et al. | ............ 546/153 |

FOREIGN PATENT DOCUMENTS

| | | |
|---|---|---|
| JP | 2001-089412 | 4/2001 |
| JP | 2001-089450 | 4/2001 |
| WO | WO-99/48871 | 9/1999 |

OTHER PUBLICATIONS

Wu et al. Molecules vol. 17, p. 1373-1387 (2012).*
International Search Report from the European Patent Office for International Application No. PCT/JP2008/070153 (Mailed Apr. 27, 2009).

* cited by examiner

*Primary Examiner* — Emily Bernhardt
(74) *Attorney, Agent, or Firm* — Finnegan, Henderson, Farabow, Garrett & Dunner, L.L.P.

(57) ABSTRACT

The present invention provides a heterocyclic compound represented by General Formula (1):

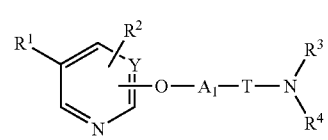

(1)

wherein $R^1$ is a group $R^5-Z_1-$, etc., $Z_1$ is a lower alkylene group, etc., and $R^5$ is a group represented by General Formula;

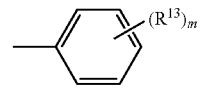

wherein $R^{13}$ is a hydrogen atom, etc., m is an integer from 1 to 5;
$R^2$ is a hydrogen atom:
Y is CH or N:
$A_1$ is a heterocyclic ring selected from the group consisting of indolediyl groups, wherein the heterocyclic ring may have at least one substituent:
T is a group —CO—, etc.:
$R^3$ is a hydrogen atom, etc.:
$R^4$ is a lower alkyl group optionally substituted by one or more hydroxy groups, etc.:
$R^3$ and $R^4$, together with the nitrogen atom to which they bind, may bind to each other and form a 5- to 10-membered saturated heterocyclic ring, wherein the heterocyclic ring may have at least one substituent. The heterocyclic compound of the present invention has excellent effects of suppressing the production of collagen and/or treating tumors.

6 Claims, No Drawings

HETEROCYCLIC COMPOUND AND PHARMACEUTICAL COMPOSITION THEREOF

TECHNICAL FIELD

The present invention relates to a heterocyclic compound, and a pharmaceutical composition thereof.

BACKGROUND ART

Currently, it is said that the disease known as fibrosis includes 130 types or more of diseases, if rare diseases are also included therein. Representative examples of such fibrosis include lung fibrosis, hepatic fibrosis, and glomerulosclerosis.

In general, lung fibrosis refers to a group of diseases associated with loss of lung functions due to a lesion regarding the reconstruction of an alveolar region, which is caused by the phenomenon whereby the alveolar structure is destroyed by an inflammatory reaction, and as a result, growth of fibroblasts and an excessive increase in extracellular matrix mainly composed of collagen take place, so that the lung becomes hardened.

Moreover, hepatic fibrosis refers to a pathologic condition associated with fibrosis of the liver, which is caused by the phenomenon whereby hepatic cells are necrotized by various types of hepatopathy such as chronic viral hepatitis or alcoholic hepatitis, and thereafter, extracellular matrix increases to replenish the necrotized portion, resulting in such fibrosis of the liver. This pathologic condition finally leads to hepatic cirrhosis, in which the entire hepatic fibers shrink and become hardened.

In order to suppress the aforementioned hepatic fibrosis, drugs such as Penicillamine or Lufironil have been used. Penicillamine has been known as a drug for treating Wilkinson's disease that is developed as a result of accumulation of copper in the liver due to abnormality of copper metabolism. Lufironil has been studied for its use as a proline hydroxylase inhibitor.

However, taking into consideration their side effects and effectiveness, the aforementioned drugs do not sufficiently function as drugs for preventing fibrosis of the liver. Thus, as a matter of fact, neither therapeutic agents nor methods for treating fibrosis, which are effective for fibrosis, including hepatic fibrosis as a representative example, have been established to date. A method of specifically inhibiting a process of developing fibrosis has become a focus of attention in the research field.

As stated above, it has been known that an excessive increase in extracellular matrix mainly composed of collagen takes place during a process of development of fibrosis in the lung tissues or hepatic tissues. Moreover, it has also been known that such an increase in extracellular matrix in hepatic cells takes place mainly in sinusoidal wall Disse's space, and that Ito cells that are mesenchymal cells in the liver are main sources for production of such extracellular matrix.

Accordingly, in order to suppress fibrosis occurring in the liver, the lung, or other organs, it is important to suppress an excessive increase in extracellular matrix (namely, collagen). JP-A-2002507601 and JP-A-200189450 disclose that a certain type of pyridine derivative has an effect of suppressing the production of collagen and thus is effective for fibrosis. JP-A-200189412 discloses that a certain type of benzene derivative has an effect of suppressing the production of collagen and thus is effective for fibrosis. However, there still remains a demand for a development of a compound that exhibits a better effects in suppressing the production of collagen with little side effect in a high safely manner.

In 1940s, nitrogen mustard was clinically used as an anticancer drug for the first time in the world. Since then, various anticancer drugs have been developed in the field of cancer treatment. For example, 5-fluorouracil and like antimetabolites, adriamycin and like antitumor antibiotics, cisplatin and like platinum complexes, vindesine and like plant origin anticancer agents, etc., are actually used.

However, these anticancer agents also exhibit cytotoxicity towards healthy cells and often result in digestive system disorders, bone marrow depression, hair loss and similar critical side effects. Due to these side effects, their usage is limited and their therapeutic effect itself is often effective only partially and in a short term.

Although various attempts have been made to develop novel anticancer agents which can take place these known anticancer agents, there are no satisfactory results obtained so far.

DISCLOSURE OF THE INVENTION

Problems to be Solved by the Invention

It is an object of the present invention to provide a novel compound that has a superior effect of suppressing the production of collagen and that exhibits an oncotherapeutic effect such as preventing and treating malignant tumor.

Means for Solving the Problems

As a result of intensive studies directed towards achieving the aforementioned object, the present inventors have found that a heterocyclic compound represented by the following General Formula (1) and a salt thereof have a superior effect of suppressing the production of collagen, and useful as a pharmaceutical composition being useful for preventing and treating fibrosis such as lung fibrosis, hepatic fibrosis, glomerulosclerosis and the like. The present inventors have further found that the compound represented by the following General Formula (1) and the salt thereof exhibit antitumor effects. The present invention has been completed based on these findings.

The present invention provides a heterocyclic compound or a salt thereof represented by General Formula (1):

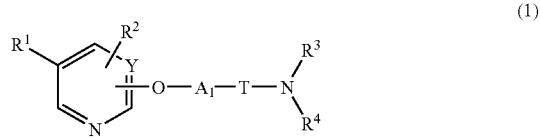

(1)

wherein $R^1$ is a group $R^5-Z_1-$, a group $R^5-B-N(R^6)-$, a group $R^5-N(R^6)-B-$, a group $R^5-N(R^7)-$, a group $R^5-N(R^8)-CO-N(R^9)-$, a group $R^5-N(R^{10}-CS-N(R^{11})-$, a group $R^5-SO_2-N(R^{12})-$, a group $R^5-CO-B_1-$, a group $R^5-B_2-CO-N(R^{12a})-$, a group $R^5-B_9-SO_2-N(R^{47})-$, a group $R^5-O-B_{10}-SO_2-N(R^{48})-$ or a group represented by General Formula:

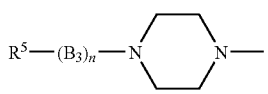

where $Z_1$ is a lower alkylene group or a lower alkenylene group:

$R^5$ is a 5- to 15-membered monocyclic, dicyclic, or tricyclic saturated or unsaturated heterocyclic group having 1 to 4 nitrogen atoms, oxygen atoms, or sulfur atoms (wherein the heterocyclic ring may be substituted by 1 to 3 groups selected from the group consisting of oxo group; lower alkoxy groups optionally substituted by one or more halogen atoms; lower alkyl groups optionally substituted by one or more halogen atoms; halogen atoms; lower alkylsulfonyl groups; phenyl groups optionally substituted, on the phenyl ring, by one or more optionally halogenated lower alkyl groups; lower alkylthio groups; pyrrolyl groups; benzoyl group; lower alkanoyl groups; lower alkoxycarbonyl groups; lower alkylenedioxy groups; pyridyl groups; and amino groups that may have at least one substituent selected from the group consisting of lower alkyl groups and lower alkanoyl groups), optionally halogenated lower alkyl groups, cycloalkyl groups, naphthyl group that may have, on the naphthalene ring, 1 to 3 substituents selected from the group consisting of lower alkyl groups, halogen atoms, and amino groups optionally substituted by at least one substituent selected from the group consisting of lower alkyl groups and lower alkanoyl groups, or a group represented by General Formula:

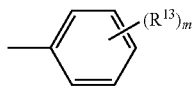

wherein $R^{13}$ is a hydrogen atom, a hydroxy group, a carboxy group, a halogen atom, a lower alkyl group optionally substituted by one or more halogen atoms, a lower alkoxy group optionally substituted by one or more halogen atoms or lower alkoxy groups, a lower alkanoyloxy group, a lower alkoxycarbonyl group, a lower alkoxycarbonyl group-substituted lower alkyl group, a cyano group, a phenyl group, a nitro group, a lower alkanoylamino group, a lower alkylenedioxy group, a phenoxy group, a pyrazolyl group optionally substituted by one or more lower alkyl groups, an oxazolyl group, or a pyrrolyl group:

m is an integer from 1 to 5, when m is any one of 2 to 5, the 2 to 5 of $R^{13}$s may be the same or different;

$R^{47}$ and $R^{48}$ are a hydrogen atom or a lower alkyl group;

$R^6$ is a hydrogen atom, a lower alkyl group optionally substituted by one or more lower alkoxy groups, a lower alkanoyl group, a lower alkylsulfonyl group, or a phenyl lower alkyl group:

B is a group —CO— or a lower alkylene group:

$R^7$ is a hydrogen atom or a lower alkyl group:

$R^8$, $R^9$, $R^{10}$ and $R^{11}$ are a hydrogen atom or a lower alkyl group:

$R^{12}$ and $R^{12a}$ are a hydrogen atom or a lower alkyl group:

$B_1$ and $B_3$ are a lower alkylene group:

n is 0 or 1:

$B_2$ is a lower alkenylene group:

$B_9$ is a lower alkylene group or a lower alkenylene group:

$B_{10}$ is a lower alkylene group:

$R^2$ is a hydrogen atom or a lower alkyl group:

Y is CH or N:

$A_1$ is a heterocyclic ring selected from the group consisting of indolediyl groups and indolinediyl groups, wherein the heterocyclic ring may have at least one substituent:

T is a group —N($R^{14}$)—$B_4$—CO—, a group —$B_5$—CO— or a group —CO—:

$R^{14}$ is a hydrogen atom, a lower alkyl group optionally substituted by one or more halogen atoms, a cycloalkyl group, a cycloalkylcarbonyl group, a lower alkanoyl group optionally substituted by one or more halogen atoms, a lower alkenyl group, an amino substituted lower alkanoyl group optionally substituted by one or more lower alkyl groups, or a lower alkylsulfonyl group:

$B_4$ is a lower alkylene group:

$B_5$ is a lower alkenylene group or a lower alkylene group optionally substituted by one or more hydroxy groups:

$R^3$ is a hydrogen atom or an alkyl group (the alkyl group may be substituted by one or more phenyl groups or amino groups optionally substituted by one or more lower alkyl groups):

$R^4$ is (4-1) a lower alkyl group optionally substituted by one or more hydroxy groups: (4-2) a cycloalkyl group optionally substituted by at least one substituent selected from the group consisting of hydroxy group and lower alkyl groups; (4-3) a phenyl group optionally substituted, on the phenyl ring, by 1 to 3 groups selected from the group consisting of lower alkyl groups; lower alkoxy groups optionally substituted by one or more halogen atoms; halogen atoms; amino lower alkoxy groups optionally substituted by one or more lower alkyl groups; hydroxy group-substituted lower alkyl groups; phenyl lower alkyl groups; lower alkynyl groups; amino groups optionally substituted by one or more lower alkyl groups or lower alkylsulfonyl groups; lower alkylthio groups; cycloalkyl groups; phenylthio group; adamantyl groups; anilino groups optionally substituted by one or more halogen atoms on the phenyl ring; lower alkoxycarbonyl groups; pyrrolidinyl groups optionally substituted by one or more oxo groups on the pyrrolidine ring; lower alkanoylamino groups; cyano group; and phenoxy group; (4-4) a phenyl lower alkyl group optionally substituted, on the phenyl ring, by 1 to 3 groups selected from the group consisting of halogen atoms; lower alkoxy groups optionally substituted by one or more halogen atoms; lower alkyl groups; and tetrazolyl groups optionally substituted by one or more lower alkyl groups or lower alkoxy lower alkyl groups; (4-5) a lower alkoxy carbonyl-substituted lower alkyl group; (4-6) a 1,2,3,4-tetrahydroquinolyl group that may have, on the tetrahydroquinoline ring, 1 to 3 substituents selected from the group consisting of oxo group, lower alkoxy groups and lower alkylenedioxy groups; (4-7) a cycloalkyl lower alkyl group; (4-8) a pyridyl lower alkyl group; (4-9) an amino group substituted lower alkyl group optionally substituted by at least one substituent selected from the group consisting of lower alkyl groups and lower alkanoyl groups; (4-10) a pyrrolidinyl lower alkyl group; (4-11) a phenyl lower alkenyl group; (4-12) an anilinocarbonyl lower alkyl group optionally substituted by one or more lower alkyl groups on the phenyl ring; (4-13) an indolyl group; (4-14) a piperazinyl lower alkyl group that may have, as a substituent on the piperazine ring, a group selected from the group consisting of lower alkyl groups and phenyl lower alkyl groups optionally substituted by one or more lower alkylenedioxy groups on the phenyl ring; (4-15) an amidino lower alkyl group optionally substituted by one or more lower alkyl groups; (4-16) a fluorenyl group; (4-17) a carbazolyl group optionally substituted by one or more lower alkyl groups on the carbazole ring; (4-18) a cyano-substituted lower alkyl group; or (4-19) a 2,3-dihydrobenzo[d]imidazo[2,1-b]thiazolyl group:

$R^3$ and $R^4$, together with the nitrogen atom to which they bind, may bind to each other, directly or via a nitrogen atom, or sulfur atom, and form a 5- to 10-membered saturated or unsaturated heterocyclic ring or a group represented by General Formula:

where the saturated heterocyclic ring may have at least one substituent.

Examples of the substituent formed on the heterocyclic ring by $R^3$ and $R^4$ include the groups described in (1) to (32) below:

(1) lower alkyl groups having 1 to 2 phenyl groups that may have, on the phenyl ring, 1 to 3 substituents selected from the group consisting of cyano group, nitro group, halogen atoms, lower alkyl groups optionally substituted by one or more halogen atoms or lower alkoxy groups, lower alkoxy groups optionally substituted by one or more halogen atoms or cycloalkyl groups, hydroxy group, aminosulfonyl groups optionally substituted by one or more lower alkyl groups, lower alkylaminocarbonyl groups, tetrazolyl groups optionally substituted by one or more lower alkyl groups or lower alkoxy lower alkyl groups, lower alkynyl groups, lower alkylsulfonyl groups, lower alkylsulfonylamino groups, 1,2,4-triazolyl groups, imidazolyl groups, piperidinyl groups, thiadiazolyl groups, and lower alkylenedioxy groups optionally substituted by one or more halogen atoms include;

(2) pyridyl lower alkyl groups that may have, on the pyridine ring, 1 to 3 substituents selected from the group consisting of hydroxy group, lower alkyl groups optionally substituted by one or more hydroxy groups, halogen atoms, lower alkoxy groups, and cyano group;

(3) pyrrolyl lower alkyl groups that may have 1 to 3 lower alkyl groups as substituents on the pyrrole ring;

(4) benzoyl group optionally substituted on the phenyl ring with at least one substituent selected from the group consisting of cyano group, lower alkoxy groups, and amino groups optionally substituted by one or more lower alkylsulfonyl groups;

(5) pyrimidinyl group;

(6) pyrazinyl group;

(7) pyridyl group optionally substituted by one or more lower alkyl groups (wherein the lower alkyl group may be substituted by one or more halogen atoms);

(8) lower alkoxycarbonyl group;

(9) lower alkyl group that may have at least one substituent selected from the group consisting of hydroxy groups and halogen atoms;

(10) phenyl group optionally substituted on the phenyl ring with 1 to 3 groups selected from the group consisting of halogen atoms, lower alkyl groups optionally substituted by one or more halogen atoms, and cyano group;

(11) phenoxy group that may have a lower alkoxy group (a lower alkoxy group optionally substituted by one or more halogen atoms thereon);

(12) group-$(B_6CO)_t$—$N(R^{15})R^{16}$ (wherein $B_6$ is a lower alkylene group. t is 0 or 1. $R^{15}$ and $R^{16}$ may be the same or different and represent a hydrogen atom, a lower alkanoyl group optionally substituted by one or more halogen atoms, a lower alkyl group, a phenyl lower alkyl group optionally substituted, on the phenyl ring, by one or more lower alkoxy groups, a phenyl group optionally substituted, on the phenyl ring, by one or more lower alkoxy groups, or a pyridyl group. $R^{15}$ and $R^{16}$, together with the nitrogen atom to which they bind, may form 6-membered saturated heterocyclic ring by binding to each other, directly or via a nitrogen atom or oxygen atom, wherein the heterocyclic ring may be substituted by 1 to 3 lower alkyl groups.)

(13) quinolyl lower alkyl group;

(14) thiazolyl lower alkyl group that may have a phenyl group (the phenyl group may be substituted on the phenyl ring with at least one lower alkyl group optionally substituted by one or more halogen atoms) as a substituent on the thiazole ring;

(15) benzimidazolyl lower alkyl group that may have 1 to 3 lower alkyl groups as substituents on the benzimidazole ring;

(16) 1,2,4-oxadiazolyl lower alkyl group that may have an oxo group as a substituent on the 1,2,4-oxadiazole ring;

(17) cycloalkyl lower alkyl group;

(18) tetrahydropyranyl group;

(19) thienyl lower alkyl group optionally substituted by one or more lower alkyl groups on the thiophene ring;

(20) hydroxy group;

(21) imidazolyl lower alkyl group that may have, on the imidazole ring, 1 to 3 substituents selected from the group consisting of lower alkyl groups and halogen atoms;

(22) benzothienyl group;

(23) 1,2,3,4-tetrahydroquinolyl group optionally substituted by one or more oxo groups on the tetrahydroquinoline ring;

(24) isoxazolyl lower alkyl group that may have 1 to 3 lower alkyl groups as substituents on the isoxazole ring;

(25) imidazo[2,1-b]thiazolyl lower alkyl group;

(26) 3,4-dihydro-2H-benzo[1,4]oxazinyl lower alkyl group optionally substituted by one or more lower alkyl groups as substituents on the 3,4-dihydro-2H-benzo[1,4]oxazine ring;

(27) pyrazolyl lower alkyl group that may have, on the pyrazole ring, 1 to 3 substituents selected from the group consisting of lower alkyl groups and halogen atoms;

(28) dihydropyridyl lower alkyl group that may have an oxo group as a substituent on the dihydropyridine ring;

(29) morpholino lower alkyl group;

(30) phenyl lower alkenyl group optionally substituted by one or more lower alkoxy groups on the phenyl ring;

(31) pyridylcarbonyl group; and

(32) N-oxide group.

The heterocyclic ring may have 1 to 3 substituents mentioned in (1) to (32) above. These substituents on the heterocyclic ring may be the same or different.

It is preferable that $R^3$ and $R^4$, together with the nitrogen atom to which they bind, bind to each other, directly or via a nitrogen atom, or sulfur atom, and form a 5- to 10-membered saturated or unsaturated heterocyclic ring, wherein the saturated heterocyclic ring is a piperidine ring that may have at least one substituent or a piperazine ring that may have at least one substituent.

It is also preferable that $R^3$ and $R^4$, together with the nitrogen atom to which they bind, bind to each other, directly or via a nitrogen atom, or sulfur atom, and form a 5- to 10-membered saturated heterocyclic ring, wherein the saturated heterocyclic ring has one benzyl group, and the benzyl group has a lower alkoxy group optionally substituted by one or more halogen atoms; or a lower alkyl group optionally substituted by one or more halogen atoms.

It is also preferable that $R^1$ is a group $R^5$—$SO_2$—$N(R^{12})$— or group $R^5$—B—$N(R^6)$— wherein $R^5$ is a group shown below:

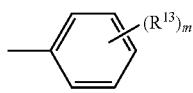

where m, B, $R^{13}$, $R^{12}$ and $R^6$ are the same as described above.

The present invention provides a pharmaceutical composition comprising the heterocyclic compound or a salt thereof represented by the General Formula (1):

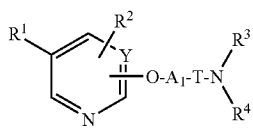

The pharmaceutical composition is preferably used for preventing or treating fibrosis.

The pharmaceutical composition is also preferably used for preventing or treating tumors.

The present invention also provides a heterocyclic compound or a salt thereof represented by the General Formula (1):

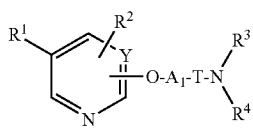

which are used as a pharmaceutical composition.

The present invention also provides a use of the heterocyclic compound or a salt thereof represented by the above General Formula (1) for producing a pharmaceutical composition.

The present invention further provides a method for preventing and/or treating fibrosis and/or tumors comprising administering an effective amount of the heterocyclic compound or a salt thereof represented by the above General Formula (1) to a patient.

The groups disclosed in the present specification are as below.

Examples of the lower alkylene group include linear or branched alkylene groups having 1 to 6 carbon atoms such as methylene, ethylene, trimethylene, 2-methyltrimethylene, 2,2-dimethylethylene, 2,2-dimethyltrimethylene, 1-methyltrimethylene, methylmethylene, ethylmethylene, tetramethylene, pentamethylene, and hexamethylene groups.

Examples of the lower alkenylene group include linear or branched alkenylene groups having 2 to 6 carbon atoms which have 1 to 3 double bonds, such as vinylene, 1-propenylene, 1-methyl-1-propenylene, 2-methyl-1-propenylene, 2-propenylene, 2-butenylene, 1-butenylene, 3-butenylene, 2-pentenylene, 1-pentenylene, 3-pentenylene, 4-pentenylene, 1,3-butadienylene, 1,3-pentadienylene, 2-penten-4-ynylene, 2-hexenylene, 1-hexenylene, 5-hexenylene, 3-hexenylene, 4-hexenylene, 3,3-dimethyl-1-propenylene, 2-ethyl-1-propenylene, 1,3,5-hexatrienylene, 1,3-hexadienylene, and 1,4-hexadienylene groups.

Examples of the 5- to 15-membered monocyclic, dicyclic, or tricyclic, saturated or unsaturated heterocyclic group having 1 to 4 nitrogen atoms, oxygen atoms, or sulfur atoms include pyrrolidinyl, piperidinyl, piperazinyl, morpholinyl, pyridyl, 1,2,5,6-tetrahydropyridyl, 1,2,4-triazolyl, 1,2,3-triazolyl, 1,2,5-triazolyl, thiazolidinyl, 1,2,3,4-tetrazolyl, thienyl, quinolyl, 1,4-dihydroquinolyl, benzothiazolyl, pyrazinyl, pyrimidyl, pyridazyl, 2H-pyrrolyl, pyrrolyl, 1,3,4-oxadiazolyl, tetrahydropyranyl, tetrahydrofuryl, furazanyl, carbostyril, 3,4-dihydrocarbostyril, 1,2,3,4-tetrahydroquinolyl, 1,2,3,4-tetrahydroisoquinolyl, indolyl, isoindolyl, indolinyl, benzimidazolyl, benzoxazolyl, imidazolidinyl, isoquinolyl, quinazolidinyl, quinoxalinyl, cinnolinyl, phthalazinyl, carbazoyl, acridinyl, chromanyl, isoindolinyl, isochromanyl, pyrazolyl, imidazolyl, pyrazolidinyl, phenothiazinyl, benzofuryl, 2,3-dihydrobenzo[b]furyl, benzothienyl, phenoxathiinyl, phenoxazinyl, 4H-chromenyl, IH-indazolyl, phenazinyl, xanthenyl, thianthrenyl, 2-imidazolinyl, 2-pyrrolinyl, furyl, oxazolyl, isoxazolyl, isoxazolidinyl, thiazolyl, isothiazolyl, pyranyl, 2-thiazolinyl, 2-pyrazolinyl, quinuclidinyl, 1,4-benzoxadinyl, 3,4,-dihydro-2H-1,4-benzoxadinyl, 3,4-dihydro-2H-I,4-benzothiazinyl, 1,4-benzothiazinyl, 1,2,3,4-tetrahydroquinoxalinyl, 1,3-dithia-2,4-dihydronaphthalenyl, phenanthridinyl, 1,4-dithianaphthalenyl, dibenz[b,e]azepine, 6,11-dihydro-5H-dibenz[b,e]azepine, and imidazo[2,1-b]thiazolyl groups.

Examples of the halogen atom are a fluorine atom, chlorine atom, bromine atom and iodine atom.

Examples of the lower alkyl group include linear or branched alkyl groups having 1 to 6 carbon atoms such as methyl, ethyl, propyl, isopropyl, 2,2-dimethylpropyl, 1-ethylpropyl, butyl, isobutyl, tert-butyl, isopentyl, pentyl, and hexyl groups.

Examples of the lower alkyl group optionally substituted by one or more halogen atoms include linear or branched alkyl groups having 1 to 6 carbon atoms that may have 1 to 3 halogen atoms as substituents. In addition to the above described lower alkyl groups, specific example thereof include trifluoromethyl, trichloromethyl, chloromethyl, bromomethyl, fluoromethyl, iodomethyl, difluoromethyl, dibromomethyl, dichloromethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, and 5,6-dibromohexyl groups.

Examples of the lower alkoxy group include linear or branched alkoxy groups having 1 to 6 carbon atoms such as methoxy, ethoxy, propoxy, isopropoxy, butoxy, tert-butoxy, pentyloxy, and hexyloxy groups.

Examples of the lower alkoxy group optionally substituted by one or more halogen atoms or lower alkoxy groups include methoxy, ethoxy, propoxy, isopropoxy, butoxy, tert-butoxy, pentyloxy, hexyloxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 6-bromohexyloxy, 5,6-dichlorohexyloxy, methoxymethoxy, ethoxymethoxy, propoxymethoxy, butoxymethoxy, tert-butoxymethoxy, pentyloxymethoxy, hexyloxymethoxy, 1-methoxyethoxy, 2-methoxyethoxy, 1-ethoxyethoxy, 2-ethoxyethoxy, 2-propoxyethoxy, 1-methoxypropoxy, 2-methoxypropoxy, 3-ethoxypropoxy, 4-methoxybutoxy, 4-ethoxybutoxy, 5-methoxypentyloxy, 3-isopropoxypropoxy, 6-methoxyhexyloxy, and 6-ethoxyhexyloxy groups. In other words, the lower alkoxy group optionally substituted by one or more halogen atoms or lower alkoxy groups is a linear or branched alkoxy group having 1 to 6 carbon atoms that may have 1 to 3 substituents selected from the group consisting of halogen atom and linear or branched alkoxy groups having 1 to 6 carbon atoms.

Examples of the lower alkyl group optionally substituted by one or more lower alkoxy groups include linear or branched alkyl groups having 1 to 6 carbon atoms optionally substituted by one or more linear or branched alkoxy groups having 1 to 6 carbon atoms. Specific examples thereof include, in addition to the above described lower alkyl groups, methoxymethyl, 1-ethoxyethyl, 2-methoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, and 3-methoxypropyl groups.

Examples of the lower alkanoyl group include liner or branched alkanoyl groups having 1 to 6 carbon atoms such as a formyl group, acetyl group, propionyl group, butyryl group, isobutyryl group, pentanoyl group, tert-butylcarbonyl, and hexanoyl group.

Examples of the lower alkylsulfonyl group include linear or branched alkylsulfonyl groups having 1 to 6 carbon atoms such as a methylsulfonyl group, ethylsulfonyl group, propylsulfonyl group, isopropylsulfonyl group, butylsulfonyl group, tert-butylsulfonyl group, pentylsulfonyl group, and hexylsulfonyl group.

Examples of the phenyl lower alkyl group include phenylalkyl groups of which alkyl moiety is a linear or branched alkyl group having 1 to 6 carbon atoms such as a benzyl group, 2-phenylethyl group, 1-phenylethyl group, 3-phenylpropyl group, 4-phenylbutyl group, 5-phenylpentyl group, 6-phenylhexyl group, 1,1-dimethyl-2-phenylethyl group, and 2-methyl-3-phenylpropyl group.

Examples of the indolediyl group represented by $A_1$ are indole-(1,2-, 1,3-, 1,4-, 1,5-, 1,6-, 1,7-, 2,3-, 2,4-, 2,5-, 2,6-, 2,7-, 3,4-, 3,5-, 3,6-, 3,7-, 4,5-, 4,6-, 4,7-, 5,6-, 5,7- or 6,7-) diyl groups.

Examples of the indolinediyl group represented by $A_1$ are indoline-(1,2-, 1,3-, 1,4-, 1,5-, 1,6-, 1,7-, 2,3-, 2,4-, 2,5-, 2,6-, 2,7-, 3,4-, 3,5-, 3,6-, 3,7-, 4,5-, 4,6-, 4,7-, 5,6-, 5,7- or 6,7-) diyl groups.

Examples of the substituent on the heterocyclic ring represented by $A_1$ include oxo group, methyl, ethyl, propyl, isopropyl, 2,2-dimethylpropyl, 1-ethylpropyl, butyl, isobutyl, tert-butyl, isopentyl, pentyl, hexyl, methoxymethyl, 1-ethoxyethyl, 2-methoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, and 3-methoxypropyl groups. In other words, the substituent on the heterocyclic ring represented by $A_1$ is oxo group or a linear or branched alkyl having 1 to 6 carbon atoms that may have 1 to 3 linear or branched alkoxy groups having 1 to 6 carbon atoms. The heterocyclic ring may have 1 to 4 of these substituents. When the heterocyclic ring has two or more substituents, they may be the same or different.

Examples of the cycloalkyl group include cycloalkyl groups having 3 to 16 carbon atoms such as cyclopropyl group, cyclobutyl group, cyclopentyl group, cyclohexyl group, cycloheptyl group, cyclooctyl group, cyclononyl group, cyclodecyl group, cycloundecyl group, cyclododecyl group, cyclotridecyl group, cyclotetradecyl group, cyclopentadecyl group, and cyclohexadecyl group.

Examples of the cycloalkylcarbonyl group include cycloalkylcarbonyl groups of which cycloalkyl moiety is a cycloalkyl group having 3 to 16 carbon atoms such as a cyclopropylcarbonyl group, cyclobutylcarbonyl group, cyclopentylcarbonyl group, cyclohexylcarbonyl group, cycloheptylcarbonyl group, cyclooctylcarbonyl group, cyclononylcarbonyl group, cyclodecylcarbonyl group, cycloundecylcarbonyl group, cyclododecylcarbonyl group, cyclotridecylcarbonyl group, cyclotetradecylcarbonyl group, cyclopentadecylcarbonylgroup, and cyclohexadecylcarbonyl group.

Examples of the naphthyl group include (1- or 2-) naphthyl, 1-methyl-(2-, 3-, 4-, 5-, 6-, 7- or 8-)naphthyl, 2-ethyl-(1-, 3-, 4-, 5-, 6-, 7- or 8-)naphthyl, 3-n-propyl-(1-, 2-, 4-, 5-, 6-, 7- or 8-)naphthyl, 4-n-butyl-(1-, 2-, 3-, 5-, 6-, 7- or 8-)naphthyl, 4-methyl-(1-, 2-, 3-, 5-, 6-, 7- or 8-)naphthyl, 5-n-pentyl-(1-, 2-, 3-, 4-, 6-, 7- or 8-)naphthyl, 6-n-hexyl-(1-, 2-, 3-, 4-, 5-, 7- or 8-)naphthyl, 1,7-dimethyl-(2-, 3-, 4-, 5-, 6- or 8-)naphthyl, 1,2,8-trimethyl-(3-, 4-, 5-, 6- or 7-) naphthyl, 1-dimethylamino-(2-, 3-, 4-, 5-, 6-, 7- or 8-)naphthyl, 2-dimethylamino-(1-, 3-, 4-, 5-, 6-, 7- or 8-)naphthyl, 3-methylamino-(1-, 2-, 4-, 5-, 6-, 7- or 8-)naphthyl, 5-amino-(1-, 2-, 3-, 4-, 6-, 7- or 8-)naphthyl, 5-dimethylamino-(1-, 2-, 3-, 4-, 6-, 7- or 8-)naphthyl, 4-(N-methyl-N-ethylamino)-(1-, 2-, 3-, 5-, 6-, 7- or 8-)naphthyl, 1-methyl-2-dimethylamino-(3-, 4-, 5-, 6-, 7- or 8-)naphthyl, 1-chloro-(2-, 3-, 4-, 5-, 6-, 7- or 8-) naphthyl, and 1-acetylamino-(2-, 3-, 4-, 5-, 6-, 7- or 8-) naphthyl group. Specifically, these naphthyl group may have on the naphthalene ring, 1 to 3 substituents selected from the group consisting of linear or branched alkyl groups having 1 to 6 carbon atoms, halogen atoms, and amino groups that may have 1 or 2 substituents selected from the group consisting of linear or branched alkyl groups having 1 to 6 carbon atoms and linear or branched alkanoyl groups having 1 to 6 carbon atoms.

Examples of the lower alkanoyl group optionally substituted by one or more halogen atoms include linear or branched alkanoyl groups having 2 to 6 carbon atoms that may have 1 to 3 halogen atoms as substituents. Specific examples thereof include, in addition to the above described lower alkanoyl groups, 2,2,2-trifluoroacetyl, 2,2,2-trichloroacetyl, 2-chloroacetyl, 2-bromoacetyl, 2-fluoroacetyl, 2-iodoacetyl, 2,2-difluoroacetyl, 2,2-dibromoacetyl, 3,3,3-trifluoropropionyl, 3,3,3-trichloropropionyl, 3-chloropropionyl, 2,3-dichloropropionyl, 4,4,4-trichlorobutyryl, 4-fluorobutyryl, 5-chloropentanoyl, 3-chloro-2-methylpropionyl, 6-bromohexanoyl, and 5,6-dibromohexanoyl groups.

Examples of the lower alkenyl group include linear or branched alkenyl groups having 2 to 6 carbon atoms that have 1 to 3 double bonds such as vinyl, 1-propenyl, 1-methyl-1-propenyl, 2-methyl-1-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl groups.

Examples of the amino substituted lower alkanoyl group optionally substituted by one or more lower alkyl groups include linear or branched alkanoyl groups having 2 to 6 carbon atoms substituted with an amino group that may have 1 or 2 linear or branched alkyl groups having 1 to 6 carbon atoms as substituents such as aminoacetyl, 2-aminopropionyl, 3-aminopropionyl, 4-aminobutyryl, 5-aminopentanoyl, 6-aminohexanoyl, 2,2-dimethyl-3-aminopropionyl, 2-methyl-3-aminopropionyl, methylaminoacetyl, 2-ethylaminopropionyl, 3-propylaminopropionyl, 3-isopropylaminopropionyl, 4-butylaminobutyryl, 5-pentylaminopentanoyl, 6-hexylaminohexanoyl, dimethylaminoacetyl, 3-diisopropylaminopropionyl, (N-ethyl-N-propylamino)acetyl, and 2-(N-methyl-N-hexylamino)acetyl groups.

Examples of the lower alkylene group optionally substituted by one or more hydroxy groups include linear or branched alkylene groups having 1 to 6 carbon atoms that may have 1 to 3 hydroxy groups as substituents. Specific examples thereof include, in addition to the above described lower alkylene groups, 1-hydroxymethylene, 1-hydroxyethylene, 2-hydroxytrimethylene, 1-hydroxytrimethylene, 1-hydroxy-2-methyltrimethylene, 1-hydroxy-2,2-dimethyltrimethylene, 3-hydroxy-1-methyltrimethylene, 2-hydroxy-1-methyltrimethylene, 1-hydroxymethylmethylene, hydroxymethylmethylene, 2-hydroxymethyltrimethylene, 2-hydroxymethyl-2-methyltrimethylene, (2-hydroxyethyl)methylene, (1-hydroxyethyl)methylene, 2-hydroxytetramethylene, 1-hydroxytetramethylene, 3-hydroxypentamethylene, 2-hydroxypentamethylene, 1-hydroxypentamethylene, 3-hydroxyhexamethylene, 2-hydroxyhexamethylene, 1-hydroxyhexamethylene, 1,2-dihydroxytrimethylene, 2,2,4-trihydroxytetramethylene, 1,2,6-trihydroxyhexamethylene and 3,4,5-trihydroxypentamethylene groups.

Examples of the alkyl group (optionally substituted by one or more amino groups optionally substituted by phenyl group or lower alkyl group include the above-explained lower alkyl group that may have 1 to 3, preferably one, phenyl group or amino group as a substituent. The amino group may have 1 or 2 lower alkyl groups explained above. Specific examples of such an alkyl group (optionally substituted by one or more amino groups optionally substituted by phenyl group or lower alkyl group) include methyl, ethyl, propyl, isopropyl, 2,2-dimethylpropyl, 1-ethylpropyl, butyl, isobutyl, tert-butyl, isopentyl, pentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, icosanyl, benzyl, 2-phenylethyl, 1-phenylethyl, 3-phenylpropyl, 4-phenylbutyl, 5-phenylpentyl, 6-phenylhexyl, 7-phenylheptyl, 8-phenyloctyl, 9-phenylnonyl, 10-phenyldecanyl, 11-phenylundecanyl, 12-phenyldodecanyl, 13-phenyltridecanyl, 14-phenyltetradecanyl, 15-phenylpentadecanyl, 16-phenylhexadecanyl, 17-phenylheptadecanyl, 18-phenyloctadecanyl, 19-phenylnonadecanyl, 20-phenylicosanyl, 1,1-dimethyl-2-phenylethyl, 2-methyl-3-phenylpropyl, 2-aminoethyl, 1-aminoethyl, 3-aminopropyl, 4-aminobutyl, 5-aminopentyl, 6-aminohexyl, 7-aminoheptyl, 8-aminooctyl, 9-aminononyl, 10-aminodecanyl, 11-aminoundecanyl, 12-aminododecanyl, 13-aminotridecanyl, 14-aminotetradecanyl, 15-aminopentadecanyl, 16-aminohexadecanyl, 17-aminoheptadecanyl, 18-aminooctadecanyl, 19-aminononadecanyl, 20-aminoicosanyl, 1,1-dimethyl-2-aminoethyl, 2-methyl-3-aminopropyl, N-methylamino-methyl, 2-(N-methylamino)ethyl, 3-(N-methylamino)propyl, 4-(N-ethylamino)benzyl, 5-(N-methylamino)pentyl, 6-(N-propylamino)hexyl, 3-(N,N-dimethylamino)propyl, and 3-(N,N-diethylamino)propyl.

Examples of the lower alkyl group optionally substituted by one or more hydroxy groups include linear or branched alkyl groups having 1 to 6 carbon atoms that have 1 to 3 hydroxy groups as substituents. Specific examples thereof include, in addition to the above described lower alkyl groups, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the cycloalkyl group optionally substituted by one or more substituents selected from the group consisting of hydroxy group and lower alkyl groups include cycloalkyl groups having 3 to 16 carbon atoms that may have 1 to 3 substituents selected from the group consisting of hydroxy group and linear or branched alkyl groups having 1 to 6 carbon atoms. Specific examples thereof include, in addition to the above described cycloalkyl groups, 2-hydroxycyclopropyl, 3-hydroxycyclobutyl, 3-hydroxycyclopentyl, 2-hydroxycyclohexyl, 4-hydroxycyclohexyl, 3-hydroxycycloheptyl, 4-hydroxycyclooctyl, 5-hydroxycyclononyl, 3-hydroxycyclodecyl, 4-hydroxycycloundecyl, 5-hydroxycyclododecyl, 6-hydroxycyclotridecyl, 7-hydroxycyclotetradecyl, 6-hydroxycyclopentadecyl, 8-hydroxycyclohexadecyl, 2,4-dihydroxycyclohexyl, 2,4,6-trihydroxycyclohexyl, 1-methylcyclopentyl, 2-ethylcyclopropyl, 3-n-propylcyclobutyl, 2-n-butylcyclohexyl, 4-n-pentylcycloheptyl, 4-n-hexylcyclooctyl, 2,3-dimethylcyclohexyl, 2,3,4-trimethylcyclohexyl, and 2-methyl-4-hydroxycyclohexyl groups.

Examples of the amino lower alkoxy group optionally substituted by one or more lower alkyl groups include linear or branched alkoxy groups having 1 to 6 carbon atoms substituted with an amino group that may have 1 or 2 linear or branched alkyl groups having 1 to 6 carbon atoms such as aminomethoxy, 2-aminoethoxy, 1-aminoethoxy, 3-aminopropoxy, 4-aminobutoxy, 5-aminopentyloxy, 6-aminohexyloxy, 1,1-dimethyl-2-aminoethoxy, 2-methyl-3-aminopropoxy, methylaminomethoxy, 1-ethylaminoethoxy, 2-propylaminoethoxy, 3-isopropylaminopropoxy, 4-butylaminobutoxy, 5-pentylaminopentyloxy, 6-hexylaminohexyloxy, dimethylaminomethoxy, 2-diethylaminoethoxy, 2-diisopropylaminoethoxy, (N-ethyl-N-propylamino)methoxy, and 2-(N-methyl-N-hexylamino)ethoxy groups.

Examples of the hydroxy group substituted lower alkyl group include linear or branched alkyl groups having 1 to 6 carbon atoms which have 1 to 3 hydroxy groups as substituents such as a hydroxymethyl, 1-hydroxyethyl, 2-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, and 2-methyl-3-hydroxypropyl groups.

Examples of the lower alkynyl group include linear or branched alkynyl groups having 2 to 6 carbon atoms such as ethynyl, 2-propynyl, 2-butynyl, 3-butynyl, 1-methyl-2-propynyl, 2-pentynyl, and 2-hexynyl groups.

Examples of the amino group optionally substituted by one or more lower alkyl groups or lower alkylsulfonyl groups include amino groups that may have 1 or 2 linear or branched alkyl groups having 1 to 6 carbon atoms or linear or branched alkylsulfonyl groups having 1 to 6 carbon atoms as substituents such as amino, methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino, N-methyl-N-hexylamino, methylsulfonylamino, ethylsulfonylamino, propylsulfonylamino, isopropylsulfonylamino, butylsulfonylamino, tert-butylsulfonylamino, pentylsulfonylamino, hexylsulfonylamino, dimethylsulfonylamino, diethylsulfonylamino, dipropylsulfonylamino, dibutylsulfonylamino, dipentylsulfonylamino, dihexylsulfonylamino, N-methylsulfonyl-N-ethylsulfonylamino, N-ethylsulfonyl-N-propylsulfonylamino, N-methylsulfonyl-N-butylsulfonylamino, and N-methylsulfonyl-N-hexylsulfonylamino groups.

Examples of the lower alkylthio group include linear or branched alkylthio groups having 1 to 6 carbon atoms such as a methylthio group, ethylthio group, propylthio group, isopropylthio group, butylthio group, tert-butylthio group, pentylthio group, and hexylthio group.

Examples of the anilino group optionally substituted by one or more halogen atoms on the phenyl ring include anilino groups that may have 1 to 3 halogen atoms as substituents on the phenyl ring such as anilino, 2-fluoroanilino, 3-fluoroanilino, 4-fluoroanilino, 2-bromoanilino, 3-bromoanilino, 4-bromoanilino, 2-iodoanilino, 3-iodoanilino, 4-iodoanilino, 2,3-dibromoanilino, 2,4-diiodoanilino, 2,5-difluoroanilino, 2,6-dichloroanilino, 2,4,6-trichloroanilino, 2,6-difluoroanilino, 3,5-difluoroanilino, 2,6-difluoroanilino, 2-chloroanilino, 3-chloroanilino, 4-chloroanilino, 2,3-dichloroanilino, 2,4-dichloroanilino, 2,5-dichloroanilino, 3,4-dichloroanilino, 2,6-dichloroanilino, 3,5-dichloroanilino, 2,4,6-trifluoroanilino, 2,4-difluoroanilino, and 3,4-difluoroanilino groups.

Examples of the lower alkoxycarbonyl group include linear or branched alkoxycarbonyl groups having 1 to 6 carbon atoms such as methoxycarbonyl, ethoxycarbonyl, propoxycarbonyl, isopropoxycarbonyl, butoxycarbonyl, tert-butoxycarbonyl, pentyloxycarbonyl, and hexyloxycarbonyl groups.

Examples of the pyrrolidinyl group optionally substituted by one or more oxo groups on the pyrrolidine ring include pyrrolidinyl groups that may have 1 or 2 oxo groups as substituents on the pyrrolidine ring such as (1-, 2- or 3-) pyrrolidinyl, 2-oxo-(1-, 3-, 4- or 5-)pyrrolidinyl, 3-oxo-(1-, 2-, 4- or 5-)pyrrolidinyl, 2,3-dioxo-(1-, 4- or 5-)pyrrolidinyl, and 2,5-dioxo-(1-, 3- or 4-)pyrrolidinyl groups.

Examples of the lower alkanoylamino group include linear or branched alkanoylamino groups having 2 to 6 carbon atoms such as acetylamino, propionylamino, butyrylamino, pentanoylamino, 2-methylpropionylamino, and hexanoylamino groups.

Examples of the phenyl group optionally substituted on the phenyl ring with 1 to 3 groups selected from the group consisting of lower alkyl groups; lower alkoxy groups optionally substituted by one or more halogen atoms; halogen atoms; amino lower alkoxy groups optionally substituted by one or more lower alkyl groups; hydroxy groups substituted lower alkyl groups; phenyl lower alkyl groups; lower alkynyl groups; amino groups optionally substituted by one or more lower alkyl or lower alkylsulfonyl groups; lower alkylthio groups; cycloalkyl groups; phenylthio group; adamantyl groups; anilino groups optionally substituted by one or more halogen atoms on the phenyl ring; lower alkoxycarbonyl groups; pyrrolidinyl groups optionally substituted by one or more oxo groups on the pyrrolidine ring; lower alkanoylamino groups; cyano group; and phenoxy group include phenyl groups optionally substituted on the phenyl ring with 1 to 3 groups selected from the group consisting of linear or branched alkyl groups having 1 to 6 carbon atoms; linear or branched alkoxy groups having 1 to 6 carbon atoms that may have 1 to 3 halogen atoms; halogen atoms; aminoalkoxy groups of which alkoxy moiety is a linear or branched alkoxy group having 1 to 6 carbon atoms and that may have 1 or 2 linear or branched alkyl groups having 1 to 6 carbon atom as substituents; linear or branched alkyl groups having 1 to 6 carbon atoms that may have 1 to 3 hydroxy groups as substituents; phenylalkyl groups of which alkyl moiety is a linear or branched alkyl group having 1 to 6 carbon atoms; linear or branched alkynyl groups having 2 to 6 carbon atoms; amino groups optionally substituted by 1 or 2 linear or branched alkyl or alkylsulfonyl groups having 1 to 6 carbon atoms; linear or branched alkylthio groups having 1 to 6 carbon atoms; cycloalkyl groups having 3 to 16 carbon atoms; phenylthio group; adamantyl groups; anilino groups optionally substituted by 1 to 3 halogen atoms on the phenyl ring; linear or branched alkoxycarbonyl groups having 1 to 6 carbon atoms; pyrrolidinyl groups that may have 1 or 2 oxo groups as substituents on the pyrrolidine ring; amino groups that may have 1 or 2 linear or branched alkanoyl groups having 2 to 6 carbon atoms; cyano group; and phenoxy group, such as phenyl, 2-methylphenyl, 3-methylphenyl, 4-methylphenyl, 2-ethylphenyl, 3-ethylphenyl, 4-ethylphenyl, 2-isopropylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 3-butoxyphenyl, 4-pentyloxyphenyl, 4-hexyloxyphenyl, 3,4-dimethoxyphenyl, 3,4-diethoxyphenyl, 2,4-dimethoxyphenyl, 2,5-dimethoxyphenyl, 2,6-dimethoxyphenyl, 3,4,5-trimethoxyphenyl, 2-trifluoromethoxyphenyl, 3-trifluoromethoxyphenyl, 4-trifluoromethoxyphenyl, 2-(bromomethoxy)phenyl, 3-(2-chloroethoxy)phenyl, 4-(2,3-dichloropropoxy)phenyl, 4-(4-fluorobutoxy)phenyl, 3-(5-chloropentyloxy)phenyl, 4-(5-bromohexyloxy)phenyl, 4-(5,6-dibromohexyloxy)phenyl, 3,4-di(trifluoromethoxy)phenyl, 3,4-di(4,4,4-trichlorobutoxy)phenyl, 2,4-di(3-chloro-2-methoxypropyl)phenyl, 2,5-di(3-chloropropoxy)phenyl, 2,6-di(2,2,2-trifluoroethoxy)phenyl, 3,4,5-tri(trifluoromethoxy)phenyl, 4-(2,2,2-trichloroethoxy)phenyl, 2-methyl-4-trifluoromethoxyphenyl, 3-ethyl-4-trichloromethoxyphenyl, 2-methoxy-4-trifluoromethoxyphenyl, 3-ethoxy-4-trichloromethoxyphenyl, 2-methyl-3-trifluoromethoxy-4-trifluoromethoxyphenyl, 2-phenoxyphenyl, 3-phenoxyphenyl, 4-phenoxyphenyl, 2,3-diphenoxyphenyl, 3,4-diphenoxyphenyl, 2,6-diphenoxyphenyl, 3,4,5-triphenoxyphenyl, 2-methyl-4-phenoxyphenyl, 3-ethyl-4-phenoxyphenyl, 2-methoxy-4-phenoxyphenyl, 3-ethoxy-4-phenoxyphenyl, 2-methyl-3-phenoxy-4-trifluoromethoxyphenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 4-methylthiophenyl, 4-cyclohexylphenyl, 4-chloro-2-anilinophenyl, 2-(4-chloroanilino)-5-ethoxycarbonylphenyl, 4-[2-(N,N-diethylamino)ethoxy]phenyl, 4-(2-oxo-1-pyrrolidinyl)phenyl, 4-methylaminophenyl, 4-methylsulfonylaminophenyl, 4-(2-hydroxyethyl)phenyl, 4-benzylphenyl, 4-ethinylphenyl, 4-phenylthiophenyl, 4-(1-adamantyl)phenyl, 5-acetylamino-2-chlorophenyl, 2-propanoylaminophenyl, 3-cyanophenyl, 2-cyanophenyl, 4-cyanophenyl, 3,4-dicyanophenyl, and 3,4,5-tricyanophenyl groups.

Examples of the lower alkyl group optionally substituted by one or more lower alkoxy groups include linear or branched alkyl groups having 1 to 6 carbon atoms optionally substituted by one or more linear or branched alkoxy groups having 1 to 6 carbon atoms, such as methoxymethyl, 1-ethoxyethyl, 2-methoxyethyl, 2-propoxyethyl, 3-isopropoxypropyl, 4-butoxybutyl, 5-pentyloxypentyl, 6-hexyloxyhexyl, 1,1-dimethyl-2-methoxyethyl, 2-methyl-3-ethoxypropyl, and 3-methoxypropyl groups.

Examples of the tetrazolyl group optionally substituted by one or more lower alkyl groups or lower alkoxy lower alkyl groups include (1- or 5-)tetrazolyl, 1-methyltetrazol-5-yl, 5-methyltetrazol-1-yl, 1-ethyltetrazol-5-yl, 5-ethyltetrazol-1-yl, 1-propyltetrazol-5-yl, 5-propyltetrazol-1-yl, 1-isopropyltetrazol-5-yl, 5-isopropyltetrazol-1-yl, 1-(2,2-dimethylpropyl)tetrazol-5-yl, 5-(2,2-dimethylpropyl)tetrazol-1-yl, 1-(1-ethylpropyl)tetrazol-5-yl, 5-(1-ethylpropyl)tetrazol-1-yl, 1-butyltetrazol-5-yl, 5-butyltetrazol-1-yl, 1-isobutyltetrazol-5-yl, 5-isobutyltetrazol-1-yl, 1-tert-butyltetrazol-5-yl, 5-tert-butyltetrazol-1-yl, 1-isopentyltetrazol-5-yl, 5-isopentyltetrazol-1-yl, 1-pentyltetrazol-5-yl, 5-pentyltetrazol-1-yl, 1-hexyltetrazol-5-yl, 5-hexyltetrazol-1-yl, 1-methoxymethyltetrazol-5-yl, 5-methoxymethyltetrazol-1-yl, 1-(1-ethoxyethyl)tetrazol-5-yl, 5-(1-ethoxyethyl)tetrazol-1-yl, 1-(2-methoxyethyl)tetrazol-5-yl, 5-(2-methoxyethyl)tetrazol-1-yl, 1-(2-propoxyethyl)tetrazol-5-yl, 5-(2-propoxyethyl) tetrazol-1-yl, 1-(3-isopropoxypropyl)tetrazol-5-yl, 5-(3-isopropoxypropyl)tetrazol-1-yl, 1-(4-butoxybutyl)tetrazol-5-yl, 5-(4-butoxybutyl)tetrazol-1-yl, 1-(5-pentyloxypentyl)tetrazol-5-yl, 5-(5-pentyloxypentyl)tetrazol-1-yl, 1-(6-hexyloxyhexyl)tetrazol-5-yl, 5-(6-hexyloxyhexyl)tetrazol-1-yl, 1-(1,1-dimethyl-2-methoxyethyl)tetrazol-5-yl, 5-(1,1-dimethyl-2-methoxyethyl)tetrazol-1-yl, 1-(2-methyl-3-ethoxypropyl)tetrazol-5-yl, 5-(2-methyl-3-ethoxypropyl)tetrazol-1-yl, 1-(3-methoxypropyl)tetrazol-5-yl, 5-(3-methoxypropyl)tetrazol-1-yl and like tetrazolyl groups that may have one of the above-described lower alkyl groups or lower alkoxy lower alkyl groups.

Examples of the phenyl lower alkyl group optionally substituted on the phenyl ring with 1 to 3 groups selected from the group consisting of halogen atoms, lower alkoxy groups optionally substituted by one or more halogen atoms, lower alkyl groups, and tetrazolyl groups optionally substituted by one or more lower alkyl groups or lower alkoxy lower alkyl groups include, in addition to the above described phenyl lower alkyl groups, 4-fluorobenzyl, 2-chlorobenzyl, 3-chlorobenzyl, 4-chlorobenzyl, 2-(2-fluorophenyl)ethyl, 2-(4-fluorophenyl)ethyl, 2-(4-chlorophenyl)ethyl, 3,4-dibromobenzyl, 3,4-diiodobenzyl, 2,4-difluorobenzyl, 2,5-dichlorobenzyl, 2,6-dichlorobenzyl, 3,4,5-trifluorobenzyl, 3-(4-chlorophenyl)propyl, 1-(2-bromophenyl)ethyl, 4-(3-fluorophenyl)butyl, 5-(4-iodophenyl)pentyl, 6-(4-chlorophenyl)hexyl, 1,1-dimethyl-2-(3-fluorophenyl)ethyl, 2-methyl-3-(4-chlorophenyl)propyl, 2-methylbenzyl, 2-(3-methylphenyl)ethyl, 3-(4-methylphenyl)propyl, 1-(2-ethylphenyl)ethyl, 4-(3-ethylphenyl)butyl, 5-(4-ethylphenyl)pentyl, 6-(4-isopropylphenyl)hexyl, 1,1-dimethyl-2-(3-butylphenyl)ethyl, 2-methyl-3-(4-pentylphenyl)propyl, 4-hexylbenzyl, 3,4-dimethylbenzyl, 3,4-diethylbenzyl, 2,4-dimethylbenzyl, 2,5-dimethylbenzyl, 2,6-dimethylbenzyl, 3,4,5-trimethylbenzyl, 2-methoxybenzyl, 2-(2-methoxyphenyl)ethyl, 2-(3-methoxyphenyl)ethyl, 2-(4-methoxyphenyl)ethyl, 4-methoxybenzyl, 1-(2-ethoxyphenyl)ethyl, 3-(3-ethoxyphenyl)propyl, 4-(4-ethoxyphenyl)butyl, 5-(4-isopropoxyphenyl)pentyl, 6-(3-butoxyphenyl)hexyl, 1,1-dimethyl-2-(4-pentyloxyphenyl)ethyl, 2-methyl-3-(4-hexyloxyphenyl)propyl, 3,4-dimethoxybenzyl, 3,4-diethoxybenzyl, 2,4-dimethoxybenzyl, 2,5-dimethoxybenzyl, 2,6-dimethoxybenzyl, 3,4,5-trimethoxybenzyl, 2-trifluoromethoxybenzyl, 3-trifluoromethoxybenzyl, 4-trifluoromethoxybenzyl, 2-[2-(bromomethoxy)phenyl]ethyl, 1-[3-(2-chloroethoxy)phenyl]ethyl, 3-[4-(2,3-dichloropropoxy)phenyl]propyl, 4-[4-(4-fluorobutoxy)phenyl]butyl, 5-[3-(5-chloropentyloxy)phenyl]pentyl, 6-[4-(5-bromohexyloxy)phenyl]hexyl, 1,1-dimethyl-2-[4-(5,6-dibromohexyloxy)phenyl]ethyl, 3,4-di(trifluoromethoxy)benzyl, 3,4-di(4,4,4-trichlorobutoxy)benzyl, 2,4-di(3-chloro-2-methoxypropyl)benzyl, 2,5-di(3-chloropropoxy)benzyl, 2,6-di(2,2,2-trifluoroethoxy)benzyl, 3,4,5-tri(trifluoromethoxy)benzyl, 4-(2,2,2-trichloroethoxy)benzyl, 2-methyl-4-trifluoromethoxybenzyl, 3-ethyl-4-trichloromethoxybenzyl, 2-methoxy-4-trifluoromethoxybenzyl, 3-ethoxy-4-trichloromethoxybenzyl, 2-methyl-3-trifluoromethoxy-4-trifluoromethoxybenzyl, 2-chloro-3-methylbenzyl, 4-fluoro-2-trifluoromethoxybenzyl, 3-chloro-2-methyl-4-methoxybenzyl, (1- or 5-)tetrazolyl benzyl, 1-methyltetrazol-5-ylbenzyl, 5-methyltetrazol-1-ylbenzyl, 1-ethyltetrazol-5-ylbenzyl, 5-ethyltetrazol-1-ylbenzyl, 5-pentyltetrazol-1-ylbenzyl, 1-hexyltetrazol-5-ylbenzyl, 5-methoxymethyltetrazol-1-ylbenzyl, and 1-(1-ethoxyethyl)tetrazol-5-ylbenzyl groups. Specifically, these are phenylalkyl groups optionally substituted on the phenyl ring with 1 to 3 groups selected from the group consisting of halogen atoms, linear or branched alkoxy groups having 1 to 6 carbon atoms that may have 1 to 3 halogen atoms as substituents, linear or branched alkyl groups having 1 to 6 carbon atoms, and tetrazolyl groups optionally substituted by one or more linear or branched alkyl groups having 1 to 6 carbon atoms or one or more linear or branched alkoxy groups having 1 to 6 carbon atoms, wherein the alkyl moiety is a linear or branched alkyl group having 1 to 6 carbon atoms.

Examples of the lower alkoxycarbonyl-substituted lower alkyl group include methoxycarbonylmethyl, 1-ethoxycarbonylethyl, 2-methoxycarbonylethyl, 2-propoxycarbonylethyl, 3-isopropoxycarbonylpropyl, 4-butoxycarbonylbutyl, 5-pentyloxycarbonylpentyl, 6-hexyloxycarbonylhexyl, 1,1-dimethyl-2-methoxycarbonylethyl, 2-methyl-3-ethoxycarbonylpropyl, 3-methoxycarbonylpropyl, and 6,6,6-trimethoxycarbonylhexyl groups.

Specifically, the lower alkoxycarbonyl-substituted lower alkyl groups are alkyl groups wherein 1 to 3 alkoxycarbonyl groups are substituted, the alkoxy moiety thereof is a linear or branched alkoxy group having 1 to 6 carbon atoms and the alkyl moiety thereof is a linear or branched alkyl group having 1 to 6 carbon atoms.

Examples of the 1,2,3,4-tetrahydroquinolyl group that may have, on the tetrahydroquinoline ring, 1 to 3 substituents selected from the group consisting of oxo group, lower alkoxy groups, and lower alkylenedioxy groups include 1,2,3,4-tetrahydroquinolyl groups that may have, on the tetrahydroquinoline ring, 1 to 3 substituents selected from the group consisting of oxo group, linear or branched alkoxy groups having 1 to 6 carbon atoms, and linear or branched alkylenedioxy groups having 1 to 4 carbon atoms such as (1, 2, 3, 4, 5, 6, 7, or 8-)1,2,3,4-tetrahydroquinolyl, 2-oxo-(1, 3, 4, 5, 6, 7, or 8-) 1,2,3,4-tetrahydroquinolyl, 2-oxo-6,7-methylenedioxy-(1, 3, 4, 5, or 8-)1,2,3,4-tetrahydroquinolyl, 4-oxo-(1, 2, 3, 5, 6, 7, or 8-) 1,2,3,4-tetrahydroquinolyl, 2,4-dioxo-(1, 3, 5, 6, 7, or 8-) 1,2,3,4-tetrahydroquinolyl, 2,4-dioxo-6,7-methylenedioxy-(1, 3, 5, or 8-)1,2,3,4-tetrahydroquinolyl, 5,6-ethylenedioxy-(1, 2, 3, 4, 7, or 8-)1,2,3,4-tetrahydroquinolyl, 7,8-trimethylenedioxy-(1, 2, 3, 4, 5, or 6-)1,2,3,4-tetrahydroquinolyl, 6,7-tetramethylenedioxy-(1, 2, 3, 4, 5, or 8-)1,2,3,4-tetrahydroquinolyl, 5-methoxy-2-oxo-(1, 3, 4, 6, 7, or 8-) 1,2,3,4-tetrahydroquinolyl, and 2-oxo-6,7-ethylenedioxy-(1, 3, 4, 5, or 8-)1,2,3,4-tetrahydroquinolyl groups.

Examples of the cycloalkyl lower alkyl group include cycloalkylalkyl groups having 3 to 16 carbon atoms of which alkyl moiety is a linear or branched alkyl group having 1 to 6 carbon atoms such as a cyclopropylmethyl, cyclohexylmethyl, 2-cyclopropylethyl, 1-cyclobutylethyl, 3-cyclopentylpropyl, 4-cyclohexylbutyl, 5-cycloheptylpentyl, 6-cyclooctylhexyl, 1,1-dimethyl-2-cyclononylethyl, 2-methyl-3-cyclodecylpropyl, cycloundecylmethyl, 2-cyclododecylethyl, 1-cyclotridecylethyl, 3-cyclotetradecylpropyl, 4-cyclopentadecylbutyl, and 5-cyclohexadecylpentyl groups.

Examples of the pyridyl lower alkyl group include pyridylalkyl groups of which alkyl moiety is a linear or branched alkyl group having 1 to 6 carbon atoms such as (2, 3 or 4-)pyridylmethyl, 2-[(2, 3 or 4-)pyridyl]ethyl, 1-[(2, 3 or 4-)pyridyl]ethyl, 3-[(2, 3 or 4-)pyridyl]propyl, 4-[(2, 3 or 4-)pyridyl]butyl, 1,1-dimethyl-2-[(2, 3 or 4-)pyridyl]ethyl, 5-[(2, 3 or 4-)pyridyl]pentyl, 6-[(2, 3 or 4-)pyridyl]hexyl, 1-[(2, 3 or 4-) pyridyl]isopropyl, and 2-methyl-3-[(2, 3 or 4-)pyridyl]propyl groups.

Examples of the amino substituted lower alkyl groups optionally substituted by one or more substituents selected from the group consisting of lower alkyl groups and lower alkanoyl groups include aminomethyl, 2-aminoethyl, 1-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, 1-ethylaminoethyl, 2-propylaminoethyl, 3-isopropylaminopropyl, 4-butylaminobutyl, 5-pentylaminopentyl, 6-hexylaminohexyl, dimethylaminomethyl, 2-diisopropylaminoethyl, (N-ethyl-N-propylamino)methyl, 2-(N,N-dimethylamino)ethyl, 2-(N-methyl-N-hexylamino)ethyl, formylaminomethyl, acetylaminomethyl, 1-propionylaminoethyl, 2-acetylaminoethyl, 3-butyrylaminopropyl, 4-pentanoylaminobutyl, 5-hexanoylaminopentyl, 6-acetylaminohexyl, N-methyl-N-acetylaminomethyl, 2-(N-ethyl-N-propanoylamino)ethyl, (N-ethyl-N-butyrylamino)methyl, 2-(N-methyl-N-hexanoylamino)ethyl, and 3-(N,N-dimethylamino)propyl groups. These groups are linear or branched alkyl groups having 1 to 6 carbon atoms optionally substituted by one or more amino groups optionally substituted by 1 or 2 substituents selected from the group consisting of linear or branched alkyl groups having 1 to 6 carbon atoms and linear or branched alkanoyl groups having 1 to 6 carbon atoms.

Examples of the pyrrolidinyl lower alkyl group include pyrrolidinylalkyl groups of which alkyl moiety is a linear or branched alkyl group having 1 to 6 carbon atoms, such as a (1-, 2-, or 3-)pyrrolydinylmethyl group, 2-[(1-, 2-, or 3-)pyrrolydinyl]ethyl group, 1-[(1-, 2-, or 3-)pyrrolydinyl]ethyl group, 3-[(1-, 2-, or 3-)pyrrolydinyl]propyl group, 4-[(1-, 2-, or 3-)pyrrolydinyl]butyl group, 5-[(1-, 2-, or 3-) pyrrolydinyl] pentyl group, 6-[(1-, 2-, or 3-)pyrrolydinyl]hexyl group, 1,1-dimethyl-2-[(1-, 2-, or 3-)pyrrolydinyl]ethyl group, and 2-methyl-3-[(1-, 2-, or 3-)pyrrolydinyl]propyl group.

Examples of the phenyl lower alkenyl group include styryl group, 3-phenyl-2-propenyl group (trivial name: cinnamyl group), 4-phenyl-2-butenyl group, 4-phenyl-3-butenyl group, 5-phenyl-4-pentenyl group, 5-phenyl-3-pentenyl group, 6-phenyl-5-hexenyl group, 6-phenyl-4-hexenyl group, 6-phenyl-3-hexenyl group, 4-phenyl-1,3-butadienyl group, and 6-phenyl-1,3,5-hexatrienyl group. These phenylalkenyl groups have 1 to 3 double bonds wherein the alkenyl moiety thereof is a linear or branched alkenyl group having 2 to 6 carbon atoms.

Examples of the anilinocarbonyl lower alkyl group optionally substituted by one or more lower alkyl groups on the phenyl ring include anilinocarbonylmethyl, 2-anilinocarbonylethyl, 1-anilinocarbonylethyl, 3-anilinocarbonylpropyl, 4-anilinocarbonylbutyl, 5-anilinocarbonylpentyl, 6-anilinocarbonylhexyl, 1,1-dimethyl-2-anilinocarbonylethyl, 2-methyl-3-anilinocarbonylpropyl, (4-methylanilinocarbonyl)methyl, 2-(3-methylanilinocarbonyl)ethyl, 3-(4-methylanilinocarbonyl)propyl, 1-(2-ethylanilinocarbonyl)ethyl, 4-(3-ethylanilinocarbonyl)butyl, 5-(4-ethylanilinocarbonyl)pentyl, 6-(4-isopropylanilinocarbonyl)hexyl, 1,1-dimethyl-2-(3-butylanilinocarbonyl)ethyl, 2-methyl-3-(4-pentylanilinocarbonyl)propyl, 4-hexylanilinocarbonylmethyl, 3,4-dimethylanilinocarbonylmethyl, 3,4-diethylanilinocarbonylmethyl, 2,4-dimethylanilinocarbonylmethyl, 2,5-dimethylanilinocarbonylmethyl, 2,6-dimethylanilinocarbonylmethyl, and 3,4,5-trimethylanilinocarbonylmethyl groups. These anilinocarbonylalkyl groups may have 1 to 3 linear or branched alkyl groups having 1 to 6 carbon atoms as substituents on the phenyl ring wherein the alkyl moiety has one or more linear or branched alkyl groups having 1 to 6 carbon atoms.

Examples of the piperazinyl lower alkyl group that may have, on the piperazine ring, at least one substituent selected from the group consisting of lower alkyl groups and phenyl lower alkyl groups optionally substituted by one or more lower alkylenedioxy groups on the phenyl ring include piperazinylalkyl groups of which alkyl moiety is a linear or branched alkyl group having 1 to 6 carbon atoms and that may have, on the piperazine ring, 1 to 3 substituents selected from the group consisting of linear or branched alkyl groups having 1 to 6 carbon atoms and phenylalkyl groups optionally substituted by one or more linear or branched alkylenedioxy groups having 1 to 4 carbon atoms on the phenyl ring, wherein the alkyl moiety thereof is a linear or branched alkyl group having 1 to 6 carbon atoms. Specific examples thereof include [(1-, 2-, or 3-)piperazinyl]methyl, 2-[(1-, 2-, or 3-)piperazinyl]ethyl, 1-[(1-, 2-, or 3-) piperazinyl]ethyl, 3-[(1-, 2-, or 3-)piperazinyl]propyl, 4-[(1-, 2-, or 3-)piperazinyl]butyl, 5-[(1-, 2-, or 3-)piperazinyl]pentyl, 6-[(1-, 2-, or 3-)piperazinyl]hexyl, 1,1-dimethyl-2-[(1-, 2-, or 3-)piperazinyl]ethyl, 2-methyl-3-[(1-, 2-, or 3-) piperazinyl]propyl, [1-methyl-(2-, 3-, or 4-)piperazinyl]methyl, 2-[1-ethyl-(2-, 3-, or 4-)piperazinyl]ethyl, 1-[4-propyl-(1-, 2-, or 3-)piperazinyl]ethyl, 3-[3-isopropyl-(1-, 2-, 4-, 5-, or 6-) piperazinyl]propyl, 4-[2-butyl-(1-, 3-, 4-, 5-, or 6-) piperazinyl]butyl, 5-[1-isobutyl-(2-, 3-, or 4-) piperazinyl]pentyl, 3-[4-methyl-(1-, 2-, or 3-) piperazinyl]propyl, 6-[1-tert-butyl-(2-, 3-, or 4-) piperazinyl]hexyl, 1,1-dimethyl-2-[4-pentyl-(1-, 2-, or 3-) piperazinyl]ethyl, [1,2-dimethyl-(3-, 4-, 5-, or 6-) piperazinyl]methyl, [1,2,6-trimethyl-(3-, 4-, or 5-) piperazinyl]methyl, and 2-[4-(3,4-methylenedioxybenzyl)-(1-, 2-, or 3-)piperazinyl]ethyl groups.

Examples of the amidino lower alkyl group optionally substituted by one or more lower alkyl groups include amidinoalkyl groups of which alkyl moiety is a linear or branched alkyl group having 1 to 6 carbon atoms and that may have 1 or 2 linear or branched alkyl groups having 1 to 6 carbon atoms, such as amidinomethyl, 2-amidinoethyl, 1-amidinoethyl, 3-amidinopropyl, 4-amidinobutyl, 5-amidinopentyl, 6-amidinohexyl, 1,1-dimethyl-2-amidinoethyl, 2-methyl-3-amidinopropyl, N,N-dimethylamidinomethyl, 2-(N,N-dimethylamidino)ethyl, 1-(N-methylamidino)ethyl, 3-(N-ethylamidino)propyl, 4-(N-n-propylamidino)propyl, 5-(N-n-pentylamidino)pentyl, 6-(N-n-hexylamidino)hexyl, and (N-methyl-N-ethylamidino) methyl groups.

Examples of the carbazolyl group optionally substituted by one or more lower alkyl groups on the carbazole ring include carbazolyl groups that may have 1 to 3 linear or branched alkyl groups having 1 to 6 carbon atoms as substituents on the carbazole ring such as (1-, 2-, 3-, or 4-)carbazolyl, 9-methyl-(1-, 2-, 3-, or 4-)carbazolyl, 9-ethyl-(1-, 2-, 3-, or 4-) carbazolyl, 1-ethyl-(2-, 3-, 4-, 5-, 6-, 7-, 8-, or 9-) carbazolyl, 2-n-propyl-(1-, 3-, 4-, 5-, 6-, 8-, or 9-)carbazolyl, 3-n-butyl-(1-, 2-, 4-, 5-, 6-, 7-, 8-, or 9-)carbazolyl, 4-n-pentyl-(1-, 2-, 3-, 5-, 6-, 7-, 8-, or 9-)carbazolyl, 5-n-hexyl-(1-, 2-, 3-, 4-, 6-, 7-, 8-, or 9-)carbazolyl, 6,9-dimethyl-(1-, 2-, 3-, 4-, 5-, 7-, or 8-)carbazolyl, and 1,7,8-trityl-(2-, 3-, 4-, 5-, 6-, 7-, 8-, or 9-)carbazolyl groups.

Examples of the cyano substituted lower alkyl group include cyanoalkyl groups of which alkyl moiety is a linear or branched alkyl group having 1 to 6 carbon atoms, such as cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, and 2-methyl-3-cyanopropyl groups.

Examples of the 5- to 10-membered saturated heterocyclic group formed by binding $R^3$ and $R^4$ each other, together with nitrogen atoms bound to them, through or not through a nitrogen atom, or a sulfur atom, include 1,2,3,4,5,6-hexahydropyrimidinyl, pyrrolidinyl, piperidinyl, piperazinyl, thiomorpholino, homopiperazinyl, homopiperidinyl, 6-azabicyclo[3,2,1]octyl, 3-aza-spiro[5,5]undecyl, and thiazolidinyl groups.

Examples of the phenyl substituted lower alkyl group that has 1 or 2 phenyl groups optionally substituted on the phenyl ring with 1 to 3 substituents selected from the group consisting of cyano group, nitro group, halogen atoms, lower alkyl groups optionally substituted by one or more halogen atoms or a lower alkoxy groups, lower alkoxy groups optionally substituted by one or more substituents selected from the group consisting of halogen atoms and cycloalkyl groups, hydroxy group, aminosulfonyl groups optionally substituted by one or more lower alkyl groups, lower alkylaminocarbonyl groups, tetrazolyl groups optionally substituted by one or more lower alkyl groups or lower alkoxy lower alkyl groups, lower alkynyl groups, lower alkylsulfonyl groups, lower alkylsulfonylamino groups, 1,2,4-triazolyl groups, imidazolyl groups, piperidinyl groups, thiadiazolyl groups, and lower alkylenedioxy groups optionally substituted by one or more halogen atoms include phenyl substituted alkyl groups which have 1 or 2 phenyls optionally substituted on the phenyl ring with 1 to 3 substituents selected from the group consisting of cyano group, nitro group, halogen atoms, linear or branched alkyl groups having 1 to 6 carbon atoms that may have 1 to 3 halogen atoms or linear or branched alkoxy groups having 1 to 6 carbon atoms as substituents, linear or branched alkoxy groups having 1 to 6 carbon atoms that may have 1 to 3 substituents selected from the group consisting of halogen atoms and cycloalkyl groups having 3 to 16 carbon atoms, hydroxy group, aminosulfonyl groups optionally substituted by one or more linear or branched lower alkyl groups having 1 to 6 carbon atoms, alkylaminocarbonyl groups wherein the alkyl moiety is one or more linear or branched alkyl groups having 1 to 6 carbon atoms, tetrazolyl groups optionally substituted by one or more linear or branched alkyl groups having 1 to 6 carbon atoms or linear or branched alkoxy-substituted alkyl groups wherein the alkoxy moiety is a linear or branched alkoxy group having 1 to 6 carbon atoms and the alkyl moiety a linear or branched alkyl group having 1 to 6 carbon atoms, linear or branched alkynyl groups having 1 to 6 carbon atoms, linear or branched alkylsulfonyl groups having 1 to 6 carbon atoms, linear or branched alkylsulfonylamino groups having 1 to 6 carbon atoms, 1,2,4-triazolyl groups, imidazolyl groups, piperidinyl groups, thiadiazolyl groups, and a linear or branched alkylenedioxy groups having 1 to 4 carbon atoms optionally substituted by one or more halogen atoms. Specific examples thereof include, in addition to the above described phenyl lower alkyl groups, 1,1-diphenylmethyl, 1,1-di(4-fluorophenyl)methyl, 1-phenyl-1-(4-methoxyphenyl)methyl, 3,4-methylenedioxybenzyl, 3,4-ethylenedioxybenzyl, 3,4-trimethylenedioxybenzyl, (2,2-difluorobenzo[1,3]dioxol-5-yl)methyl, 2,5-difluorobenzyl, 2,4-difluorobenzyl, 3,4-difluorobenzyl, 3,5-difluorobenzyl, 2,6-difluorobenzyl, 3-trifluoromethylbenzyl, 2-trifluoromethylbenzyl, 4-trifluoromethylbenzyl, (2-, 3-, or 4-)methoxymethylbenzyl, 3-(1-ethoxyethyl)benzyl, 4-(2-methoxyethyl)benzyl, 2-(2-propoxyethyl)benzyl, 3-(3-isopropoxypropyl)benzyl, 4-(4-butoxybutyl)benzyl, 2-(5-pentyloxypentyl)benzyl, 3-(6-hexyloxyhexyl)benzyl, 4-(1,1-dimethyl-2-methoxyethyl)benzyl, 2-(2-methyl-3-ethoxypropyl)benzyl, 3-(3-methoxypropyl)benzyl, 3,4-dimethoxybenzyl, 3,5-dimethoxybenzyl, 2-chlorobenzyl, 3-chlorobenzyl, 4-chlorobenzyl, 2-methylbenzyl, 3-methylbenzyl, 4-methylbenzyl, (2-, 3-, or 4-)isobutylbenzyl, (2-, 3-, or 4-) octylbenzyl, 3,4-dimethylbenzyl, 2,3-dimethylbenzyl, 2-methoxybenzyl, 3-methoxybenzyl, (2-, 3-, or 4-)ethoxybenzyl, (2-, 3-, or 4-)propoxybenzyl, (2-, 3-, or 4-)isopropoxybenzyl, (2-, 3-, or 4-)(3-methylbutoxy)benzyl, (2-, 3-, or 4-)cyclopropylmethoxybenzyl, (2-, 3-, or 4-)-2-fluoroethoxy benzyl, (2-, 3-, or 4-)2,2,2-trifluoroethoxybenzyl, (2-, 3-, or 4-)difluoromethoxybenzyl, (2-, 3-, or 4-)2,2-difluoroethoxybenzyl, (2-, 3-, or 4-)(2-fluoro-1-fluoromethylethoxy)benzyl, (2-, 3-, or 4-)1,1,2,2-tetrafluoroethoxybenzyl, 3-methoxy-4-(2,2-difluoroethoxy)benzyl, (2-, 3-, or 4-)propylbenzyl, (2-, 3-, or 4-) [1,2,3]thiadiazol-4-ylbenzyl, 2-fluoro-4-isopropoxybenzyl, 3-fluoro-4-isopropoxybenzyl, 4-cyanobenzyl, 2-cyanobenzyl, 3-cyanobenzyl, 4-methoxybenzyl, 2,3-dichlorobenzyl, 2,4-dichlorobenzyl, 2,5-dichlorobenzyl, 3,4-dichlorobenzyl, 2,6-dichlorobenzyl, 4-fluorobenzyl, 3-fluorobenzyl, 2-fluorobenzyl, 4-nitrobenzyl, 3-nitrobenzyl, 2-nitrobenzyl, 3-trifluoromethoxybenzyl, 4-trifluoromethoxybenzyl, 2-trifluoromethoxybenzyl, 4-tert-butylbenzyl, 4-ethylbenzyl, (2-, 3-, or 4-)isopropylbenzyl, 4-methoxy-3-chlorobenzyl, 2-(4-methoxyphenyl)ethyl, 2-(4-fluorophenyl)ethyl, 2-(4-chlorophenyl)ethyl, 2-(3-methoxyphenyl)ethyl, 2-(4-methylphenyl)ethyl, 3,3-diphenylpropyl, 3-methyl-4-nitrobenzyl, 4-(4-methoxyphenyl)butyl, 2-(4-methylphenyl)ethyl, 3-chloro-6-methoxybenzyl, 4-nitro-3-methylbenzyl, 4-hydroxybenzyl, 3-hydroxybenzyl, 2-hydroxybenzyl, 2-(2-cyanophenyl) ethyl, 1-(3-cyanophenyl)ethyl, 3-(4-cyanophenyl)propyl, 4-(2-cyanophenyl)butyl, 5-(3-cyanophenyl)pentyl, 6-(4-cyanophenyl)hexyl, 1,1-dimethyl-2-(2,4-dicyanophenyl)ethyl, 2-methyl-3-(2,4,6-tricyanophenyl)propyl, 2-(2-nitrophenyl) ethyl, 1-(3-nitrophenyl)ethyl, 3-(4-nitrophenyl)propyl, 4-(2-nitrophenyl)butyl, 5-(3-nitrophenyl)pentyl, 6-(4-nitrophenyl)hexyl, 1,1-dimethyl-2-(2,4-dinitrophenyl)ethyl, 2-methyl-3-(2,4,6-trinitrophenyl)propyl, 2-(2-fluorophenyl) ethyl, 1-(3-bromophenyl)ethyl, 3-(4-iodophenyl)propyl, 4-(2-bromophenyl)butyl, 5-(3-chlorophenyl)pentyl, 6-(4-bromophenyl)hexyl, 1,1-dimethyl-2-(2,4-dichlorophenyl) ethyl, 2-methyl-3-(2,4,6-trifluorophenyl)propyl, 2-(2-ethylphenyl)ethyl, 1-(3-propylphenyl)ethyl, 3-(4-butylphenyl) propyl, 4-(2-pentylphenyl)butyl, 5-(3-hexylphenyl)pentyl, 6-(4-trifluoromethylphenyl)hexyl, 1,1-dimethyl-2-(2,4-dimethylphenyl)ethyl, 2-methyl-3-[2,4,6-tri(trifluoromethyl) phenyl]propyl, 2-(2-ethoxyphenyl)ethyl, 1-(3-propoxyphenyl)ethyl, 3-(4-butoxyphenyl)propyl, 4-(2-pentyloxyphenyl) butyl, 5-(3-hexyloxyphenyl)pentyl, 6-(4-trifluoromethoxyphenyl)hexyl, 1,1-dimethyl-2-(2,4-dimethoxyphenyl)ethyl, 2-methyl-3-[2,4,6-tri (trifluoromethoxy)phenyl]propyl, 2-(2-hydroxyphenyl) ethyl, 1-(3-hydroxyphenyl)ethyl, 3-(4-hydroxyphenyl) propyl, 4-(2-hydroxyphenyl)butyl, 5-(3-hydroxyphenyl) pentyl, 6-(4-hydroxyphenyl)hexyl, 1,1-dimethyl-2-(2,4-dihydroxyphenyl)ethyl, 2-methyl-3-(2,4,6-trihydroxyphenyl)propyl, 2-aminosulfonylbenzyl, 2-(3-methylaminosulfonylphenyl)ethyl, 3-(4-ethylaminosulfonylphenyl)propyl, 4-(2-propylaminosulfonylphenyl)butyl, 5-(3-isopropylaminosulfonylphenyl)pentyl, 6-[4-(2,2-dimethylpropylaminosulfonyl)phenyl]hexyl, 2-(1-ethylpropylaminosulfonyl)benzyl, 2-(3-butylaminosulfonylphenyl)ethyl, 3-(4-isobutylaminosulfonylphenyl)propyl, 4-(2-tert-butylaminosulfonylphenyl)butyl, 5-(3-isopentylaminosulfonylphenyl)pentyl, 6-(4-pentylaminosulfonylphenyl)hexyl, 3-hexylaminosulfonylbenzyl, 2-(4-N,N-dimethylaminosulfonylphenyl)ethyl, 3-(2-N-methyl-N-ethylaminosulfonylphenyl)propyl, 4-(3-N,N-diethylaminosulfonylphenyl)butyl, 5-(4-aminocarbonylphenyl)pentyl, 6-(2-methylaminocarbonylphenyl)hexyl, 3-ethylaminocarbonylbenzyl, 2-(4-propylaminocarbonylphenyl)ethyl, 3-(2-isopropylaminocarbonylphenyl)propyl, 4-[3-(2,2-dimethylpropylaminocarbonyl)phenyl]butyl, 5-[4-(1-ethylpropylaminocarbonyl)phenyl]pentyl, 6-(2-butylaminocarbonylphenyl)hexyl, 4-isobutylaminocarbonylbenzyl, 2-(2-tert-butylaminocarbonylphenyl)ethyl, 3-(3-isopentylaminocarbonylphenyl)propyl, 4-(2-pentylaminocarbonylphenyl)butyl, 5-(3-hexylaminocarbonylphenyl)pentyl, 6-(4-N,N-dimethylaminocarbonylphenyl)hexyl, 2-N-methyl-N-ethylaminocarbonylbenzyl, 2-(3-N,N-diethylaminocarbonylphenyl)ethyl, 3-[4-(1H-tetrazolyl)phenyl]propyl, 4-[2-(2H-tetrazolyl)phenyl]butyl, 5-[3-(5H-tetrazolyl)phenyl]pentyl, 6-[4-(5-methyl-1H-tetrazol-1-yl)phenyl]hexyl, 3-(5-methyl-2H-tetrazol-2-yl)benzyl, 2-[4-(5-methyl-5H-tetrazol-5-yl)phenyl]ethyl, 3-[2-(5-ethyl-1H-tetrazol-1-yl)phenyl]propyl, 4-[3-(5-ethyl-1H-tetrazol-1-yl)phenyl]butyl, 5-[4-(5-propyl-1H-tetrazol-1-yl)phenyl]pentyl, 6-[2-(5-isopropyl-1H-tetrazol-1-yl)phenyl]hexyl, 4-[5-(2,2-dimethylpropyl)-1H-tetrazol-1-yl]benzyl, 2-{2-[5-(1-ethylpropyl)-1H-tetrazol-1-yl]phenyl}ethyl, 3-[3-(5-butyl-1H-tetrazol-1-yl)phenyl]propyl, 4-[4-(5-isobutyl-1H-tetrazol-1-yl)phenyl]butyl, 5-[2-(5-tert-butyl-1H-tetrazol-1-yl)phenyl]pentyl, 6-[3-(5-isopentyl-1H-tetrazol-1-yl)phenyl]hexyl, 2-(5-pentyl-1H-tetrazol-1-yl)benzyl, 2-[3-(5-hexyl-1H-tetrazol-1-yl)phenyl]ethyl, 3-[4-(5-methoxy-1H-tetrazol-1-yl)phenyl]propyl, 4-[2-(5-ethoxy-1H-tetrazol-1-yl)phenyl]butyl, 5-[3-(5-propoxy-1H-tetrazol-1-yl)phenyl]pentyl, 6-[4-(5-isopropoxy-1H-tetrazol-1-yl)phenyl]hexyl, 3-(5-butoxy-1H-tetrazol-1-yl)benzyl, 2-[4-(5-tert-butoxy-1H-tetrazol-1-yl)phenyl]ethyl, 3-[2-(5-pentyloxy-1H-tetrazol-1-yl)phenyl]propyl, 4-[3-(5-hexyloxy-1H-tetrazol-1-yl)phenyl]butyl, 5-(4-ethynylphenyl)pentyl, 6-[2-(2-propynyl)phenyl]hexyl, 4-(2-butynyl)benzyl, 2-[3-(3-butynyl)phenyl]ethyl, 3-[4-(1-methyl-2-propynyl)phenyl]propyl, 4-[2-(2-pentynyl)phenyl]butyl, 5-[3-(2-hexynyl)phenyl]pentyl, 6-(4-methylsulfonylphenyl)hexyl, 3-ethylsulfonylbenzyl, 2-(4-propylsulfonylphenyl)ethyl, 3-(2-isopropylsulfonylphenyl)propyl, 4-[3-(2,2-dimethylpropylsulfonyl)phenyl]butyl, 5-[4-(1-ethylpropylsulfonyl)phenyl]pentyl, 6-(2-butylsulfonylphenyl)hexyl, 4-isobutylsulfonylbenzyl, 2-(2-tert-butylsulfonylphenyl)ethyl, 3-(3-isopentylsulfonylphenyl)propyl, 4-(4-pentylsulfonylphenyl)butyl, 5-(2-hexylsulfonylphenyl)pentyl, 6-(3-methylsulfonylaminophenyl)hexyl, 2-ethylsulfonylaminobenzyl, 2-(3-propylsulfonylaminophenyl)ethyl, 3-(4-isopropylsulfonylaminophenyl)propyl, 4-(2-butylsulfonylaminophenyl)butyl, 5-(3-tert-butylsulfonylaminophenyl)pentyl, 6-(4-pentylsulfonylaminophenyl)hexyl, 3-hexylsulfonylaminobenzyl, 2-(4-N,N-dimethylsulfonylaminophenyl)ethyl, 3-(2-N,N-diethylsulfonylaminophenyl)propyl, 4-(3-N-methylsulfonyl-N-ethylsulfonylaminophenyl)butyl, 2-(3,4-methylenedioxyphenyl)ethyl, 1-(2,3-ethylenedioxyphenyl)ethyl, 3-(3,4-trimethylenedioxyphenyl)propyl, 4-(3,4-tetramethylene dioxyphenyl)butyl, 5-(3,4-methylenedioxyphenyl)pentyl, 6-(3,4-ethylenedioxyphenyl)hexyl, 1,1-dimethyl-2-(3,4-methylenedioxy)ethyl, and 2-methyl-3-(3,4-methylenedioxyphenyl) propyl groups.

Examples of the pyridyl lower alkyl group that may have, on the pyridine ring, 1 to 3 substituents selected from the group consisting of hydroxy group, lower alkyl groups optionally substituted by one or more hydroxy groups, halogen atoms, lower alkoxy groups, and cyano group include pyridylalkyl groups that may have, on the pyridine ring, 1 to 3 substituents selected from the group consisting of hydroxy groups, linear or branched alkyl groups having 1 to 6 carbon atoms that may have 1 to 3 hydroxy groups as substituents, halogen atoms, linear or branched alkoxy groups having 1 to 6 carbon atoms, and cyano group; and of which alkyl moiety is a linear or branched alkyl group having 1 to 6 carbon atoms. Specific examples thereof include, in addition to the above described pyridyl lower alkyl groups, [2-methyl-(3, 4, 5, or 6-)pyridyl]methyl, [2-methyl-3-hydroxy-5-hydroxymethyl-(4 or 6-)pyridyl]methyl, 2-[3-ethyl-(2, 4, 5, or 6-)pyridyl]ethyl, 1-[4-propyl-(2, 3, 5, or 6-)pyridyl]ethyl, 3-[2-butyl-(3, 4, 5, or 6-)pyridyl]propyl, 4-[3-pentyl-(2, 4, 5, or 6-)pyridyl]butyl, 1,1-dimethyl-2-[4-hexyl-(2, 3, 5, or 6-)pyridyl]ethyl, 5-[2,3-dimethyl-(4, 5, or 6-)pyridyl]pentyl, 6-[2, 4,6-trimethyl-(3 or 5-) pyridyl]hexyl, 1-[2-hydroxy-(2, 3, 5, or 6-)pyridyl]isopropyl, 2-methyl-3-[hydroxy-(2, 4, 5, or 6-)pyridyl]propyl, [2-hydroxy-(3, 4, 5, or 6-)pyridyl]methyl, 2-[3-hydroxy-(2, 4, 5, or 6-) pyridyl]ethyl, 1-[4-hydroxy-(2, 3, 5, or 6-)pyridyl]ethyl, 3-[2-hydroxy-(3, 4, 5, or 6-)pyridyl]propyl, 4-[3-hydroxy-(2, 4, 5, or 6-)pyridyl]butyl, 1,1-dimethyl-2-[4-hydroxy-(2, 3, 5, or 6-) pyridyl]ethyl, 5-[2,3-dihydroxy-(4, 5, or 6-)pyridyl]pentyl, 6-[2,4,6-trihydroxy-(3 or 5-)pyridyl]hexyl, [2-hydroxymethyl-(3, 4, 5, or 6-)pyridyl]methyl, 2-[3-(2-hydroxyethyl)-(2, 4, 5, or 6-) pyridyl]ethyl, 1-[4-(3-hydroxypropyl)-(2, 3, 5, or 6-) pyridyl]ethyl, 3-[2-(4-hydroxybutyl)-(3, 4, 5, or 6-) pyridyl]propyl, 4-[3-(5-hydroxypentyl)-(2, 4, 5, or 6-) pyridyl]butyl, 1,1-dimethyl-2-[4-(6-hydroxyhexyl)-(2, 3, 5, or 6-)pyridyl]ethyl, 5-[2,3-di(hydroxymethyl)-(4, 5, or 6-) pyridyl]pentyl, 6-[2,4,6-tri(hydroxymethyl)-(3 or 5-) pyridyl]hexyl, 1-[2-hydroxymethyl-(2, 3, 5, or 6-) pyridyl]isopropyl, 2-methyl-3-[3-(2,3-dihydroxypropyl)-(2, 4, 5, or 6-)pyridyl]propyl, [2-methyl-3-(2,2,4-trihydroxybutyl)-(4, 5, or 6-)pyridyl]methyl, [2-methyl-5-hydroxymethyl-(3, 4, or 6-) pyridyl]methyl, [2-chloro-(3-, 4-, 5-, or 6-)pyridyl]methyl, [3-fluoro-(2-, 4-, 5-, or 6-)pyridyl]methyl, [2-bromo-(3-, 4-, 5-, or 6-)pyridyl]methyl, [2-methoxy-(3-, 4-, 5-, or 6-) pyridyl]methyl, [3-methoxy-(2-, 4-, 5-, or 6-)pyridyl]methyl, [4-methoxy-(2-, or 3-)pyridyl]methyl, [2-ethoxy-(3,4-, 5-, or 6-) pyridyl]methyl, [3-ethoxy-(2-, 4-, 5-, or 6-)pyridyl]methyl, [2-isopropoxy-(3-, 4-, 5-, or 6-)pyridyl]methyl, [3-methoxymethoxy-(2-, 4-, 5-, or 6-)pyridyl]methyl, [3-cyano-(2-, 4-, 5-, or 6-) pyridyl]methyl, [3,5-dichloro-(2-, or 4-) pyridyl]methyl, [2,6-dichloro-(3-, or 4-)pyridyl]methyl, and [2-cyano-(3-, 4-, 5-, or 6-)pyridyl]methyl groups.

Examples of the pyrrolyl lower alkyl group that may have 1 to 3 lower alkyl groups as substituents on the pyrrole ring include pyrrolylalkyl groups that may have 1 to 3 linear or branched alkyl groups having 1 to 6 carbon atoms as substituents on the pyrrole ring and of which alkyl moiety is a linear or branched alkyl group having 1 to 6 carbon atoms such as [(1, 2, or 3-)pyrrolyl]methyl, 2-[(1, 2, or 3-)pyrrolyl]ethyl, 1-[(1, 2, or 3-)pyrrolyl]ethyl, 3-[(1, 2, or 3-)pyrrolyl]propyl, 4-[(1, 2, or 3-)pyrrolyl]butyl, 5-[(1, 2, or 3-)pyrrolyl]pentyl, 6-[(1, 2, or 3-)pyrrolyl]hexyl, 1,1-dimethyl-2-[(1, 2, or 3-)pyrrolyl]ethyl, 2-methyl-3-[(1, 2, or 3-)pyrrolyl]propyl, [1-methyl-(2 or 3-) pyrrolyl]methyl, 2-[2-ethyl-(1, 3, 4, or 5-)pyrrolyl]ethyl, 1-[3-propyl-(1, 2, 4, or 5-)pyrrolyl]ethyl, 3-[1-butyl-(2, 3, or 4-) pyrrolyl]propyl, 4-[2-pentyl-(1, 3, 4, or 5-)pyrrolyl]butyl, 5-[3-hexyl-(1, 2, 4, or 5-)pyrrolyl]pentyl, 6-[1,2-dimethyl-(3, 4, or 5-)pyrrolyl]hexyl, 1,1-dimethyl-2-[1,2,3-trimethyl-(4 or 5-) pyrrolyl]ethyl, and 2-methyl-3-[1-ethyl-2-methyl-(3, 4, or 5-) pyrrolyl]propyl group.

Examples of the benzoyl group optionally substituted on the phenyl ring with at least one substituent selected from the group consisting of cyano group, lower alkoxy groups, and amino groups that may have at least one lower alkylsulfonyl group as a substituent include benzoyl groups optionally substituted on the phenyl ring with 1 to 3 groups selected from the group consisting of cyano group, linear or branched alkoxy groups having 1 to 6 carbon atoms, and amino groups that may have 1 or 2 linear or branched alkylsulfonyl groups having 1 to 6 carbon atoms as substituents, such as benzoyl, 4-cyanobenzoyl, 2-aminobenzoyl, 3-aminobenzoyl, 4-aminobenzoyl, 3,4-diaminobenzoyl, 2,4,6-triaminobenzoyl, 3-cyanobenzoyl, 2-cyanobenzoyl, 2,3-dicyanobenzoyl, 3,4,5-tricyanobenzoyl, (2-, 3-, or 4-) methoxybenzoyl, 2-methylsulfonylaminobenzoyl, 3-methylsulfonylaminobenzoyl, 4-ethylsulfonylaminobenzoyl, 2-propylsulfonylaminobenzoyl, 3-isopropylsulfonylaminobenzoyl, 4-(2,2-dimethylpropylsulfonylamino)benzoyl, 2-(1-ethylpropylsulfonylamino)benzoyl, 3-butylsulfonylaminobenzoyl, 4-isobutylsulfonylaminobenzoyl, 2-tert-butylsulfonylaminobenzoyl, 3-isopentylsulfonylaminobenzoyl, 4-pentylsulfonylaminobenzoyl, 2-hexylsulfonylaminobenzoyl, and 2-N,N-dimethylsulfonylaminobenzoyl groups.

Examples of the pyridyl group optionally substituted by one or more lower alkyl groups (wherein the lower alkyl group may be substituted by one or more halogen atoms) as a substituent include pyridyl group that may have 1 to 3 of the above explained lower alkyl groups. Such lower alkyl groups may have 1 to 5 halogen atoms as substituents. Specific examples of the pyridyl group optionally substituted by one or more lower alkyl groups (wherein the lower alkyl group may be substituted by one or more halogen atoms) as a substituent include (2-, 3- or 4-)pyridyl, 2-methyl-(3-, 4-, 5- or 6-)pyridyl, 3-ethyl-(2-, 4-, 5- or 6-)pyridyl, 4-propyl-(2- or 3-)pyridyl, 2-butyl-(2-, 3-, 5- or 6-)pyridyl, 3-tert-butyl-(2-, 4-, 5- or 6-)pyridyl, 4-pentyl-(2- or 3-)pyridyl, 2-hexyl-(3-, 4-, 5- or 6-)pyridyl, and 3-trifluoromethyl-(2-, 4-, 5- or 6-)pyridyl groups.

Examples of the lower alkyl group optionally substituted by one or more substituents selected from the group consisting of hydroxy group and halogen atoms include linear or branched alkyl groups having 1 to 6 carbon atoms that may have 1 to 3 substituents selected from the group consisting of hydroxy group and halogen atoms. Specific examples thereof include, in addition to the above described lower alkyl groups, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl, 2-hydroxy-3-fluoropropyl, and 2,2-dichloro-3-hydroxybutyl groups.

Examples of the phenyl group optionally substituted on the phenyl ring with 1 to 3 groups selected from the group consisting of halogen atoms, lower alkyl groups optionally substituted by one or more halogen atoms, and cyano group include phenyl groups optionally substituted on the phenyl group with 1 to 3 groups selected from the group consisting of halogen atoms, linear or branched alkyl groups having 1 to 6 carbon atoms optionally substituted by 1 to 3 halogen atoms, and cyano group such as phenyl, 2-chlorophenyl, 3-chlorophenyl, 4-chlorophenyl, 2,3-dichlorophenyl, 2,4-dichlorophenyl, 2,5-dichlorophenyl, 3,4-dichlorophenyl, 2,6-dichlorophenyl, 3,5-dichlorophenyl, 2,4,6-trichlorophenyl, 2-fluorophenyl, 3-fluorophenyl, 4-fluorophenyl, 2,5-difluorophenyl, 2,4-difluorophenyl, 3,4-difluorophenyl, 3,5-difluorophenyl, 2,6-difluorophenyl, 2,4,6-trifluorophenyl, 2-bromophenyl, 3-bromophenyl, 4-bromophenyl, 2-iodophenyl, 3-iodophenyl, 4-iodophenyl, 2,3-dibromophenyl, 2,4-diiodophenyl, 2-trifluoromethylphenyl, 3-trifluoromethylphenyl, 4-trifluoromethylphenyl, 2-(bromomethyl)phenyl, 3-(2-chloroethyl)phenyl, 4-(2,3-dichloropropyl)phenyl, 4-(4-fluorobutyl)phenyl, 3-(5-chloropentyl)phenyl, 4-(5-bromohexyl)phenyl, 4-(5,6-dibromohexyl)phenyl, 3,4-di(trifluoromethyl)phenyl, 3,4-di(4,4,4-trichlorobutyl)phenyl, 2,4-di(3-chloro-2-methylpropyl)phenyl, 2,5-di(3-chloropropyl)phenyl, 2,6-di(2,2,2-trifluoroethyl)phenyl, 3,4,5-tri(trifluoromethyl)phenyl, 4-(2,2,2-trichloroethyl)phenyl, 2-methyl-4-trifluoromethylphenyl, 3-ethyl-4-trichloromethylphenyl, 2-cyanophenyl, 3-cyanophenyl, 4-cyanophenyl, 3,4-dicyanophenyl, 3,5-dicyanophenyl, 2,4-dicyanophenyl, 2,5-dicyanophenyl, 2,6-dicyanophenyl, and 3,4,5-tricyanophenyl groups.

Examples of the phenoxy group optionally substituted by one or more lower alkoxy groups (a lower alkoxy group optionally substituted by one or more halogen atoms thereon) include phenoxy group optionally substituted on the phenyl group with 1 to 3 linear or branched alkoxy groups having 1 to 6 carbon atoms that may have 1 to 3 halogen atoms as substituents, such as phenoxy, 2-methoxyphenoxy, 3-methoxyphenoxy, 4-methoxyphenoxy, 2-ethoxyphenoxy, 3-ethoxyphenoxy, 4-ethoxyphenoxy, 4-isopropoxyphenoxy, 3-butoxyphenoxy, 4-pentyloxyphenoxy, 4-hexyloxyphenoxy, 3,4-dimethoxyphenoxy, 3,4-diethoxyphenoxy, 2,4-dimethoxyphenoxy, 2,5-dimethoxyphenoxy, 2,6-dimethoxyphenoxy, 3,4,5-trimethoxyphenoxy, 2-trifluoromethoxyphenoxy, 3-trifluoromethoxyphenoxy, 4-trifluoromethoxyphenoxy, 2-(bromomethoxy)phenoxy, 3-(2-chloroethoxy)phenoxy, 4-(2,3-dichloropropoxy)phenoxy, 4-(4-fluorobutoxy)phenoxy, 3-(5-chloropentyloxy)phenoxy, 4-(5-bromohexyloxy)phenoxy, 4-(5,6-dibromohexyloxy)phenoxy, 3,4-di(trifluoromethoxy)phenoxy, 3,4-di(4,4,4-trichlorobutoxy)phenoxy, 2,4-di(3-chloro-2-methoxypropyl)phenoxy, 2,5-di(3-chloropropoxy)phenoxy, 2,6-di(2,2,2-trifluoroethoxy)phenoxy, 3,4,5-tri(trifluoromethoxy)phenoxy, 4-(2,2,2-trichloroethoxy)phenoxy, 2-methoxy-4-trifluoromethoxyphenoxy, and 3-ethoxy-4-trichloromethoxyphenoxy groups.

Examples of the 6-membered saturated heterocyclic ring formed by $R^{15}$ and $R^{16}$, together with the nitrogen atom to which they bind, by binding to each other, directly or via a nitrogen atom or oxygen atom include piperidinyl, piperazinyl, and morpholinyl groups.

Examples of the quinolyl lower alkyl group include quinolylalkyl groups of which alkyl moiety is a linear or branched alkyl group having 1 to 6 carbon atoms such as a (2, 3, 4, 5, 6, 7 or 8-)quinolylmethyl group, 2-[(2, 3, 4, 5, 6, 7 or 8-) quinolyl]ethyl group, 1-[(2, 3, 4, 5, 6, 7 or 8-)quinolyl] ethyl group, 3-[(2, 3, 4, 5, 6, 7 or 8-)quinolyl]propyl group, 4-[(2, 3, 4, 5, 6, 7 or 8-)quinolyl]butyl group, 5-[(2, 3, 4, 5, 6, 7 or 8-)quinolyl]pentyl group, and 6-[(2, 3, 4, 5, 6, 7 or 8-) quinolyl]hexyl group.

Examples of the thiazolyl lower alkyl group optionally substituted by one or more phenyl groups (the phenyl group may be substituted on the phenyl ring with at least one lower alkyl group optionally substituted by one or more halogen atoms) as a substituent on the thiazole ring include thiazolylalkyl groups that may have 1 or 2 phenyl groups (the phenyl group may be substituted on the phenyl ring with at least one linear or branched alkyl group having 1 to 6 carbon atoms that may have 1 to 3 halogen atoms as substitutes) as substituents on the thiazole ring and of which alkyl moiety is a linear or branched alkyl group having 1 to 6 carbon atoms such as [(2, 4, or 5-) thiazolyl]methyl, 2-[(2, 4, or 5-)thiazolyl]ethyl, 1-[(2, 4, or 5-)thiazolyl]ethyl, 3-[(2, 4, or 5-)thiazolyl]propyl, 4-[(2, 4, or 5-)thiazolyl]butyl, 5-[(2, 4, or 5-)thiazolyl]pentyl, 6-[(2, 4, or 5-)thiazolyl]hexyl, 1,1-dimethyl-2-[(2, 4, or 5-)thiazolyl]ethyl, 2-methyl-3-[(2, 4, or 5-)thiazolyl]propyl, [2-phenyl-(4 or 5-)thiazolyl]methyl, 2-[4-phenyl-(2 or 5-)thiazolyl]ethyl, 1-[5-phenyl-(2 or 4-)thiazolyl]ethyl, 3-[2-phenyl-(2 or 5-)thiazolyl]propyl, 4-(2,4-diphenyl-5-thiazolyl)butyl, 5-(2,5-diphenyl-4-thiazolyl)pentyl, 6-(4,5-diphenyl-2-thiazolyl)hexyl, 1,1-dimethyl-2-[2-phenyl-(4 or 5-)thiazolyl]ethyl, 2-methyl-3-[4-phenyl-(2 or 5-) thiazolyl]propyl, [4-phenyl-(2 or 5-)thiazolyl]methyl, [5-phenyl-(2 or 4-)thiazolyl]methyl, (2,4-diphenyl-5-thiazolyl)methyl, (2,5-diphenyl-4-thiazolyl)methyl, (4,5-diphenyl-2-thiazolyl)methyl, and [2-(4-trifluoromethylphenyl)thiazol-5-yl]methyl groups.

Examples of the benzimidazolyl lower alkyl group that may have 1 to 3 lower alkyl groups as substituents on the benzimidazole ring include benzimidazolyl alkyl group that may have 1 to 3 linear or branched alkyl groups having 1 to 6 carbon atoms as substituents on the benzimidazole ring, and the alkyl moiety is a linear or branched alkyl group having 1 to 6 carbon atoms such as (1-, 2-, 4-, 5-, 6-, or 7-)benzimidazolylmethyl, 1-methyl-(2-, 4-, 5-, 6-, or 7-)benzimidazolylmethyl, 2-[1-methyl-(2-, 4-, 5-, 6-, or 7-)benzimidazolylmethyl]ethyl, 3-[1-methyl-(2-, 4-, 5-, 6-, or 7-)benzimidazolylmethyl]propyl, 4-[1-methyl-(2-, 4-, 5-, 6-, or 7-)benzimidazolylmethyl]butyl, 5-[1-methyl-(2-, 4-, 5-, 6-, or 7-)benzimidazolylmethyl]pentyl, 6-[1-methyl-(2-, 4-, 5-, 6-, or 7-)benzimidazolylmethyl]hexyl, 2-[2-ethyl-(1-, 4-, 5-, 6-, or 7-)benzimidazolyl]ethyl, 4-propyl-(1-, 2-, 5-, 6-, or 7-)benzimidazolylmethyl, 5-butyl-(1-, 2-, 4-, 6-, or 7-)benzimidazolylmethyl, 2-[6-pentyl-(1-, 2-, 4-, 5-, or 7-)benzimidazolyl]ethyl, 3-[7-hexyl-(1-, 2-, 4-, 5-, or 6-)benzimidazolyl]propyl, 1-ethyl-(2-, 4-, 5-, 6-, or 7-)benzimidazolylmethyl, 1-butyl-(2-, 4-, 5-, 6-, or 7-)benzimidazolylmethyl, 1-isopropyl-(2-, 4-, 5-, 6-, or 7-)benzimidazolylmethyl, 1,2-dimethyl-(4-, 5-, 6-, or 7-)benzimidazolylmethyl, 1-methyl-4-ethyl-(2-, 5-, 6-, or 7-)benzimidazolylmethyl, 1-propyl-5-methyl-(2-, 4-, 6-, or 7-)benzimidazolylmethyl, and 1, 2 and 5-trimethyl-(4-, 6-, or 7-)benzimidazolylmethyl groups.

Examples of the 1,2,4-oxadiazolyl lower alkyl group that may have an oxo group as a substituent on the 1,2,4-oxadiazole ring include 1,2,4-oxadiazolylalkyl groups that may have an oxo group as a substituent on the 1,2,4-oxadiazole ring and of which alkyl moiety is a linear or branched alkyl group having 1 to 6 carbon atoms such as (2 or 5-) 1,2,4-oxadiazolylmethyl, 2-[(2 or 5-) 1,2,4-oxadiazolyl]ethyl, 1-[(2 or 5-)1,2,4-oxadiazolyl]ethyl, 3-[(2 or 5-)1,2,4-oxadiazolyl]propyl, 4-[(2 or 5-)1,2,4-oxadiazolyl]butyl, 5-[(2 or 5-)1,2,4-oxadiazolyl]pentyl, 6-[(2 or 5-)1,2,4-oxadiazolyl]hexyl, 1,1-dimethyl-2-[(2 or 5-)1,2,4-oxadiazolyl]ethyl, 2-methyl-3-[(2 or 5-)1,2,4-oxadiazolyl]propyl, 2-oxo-[(3 or 5-)1,2,4-oxadiazolyl]methyl, 5-oxo-[(2 or 3-)1,2,4-oxadiazolyl]methyl, 2-[2-oxo-(3 or 5-)(1,2,4-oxadiazolyl)]ethyl, 1-[5-oxo-(2 or 3-) 1,2,4-oxadiazolyl]ethyl, 3-[(2 or 5-)1,2,4-oxadiazolyl]propyl, 4-[2-oxo-(3 or 5-)1,2,4-oxadiazolyl]butyl, 5-[5-oxo-(2 or 3-) 1,2,4-oxadiazolyl]pentyl, 6-[2-oxo-(3 or 5-)1,2,4-oxadiazolyl]hexyl, 1,1-dimethyl-2-[5-oxo-(2 or 3-)1,2,4-oxadiazolyl]ethyl, and 2-methyl-3-[2-oxo-(3 or 5-)1,2,4-oxadiazolyl]propyl groups.

Examples of the thienyl lower alkyl group optionally substituted by one or more lower alkyl groups on the thiophene ring include (2- or 3-)thienylmethyl, 2-[(2- or 3-)thienyl]ethyl, 1-[(2- or 3-)thienyl]ethyl, 3-[(2- or 3-)thienyl]propyl, 4-[(2- or 3-)thienyl]butyl, 5-[(2- or 3-)thienyl]pentyl, 6-[(2- or 3-) thienyl]hexyl, 1,1-dimethyl-2-[(2- or 3-)thienyl]ethyl, 2-methyl-3-[(2- or 3-)thienyl]propyl, [5-methyl-(2-, 3- or 4-)thienyl]methyl, 2-[5-methyl-(2-, 3- or 4-)thienyl]ethyl, 1-[4-methyl-(2-, 3- or 5-) thienyl]ethyl, 3-[5-methyl-(2-, 3- or 4-)thienyl]propyl, 4-[4-ethyl-(2-, 3- or 5-)thienyl]butyl, 5-[5-propyl-(2-, 3- or 4-) thienyl]pentyl, 6-[4-butyl-(2-, 3- or 5-)thienyl]hexyl, 1,1-dimethyl-2-[4,5-dimethyl-(2- or 3-)thienyl]ethyl, and 2-methyl-3-[4-methyl-(2-, 3- or 5-)thienyl]propyl group. Specific examples thereof include thienylalkyl group wherein the thiophene ring may have one or more linear or branched alkyl groups having 1 to 6 carbon atoms and the alkyl moiety is a linear or branched alkyl group having 1 to 6 carbon atoms.

Examples of the imidazolyl lower alkyl group that may have, on the imidazole ring, 1 to 3 members selected from the group consisting of lower alkyl groups and halogen atoms as substituents include (1-, 2-, 4- or 5-)imidazolyl methyl, 2-[(1-, 2-, 4- or 5-)imidazolyl]ethyl, 1-[(1-, 2-, 4- or 5-) imidazolyl]ethyl, 3-[(1-, 2-, 4- or 5-)imidazolyl]propyl, 4-[(1-, 2-, 4- or 5-)imidazolyl]butyl, 5-[(1-, 2-, 4- or 5-) imidazolyl] pentyl, 6-[(1-, 2-, 4- or 5-)imidazolyl]hexyl, 1,1-dimethyl-2-[(1-, 2-, 4- or 5-)imidazolyl]ethyl, 2-methyl-3-[(1-, 2-, 4- or 5-)imidazolyl]propyl, 1-methyl-(2-, 4- or 5-)imidazolyl methyl, 2-methyl-(1-, 4- or 5-)imidazolyl methyl, 4-methyl-(1-, 2- or 5-)imidazolyl methyl, 5-methyl-(1-, 2- or 4-)imidazolyl methyl, 2-[1-methyl-(2-, 4- or 5-)imidazolyl]ethyl, 2-[2-methyl-(1-, 4- or 5-)imidazolyl]ethyl, 2-[4-methyl-(1-, 2- or 5-) imidazolyl]ethyl, 2-[5-methyl-(1-, 2- or 4-)imidazolyl]ethyl, 1-[1-methyl-(2-, 4- or 5-)imidazolyl]ethyl, 3-[2-methyl-(1-, 4- or 5-) imidazolyl]propyl, 4-[4-methyl-(1-, 2- or 5-)imidazolyl]butyl, 5-[5-methyl-(1-, 2- or 4-)imidazolyl] pentyl, 6-[1-methyl-(2-, 4- or 5-)imidazolyl]hexyl, 1,1-dimethyl-2-[2-methyl-(1-, 4- or 5-) imidazolyl]ethyl, 2-methyl-3-[4-methyl-(1-, 2- or 5-)imidazoly]propyl, 1-chloro-(2-, 4- or 5-)imidazolyl methyl, 2-chloro-(1-, 4- or 5-)imidazolyl methyl, 4-chloro-(1-, 2- or 5-) imidazolyl methyl, 5-chloro-(1-, 2- or 4-)imidazolyl methyl, 1-fluoro-(2-, 4- or 5-)imidazolyl methyl, 2-bromo-(1-, 4- or 5-) imidazolyl methyl, 4-iodo-(1-, 2- or 5-)imidazolyl methyl, 5-fluoro-(1-, 2- or 4-)imidazolyl methyl, and 1,2,4-trichloro-5-imidazolyl methyl group. Specifically, these groups may have, on the imidazole ring, 1 to 3 members selected from the group consisting of linear or branched alkyl groups having 1 to 6 carbon atoms and halogen atoms as substituents, wherein the alkyl moiety is a linear or branched alkyl group having 1 to 6 carbon atoms.

Examples of the 1,2,3,4-tetrahydroquinolyl group optionally substituted by one or more oxo groups on the tetrahydroquinoline ring include 1,2,3,4-tetrahydroquinolyl groups that may have 1 or 2 oxo groups on the tetrahydroquinoline ring such as (1, 3, 4, 5, 6, 7 or 8-)1,2,3,4-tetrahydroquinolyl, 2-oxo-(1, 3, 4, 5, 6, 7 or 8-)1,2,3,4-tetrahydroquinolyl, 4-oxo-(1, 2, 3, 5, 6, 7 or 8-)1,2,3,4-tetrahydroquinolyl, and 2,4-dioxo-(1, 3, 5, 6, 7 or 8-)1,2,3,4-tetrahydroquinolyl groups.

Examples of the isoxazolyl lower alkyl group that may have 1 to 3 lower alkyl groups as substituents on the isoxazole ring include (3-, 4-, or 5-)isoxazolylmethyl, 2-[(3-, 4-, or 5-) isoxazolyl]ethyl, 1-[(3-, 4-, or 5-)isoxazolyl]ethyl, 3-[(3-, 4-, or 5-)isoxazolyl]propyl, 4-[(3-, 4-, or 5-)isoxazolyl]butyl, 5-[(3-, 4-, or 5-)isoxazolyl]pentyl, 6-[(3-, 4-, or 5-) isoxazolyl]hexyl, 1,1-dimethyl-2-[(3-, 4-, or 5-) isoxazolyl]ethyl, 2-methyl-3-[(3-, 4-, or 5-)isoxazolyl]propyl, 5-methyl-(3- or 4-)isoxazolylmethyl, and 3,5-dimethyl-4-isoxazolylmethyl groups. Specific examples thereof include isoxazolyl alkyl groups that may have 1 or 2 aforesaid lower alkyl groups as substituents on the isoxazole ring.

Examples of the imidazo[2,1-b]thiazolyl lower alkyl group include imidazo[2,1-b]thiazol-(2-, 3-, 5-, or 6-)ylmethyl, 2-[imidazo[2,1-b]thiazol-(2-, 3-, 5-, or 6-)yl]ethyl, 1-[imidazo[2,1-b]thiazol-(2-, 3-, 5-, or 6-)yl]ethyl, 3-[imidazo[2,1-b]thiazol-(2-, 3-, 5-, or 6-)yl]propyl, 4-[imidazo[2,1-b]thiazol-(2-, 3-, 5-, or 6-)yl]butyl, 5-[imidazo[2,1-b]thiazol-(2-, 3-, 5-, or 6-)yl]pentyl, 6-[imidazo[2,1-b]thiazol-(2-, 3-, 5-, or 6-)yl]hexyl, 1,1-dimethyl-2-[imidazo[2,1-b]thiazol-(2-, 3-, 5-, or 6-)yl]ethyl, and 2-methyl-3-[imidazo[2,1-b]thiazol-(2-, 3-, 5-, or 6-)yl]propyl groups. Specific examples thereof include imidazo[2,1-b]thiazolyl alkyl groups wherein the alkyl moiety is a linear or branched alkyl group having 1 to 6 carbon atoms.

Examples of the 3,4-dihydro-2H-1,4-benzoxazinyl lower alkyl group optionally substituted by one or more lower alkyl groups on the 3,4-dihydro-2H-1,4-benzoxazine ring include 3,4-dihydro-2H-1,4-benzoxazin-(2-, 3-, 4-, 5-, 6-, 7-, or 8-)ylmethyl, 2-[3,4-dihydro-2H-1,4-benzoxazin-(2-, 3-, 4-, 5-, 6-, 7-, or 8-) yl]ethyl, 1-[3,4-dihydro-2H-1,4-benzoxazin-(2-, 3-, 4-, 5-, 6-, 7-, or 8-)yl]ethyl, 3-[3,4-dihydro-2H-1,4-benzoxazin-(2-, 3-, 4-, 5-, 6-, 7-, or 8-)yl]propyl, 4-[3,4-dihydro-2H-1,4-benzoxazin-(2-, 3-, 4-, 5-, 6-, 7-, or 8-)yl]butyl, 5-[3,4-dihydro-2H-1,4-benzoxazin-(2-, 3-, 4-, 5-, 6-, 7-, or 8-)yl]pentyl, 6-[3,4-dihydro-2H-1,4-benzoxazin-(2-, 3-, 4-, 5-, 6-, 7-, or 8-)yl]hexyl, 1,1-dimethyl-2-[3,4-dihydro-2H-1,4-benzoxazin-(2-, 3-, 4-, 5-, 6-, 7-, or 8-)yl]ethyl, 2-methyl-3-[3,4-dihydro-2H-1,4-benzoxazin-(2-, 3-, 4-, 5-, 6-, 7-, or 8-)yl]propyl, and [4-methyl-3,4-dihydro-2H-1,4-benzoxazin-(2-, 3-, 4-, 5-, 6-, 7-, or 8-)yl]methyl group. Specific examples thereof include 3,4-dihydro-2H-1,4-benzoxazinyl alkyl groups that may have 1 to 3 linear or branched alkyl groups having 1 to 6 carbon atoms as substituents on the 3,4-dihydro-2H-1,4-benzoxazine ring, wherein the alkyl moiety is a linear or branched alkyl group having 1 to 6 carbon atoms.

Examples of the pyrazolyl lower alkyl group that may have, on the pyrazole ring, 1 to 3 members selected from the group consisting of lower alkyl groups and halogen atoms as substituents include pyrazolyl alkyl groups wherein the alkyl moiety is a linear or branched alkyl group having 1 to 6 carbon atoms. Such pyrazolyl lower alkyl groups may have, on the pyrazole ring, 1 to 3 members selected from the group consisting of the aforesaid lower alkyl groups and the aforesaid halogen atoms. Specific examples of the pyrazolyl lower alkyl group that may have, on the pyrazole ring, 1 to 3 members selected from the group consisting of lower alkyl groups and halogen atoms as substituents include pyrazol(1-, 3-, 4-, or 5-)ylmethyl, 2-[pyrazol-(1-, 3-, 4-, or 5-)yl]ethyl, 1-[pyrazol-(1-, 3-, 4-, or 5-)yl]ethyl, 3-[pyrazol-(1-, 3-, 4-, or 5-)yl]propyl, 4-[pyrazol-(1-, 3-, 4-, or 5-)yl]butyl, 5-[pyrazol-(1-, 3-, 4-, or 5-) yl]pentyl, 6-[pyrazol-(1-, 3-, 4-, or 5-)yl]hexyl, 1,1-dimethyl-2-[pyrazol-(1-, 3-, 4-, or 5-)yl]ethyl, 2-methyl-3-[pyrazol-(1-, 3-, 4-, or 5-)yl]propyl, [(1,3-, 1,4-, or 3,4-)dimethylpyrazol-5-yl]methyl, 2-[(1,3-, 1,4-, or 3,4-)dimethylpyrazol-5-yl]ethyl, [1-methyl-4-chloropyrazol-(3- or 5-)yl]methyl, and 2-[1-methyl-4-chloropyrazol-(3- or 5-)yl]ethyl groups.

Examples of the dihydropyridyl lower alkyl group that may have an oxo group as a substituent on the dihydropyridine ring include dihydropyridyl alkyl groups wherein the alkyl moiety is a linear or branched alkyl group having 1 to 6 carbon atoms. Such a dihydropyridyl lower alkyl group may have one oxo group as a substituent on the dihydropyridine ring. Specific examples of the dihydropyridyl lower alkyl group that may have an oxo group as a substituent on the dihydropyridine ring include 1,2-dihydropyridin-(1-, 2-, 3-, 4-, 5-, or 6-)ylmethyl, 2-oxo-1,2-dihydropyridin-(1-, 3-, 4-, 5-, or 6-)ylmethyl, 2-[1,2-dihydropyridin-(1-, 2-, 3-, 4-, 5-, or 6-)yl]ethyl, 1-[1,2-dihydropyridin-(1-, 2-, 3-, 4-, 5-, or 6-)yl]ethyl, 3-[1,2-dihydropyridin-(1-, 2-, 3-, 4-, 5-, or 6-)yl]propyl, 4-[1,2-dihydropyridin-(1-, 2-, 3-, 4-, 5-, or 6-)yl]butyl, 5-[1,2-dihydropyridin-(1-, 2-, 3-, 4-, 5-, or 6-)yl]pentyl, 6-[1,2-dihydropyridin-(1-, 2-, 3-, 4-, 5-, or 6-)yl]hexyl, 1,1-dimethyl-2-[1,2-dihydropyridin-(1-, 2-, 3-, 4-, 5-, or 6-)yl]ethyl, and 2-methyl-3-[1,2-dihydropyridin-(1-, 2-, 3-, 4-, 5-, or 6-)yl]propyl groups.

Examples of the morpholino lower alkyl group include morpholinomethyl, 2-morpholinoethyl, 1-morpholinoethyl, 3-morpholinopropyl, 4-morpholinobutyl, 5-morpholinopentyl, 6-morpholinohexyl, 1,1-dimethyl-2-morpholinoethyl, and 2-methyl-3-morpholinopropyl group. Specific examples thereof include morpholino alkyl groups wherein the alkyl moiety is a linear or branched alkyl group having 1 to 6 carbon atoms.

Examples of the phenyl lower alkenyl group optionally substituted by one or more lower alkoxy groups on the phenyl ring include phenyl alkenyl groups having 1 to 3 doble bonds wherein the alkenyl moiety is a linear or branched alkenyl group having 2 to 6 carbon atoms. Such phenyl lower alkenyl groups may have 1 to 3 aforesaid lower alkoxy groups on the phenyl ring. Specific examples of the phenyl lower alkenyl groups optionally substituted by one or more lower alkoxy groups on the phenyl ring include styryl, 3-phenyl-2-propenyl (trivial name: cinnamyl), 4-phenyl-2-butenyl, 4-phenyl-3-butenyl, 5-phenyl-4-pentenyl, 5-phenyl-3-pentenyl, 6-phenyl-5-hexenyl, 6-phenyl-4-hexenyl, 6-phenyl-3-hexenyl, 4-phenyl-1,3-butadienyl, 6-phenyl-1,3,5-hexatrienyl, 2-[(2-, 3-, or 4-)methoxyphenyl]vinyl, 2-[(2-, 3-, or 4-)ethoxyphenyl]vinyl, 3-[(2-, 3-, or 4-)methoxyphenyl]-2-propenyl, 3-[(2-, 3-, or 4-)ethoxyphenyl]-2-propenyl, 3-[(2,3-, 2,4-, 2,5-, 2,6-, 3,4-, or 3,5-)dimethoxyphenyl]-2-propenyl, and 4-[(2,3,4-, 2,3,5-, 2,3,6-, 2,4,5- or 2,4,6-)triethoxyphenyl]-2-butenyl groups.

Examples of the lower alkanoyloxy groups are liner or branched alkanoyloxy groups having 1 to 6 carbon atoms.

The methods for producing the compounds according to the invention are explained below.

The compound of the present invention is produced as shown in Reaction Formulas 1 to 13, for example.

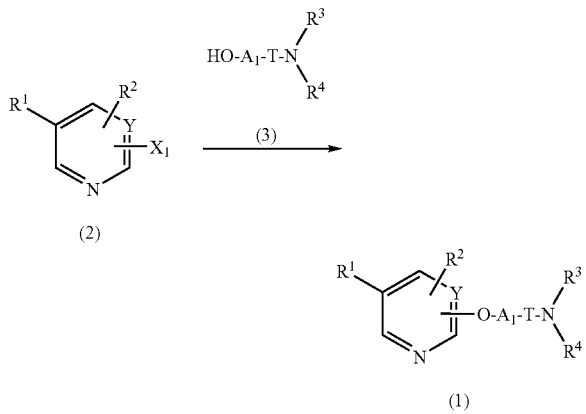

Reaction Formula 1 wherein $R^1$, $R^2$, $R^3$, $R^4$, Y, T, and $A_1$ are as defined above, and $X_1$ is a halogen atom.

The reaction of the compound (2) with the compound (3) is carried out in an appropriate solvent or with no solvent in the presence or absence of a basic compound.

Examples of the inert solvent used include aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, dimethylsulfoxide, N,N-dimethylformamide, N-methylpyrrolidone, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, sodium hydride, potassium hydride, potassium, sodium, sodium amide, metal alcoholates such as sodium methylate, sodium ethylate, and sodium n-butoxide, and organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

When the reaction is carried out in the presence of a basic compound, the basic compound is used in an amount typically equimolar to the compound (2), and preferably 1 to 10 times of the compound (2) on a molar basis.

The compound (3) is used in an amount typically at least equimolar to the compound (2), and preferably 1 to 10 times of the compound (2) on a molar basis.

The reaction is carried out typically at −30 to 200° C., and preferably at about −30 to 150° C., and is generally completed in about 5 minutes to 80 hours.

To this reaction system, an alkali metal halide such as sodium iodide or potassium iodide may be added, and a phase-transfer catalyst may be added.

Examples of the phase-transfer catalyst include quaternary ammonium salts substituted with a group selected from the group consisting of a linear or branched alkyl group having 1 to 18 carbon atoms, a phenyl alkyl group which the alkyl moiety is a linear or branched alkyl group having 1 to 6 carbon atoms and a phenyl group, such as tetrabutylammonium chloride, tetrabutylammonium bromide, tetrabutylammonium fluoride, tetrabutylammonium iodide, tetrabutylammonium hydroxide, tetrabutylammonium hydrogensulfite, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, tetramethylammonium chloride; phosphonium salts substituted with a linear or branched alkyl group having 1 to 18 carbon atoms such as tetrabutylphosphonium chloride; and pyridinium salts substituted with a linear or branched alkyl group having 1 to 18 carbon atoms such as 1-dodecanylpyridinium chloride. These phase-transfer catalysts are used singly or in a combination of two or more.

Typically the phase-transfer catalyst is used in an amount of 0.1 to 1 times of the compound (2), and preferably 0.1 to 0.5 times of the compound (2).

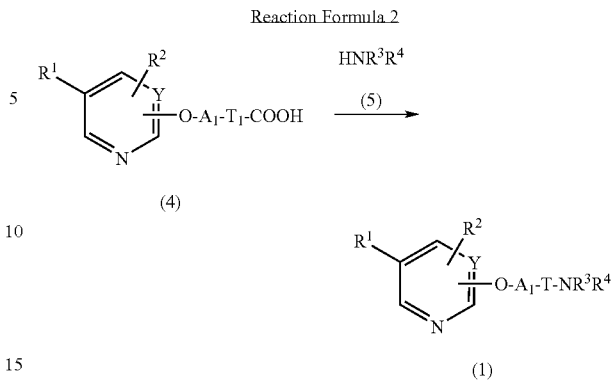

wherein $R^1$, $R^2$, $R^3$, $R^4$, Y and $A_1$ are as defined above, and $T_1$ is a group-$N(R^{14})$—$B_4$—, a group-$B_5$— or a direct bond, wherein $R^{14}$, $B_4$ and $B_5$ are as defined above.

Known reactions for producing an amide bond may be applied to the reaction of the compound (4) with the compound (5). Specific methods thereof include: (a) a mixed acid anhydride method, specifically, a method of reacting an alkylhalocarboxylic acid with the carboxylic acid (4) to prepare a mixed acid anhydride, and then reacting the amine (5) with the mixed acid anhydride; (b) an active ester method, specifically, a method of preparing, from the carboxylic acid (4), an active ester such as a phenyl ester, p-nitrophenyl ester, N-hydroxysuccinimide ester, and 1-hydroxybenzotriazole ester, or an active amide with benzoxazoline-2-thione, and then reacting the active ester or amide with the amine (5); (c) a carbodiimide method, specifically, a method of condensation reaction of the carboxylic acid (4) with the amine (5) in the presence of an activator such as dicyclohexylcarbodiimide, 1-(3-dimethylaminopropyl)-3-ethylcarbodiimide (WSC), and carbonyldiimidazole; (d) other methods, for example, a method of preparing carboxylic anhydride from the carboxylic acid (4) by the action of a dehydrator such as acetic anhydride, and then reacting the carboxylic anhydride with the amine (5), a method of reacting an ester of the carboxylic acid (4) with a lower alcohol with the amine (5) at a high pressure and a high temperature, and a method of reacting an acid halide of the carboxylic acid (4), that is, carboxylic acid halide, with the amine (5).

The mixed acid anhydride used in the mixed anhydride method (a) described above, may be obtained by a typical Schotten-Baumann reaction, and the compound of the present invention of General Formula (I) can be produced by reacting the amine (5) with the mixed acid anhydride without isolation.

The Schotten-Baumann reaction described above is carried out in the presence of a basic compound.

The basic compounds used include compounds commonly used in Schotten-Baumann reaction, for example, organic bases such as triethylamine, trimethylamine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and inorganic bases such as carbonates such as sodium carbonate, potassium carbonate, sodium bicarbonate, and potassium bicarbonate, metal hydroxides such as sodium hydroxide, potassium hydroxide, and calcium hydroxide, potassium hydride, sodium hydride, potassium, sodium, sodium amide, and metal alcoholates such as sodium methylate and sodium ethylate. These basic compounds are used singly or in a combination of two or more. The reaction is carried out at typically about −20 to 100° C., and preferably about 0 to 50° C., and the reaction time is about 5 minutes to 10 hours, and preferably about 5 minutes to 2 hours.

The resulting mixed acid anhydride is reacted with the amine (5) at typically about −20 to 150° C., preferably about 10 to 50° C., and the reaction time is about 5 minutes to 10 hours, and preferably about 5 minutes to 5 hours.

The mixed acid anhydride method is, in general, carried out in a solvent. Any of the solvent conventionally used for the mixed acid anhydride method may be used. Specific examples of the solvent include halogenated hydrocarbons such as chloroform, dichloromethane, dichloroethane, and carbon tetrachloride, aromatic hydrocarbons such as benzene, toluene and xylene, ethers such as diethyl ether, diisopropyl ether, tetrahydrofuran, and dimethoxyethane, esters such as methyl acetate, ethyl acetate, and isopropyl acetate, and aprotic polar solvents such as N,N-dimethylformamide, dimethylsulfoxide, and hexamethylphosphoric acid triamide, and a mixture thereof.

Examples of the alkylhalocarboxylic acid used in the mixed acid anhydride method include methyl chloroformate, methyl bromoformate, ethyl chlorformate, ethyl bromoformate, and isobutyl chloroformate.

In the mixed acid anhydride method, it is typically preferable to use the carboxylic acid (4), alkylhalocarboxylic acid and the amine (5) equimolar to each other. However, each of alkyl halocarboxylic acid and the carboxylic acid (4) may be used 1 to 1.5 times of the amine (5) on a molar basis, respectively.

In the above described method (c) of condensation reaction in the presence of an activator, the reaction is carried out in an appropriate solvent in the presence or absence of a basic compound. Any of the solvents and basic compounds used in the reaction in the other methods (d) described below of reacting carboxylic acid halide with the amine (5) may be used for this reaction. It is appropriate to use the activator in an amount typically at least equimolar to the compound (5), and preferably 1 to 5 times of the compound (5) on a molar basis. When WSC is used as an activator, the reaction may be carried out advantageously by adding 1-hydroxybenzotriazole and/or an acid such as hydrochloric acid into the reaction system. This reaction is carried out at typically about −20 to 180° C., and preferably about 0 to 150° C., and is completed typically in about 5 minutes to 90 hours.

In the other method (d) described above, wherein the amine (5) is reacted with carboxylic acid halide, the reaction is carried out in an appropriate solvent in the presence of a basic compound. As such a basic compound, known basic compounds may be widely used, and, for example, any of compounds used for the Shotten-Baumann reaction described above may be used. Examples of the solvent include, in addition to the solvents used in the mixed acid anhydride method described above, alcohols such as methanol, ethanol, isopropanol, propanol, butanol, 3-methoxy-1-butanol, ethyl cellosolve, and methyl cellosolve, acetonitrile, pyridine, acetone, and water. The ratio of the amine (5) to the carboxylic acid halide in the reaction is not specified and may be appropriately selected in a wide range. Typically, the carboxylic acid halide may be used in an amount at least about equimolar to the amine, and preferably about 1 to 5 times of the amine on a molar basis. This reaction is carried out at typically about −20 to 180° C., and preferably about 0 to 150° C., and is completed typically in 5 minutes to 50 hours.

Further, the reaction for producing an amide bond shown in the above described reaction formula 2 may be carried out by reacting the carboxylic acid (4) and the amine (5) in the presence of a condensation agent of a phosphorus compound such as triphenylphosphine, diphenylphosphinyl chloride, phenyl-N-phenylphosphoramide chloridate, diethyl chlorophosphate, diethyl cyanophosphate, diphenylphosphoric acid azide, and bis(2-oxo-3-oxazolidinyl)phosphinic chloride. The condensation agent described above is used singly or in a combination of two or more.

The above described reaction is carried out, in the presence of the solvent and the basic compound which are used in the method for reacting the carboxylic acid halide with the amine (5) described above, at typically about −20 to 150° C., and preferably about 0 to 100° C., and is completed typically in 5 minutes to about 30 hours. The condensation agent and the carboxylic acid (4) may be used respectively in an amount at least about equimolar to the amine (5), and preferably about 1 to 2 times of the amine (5) on a molar basis.

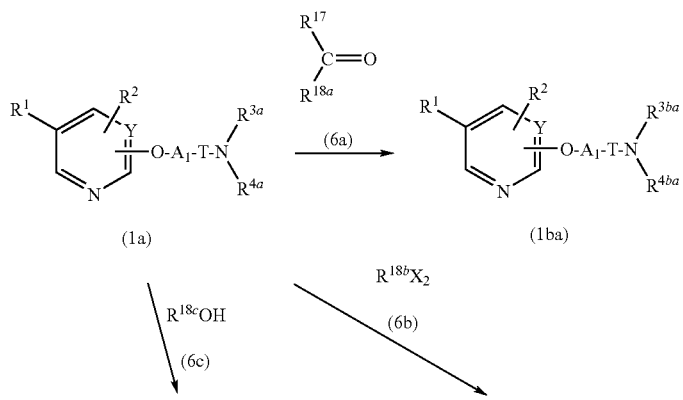

Reaction Formula 3

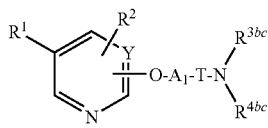

(1bc)

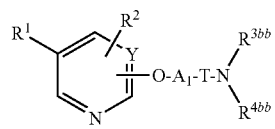

(1bb)

wherein $R^1$, $R^2$, Y, T, and $A_1$ are as defined above, $R^{3a}$ and $R^{4a}$ are the same as the saturated heterocyclic group of 5- to 10-membered ring defined in the $R^3$ and $R^4$ above except that they have at least one secondary amine on the heterocyclic group, $R^{3a}$ and $R^{4a}$ are the same as the saturated heterocyclic group of 5- to 10-membered ring defined in the $R^3$ and $R^4$ above except that they have at least one tertiary amine substituted with a group $R^{17}(R^{18a})CH$— on the heterocyclic group, $R^{17}$ is a hydrogen atom or a lower alkyl group, and $R^{18a}$ is a hydrogen atom; a lower alkyl group that has, 1 or 2 phenyl groups that may be substituted with 1 to 3 groups selected from the group consisting of cyano group, nitro group, halogen atoms, and lower alkyl groups that may have one or more halogen atoms or lower alkoxy groups, lower alkoxy groups that may have one or more halogen atoms, hydroxy group, aminosulfonyl groups that may have one or more lower alkyl groups, lower alkylamino carbonyl groups, tetrazolyl groups that may have one or more lower alkyl groups or lower alkoxy-lower alkyl groups, lower alkynyl groups, lower alkyl sulfonyl groups, lower alkyl sulfonylamino groups, 1,2,4-triazolyl groups, imidazolyl groups, piperidinyl groups, and lower alkylenedioxy groups; phenyl groups that may have, on the phenyl ring, 1 to 3 groups elected from the group consisting of cyano group, nitro group, halogen atoms, lower alkyl groups that may have one or more halogen atoms or lower alkoxy groups, lower alkoxy groups that may have one or more halogen atoms, hydroxy group, aminosulfonyl groups that may have one or more lower alkyl groups, lower alkylamino carbonyl groups, tetrazolyl groups that may have one or more lower alkyl groups or lower alkoxy-lower alkyl groups, lower alkynyl groups, lower alkyl sulfonyl groups, lower alkyl sulfonylamino groups, 1,2,4-triazolyl groups, imidazolyl groups, piperidinyl groups, and lower alkylenedioxy groups; pyridyl lower alkyl groups that may have, on the pyridine ring, 1 to 3 groups selected from the group consisting of: hydroxyl group, lower alkyl groups that may have one or more hydroxyl groups, halogen atoms, lower alkyl groups and cyano group; pyridyl groups that may have, on the pyridine ring, 1 to 3 groups selected from the group consisting of hydroxy groups, lower alkyl groups that may have one or more hydrogen groups, lower alkyl groups that may have one or more hydroxyl groups, halogen atoms, lower alkoxy groups, and cyano group; pyrrolyl lower alkyl groups that may have, on the pyrrole ring, 1 to 3 lower alkyl groups as substituents; pyrrolyl groups that may have, on the pyrrole ring, 1 to 3 lower alkyl groups as substituents; lower alkyl groups that may have one or more groups selected from the group consisting of: hydroxy group and halogen atoms, as substituents; group-$(B_6CO)t$-$N(R^{15})R^{16}$; quinolyl lower alkyl groups; quinolyl groups; thiazolyl lower alkyl groups that may have, on the thiazole ring, one or more phenyl groups; thiazolyl groups that may have, on the thiazole ring, one or more phenyl groups; benzimidazolyl lower alkyl groups that may have, on the benzimidazole ring, 1 to 3 lower alkyl groups as substituents; benzimidazolyl groups that may have, on the benzimidazole ring, 1 to 3 lower alkyl groups as substituents; 1,2,4-oxadiazolyl lower alkyl groups that may have, on the 1,2,4-oxadiazole ring, one or more oxo groups; 1,2,4-oxadiazolyl groups that may have, on the 1,2,4-oxadiazole ring, one or more oxo groups; cycloalkyl lower alkyl groups; cycloalkyl groups; thienyl lower alkyl groups that may have, on the thiophene ring, one or more lower alkyl groups; thienyl group that may have, on the thiophene ring, one or more lower alkyl groups; imidazolyl lower alkyl groups that may have, on the imidazole ring, 1 to 3 groups selected from the group consisting of lower alkyl groups and halogen atoms as substituents; imidazolyl groups that may have, on the imidazole ring, 1 to 3 groups selected from the group consisting of lower alkyl groups and halogen atoms as substituents; isoxazolyl lower alkyl groups that may have, on the isoxazole ring, 1 to 3 lower alkyl groups as substituents; isoxazolyl groups that may have, on the isoxazole ring, 1 to 3 lower alkyl groups as substituents; imidazo[2,1-b]thiazolyl lower alkyl groups; imidazo[2,1-b]thiazolyl groups; 3,4-dihydro-2H-1,4-benzoxazinyl lower alkyl groups that may have, on the 3,4-dihydro-2H-1,4-benzoxazine ring, one or more lower alkyl groups; 3,4-dihydro-2H-1,4-benzoxazinyl groups that may have, on the 3,4-dihydro-2H-1,4-benzoxazine ring, one or more lower alkyl groups; pyrazolyl lower alkyl groups that may have, on the pyrazole ring, 1 to 3 groups selected from the group consisting of lower alkyl groups and halogen atoms as substituents; pyrazolyl groups that may have, on the pyrazole ring, 1 to 3 groups selected from the group consisting of lower alkyl groups and halogen atoms as substituents; dihydropyridyl lower alkyl groups that may have, on a dihydropyridine ring, one or more oxo groups; dihydropyridyl groups that may have, on the dihydropyridine ring, one or more oxo groups; morpholino lower alkyl groups; morpholino groups; or phenyl lower alkenyl groups that may have, on the phenyl ring, one or more lower alkoxy groups, $R^{17}$ and $R^{18a}$ may form a cycloalkyl group or a tetrahydro 4H-pyranyl group with the carbon atom to which they are bonded, the carbon of the alkyl moiety of the group $R^{17}(R^{18a})CH$— in the compound (1ba) is less than 6, $X_2$ is a halogen atom, a lower alkane sulfonyloxy group such as a methane sulfonyloxy group, or an arylsulfonyloxy group such as a p-toluenesulfonyloxy group, $R^{3bb}$ and $R^{4bb}$ are the same as the saturated heterocyclic group of 5- to 10-membered ring defined in the $R^3$ and $R^4$ above except that they have at least one tertiary amine substituted with a group $R^{18b}$ on the heterocyclic group, $R^{3bc}$ and $R^{4bc}$ are the same as the saturated heterocyclic group of 5- to 10-membered ring defined in the $R^3$ and $R^4$ above except that they have at least one tertiary amine substituted with a group $R^{18b}$ on the heterocyclic group, $R^{18b}$ is the same group as the (1), (2), (3), (5), (6), (7), (9), (10), and (12) (however, t is 1) (13), (14), (15), (16), (17), (18), (19), (21), (22), (23), (24), (25), (26), (27), (28), (29) or (30), which is a substituent of the heterocycle group formed by a combination of $R^3$ and $R^4$, $R^{18c}$ is the same group as the (4), (8) or (31) which is a substituent of the heterocycle group formed by a combination of $R^3$ and $R^4$.

The reaction of the compound (1a) with the compound (6a) is carried out, for example, in the presence of a reducing agent without a solvent or with an appropriate solvent. Hereinafter, this method is called "method A".

Examples of the solvent used here include water, lower alcohols such as, methanol, ethanol, isopropanol, butanol, tert-butanol, and ethylene glycol, acetonitrile, fatty acids such as formic acid, and acetic acid, ethers such as diethyl ether, tetrahydrofuran, dioxane, monoglyme, and diglyme, aromatic hydrocarbons such as benzene, toluene, and xylene, and halogenated hydrocarbons such as dichloromethane, dichloroethane, chloroform, and carbon tetrachloride, and a mixture thereof.

Examples of the reducing agent include fatty acids and alkali metal salts thereof such as formic acid, sodium formate, and sodium acetate, hydride reducing agents such as sodium borohydride, sodium cyanoborohydride, sodium triacetyloxyborohydride, and aluminum lithium hydride, or a mixture of these hydride reducing agents, and catalytic hydrogen reducing agents such as palladium black, palladium-carbon, platinum oxide, platinum black, and Raney nickel.

In using a fatty acid or an alkali metal salt thereof such as formic acid, sodium formate, and sodium acetate as a reducing agent, the appropriate reaction temperature is typically from room temperature to about 200° C., and preferably about 50 to about 150° C., and the reaction is completed generally in about 10 minutes to 10 hours. It is preferable to use a fatty acid or an alkali metal salt thereof in a large excess amount with respect to the compound (1a).

In using a hydride reducing agent, the appropriate reaction temperature is typically about −80 to 100° C., and preferably −80 to 70° C., and the reaction is completed in general in 30 minutes to 60 hours. The hydride reducing agent is used in an amount typically 1 to 20 times of the compound (1a), and preferably 1 to 6 times of the compound (1a) on a molar basis.

Especially in using aluminum lithium hydride as a hydride reducing agent, it is preferable to employ an ether such as diethyl ether, tetrahydrofuran, dioxane, monoglyme, and diglyme, or an aromatic hydrocarbon such as benzene, toluene, and xylene. To the reaction system, an amine such as trimethylamine, triethylamine, and N-ethyl-N,N-diisopropylamine, or molecular sieves such as Molecular Sieves 3A (MS-3A) or Molecular Sieves 4A (MS-4A) may be added.

In using a catalytic hydrogen reducing agent, the reaction is preferably carried out in a hydrogen atmosphere typically at a normal pressure to about 20 atm, and preferably at a normal atmosphere to about 10 atm, or in the presence of a hydrogen donor such as formic acid, ammonium formate, cyclohexene, and hydrazine hydrate, at a temperature of typically about −30 to 100° C., and preferably about 0 to 60° C. The above described reaction is in general completed in about 1 to 12 hours. The catalytic hydrogen reducing agent is used typically in an amount of about 0.1% to 40% by weight, and about 1 to 20% by weight based on the compound (1a).

In the reaction of the compound (1a) with the compound (6a), the compound (6a) is typically used in an amount at least equimolar to the compound (1a), and preferably used in an equal amount to a large excess amount of compound (1a) on a molar basis.

When the compound (6a), wherein $R^{17}$ and $R^{18a}$ are bound together with the carbon atoms to form a cycloalkyl ring or tetrahydro-4H-pyran ring, is used as a starting material, and the hydride reducing agent is used to carry out the reaction, cycloalkyloxytrialkylsilane such as [(1-ethoxycyclopropyl) oxy]trimethylsilane may be used in place of the compound (6a) as the starting material to produce the above described compound (6a) in the reaction system.

The reaction of the compound (1a) with the compound (6b) is carried out under reaction conditions similar to those of the reaction of the compound (2) with the compound (3) of the above described reaction formula 1.

The reaction of the compound (1a) with the compound (6c) is carried out under reaction conditions similar to those of the reaction of the compound (4) with the compound (5) of the above described reaction formula 2.

Reaction Formula 4

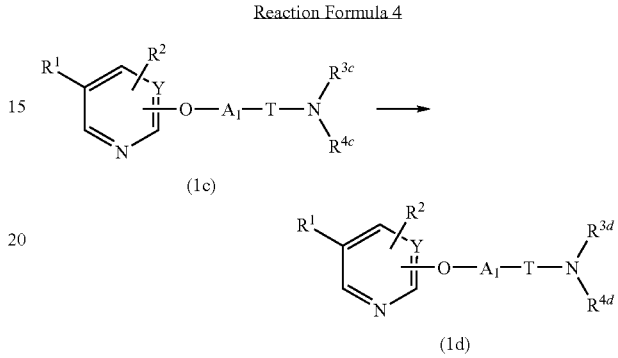

wherein $R^1$, $R^2$, Y, T, and $A_1$ are as defined above, $R^{3c}$ and $R^{4c}$ are the same as the saturated heterocyclic group of 5- to 10-membered ring defined in the $R^3$ and $R^4$ above except that they have at least one tertiary amine substituted with a lower alkoxycarbonyl group on the heterocyclic group, and $R^{3d}$ and $R^{4d}$ are the same as the saturated heterocyclic group of 5- to 10-membered ring defined in the $R^3$ and $R^4$ above except that they have at least one secondary amine on the heterocyclic group.

The reaction which converts the compound (1c) into the compound (1d) is the hydrolysis reaction (hereinafter this hydrolysis reaction is called "hydrolysis B"), and the reaction may be carried out in an appropriate solvent or without a solvent, in the presence of an acidic or basic compound.

Examples of the solvent used include water, lower alcohols such as methanol, ethanol, isopropanol, and tert-butanol, ketones such as acetone and methyl ethyl ketone, ethers such as diethyl ether, dioxane, tetrahydrofuran, monoglyme, and diglyme, fatty acids such as acetic acid and formic acid, esters such as methyl acetate and ethyl acetate, halogenated hydrocarbons such as chloroform, dichloromethane, dichloroethane, and carbon tetrachloride, dimethylsulfoxide, N,N-dimethylformamide, and hexamethylphosphoric acid triamide, and a mixture thereof.

Examples of the acid include mineral acids such as hydrochloric acid, sulfuric acid, and hydrobromic acid, organic acids such as formic acid, acetic acid, trifluoroacetic acid, and sulfonic acids including p-toluenesulfonic acid, and Lewis acids such as boron tribromide and boron trichloride. These acids are used singly or in a mixture of two or more.

Examples of the basic compound include carbonates such as sodium carbonate, potassium carbonate, sodium bicarbonate, and potassium bicarbonate, and metal hydroxides such as sodium hydroxide, potassium hydroxide, calcium hydroxide, and lithium hydroxide. These basic compounds are used singly or in a mixture of two or more.

The hydrolysis reaction is favorably carried out at typically about 0 to 200° C., and preferably about 0 to 150° C., and is completed in general in about 10 minutes to 50 hours.

37

Reaction Formula 5

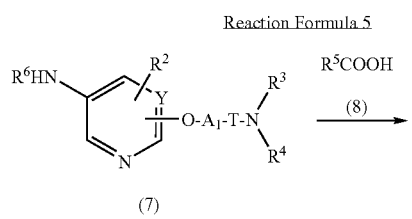

(7)

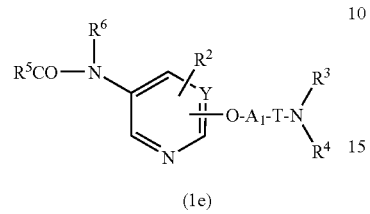

(1e)

wherein $R^2$, $R^3$, $R^4$, $R^5$, $R^6$, Y, T, and $A_1$ are as defined above.

The reaction of the compound (7) with the compound (8) is carried out under reaction conditions similar to those of the reaction of the compound (5) with the compound (4) of the above described reaction formula 2.

Reaction Formula 6

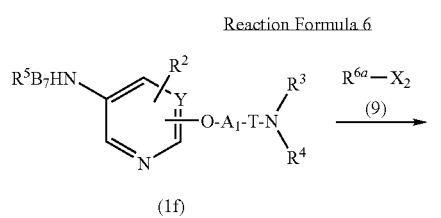

(1f)

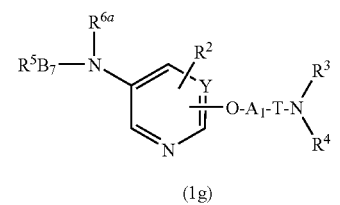

(1g)

wherein $R^2$, $R^3$, $R^4$, $R^5$, Y, T, and $A_1$ are as defined above, and $R^{6a}$ is lower alkylsulfonyl groups, phenyl lower alkyl groups or lower alkyl groups that may have lower alkoxy groups as substituents. $X_2$ is a halogen atom, a lower alkane sulfonyloxy group such as a methane sulfonyloxy group, or an arylsulfonyloxy group such as a p-toluenesulfonyloxy group, and $B_7$ is B, group-$SO_2$—, or a direct bond.

The reaction of the compound (1f) with the compound (9) is carried out under the same reaction condition as that for the reaction of the compound (2) with the compound (3) in the Reaction Formula 1.

Reaction Formula 7

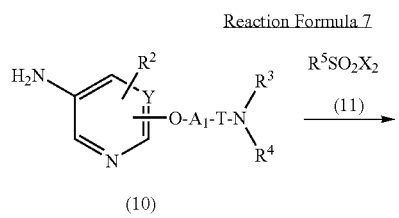

(10)

38

-continued

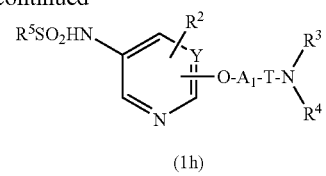

(1h)

wherein $R^2$, $R^3$, $R^4$, $R^5$, Y, T, $A_1$, and $X_2$ are as defined above.

The reaction of the compound (10) with the compound (11) is carried out under reaction conditions similar to those of the reaction of the compound (2) with the compound (3) of the above described reaction formula 1.

Reaction Formula 8

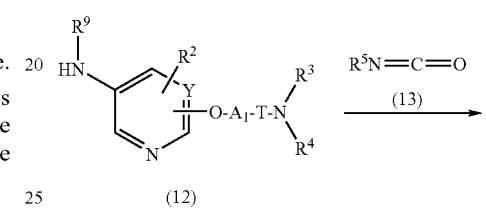

(12)

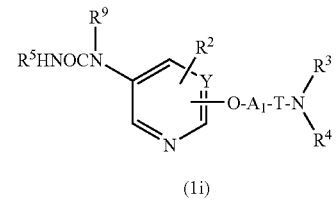

(1i)

wherein $R^2$, $R^3$, $R^4$, $R^5$, $R^9$, Y, T, and $A_1$ are as defined above.

The reaction of the compound (12) with the compound (13) is typically carried out in an appropriate inert solvent or without a solvent in the presence or absence of a basic compound, and preferably in the absence of a basic compound.

Any of the inert solvents and the basic compounds, which are used in the reaction of carboxylic acid halide with amine (5) by the method (d) of the reaction formula 2 for reacting the compound (4) with the compound (5) (reaction which produces an amide bond), may be used in this reaction.

The compound (13) may be used in an amount typically at least about 1 to 5 times, and preferably about 1 to 3 times of the compound (12) on a molar basis.

The above described reaction is carried out typically at about 0 to 200° C., and preferably at around room temperature to about 150° C. and is, in general, completed in about 5 minutes to 50 hours.

A boron compound such as a boron trifluoride-diethyl ether complex may be added to the system of the above described reaction.

Reaction Formula 9

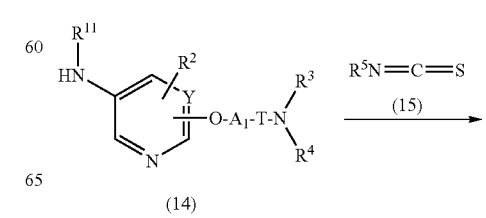

(14)

-continued

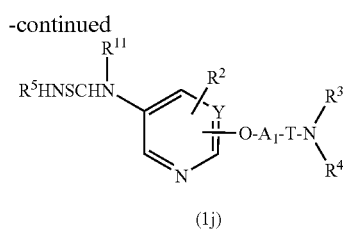

(1j)

wherein $R^2$, $R^3$, $R^4$, $R^5$, $R^{11}$, Y, T, and $A_1$ are as defined above.

The reaction of the compound (14) with the compound (15) is carried out under reaction conditions similar to those of the reaction of the compound (12) with the compound (13) of the above described reaction formula 8.

carbons such as chloroform, methylene chloride, and carbon tetrachloride, and dimethylformamide, and a mixture thereof.

When a sulfonyl halide compound is used together with a basic compound as a halogenating agent, the sulfonyl halide compound is appropriately used in an amount typically at least equimolar to the compound (16), and preferably 1 to 2 times of the compound (16) on a molar basis. The basic compound is used typically in a catalytic amount of the compound (16), and preferably in a catalytic amount to an amount equimolar to the compound (16). When another halogenating agent is used, such a halogenating agent is used at least equimolar to the compound (16), and typically used in a large excess amount.

Reaction Formula 10

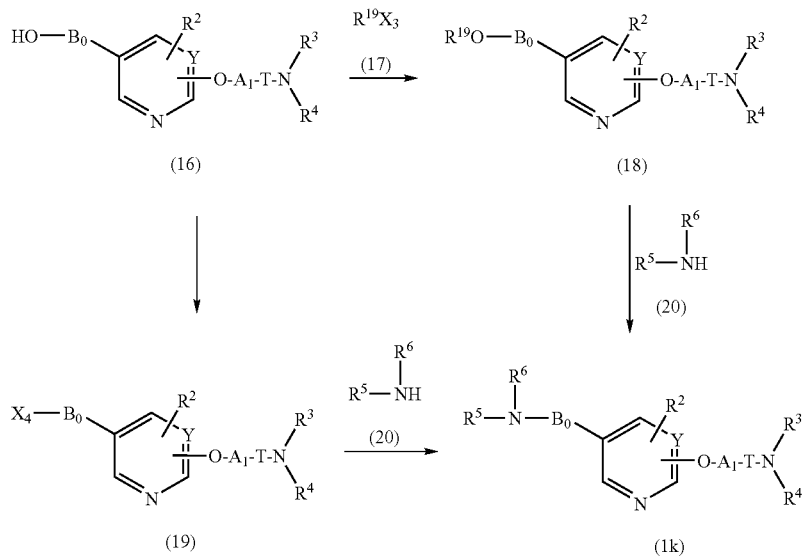

wherein $R^2$, $R^3$, $R^4$, $R^5$, $R^6$, Y, T, and $A_1$ are as defined above, and $R^{19}$ is a lower alkane sulfonyl group such as a methane sulfonyl group or an arylsulfonyl group such as a p-toluenesulfonyl group, $X_3$ and $X_4$ are a halogen atom, and $B_0$ is a lower alkylene group.

The reaction of the compound (16) with the compound (17) is carried out under reaction conditions similar to those of the reaction of the compound (2) with the compound (3) of the above described reaction formula 1.

The reaction which converts the compound (16) into the compound (19) is carried out by reacting compound (16) to a halogenating agent in an appropriate solvent or without solvent.

Examples of the halogenating agent include mineral acids such as hydrochloric acid and hydrobromic acid, N,N-diethyl-1,2,2-trichlorovinyl azide, phosphorus pentachloride, phosphorus pentabromide, phosphorus oxychloride, sulfonyl halide compounds such as thionyl chloride, mesyl chloride, and tosyl chloride, and a mixture of carbon tetra bromide with triphenylphosphine. The sulfonyl halide compound is used together with a basic compound.

Any of the basic compounds used in the reaction of the compound (2) with the compound (3) of the reaction formula 1 may be used.

Examples of the solvent used include ethers such as dioxane, tetrahydrofuran, and diethyl ether, halogenated hydro- The above described reaction proceeds favorably typically at room temperature to 200° C., and preferably at room temperature to 150° C., and in general is completed in about 1 to 80 hours.

The reaction of the compound (18) with the compound (20), and the reaction of the compound (19) with the compound (20) are carried out under reaction conditions similar to those of the reaction of the compound (2) with the compound (3) of the above described reaction formula 1.

Reaction Formula 11

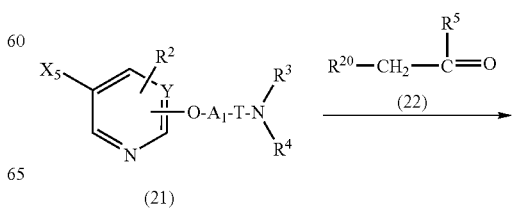

(21)

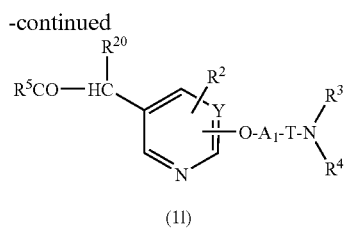

(11)

wherein $R^2$, $R^3$, $R^4$, $R^5$, Y, T, and $A_1$ are as defined above, $X_5$ is a halogen atom, and $R^{20}$ is a hydrogen atom or a lower alkyl group.

The reaction of the compound (21) with the compound (22) is carried out in an appropriate solvent, in the presence of a basic compound and a catalyst.

Examples of the inert solvent used include water, aromatic hydrocarbons such as benzene, toluene, and xylene, ethers such as diethyl ether, tetrahydrofuran, dioxane, 2-methoxyethanol, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, N-methylpyrrolidone, dimethyl sulfoxide, N,N-dimethylformamide, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, potassium phosphate, sodium phosphate, sodium hydride, potassium hydride, potassium, sodium, sodium amide, metal alcoholates such as sodium methylate, sodium ethylate, sodium n-butoxide, sodium tert-butoxide, and potassium tert-butoxide, alkylsilylamide alkali metal salts such as potassium bis(trimethylsilyl)amide, and organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

Examples of the catalyst may include palladium compounds such as palladium acetate, bis(tributyltin)/bis(dibenzylideneacetone)palladium, copper iodide/2,2'-bipyridyl, bis(dibenzylideneacetone)palladium, copper iodide/bis(triphenylphosphine)palladium dichloride, tris(dibenzylideneacetone)dipalladium, R-tris(dibenzylideneacetone)-dipalladium, S-tris(dibenzylideneacetone)dipalladium, palladium(II)acetate, [1,1'-bis(diphenylphosphino)-ferrocene]dichloropalladium (II), and tetrakis(triphenylphosphine)palladium, compounds such as R-2,2'-bis(diphenylphosphino)-1,1'-binaphthyl (R-BINAP), S-2,2'-bis(diphenylphosphino)-1,1'-binaphthyl (S-BINAP), RAC-2,2'-bis(diphenylphosphino)-1,1'-binaphthyl (RAC-BINAP), and 2,2-bis(diphenyl)midazolidinyliden), xanthene compounds such as 4,5-bis(diphenylphosphino)-9,9-dimethylxanthene, and borates such as tri-tert-butylphosphine tetrafluoroborate, and a mixture thereof.

The basic compound is appropriately used in an amount at least 0.5 times, and preferably 0.5 to 40 times of the compound (21) on a molar basis. The catalyst is appropriately used in a typical catalyst amount based on the compound (21).

The compound (22) is appropriately used in an amount at least 0.5 times, and preferably 0.5 to 3 times of the compound (21) on a molar basis.

The above described reaction is carried out typically at room temperature to 200° C., preferably at room temperature to about 150° C., and is completed in about 0.5 to 20 hours.

Reaction Formula 12

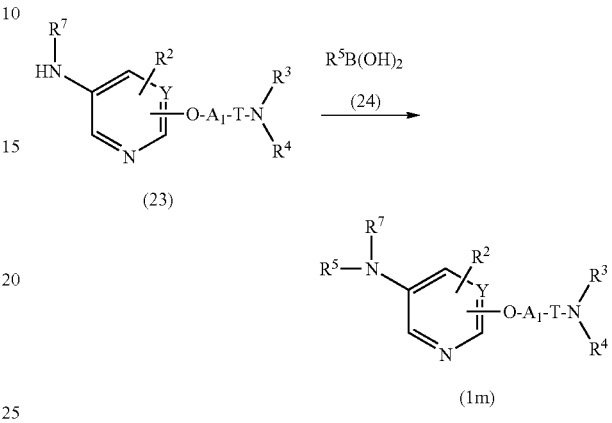

wherein $R^2$, $R^3$, $R^4$, $R^5$, $R^7$, Y, T, and $A_1$ are as defined above, and in the compound (24), B is a boron atom.

The reaction of the compound (23) with the compound (24) is carried out in an appropriate solvent, in the presence of a basic compound and a catalyst.

Examples of the solvent used include water, aromatic hydrocarbons such as benzene, toluene, and xylene, ethers such as diethyl ether, tetrahydrofuran, dioxane, 2-methoxyethanol, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as acetic acid, esters such as ethyl acetate and methyl acetate, ketones such as acetone and methyl ethyl ketone, acetonitrile, pyridine, dimethylsulfoxide, N,N-dimethylformamide, and hexamethylphosphoric acid triamide, and a mixture thereof.

Examples of the basic compound include carbonates such as sodium carbonate, potassium carbonate, sodium bicarbonate, potassium bicarbonate, and cesium carbonate, metal hydroxides such as sodium hydroxide, potassium hydroxide, and calcium hydroxide, sodium hydride, potassium hydride, potassium, sodium, sodium amide, metal alcoholates such as sodium methylate, sodium ethylate, sodium n-butoxide, sodium tert-butoxide, and potassium tert-butoxide, organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO), and a mixture thereof.

Examples of the catalyst include palladium compounds such as tetrakis(triphenylphosphine)palladium (0) and dichlorobis(triphenylphosphine)palladium (II), and copper compounds such as copper (II) acetate.

The basic compound is appropriately used in an amount at least equimolar to the compound (23), and preferably 1 to 5 times of the compound (23) on a molar basis.

The catalyst is appropriately used in an amount 0.001 to 1 times, and preferably 0.01 to 0.5 times of the compound (23) on a molar basis.

The compound (24) is appropriately used in an amount at least equimolar to the compound (23), and preferably 1 to 5 times of the compound (23) on a molar basis.

The above described reaction is carried out typically at −30 to 200° C., and preferably at 0 to 150° C. and is completed in about 0.5 to 30 hours. A molecular sieve such as Molecular Sieves 3A (MS-3A), Molecular Sieves 4A (MS-4A) or the like may be added to the reaction.

Reaction Formula 13

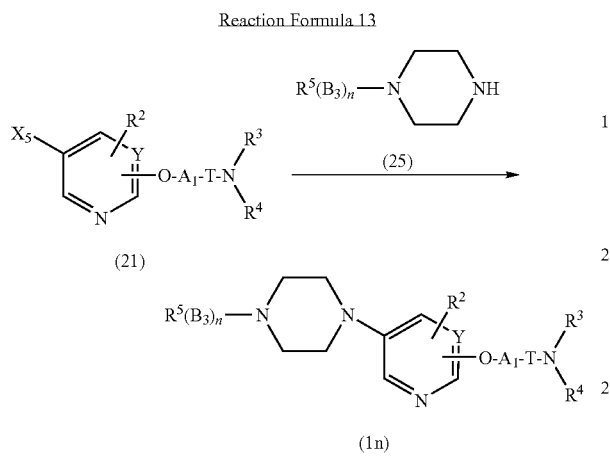

wherein $R^2$, $R^3$, $R^4$, $R^5$, Y, T, $A_1$, $X_5$, $B_3$ and n are as defined above.

The reaction of the compound (21) with the compound (25) is carried out under the same reaction condition as that for the reaction of the compound (21) with the compound (22) in the Reaction Formula 11.

Production Method for the Material Compound

The respective compounds used as starting materials in the reaction formulas are all known compounds, or are readily produced using the method according to the later-described Reference Example, the method shown in the above reaction formulas, or other similar methods. Reaction Formulas 14 through 37 are typical methods among the aforementioned various methods.

Reaction Formula 14

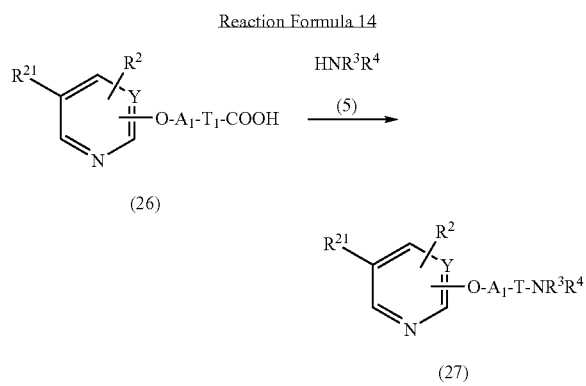

wherein $R^2$, Y, $A_1$, $T_1$, $R^3$, and $R^4$ are as defined above, and $R^{21}$ is $R^1$, an alkoxycarbonyl group, a halogen atom, or an amino group that may have, as a substituent, one or more groups selected from the group consisting of lower alkyl groups, lower alkoxycarbonyl groups and lower alkanoyl groups.

The reaction of the compound (26) with the compound (5) is carried out under the same reaction condition as that for the reaction of the compound (4) with the compound (5) in the Reaction Formula 2.

Reaction Formula 15

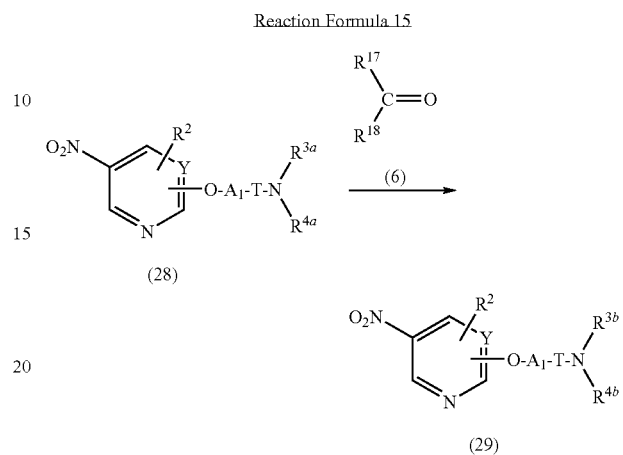

wherein $R^2$, Y, $A_1$, T, $R^{3a}$, $R^{4a}$, $R^{3b}$, $R^{4b}$, $R^{17}$ and $R^{18}$ are as defined above. The carbon of the alkyl moiety of the group $R^{17}$ ($R^{18}$) CH— in the compound (29) is less than 6.

The reaction of the compound (28) with the compound (6) is carried out under the same reaction condition as that for the reaction of the compound (1a) with the compound (6) in the Reaction Formula 3.

Reaction Formula 16

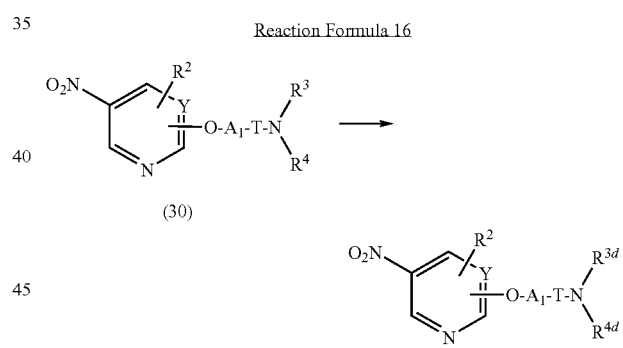

wherein $R^2$, Y, $A_1$, T, $R^{3d}$, $R^{4c}$, $R^{3d}$, and $R^{4d}$ are as defined above.

The reaction which converts the compound (30) into the compound (31) may be carried out under reaction conditions similar to those of the reaction which converts the compound (1c) into the compound (1d) of the above described reaction formula 4.

Reaction Formula 17

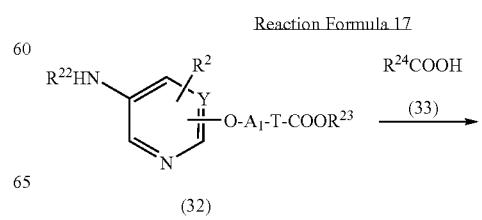

-continued

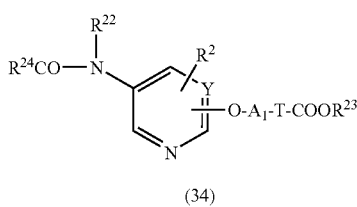

(34)

wherein $R^2$, Y, $A_1$ and $T_1$ are as defined above, $R^{22}$ is a hydrogen atom, a lower alkyl group or a lower alkoxy group, $R^{23}$ is a lower alkyl group, $R^{24}$ is $R^5$, a lower alkyl group or a lower alkoxy group, and $R^5$ is as defined above.

The reaction of the compound (32) with the compound (33) is carried out under the same reaction condition as that for the reaction of the compound (1a) with the compound (6) in the Reaction Formula 3.

Reaction Formula 18

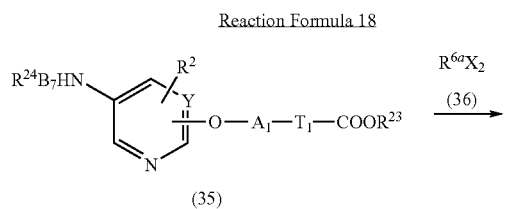

-continued

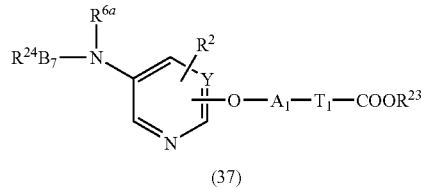

(37)

wherein $R^2$, Y, $A_1$, $T_1$, $R^{23}$, $R^{24}$, $B_7$, and $X_2$ are as defined above.

The reaction of the compound (35) with the compound (36) is carried out under reaction conditions similar to those of the reaction of the compound (2) with the compound (3) of the above described reaction formula 1.

Reaction Formula 19

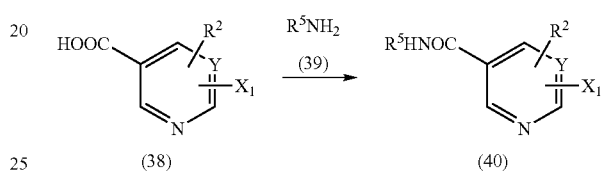

wherein $R^2$, Y, $X_1$, and $R^5$ are as defined above.

The reaction of the compound (38) with the compound (39) is carried out under reaction conditions similar to those of the reaction of the compound (4) with the compound (5) of the above described reaction formula 2.

Reaction Formula 20

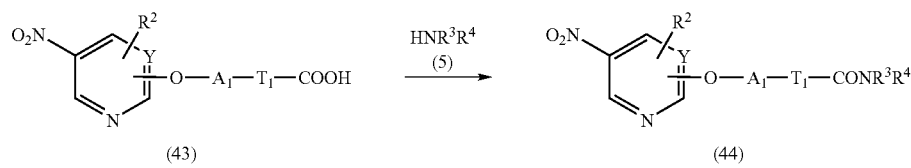

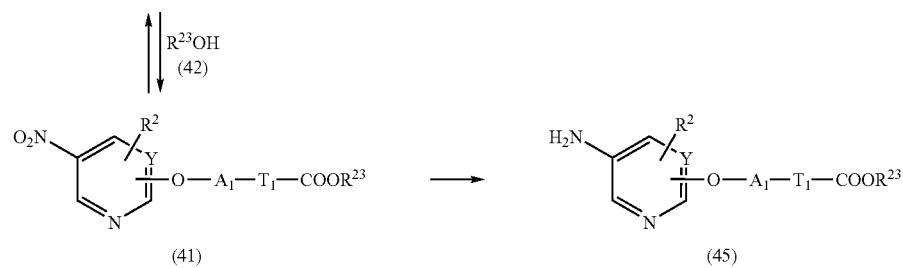

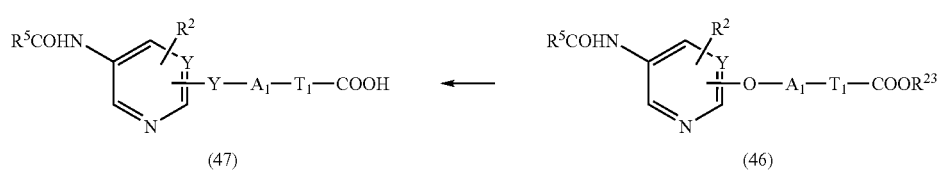

wherein $R^2$, Y, $A_1$, $T_1$, $R^3$, $R^4$, $R^5$, and $R^{23}$ are as defined above.

The reaction which converts the compound (41) into the compound (43) may be carried out under the reaction condition similar to that of the hydrolysis B as described in the above described reaction formula 4.

Any of the reaction conditions for typical esterification reaction may be used for the reaction of the compound (43) with the compound (42). For example, the above described reaction is carried out in the presence of a mineral acid such as hydrochloric acid or sulfuric acid, and a halogenation agent such as thionylchloride, phosphorus oxychloride, phosphorus pentachloride, or phosphorus trichloride. The compound (42) is used in large excess over the compound (43). The above described reaction favorably proceeds at typically about 0 to 150° C., preferably about 50 to 100° C., and is completed in general in about 1 to 10 hours.

The esterification described above may be carried out using a condensation agent such as carbodiimide in the presence of a basic compound such as dimethylaminopyridine. A typical reaction condition for generating an amide bond, which is used in the reaction of the compound (4) with the compound (5) in the reaction formula 2, may also be used.

The reaction of the compound (43) with the compound (42) may also be carried out in the presence of the same basic compound and the solvent as those used in the reaction of the compound (2) with the compound (3) of the reaction formula 1. The reaction is carried out at typically about 0 to 100° C., and preferably about 0 to 70° C., and is completed in general in about 1 to 30 hours.

The compound (41) may also be produced using a halogenated lower alkyl such as methyl iodide in place of the compound (42) under the condition similar to that of the reaction of the compound (2) with the compound (3) of the reaction formula 1.

The reaction which converts the compound (41) into the compound (45) may be carried out, for example, (1) by reducing the compound (41) with a catalytic hydride reducing agent in an appropriate solvent, or (2) by reducing the compound (41) with a reducing agent such as a mixture of a metal or a metal salt with an acid, or a mixture of a metal or a metal salt with an alkali metal hydroxide, a sulfide, an ammonium salt or the like, in an appropriate inert solvent.

Examples of the solvent in using the method (1) include water, acetic acid, alcohols such as methanol, ethanol, and isopropanol, hydrocarbons such as n-hexane and cyclohexane, ethers such as dioxane, tetrahydrofuran, diethyl ether, and diethylene glycol dimethyl ether, esters such as ethyl acetate and methyl acetate, and aprotic polar solvents such as N,N-dimethylformamide, and a mixture thereof. Examples of the catalytic hydride reducing agent used include palladium, palladium black, palladium-carbon, platinum-carbon, platinum, platinum oxide, copper chromite, and Raney nickel. These reducing agents may be used singly or in a mixture of two or more. In general, the reducing agent may be used in an amount 0.02 to 1 times of the compound (41) on a weight basis. The reaction temperature is typically about –20 to 150° C., and preferably about 0 to 100° C., and the hydrogen pressure is typically at 1 to 10 atm. In general, the above described reaction is completed in about 0.5 to 100 hours. An acid such as hydrochloric acid may be added to the above described reaction system.

The reducing agent which may be used in using the method (2) is a mixture of iron, zinc, tin or stannous chloride with a mineral acid such as hydrochloric acid or sulfuric acid; or a mixture of iron, ferrous sulfate, zinc or tin with an alkali metal hydroxide such as sodium hydroxide, a sulfate such as ammonium sulfate or an ammonium salt such as ammonium hydroxide or ammonium chloride. Examples of the inert solvent include water, acetic acid, alcohols such as methanol and ethanol, and ethers such as dioxane, and a mixture thereof. The reaction conditions may be chosen appropriately depending on the reducing agent used. For example, when stannous chloride and hydrochloric acid are used as the reducing agents, the reaction is appropriately carried out advantageously at about 0 to 150° C., and for around 0.5 to 10 hours. The above described reducing agent is used in an amount at least equal molar to the compound (41), and typically 1 to 5 times of the compound (41) on a molar basis.

The reaction of the compound (45) with the compound (8) is carried out under reaction conditions similar to those of the reaction of the compound (4) with the compound (5) of the above described reaction formula 2.

The reaction which converts the compound (46) into the compound (47) may be carried out under reaction conditions similar to those of the hydrolysis B described for the above described reaction formula 3.

The reaction of the compound (43) with the compound (5) is carried out under reaction conditions similar to those of the reaction of the compound (4) with the compound (5) of the above described reaction formula 2.

Reaction Formula 21

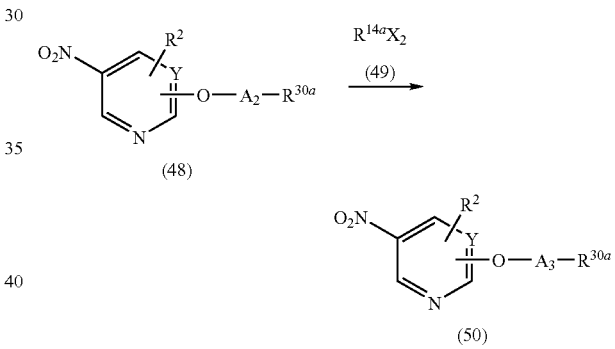

wherein $R^2$, Y, and $X_2$ are as defined above, $R^{14a}$ is the same as said $R^{14}$ except for a hydrogen atom. $R^{30a}$ is group-T-$NR^3R^4$ or group-$T_1$-$COOR^{23}$, T, $T_1$, $R^3$, $R^4$ and $R^{23}$ are as defined above, $A_2$ is a heterocyclic group as described in $A_1$ that have at least one secondary amine on the heterocyclic group, $A_3$ is a heterocyclic group as described in $A_1$ that have at least one tertiary amine substituted with $R^{14a}$ on the heterocyclic group.

The reaction of the compound (48) with the compound (49) is carried out under the same reaction condition as that for the reaction of the compound (2) with the compound (3) in the Reaction Formula 1.

Reaction Formula 22

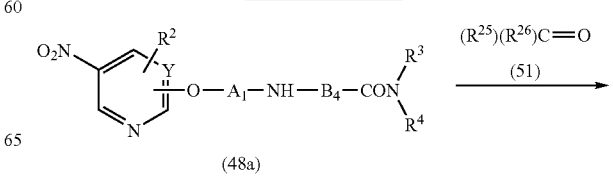

-continued

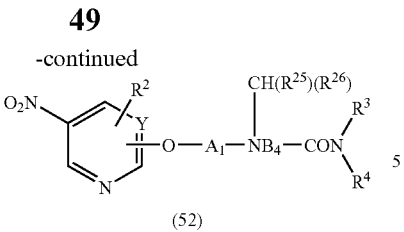

(52)

wherein $R^2$, Y, $A_1$, $B_4$, $R^3$ and $R^4$ are as defined above, $R^{25}$ and $R^{26}$ are each a hydrogen atom, a lower alkyl group, respectively.

The reaction of the compound (48a) with the compound (51) is carried out under the same reaction condition as that for the reaction of the compound (1a) with the compound (6) in the Reaction Formula 3.

Reaction Formula 23

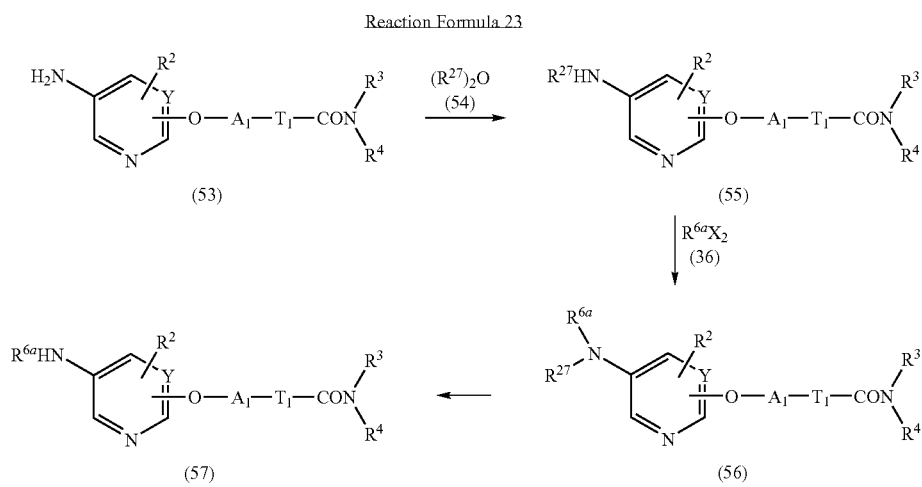

wherein $R^2$, Y, $A_1$, $T_1$, $R^3$, $R^4$, $R^{6a}$ and $X_2$ are as defined above, and $R^{27}$ is a lower alkoxycarbonyl group.

The reaction of the compound (53) with the compound (54) is carried out under the same reaction condition as that for the reaction of the compound (4) with the compound (5) in the Reaction Formula 2.

The reaction of the compound (55) with the compound (36) is carried out under reaction conditions similar to those of the reaction of the compound (2) with the compound (3) of the above described reaction formula 1.

The reaction which converts the compound (56) into the compound (57) may be carried out under reaction conditions similar to those of the hydrolysis B described for the above described reaction formula 3.

Reaction Formula 24

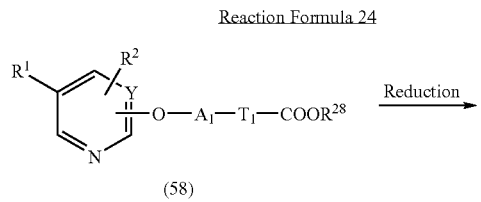

-continued

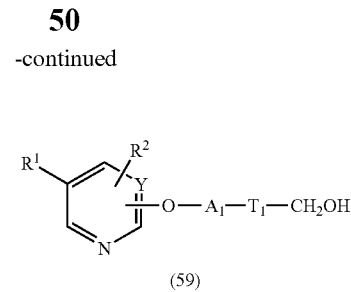

(59)

wherein $R^1$, $R^2$, Y, $A_1$ and $T_1$ are as defined above, $R^{28}$ is a halogen atom, a lower alkyl group, or a lower alkoxycarbonyl group.

The compound (59) is produced by reducing the compound (58).

In the reducing reaction described above, a reducing method employing a hydride reducing agent is favorably used.

Examples of the reducing agent used include aluminum lithium hydride, sodium borohydride, borane, diborane, and lithium borohydride-trimethoxyborane. These reducing agents are used singly or in a mixture of two or more. The reducing agent may be used in an amount typically at least equimolar to the compound (1f), and preferably 1 to 15 times of the compound (1f) on a molar basis. This reducing reaction is typically carried out in an appropriate solvent, for example, water, a lower alcohol such as methanol, ethanol, or isopropanol, an ether such as tetrahydrofuran, diethyl ether, diisopropyl ether, or diglyme, or a halogenated hydrocarbon such as dichloromethane, chloroform, or carbon tetrachloride, or a mixture thereof, at about −60 to 150° C., preferably from about −30 to 100° C., in general for about 10 minutes to 40 hours. In the case where aluminum lithium hydride or borane is used as the reducing agent, it is preferable to use an anhydrous solvent of tetrahydrofuran, diethyl ether, diisopropyl ether, diglyme, or the like.

Reaction Formula 25

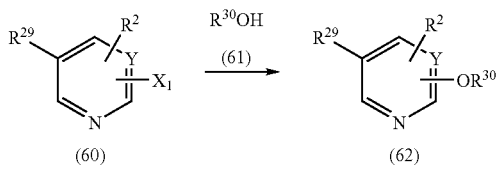

(60) → (62)

Reaction Formula 28

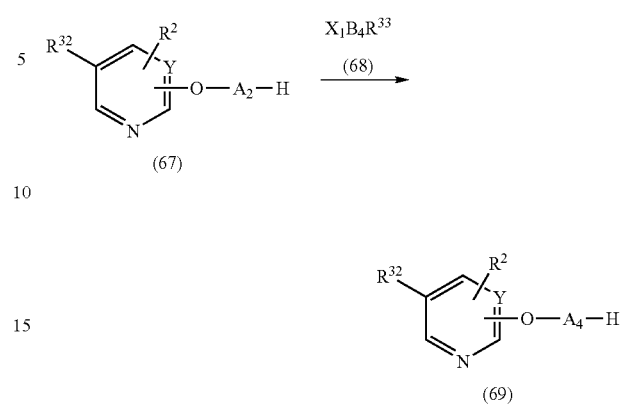

(67) → (69)

wherein $R^2$, Y, and $X_1$ are as defined above, $R^{29}$ is nitro group or a halogen atom, $R^{30}$ is group-$A_1$-T-$NR^3R^4$ or group-$A_1$-$T_1$-COOR$^{23}$, and $A_1$, T, $T_1$, $R^3$, $R^4$, and $R^{23}$ are as defined above.

The reaction of the compound (60) with the compound (61) is carried out under the same reaction condition as that for the reaction of the compound (2) with the compound (3) in the Reaction Formula 1.

Reaction Scheme 26

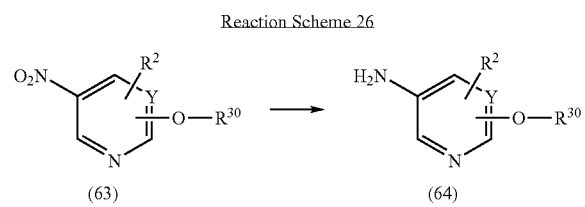

(63) → (64)

wherein $R^2$, Y, and $R^{30}$ are as defined above.

wherein $R^2$, $A_2$, Y, $X_1$ and $B_4$ are as defined above, $R^{32}$ is $R^1$, a lower alkoxycarbonyl group or nitro group, $R^{33}$ is —CONR$^3R^4$ or —COOR$^{23}$, $R^1$, $R^3$, $R^4$, and $R^{23}$ are as defined above, $A_4$ is a heterocyclic ring as defined in $A_1$ that has at least one tertiary amine substituted with a group-$B_4R^{33}$ on the heterocyclic ring.

The reaction of the compound (67) with the compound (68) is carried out under the same reaction condition as that for the reaction of the compound (2) with the compound (3) in the Reaction Formula 1.

Reaction Formula 29

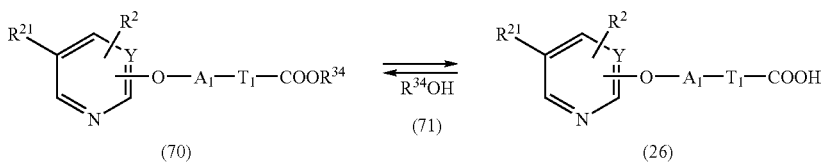

(70) ⇌ (26)

The reaction which converts the compound (63) into the compound (64) may be carried out under reaction conditions similar to those of the reaction which converts the compound (41) into the compound (45) of the above described reaction formula 20.

Reaction Formula 27

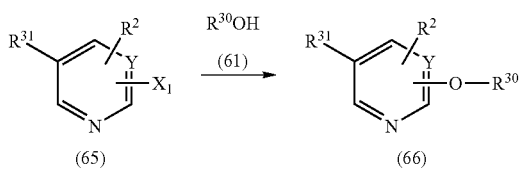

(65) → (66)

wherein $R^2$, Y, $X_1$ and $R^{30}$ are as defined above, $R^{31}$ is $R^1$ (as defined above), nitro group or a lower alkoxycarbonyl group.

The reaction of the compound (65) with the compound (61) is carried out under the same reaction condition as that for the reaction of the compound (60) with the compound (61) in the Reaction Formula 25.

wherein $R^2$, Y, $A_1$, $T_1$ and $R^{21}$ are as defined above, $R^{34}$ is a lower alkyl group or a phenyl lower alkyl group.

The reaction which converts the compound (70) into the compound (26) is carried out under the same reaction condition as that for hydrolysis B in the description of Reaction Formula 4.

The reaction of the compound (26) with the compound (71) is carried out under reaction conditions similar to those of the reaction of the compound (43) with the compound (42) of the above described reaction formula 20.

The compound (70) can be produced also by reacting lower alkyl halide such as a methyl iodide, instead of reacting the compound (71), under the same reaction condition as the reaction of the compound (2) with compound (3) in Reaction Formula 1.

Reaction Formula 30

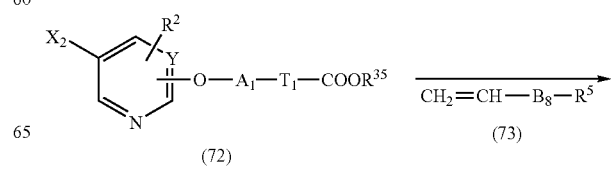

(72) → (73)

-continued

R$^5$—B$_8$—HC=HC (74)

wherein R$^2$, Y, A$_1$, T$_1$, X$_2$ and R$^5$ are as defined above, R$^{35}$ is a hydrogen atom or a lower alkyl group, and B$_8$ is a lower alkylene group or a direct bond.

The reaction of the compound (72) with the compound (73) is carried out in an appropriate inert solvent and in the presence of a condensation agent.

Examples of the inert solvent used in the above described reaction include aromatic hydrocarbons such as benzene, toluene, and xylene, ethers such as diethyl ether, tetrahydrofuran, dioxane, monoglyme, and diglyme, halogenated hydrocarbons such as dichloromethane, dichloroethane, chloroform, and carbon tetrachloride, lower alcohols such as methanol, ethanol, isopropanol, butanol, tert-butanol, and ethylene glycol, fatty acids such as α-dimethylaminoacetic acid and acetic acid, esters such as ethyl acetate and methyl acetate, ketones such as acetone and methyl ethyl ketone, acetonitrile, 1-methyl-2-pyrrolidone, pyridine, dimethyl sulfoxide, dimethylformamide, and hexamethylphosphoric acid triamide, and a mixture thereof.

Examples of the condensation agent include palladium complexes such as bis(benzonitrile)dichloropalladium (II).

The condensation agent is appropriately used in an amount typically 0.01 to 1 times, and preferably 0.01 to 0.5 times of the compound (72) on a molar basis.

The above described reaction favorably proceeds typically at 0 to 200° C., and preferably at about room temperature to about 150° C., and is, in general, completed in about 10 minutes to 20 hours.

The above described reaction proceeds advantageously by adding an alkali metal salt of fatty acid such as sodium acetate to the reaction system.

Reaction Formula 31

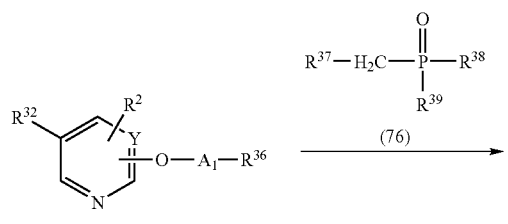

(75)

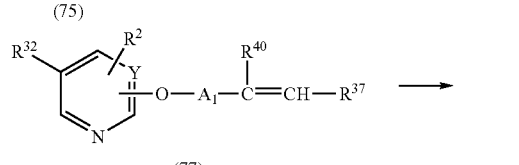

(77)

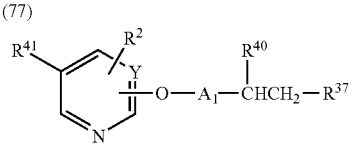

(78)

R$^2$, R$^{32}$, Y, and A$_1$ are as defined above, R$^{36}$ is a lower alkanoyl group, R$^{37}$ is a lower alkoxycarbonyl group, R$^{38}$ and R$^{39}$ are each a lower alkoxy group, R$^{40}$ is a hydrogen atom or a lower alkyl group, R$^{41}$ is an amino group, a lower alkoxycarbonyl group or R$^1$ (as defined above), and the carbon of the C(R$^{40}$)=CH moiety and the carbon of the CH(R$^{40}$)=CH$_2$ moiety are less than 6.

The reaction of the compound (75) with the compound (76) is carried out in an appropriate solvent in the presence of a basic compound.

Any of the known solvents which do not affect the reaction may be used. Examples of such a solvent include ethers such as diethyl ether, dioxane, tetrahydrofuran, monoglyme, and diglyme, aromatic hydrocarbons such as benzene, toluene, and xylene, aliphatic hydrocarbons such as n-hexane, heptane, and cyclohexane, amines such as pyridine and N,N-dimethylaniline, aprotic polar solvents such as acetonitrile, N,N-dimethylformamide, dimethyl sulfoxide, and hexamethylphosphoric acid triamide, and alcohols such as methanol, ethanol, and isopropanol, and a mixture thereof.

Examples of the basic compound include metal sodium, metal potassium, sodium hydride, sodium amide, metal hydroxides such as sodium hydroxide, potassium hydroxide, and calcium hydroxide, carbonates such as sodium carbonate, potassium carbonate, and sodium bicarbonate, metal alcoholates such as sodium methylate, sodium ethylate, and potassium tert-butoxide, alkyl and aryl lithiums or lithium amides such as methyl lithium, n-butyryl lithium, phenyl lithium, and lithium diisopropylamide, and organic bases such as pyridine, piperidine, quinoline, triethylamine, diisopropylethylamine, N,N-dimethylaniline. These basic compounds are used singly or in a mixture of two or more. The basic compound is appropriately used in an amount typically 0.1 to 10 times, and preferably 0.5 to 5 times of the compound (75) on a molar basis.

The compound (76) is appropriately used in an amount typically at least equimolar to the compound (75), and preferably 1 to 5 times of the compound (75) on a molar basis.

The above described reaction is carried out typically at –80 to 150° C., and preferably at about –80 to 120° C. and, in general, is completed in about 0.5 to 40 hours.

When an organic base is used as the basic compound, the reaction proceeds advantageously by adding a lithium salt such as lithium chloride to the reaction system.

The reaction which converts the compound (77) into the compound (78) may be carried out under reaction conditions similar to those of the reaction which converts the compound (41) into the compound (45) of the above described reaction formula 20.

Reaction Formula 32

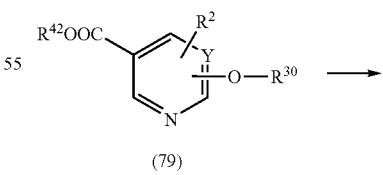

(79)

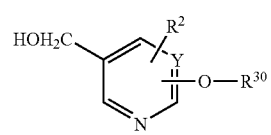

(80)

wherein $R^2$, $R^{30}$, and Y are as defined above, and $R^{42}$ is a hydrogen atom, a lower alkyl group or a lower alkoxycarbonyl group.

The reaction which converts the compound (79) into the compound (80) is carried out under the same reaction condition as the reaction for converting the compound (58) into the compound (59) in Reaction Formula 24.

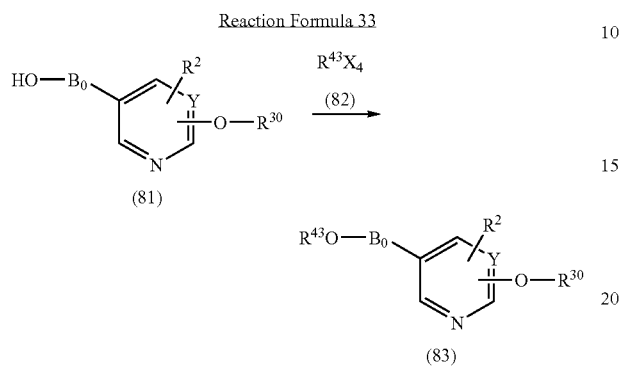

wherein $R^2$, $B_0$, $R^{30}$, Y and $X_4$ are as defined above. $R^{43}$ is a lower alkane sulfonyl group such as a methane sulfonyl group, or an aryl sulfonyl group such as a p-tosyl group.

The reaction of the compound (81) with the compound (82) is carried out under the same reaction condition as that for the reaction of the compound (2) with the compound (3) in the Reaction Formula 1.

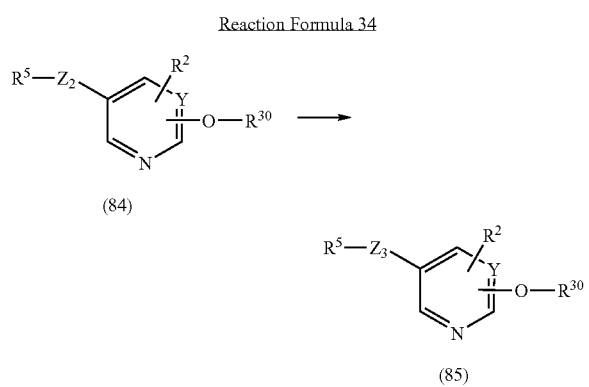

where $R^2$, $R^5$, $R^{30}$, and Y are as defined above, $Z_2$ is a lower alkenylene group, and $Z_3$ is a lower alkylene group.

The reaction which converts the compound (84) into the compound (85) is carried out in an appropriate solvent in the presence of a catalytic hydrogenation reducing agent.

Examples of the solvent used include water, fatty acids such as acetic acid, alcohols such as methanol, ethanol, and isopropanol, aliphatic hydrocarbons such as n-hexane, alicyclic hydrocarbons such as cyclohexane, ethers such as diethyl ether, dimethoxyethane, tetrahydrofuran, monoglyme, diglyme, and 1,4-dioxane, esters such as methyl acetate, ethyl acetate, and butylacetate, aprotic polar solvents such as N,N-dimethylformamide, N,N-dimethylacetoamide, and N-methylpyrrolidone, and a mixture thereof.

Examples of the catalytic hydrogen reducing agent used include palladium, palladium black, palladium-carbon, palladium hydroxide-carbon, rhodium-alumina, platinum, platinum oxide, copper chromite, Raney nickel, and palladium acetate.

The catalytic hydrogen reducing agent is favorably used generally in an amount of 0.01 to 1 time of the compound (84) on a weight basis.

The reaction temperature is typically at about −20 to 150° C., and preferably at about 0 to about 100° C. The reaction is preferably carried out at a hydrogen pressure of typically 1 to 10 atm, and is completed in general in about 0.5 to 20 hours.

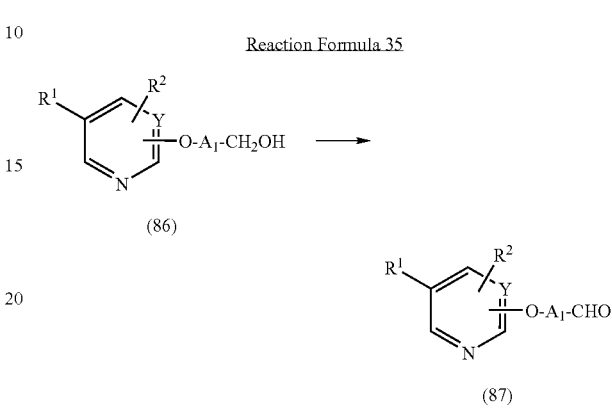

wherein $R^1$, $R^2$, Y, and $A_1$ are as defined above.

The reaction which converts the compound (86) into the compound (87) is carried out in an appropriate solvent in the presence of an oxidizing agent.

Examples of the solvent include water, fatty acids such as formic acid, acetic acid, trifluoroacetic acid, and propionic acid, esters such as ethyl acetate and methyl acetate, alcohols such as methanol, ethanol, and isopropanol, ethers such as dioxane, tetrahydrofuran, and diethyl ether, ketones such as acetone and methyl ethyl ketone, aromatic hydrocarbons such as benzene, toluene, chlorobenzene, and xylene, and halogenated hydrocarbons such as chloroform and dichloromethane, hexamethylphosphoric acid triamide, N,N-dimethylformamide, dimethyl sulfoxide, and pyridine, and a mixture thereof.

Examples of the oxidizing agent include peracids such as performic acid, peracetic acid, pertrifluoroacetic acid, perbenzoic acid, m-chloroperbenzoic acid, and o-carboxyperbenzoic acid, hydrogen peroxide, sodium metaperidodate, dichromic acid, dichromates such as sodium dichromate and potassium dichromate, manganese dioxide, permanganic acid, permanganates such as sodium permanganate and potassium permanganate, lead salts such as lead tetraacetate, silver oxide, a Dess-Martin reagent (Dess-Martin periodinane), 2-iodoxybenzoic acid, 1-hydroxy-1,2-benziodoxol-3 (1H)-one 1-oxide. The oxidizing agent is used in an amount typically at least equimolar to the compound (86), and preferably 1 to 3 times of the compound (86) on a molar basis.

Reaction Formula 36

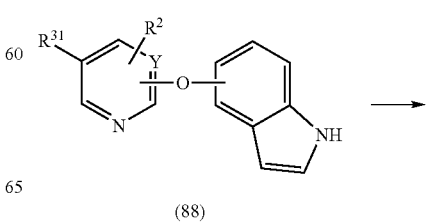

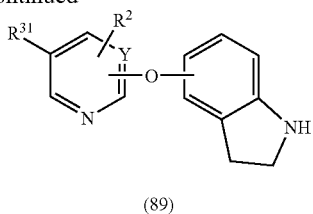

(89)

wherein $R^2$, $R^{31}$ and Y are as defined above.

The reaction which converts the compound (88) into the compound (89) is carried out under the same reaction condition as the reaction for converting the compound (58) into the compound (59) in Reaction Formula 24. In addition to the hydrogenation reducing agents mentioned in the reaction for converting the compound (58) into the compound (59), a complex such as borane-pyridine, borane-trimethylamine, etc. is also useful as a hydrogenation reducing agent. In addition to the solvent mentioned in the reaction for converting the compound (58) into the compound (59), dioxane is also useful as a solvent.

Reaction Formula 37

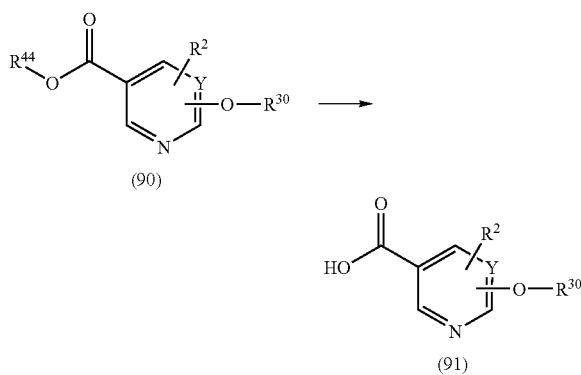

wherein $R^2$, $R^{30}$, and Y are as defined above, and $R^{44}$ is a lower alkyl group.

The reaction which converts the compound (90) into the compound (91) may be carried out under the reaction condition similar to that of the hydrolysis B as described in the above described reaction formula 4.

Reaction Formula 38

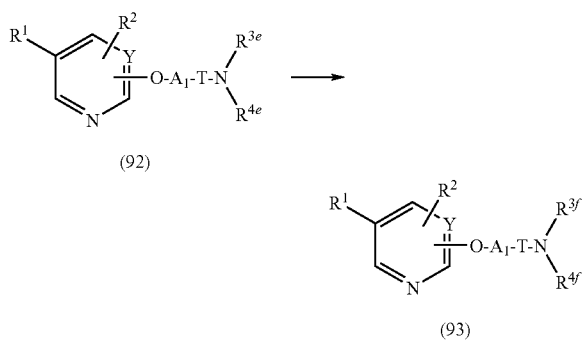

wherein $R^1$, $R^2$, Y, $A_1$, and T are as defined above.

$R^{3e}$ and $R^{4e}$ are the same as the saturated heterocyclic group of 5- to 10-membered ring defined in the $R^3$ and $R^4$ above except that they have at least another nitrogen atom in addition to the nitrogen atom bonded to T.

$R^{3f}$ and $R^{4f}$ are the same as the saturated heterocyclic group of 5- to 10-membered ring defined in the $R^3$ and $R^4$ above except that they have at least one nitrogen atom substituted with an N-oxide group in addition to the nitrogen atom bonded to T.

The reaction which converts the compound (92) into the compound (93) is carried out in an appropriate solvent in the presence of an oxidizing agent.

Examples of the oxidizing agent include peracids such as performic acid, peracetic acid, pertrifluoroacetic acid, perbenzoic acid, m-chloroperbenzoic acid, and o-carboxyperbenzoic acid, hydrogen peroxide, sodium metaperiodate, dichromic acid, dichromates such as sodium dichromate and potassium dichromate, permanganic acid, permanganates such as sodium permanganate and potassium permanganate, and lead salts such as lead tetraacetate. These oxidizing agents are used singly or in a mixture of two or more.

Examples of the solvent include water, lower alcohols such as methanol, ethanol, isopropanol, butanol, tert-butanol, and ethylene glycol, ketones such as acetone and methyl ethyl ketone, ethers such as diethyl ether, dioxane, tetrahydrofuran, monoglyme, and diglyme, and halogenated hydrocarbons such as chloroform, dichloromethane, dichloroethane, and carbon tetrachloride, aromatic hydrocarbons such as benzene, toluene, and xylene, and a mixture thereof.

The oxidizing agent is appropriately used in typically at least an equal amount, and preferably an amount 1 to 3 times of the compound (92) on a molar basis.

The above described reaction favorably proceeds typically at −30 to 200° C., and preferably at about −10 to 100° C., and is, in general, completed in about 0.5 to 30 hours.

Each of the target compounds obtained by the formulas shown above may be isolated and purified by separating the crude reaction product from the reaction mixture after cooling using an isolation procedure such as filtration, concentration, or extraction, and by purifying using a common purification procedure such as column chromatography or recrystallization.

Each starting material in the above described reaction formulae 1 to 38 may be a suitable salt or a suitable reactive derivative. Moreover, their target compounds may form suitable salts. Examples of such salts include salts equal to the heterocyclic compound (1).

Each starting material in the above described reaction formulae 14 to 38 may be a known compound or may be easily produced by following known methods.

The compound represented by General Formula (1) of the present invention contains steric isomers, optical isomers, and solvates (hydrates, ethanolates, etc.).

The compound represented by General Formula (1) of the present invention may be easily formed into an acid addition salt by the action of a pharmacologically acceptable acid, and the present invention also contains the acid addition salt. Examples of such acids include inorganic acids such as hydrochloric acid, sulfuric acid, phosphoric acid, hydrobromic acid, hydroiodic acid, and nitric acid, organic acids such as acetic acid, oxalic acid, succinic acid, maleic acid, fumaric acid, malic acid, tartaric acid, citric acid, malonic acid, methanesulfonic acid, benzoic acid, trifluoroacetic acid, benzenesulfonic acid, formic acid, toluenesulfonic acid, and lactic acid, or amino acids (e.g., arginine, aspartic acid, glutamic acid, etc.); and the like.

Among the compounds represented by General Formula (1) of the present invention, those having an acidic group can easily form salts by the action of a pharmacologically acceptable basic compound. Examples of such salts include metal salts, such as alkali metal salts (e.g., sodium salts, potassium salts, etc.) and alkaline earth metal salts (e.g., calcium salts, magnesium salts, etc.); ammonium salts; organic base salts (e.g., trimethylamine salts, triethylamine salts, pyridine salts, picoline salts, dicyclohexylamine salts, N,N'-dibenzylethylenediamine salts, etc.). Examples of basic compounds include sodium hydrate, potassium hydroxide, calcium hydroxide, sodium carbonate, potassium hydrogencarbonate, etc.

Next, medical formulations which contain the compound of the present invention as an active ingredient will be described.

The above described medical formulations, which are obtained by preparing the compound of the present invention formulated into a common pharmaceutical form, are prepared using a diluent or excipient commonly used such as a filler, expander, binder, moistener, disintegrator, surfactant, and lubricant.

Such medical formulations may be chosen from various forms according to the therapeutic objectives, and typical examples of such formulations include tablets, pills, powders, liquids, suspensions, emulsions, granules, capsules, suppositories, injections (liquids, suspensions), and ointments.

Carriers which are used for forming tablets may be chosen widely from the conventional ones, of which examples include excipients such as lactose, saccharose, sodium chloride, glucose, urea, starch, calcium carbonate, kaolin, crystalline cellulose, and silic acid, binders such as water, ethanol, propanol, simple syrup, a glucose solution, a starch solution, a gelatin solution, carboxymethylcellulose, shellac, methylcellulose, potassium phosphate, and polyvinylpyrrolidone, disintegrators such as dried starch, sodium arginate, agar powder, laminaran powder, sodium bicarbonate, calcium carbonate, polyoxyethylene sorbitan fatty acid esters, sodium lauryl sulfate, stearic acid monoglyceride, starch, and lactose, anti-disintegrators such as saccharose, stearine, cacao butter, and hydrogenated oil, sorbefacients such as quarternary ammonium base and sodium lauryl sulfate, wetting agents such as glycerol and starch, adsorbents such as starch, lactose, kaolin, bentonite, and colloidal silicate, and lubricants such as purified talc, stearate, boric acid powder, and polyethylene glycol.

Further, tablets may be made into conventional coated tablets, for example, sugar-coated tablets, gelatin-coated tablets, enteric-coated tablets, film-coated tablets, or double or multi-layered tablets.

Carriers which are used for forming pills may be chosen widely from the conventional ones, of which examples include excipients such as glucose, lactose, starch, cacao butter, hydrogenated vegetable oil, kaolin, and talc, binders such as gum arable powder, tragacanth powder, gelatin, and ethanol, and disintegrators such as laminaran and agar.

Carriers which are used for forming suppositories may be chosen widely from the conventional ones, of which examples include polyethylene glycol, cacao butter, higher alcohols, esters of higher alcohols, gelatin, and semi-synthetic glycerides.

The injection preparations in liquid, emulsion and suspension forms are preferably sterilized and isotonic with the blood. Diluents which are used for forming these liquid, emulsion and suspension preparations may be chosen widely from the conventional ones, of which examples include water, a lactic acid aqueous solution, ethanol, propylene glycol, ethoxylated isostearyl alcohol, polyoxylated isostearyl alcohol, and polyoxyethylene sorbitan fatty acid ester. In this case, the medical formulations may contain sodium chloride, glucose or glycerol enough to prepare isotonic solutions. Also, conventional solubilizers, buffers, analgestics, and the like, and, as necessary, coloring agents, preservatives, spices, flavors, sweets and the like, or other pharmaceuticals may be added.

Diluents which are used for forming pastes, creams, and gels may be chosen widely from the conventional ones in this field. Examples thereof include white vaseline, paraffin, glycerol, cellulose derivatives, polyethylene glycol, silicon, bentonite, and the like.

Although the amount of the compound of the present invention included in the medical formulation is not limited and may be selected appropriately in a wide range, it is typically preferable that the medical formulation contains the compound of the present invention at 1 to 70 wt %.

The method for administration of the medical formulation of the present invention is not limited and the administration is carried out in accordance with the conditions such as forms of the medical formulation, patient's age, sex, severity of the disease and other conditions. For example, tablets, pills, liquids, suspensions, emulsions, granules and capsules are administered orally. The injection formulations are administered intravenously singly or by mixing with a conventional fluid replacement such as a glucose solution or amino acid solution, or, as necessary, administered singly and intramuscularly, intradermally, subcutaneously or intraperitoneally. The suppositories are administered into the rectum.

The dosage for the above mentioned medical formulation may be chosen appropriately according to the usage, patient's age, sex and severity of the disease and other conditions. Typically, the compound of General Formula (1), which is an active ingredient, is administered once or in several times a day in an amount of 0.001 to 100 mg per kg body weight per day, preferably 0.001 to 50 mg per kg body weight per day.

Since the above described dosage may vary in accordance with various conditions, it may be sufficient with a dosage smaller than in the above described range, or it may be necessary to administer a dosage larger than in the above described range.

The patents, patent applications, and documents cited in the present application are inserted as reference.

The compound of the present invention has a superior effect on suppressing the production of collagen.

Therefore, the heterocyclic compound (1) or a salt thereof suitably functions as a collagen production inhibitor and a fibril formation inhibitor. They are effective for prophylaxis or treatment of diseases attended with fibrogenesis caused by excess production of collagen, for example, (i) organ diseases such as sudden and interstitial pulmonary fibrosis, pneumoconiosis, ARDS, hepatic fibrosis, neonatal hepatic fibrosis, hepatic cirrhosis, mucoviscidosis and myelofibrosis; (ii) dermal diseases such as scleroderma, elephantiasis, morphea, injury and hypertrophic cicatrix and keloid after burn injury; (iii) vascular diseases such as atherosclerosis and arteriosclerosis; (iv) ophthalmic diseases such as diabetic retinopathy, retrolental fibroplasia, vascularization arising along with corneal transplantation, glaucoma, proliferative vitreoretinopathy and corneal cicatrix after operation; renal diseases such as contracted kidney, nephrosclerosis, renal fibrosis, interstitial nephritis, IgA nephritis, glomerulosclerosis, membranoproliferative nephritis, diabetic nephropathy, chronic interstitial nephritis and chronic glomerulonephritis; and (vi) diseases in cartilage or bone, such as rheumatic arthritis, chronic arthritis and osteoarthritis. Among them, the heterocyclic compound (1) and a salt thereof of the present invention is superior in effect of inhibiting fibrogenesis attended with the organ diseases listed in the above item (i), and can be used as a preventive or a remedy for pulmonary fibrosis, hepatic fibrosis and, glomerulosclerosis.

The compound of the present invention also has a superior antitumor effect. For examples, such antitumor effect is exhibited on malignant tumors or the like.

Examples of malignant tumors include solid tumors (e.g., carcinoma and sarcoma), lymphoma and leukaemia.

More specifically, examples of malignant tumors include childhood brain tumors such as astroglioma, malignant medulloblastoma, germ cell tumor, craniopharyngioma, and ependymoma; adult brain tumors such as glioma, neuroglioma, meningioma, pituitary adenoma, neurilemoma; head and neck cancers such as maxillary sinus cancer, pharyngeal cancer (nasopharyngeal carcinoma, mesopharyngeal carcinoma, hypopharyngeal carcinoma), laryngeal cancer, oral cancer, lip cancer, tongue cancer, and parotid cancer; thoracic cancers and tumors such as small cell lung cancer, non-small cell lung cancer, thymoma, and mesothelioma; gastrointestinal cancers and tumors such as esophageal cancer, liver cancer, primary hepatic cancer, gallbladder cancer, bile duct cancer, stomach cancer, large bowel cancer, colonic cancer, rectal cancer, anal cancer, pancreatic cancer, and pancreatic endocrine tumor; urinary organ cancers and tumors such as penile cancer, renal pelvis and ureteral cancer, renal cell cancer, testicular tumor, prostatic cancer, bladder cancer, Wilms tumor, and urothelial cancer; gynecologic cancers and tumors such as vulvar cancer, uterine cervical cancer, corpus uteri cancer, endometrial cancer, uterine sarcoma, chorionic cancer, vaginal cancer, breast cancer, ovarian cancer, and ovarian germ cell tumor; adult and childhood soft tissue sarcoma; bone tumors such as osteosarcoma and Ewing's tumor; endocrine tissue cancers and tumors such as adrenocortical cancer and thyroid cancer; malignant lymphoma and leukemia such as malignant lymphoma, non-Hodgkin's lymphoma, Hodgkin's disease, multiple myeloma, plasmacytic tumor, acute myelogenous leukemia, acute lymphatic leukemia, adult T cell leukemia lymphoma, chronic myelogenous leukemia, and chronic lymphatic leukemia; skin cancers and tumors such as chronic myeloproliferative disorders, malignant melanoma, squamous cell cancer, basal cell cancer, and mycosis fungoides; and metastatic foci of these tumors and cancers.

When the compound of the present invention is used as a therapeutic agent for these diseases, agents for inhibiting collagen production, agents for inhibiting fibrosis, antiviral agents, anti-inflammatory agent, antitumor agents, and like other agents can be used simultaneously or continuously. The compound of the present invention has less side effects and an excellent safety.

BEST MODE FOR CARRYING OUT THE INVENTION

The present invention is described in more detail below with reference to reference examples, examples, and pharmaceutical test examples.

EXAMPLES

Manufacturing examples of compounds used in the invention are shown below, being followed the Pharmacological Tests results of these compounds.

Reference Example 1

Production of 6-hydroxy-1-methyl-1H-indole-2-carboxylic acid methyl ester

To a solution of 6-methoxy-1H-indole-2-carboxylic acid methyl ester (11.57 g, 56.38 mmol) in N,N-dimethylformamide (DMF) (100 mL) was added 60% sodium hydride in oil (2.93 g, 73.29 mmol) under ice cooling. After the mixture was stirred for 15 minutes, iodomethane (3.86 mL, 62.02 mmol) was added and the mixture was stirred at the same temperature for 1 hour. To the mixture were added water and diethyl ether ($Et_2O$), and then resulting precipitate was collected by filtration. The white precipitate was dissolved in dichloromethane (200 mL), and to the solution was added dropwise boron tribromide dichloromethane solution (100 mL) while ice cooling under an argon atmosphere. The reaction mixture was stirred at the same temperature for 1 hour, and then quenched with methanol (MeOH). The solvent was evaporated in vacuo, and water was added to the residue. The aqueous mixture was extracted with ethyl acetate (AcOEt). The organic layer was washed with brine, dried over anhydrous sodium sulfate, and evaporated in vacuo to give 10.19 g of the title compound as a brown powder.

$^1$H NMR ($CDCl_3$) δ 3.88 (3H, s), 3.99 (3H, s), 5.01 (1H, s), 6.72 (1H, dd, J=8.5 Hz, 2.2 Hz), 6.77 (1H, d, J=2.1 Hz), 7.23 (1H, d, J=1.0 Hz), 7.52 (1H, dd, J=8.6 Hz, 0.5 Hz).

Reference Example 2

Production of 4-(6-hydroxy-1-methyl-1H-indole-2-carbonyl)-piperazine-1-carboxylic acid tert-butyl ester To a mixture of 6-benzyloxy-1H-indole-2-carboxylic acid ethyl ester (10 g, 33.86 mmol) and iodomethane (2.32 mL, 37.10 mmol) in tetrahydrofuran (THF) (100 mL) and DMF (50 mL) was added 60% sodium hydride in oil (1.63 g, 40.75 mmol) under ice cooling and the mixture was stirred for 2 hours. After the addition of water and AcOEt, the organic layer was separated and washed with 1 M HCl and brine, dried over anhydrous magnesium sulfate and evaporated. To the residue in ethanol (EtOH) (100 mL) was added 5 M NaOH (20.3 mL, 101.5 mmol) and the mixture was refluxed for 2 hours. The reaction mixture was acidified with 6 M HCl under ice cooling and the precipitate was collected by filtration and dried. The filtrate was extracted with AcOEt and the organic layer was washed with brine, dried over anhydrous magnesium sulfate and evaporated. To a solution of this residue and the precipitate in DMF (120 mL) was added piperazine-1-carboxylic acid tert-butyl ester (7.57 g, 40.63 mmol) and the mixture was cooled to 0° C. To the mixture was added 1-ethyl-3-(3-dimethylaminopropyl)-carbodiimide hydrochloride (9.7 g, 50.60 mmol) and 1-Hydroxy-benzotiriazole monohydrate (6.1 g, 39.83 mmol) and the mixture was stirred at room temperature overnight. After the addition of water and saturated aqueous $NaHCO_3$, the mixture was stirred for 1 hour. The precipitate was collected by filtration and dissolved in $CH_2Cl_2$. The solution was washed with 1 M HCl and water, dried over anhydrous magnesium sulfate and evaporated. To a solution of the residue in 1,4-dioxane (60 mL) was added a suspension of 10% palladium/carbon (Pd/C) (1.2 g) in EtOH (60 mL) under ice cooling. The mixture was stirred under a hydrogen atmosphere (1 atm) for 3 hours at 40° C. The catalyst was filtered off using celite and the filtrate was evaporated. The residue was purified by silica gel column chromatography (n-hexane:AcOEt=1:3, in ratio by volume; hereinafter the same) and crystallized with $Et_2O$ to afford the title compound (7.23 g) as a white powder.

$^1$H NMR ($CDCl_3$) δ 1.49 (9H, s), 3.50 (4H, t, J=5.3 Hz), 3.71 (3H, s), 3.76 (4H, t, J=5.1 Hz), 5.53 (1H, s), 6.53 (1H, s), 6.69-6.72 (2H, m), 7.43 (1H, d, J=8.2 Hz).

Reference Example 3

Production of 6-hydroxy-2,3-dihydroindole-1,2-dicarboxylic acid 1-tert-butyl ester 2-ethyl ester To a suspension of 6-benzyloxy-1H-indole-2-carboxylic acid ethyl ester (3.0 g, 10 mmol) in AcOEt (30 mL) was added triethylamine (2.1 mL, 15 mmol), N,N-dimethylaminopyridine (0.12 g, 1.0 mmol) and di-tert-butyl dicarbonate (2.7 g, 12 mmol) under ice cooling and the mixture was stirred for 0.5 hour. Water (30 mL) was added to the reaction mixture and extracted with AcOEt, the organic layer was washed with 1 M HCl, saturated aqueous $NaHCO_3$ and brine, dried over anhydrous sodium sulfate and evaporated. To the residue in EtOH (40 mL) was added 10% Pd/C (0.4 g) and the mixture was stirred under a hydrogen atmosphere (1 atm) for 6 hours at 50° C. The catalyst was filtered off and the filtrate was evaporated. The residue was purified by silica gel column chromatography (n-hexane:AcOEt=4:1) to give 2.3 g of the title compound as a colorless oil.

$^1$H NMR ($CDCl_3$) δ 1.28 (3H, t, J=5.3 Hz), 1.50 (9H, d, J=1.3 Hz), 3.01 (1H, dd, J=16.0 Hz, 4.5 Hz), 3.43 (1H, dd, J=15.7 Hz, 11.4 Hz), 4.18-4.23 (2H, m), 4.82-4.87 (1H, m), 5.04 (1H, s), 6.44 (1H, d, J=7.6 Hz), 6.93 (1H, d, J=7.9 Hz), 7.46 (1H, s).

Reference Example 4

Production of 6-benzyloxy-1-methoxymethyl-1H-indole-2-carboxylic acid ethyl ester To a solution of 6-benzyloxy-1H-indole-2-carboxylic acid ethyl ester (3.00 g, 10 mmol) in DMF (30 ml) was added 60% sodium hydride in oil (0.49 g, 12 mmol) under ice cooling and the mixture was stirred for 15 minutes. Then to the mixture was added chloromethyl methyl ether (1.0 ml, 13 mmol) under ice cooling and stirred for 0.5 hour. Water (60 ml) was added to the reaction mixture and extracted with AcOEt, the organic layer was washed with saturated aqueous $NaHCO_3$ and brine, dried over anhydrous sodium sulfate and evaporated to give the title compound (3.45 g) as a pale brown oil.

$^1$H NMR ($CDCl_3$) δ 1.40 (3H, t, J=7.3 Hz), 3.27 (3H, s), 4.36 (2H, q, J=7.1 Hz), 5.14 (2H, s), 5.93 (2H, s), 6.94 (1H, dd, J=8.7 Hz, 2.1 Hz), 7.04 (1H, d, J=2.3 Hz), 7.31-7.43 (5H, m), 7.46-7.49 (2H, m), 7.55 (1H, d, J=8.9 Hz).

Reference Example 5

Production of 6-hydroxy-1-methoxymethyl-1H-indole-2-carboxylic acid ethyl ester To a solution of 6-benzyloxy-1-methoxymethyl-1H-indole-2-carboxylic acid ethyl ester (3.45 g, 10 mmol) in EtOH (35 ml) was added 10% Pd/C (0.35 g) and the mixture was stirred under a hydrogen atmosphere (1 atm) for 2 hours at 50° C. The catalyst was filtered off and the filtrate was evaporated. The residue was purified by silica gel column chromatography (n-hexane:AcOEt=4:1) to give 2.0 g of the title compound as colorless crystals.

$^1$H NMR ($CDCl_3$) δ 1.40 (3H, t, J=7.1 Hz), 3.30 (3H, s), 4.36 (2H, q, J=7.1 Hz), 4.85 (1H, s), 5.91 (2H, s), 6.77 (1H, dd, J=8.6 Hz, 2.3 Hz), 6.95 (1H, d, J=2.0 Hz), 7.30 (1H, d, J=0.7 Hz), 7.53 (1H, d, J=8.6 Hz).

Reference Example 6

Production of 6-hydroxy-1,3-dimethyl-1H-indole-2-carboxylic acid ethyl ester To a solution of 6-benzyloxy-1,3-dimethyl-1H-indole-2-carboxylic acid ethyl ester (547 mg, 1.69 mmol) in DMF (10 mL) was added sodium hydride (81 mg, 2.03 mmol) at 0° C. The mixture was stirred for 10 minutes at 0° C., and then iodomethane (116 μL, 1.86 mmol) was added to the mixture. After the reaction mixture was stirred for 1 hour under ice cooling, saturated aqueous $NH_4Cl$ was added to the mixture, and the mixture was extracted with AcOEt. The organic layer was washed with water and brine, dried over anhydrous sodium sulfate, and evaporated in vacuo. The residue was purified by silica gel column chromatography (AcOEt:n-hexane=1:20 to 1:4) to give a white powder (392 mg). This powder was dissolved in ethanol (8 mL) and dioxane (4 mL), and the mixture was hydrogenated over 10% Pd/C (40 mg) for 7 hours at 40° C. under atmospheric pressure. The catalyst was removed by filtration, and the filtrate was evaporated in vacuo to give 277 mg of the title compound as a white powder.

$^1$H NMR ($CDCl_3$) δ 1.42 (3H, t, J=7.1 Hz), 2.55 (3H, s), 3.92 (3H, s), 4.39 (2H, q, J=7.1 Hz), 4.82 (1H, s), 6.68-6.73 (2H, m), 7.51 (1H, dd, J=8.4 Hz, 0.7 Hz).

Reference Example 7

Production of 5-(5-nitropyridin-2-yloxy)-1H-indole-2-carboxylic acid methyl ester 5-Hydroxy-1H-indole-2-carboxylic acid methyl ester (0.845 g, 4.42 mmol) and 2-chloro-5-nitropyridine (0.771 g, 4.86 mmol) were dissolved in DMF (5 mL). To the solution was added anhydrous potassium carbonate (0.611 g, 4.42 mmol) and the resulting solution was stirred for 18 hours at 80° C. Water (80 mL) was added to the reaction solution and the mixture was extracted with ethyl acetate (80 mL). The organic layer was washed with brine, dried over anhydrous sodium sulfate and the solvent was removed by evaporation. The residue was purified by silica gel column chromatography (AcOEt:n-hexane=1:3), then the obtained solid was recrystallized from ethyl acetate and n-hexane to yield 0.753 g of the title compound as a yellow powder.

$^1$H NMR ($CDCl_3$) δ 3.96 (3H, s), 7.04 (1H, d, J=9.1 Hz), 7.13 (1H, dd, J=9.0 Hz, 2.2 Hz), 7.23 (1H, d, J=2.0 Hz), 7.47-7.50 (2H, m), 8.47 (1H, dd, J=9.1 Hz, 2.8 Hz), 8.96 (1H, brs), 9.05 (1H, d, J=2.8 Hz).

The following compounds were produced in the same manner as in Reference Example 7 using appropriate starting materials.

Reference Example 8

4-(5-Nitropyridin-2-yloxy)-1H-indole $^1$H NMR ($CDCl_3$) δ 6.27-6.30 (1H, m), 6.93-6.96 (1H, m), 7.02 (1H, d, J=9.1 Hz), 7.17-7.27 (2H, m), 7.34-7.38 (1H, m), 8.32 (1H, brs), 8.46 (1H, dd, J=9.1 Hz, 2.8 Hz), 9.06 (1H, d, J=2.8 Hz).

Reference Example 9

5-(5-Nitropyridin-2-yloxy)-1H-indole $^1$H NMR (CDCl$_3$) δ 6.56-6.59 (1H, m), 6.96-7.00 (2H, m), 7.28-7.30 (1H, m), 7.41-7.46 (2H, m), 8.28 (1H, brs), 8.44 (1H, dd, J=9.1 Hz, 2.8 Hz), 9.06 (1H, d, J=2.8 Hz).

Reference Example 10

6-(1H-Indol-4-yloxy)-N-(4-trifluoromethylphenyl)nicotinamide $^1$H NMR (CDCl$_3$) δ 6.26-6.28 (1H, m), 6.90-6.94 (1H, m), 6.99 (1H, d, J=8.6 Hz), 7.13-7.15 (1H, m), 7.18-7.24 (1H, m), 7.29-7.32 (1H, m), 7.60 (2H, d, J=8.7 Hz), 7.73 (2H, d, J=8.4 Hz), 8.08 (1H, brs), 8.19 (1H, dd, J=8.6 Hz, 2.5 Hz), 8.39 (1H, brs), 8.67 (1H, d, J=2.5 Hz).

Reference Example 11

4-[5-(5-Nitropyridin-2-yloxy)-1H-indole-2-carbonyl]piperazine-1-carboxylic acid tert-butyl ester $^1$H NMR (CDCl$_3$) δ 1.50 (9H, s), 3.57 (4H, t, J=5.2 Hz), 3.92 (4H, brs), 6.78 (1H, s), 7.03 (1H, d, J=9.1 Hz), 7.08 (1H, dd, J=8.9 Hz, 2.3 Hz), 7.43 (1H, d, J=2.3 Hz), 7.49 (1H, d, J=8.9 Hz), 8.46 (1H, dd, J=9.1 Hz, 2.6 Hz), 9.04 (1H, d, J=2.6 Hz), 9.41 (1H, brs).

Reference Example 12

[5-(5-Bromopyridin-2-yloxy)indol-1-yl]acetic acid ethyl ester $^1$H NMR (CDCl$_3$) δ 1.28 (3H, t, J=7.1 Hz), 4.23 (2H, q, J=7.1 Hz), 4.84 (2H, s), 6.54 (1H, dd, J=3.2 Hz, 0.7 Hz), 6.78 (1H, dd, J=8.7 Hz, 0.5 Hz), 6.99 (1H, dd, J=8.7 Hz, 2.3 Hz), 7.14 (1H, d, J=3.2 Hz), 7.21-7.31 (1H, m), 7.37 (1H, d, J=2.3 Hz), 7.71 (1H, dd, J=8.7 Hz, 2.6 Hz), 8.21 (1H, dd, J=2.6 Hz, 0.5 Hz).

Reference Example 13

6-(1H-Indol-4-yloxy)nicotinic acid ethyl ester $^1$HNMR (CDCl$_3$) δ 1.38 (3H, t, J=7.1 Hz), 4.37 (2H, q, J=7.1 Hz), 6.28-6.30 (1H, m), 6.90-6.95 (2H, m), 7.14-7.16 (1H, m), 7.19-7.25 (1H, m), 7.30-7.33 (1H, m), 8.25 (1H, dd, J=8.7 Hz, 2.5 Hz), 8.34 (1H, brs), 8.85 (1H, d, J=2.5 Hz).

Reference Example 14

4-[1-Methyl-5-(4-methyl-5-nitropyridin-2-yloxy)-1H-indole-2-carbonyl]piperazine-1-carboxylic acid tert-butyl ester $^1$H NMR (CDCl$_3$) δ 1.48 (9H, s), 2.66 (3H, s), 3.50 (4H, brs), 3.76 (4H, brs), 3.86 (3H, s), 6.59 (1H, s), 6.81 (1H, s), 7.07 (1H, dd, J=2.2 Hz, 8.9 Hz), 7.37 (1H, d, J=2.4 Hz), 7.41 (1H, d, J=8.9 Hz), 8.88 (1H, s).

Reference Example 15

4-[1-Methyl-5-(6-methyl-5-nitropyridin-2-yloxy)-1H-indole-2-carbonyl]piperazine-1-carboxylic acid tert-butyl ester $^1$H NMR (CDCl$_3$) δ 1.49 (9H, s), 2.76 (3H, s), 3.49-3.53 (4H, m), 3.75-3.80 (4H, m), 3.88 (3H, s), 6.59 (1H, s), 6.72 (1H, d, J=9.2 Hz), 7.09 (1H, dd, J=2.2 Hz, 8.9 Hz), 7.38 (1H, s), 7.40 (1H, d, J=6.2 Hz), 8.33 (1H, d, J=8.9 Hz).

Reference Example 16

4-[1-Methyl-5-(5-nitropyrimidin-2-yloxy)-1H-indole-2-carbonyl]-piperazine-1-carboxylic acid tert-butyl ester $^1$H NMR (CDCl$_3$) δ 1.49 (9H, s), 3.50 (4H, brs), 3.74-3.77 (4H, m), 3.87 (3H, s), 6.61 (1H, s), 7.13 (1H, dd, J=2.4 Hz, 8.9 Hz), 7.42-7.45 (2H, m), 9.31 (2H, s).

Reference Example 17

1-Methyl-5-(5-nitropyridin-2-yloxy)-1H-indole-2-carboxylic acid methyl ester $^1$H NMR (CDCl$_3$) δ 3.93 (3H, s), 4.11 (3H, s), 7.03 (1H, d, J=8.9 Hz), 7.15 (1H, dd, J=2.2 Hz, 9.2 Hz), 7.27 (1H, d, J=8.1 Hz), 7.44-7.47 (2H, m), 8.46 (1H, dd, J=2.7 Hz, 8.9 Hz), 9.03 (1H, d, J=2.7 Hz).

Reference Example 18

(S)-3-Methyl-4-[1-methyl-5-(5-nitropyridin-2-yloxy)-1H-indole-2-carbonyl]piperazine-1-carboxylic acid tert-butyl ester $^1$H NMR (CDCl$_3$) δ 1.31 (3H, d, J=6.8 Hz), 1.48 (9H, s), 2.88 (1H, brs), 3.05 (1H, brs), 3.28 (1H, t, J=11.3 Hz), 3.84 (3H, s), 3.92 (1H, s), 4.21 (2H, brs), 4.70 (1H, brs), 6.57 (1H, s), 7.02 (1H, dd, J=0.5 Hz, 8.9 Hz), 7.08 (1H, dd, J=2.4 Hz, 8.9 Hz), 7.39-7.43 (2H, m), 8.46 (1H, dd, J=2.7 Hz, 8.9 Hz), 9.03 (1H, dd, J=0.5 Hz, 2.7 Hz).

Reference Example 19

1-Methyl-6-(5-nitropyridin-2-yloxy)-1H-indole-2-carboxylic acid ethyl ester $^1$H NMR (CDCl$_3$) δ 1.42 (3H, t, J=7.0 Hz), 4.04 (3H, s), 4.38 (2H, q, J=7.0 Hz), 6.94 (1H, dd, J=2.2 Hz, 8.6 Hz), 7.05 (1H, d, J=8.9 Hz), 7.19 (1H, d, J=1.6 Hz), 7.32 (1H, d, J=1.6 Hz), 7.71 (1H, d, J=8.6 Hz), 8.48 (1H, dd, J=2.7 Hz, 8.9 Hz), 9.05 (1H, d, J=3.0 Hz).

Reference Example 20

1-Methyl-7-(5-nitropyridin-2-yloxy)-1H-indole-2-carboxylic acid ethyl ester $^1$H NMR (CDCl$_3$) δ 1.40 (3H, t, J=7.0 Hz), 4.09 (3H, s), 4.35 (2H, q, J=7.0 Hz), 3.94 (3H, s), 7.01 (1H, dd, J=1.1 Hz, 7.6 Hz), 7.08 (1H, d, J=8.9 Hz), 7.14 (1H, t, J=7.8 Hz), 7.35 (1H, s), 7.60 (1H, dd, J=0.8 Hz, 7.8 Hz), 8.51 (1H, dd, J=3.0 Hz, 8.9 Hz), 9.05 (1H, dd, J=0.8 Hz, 3.0 Hz).

Reference Example 21

1-Methyl-4-(5-nitropyridin-2-yloxy)-1H-indole-2-carboxylic acid ethyl ester $^1$H NMR (CDCl$_3$) δ 1.36 (3H, t, J=7.0 Hz), 4.11 (3H, s), 4.34 (2H, q, J=7.0 Hz), 6.96 (1H, dd, J=1.4 Hz, 7.3 Hz), 7.03

(1H, d, J=0.8 Hz), 7.07 (1H, dd, J=0.5 Hz, 8.9 Hz), 7.32-7.43 (2H, m), 8.48 (1H, dd, J=2.7 Hz, 8.9 Hz), 9.03 (1H, dd, J=0.8 Hz, 3.0 Hz).

Reference Example 22

1,4-Dimethyl-5-(5-nitropyridin-2-yloxy)-1H-indole-2-carboxylic acid ethyl ester $^1$H NMR (CDCl$_3$) δ 1.43 (3H, t, J=7.0 Hz), 2.35 (3H, s), 4.09 (3H, s), 4.39 (2H, q, J=7.0 Hz), 7.01 (1H, dd, J=0.5 Hz, 9.2 Hz), 7.07 (1H, d, J=8.9 Hz), 7.29 (1H, d, J=8.6 Hz), 7.35 (1H, d, J=0.8 Hz), 8.46 (1H, dd, J=2.7 Hz, 8.9 Hz), 9.02 (1H, dd, J=0.3 Hz, 2.7 Hz).

Reference Example 23

1-Methyl-6-(5-nitropyridin-2-yloxy)-1H-indole-2-carboxylic acid methyl ester $^1$H NMR (CDCl$_3$) δ 3.92 (3H, s), 4.05 (3H, s), 6.94 (1H, dd, J=8.6 Hz, 2.0 Hz), 7.06 (1H, d, J=9.1 Hz), 7.19 (1H, d, J=2.0 Hz), 7.32 (1H, s), 7.72 (1H, d, J=8.6 Hz), 8.49 (1H, dd, J=9.1 Hz, 2.8 Hz), 9.06 (1H, d, J=2.8 Hz).

Reference Example 24

1-Methyl-6-(5-nitropyrimidin-2-yloxy)-1H-indole-2-carboxylic acid ethyl ester $^1$H NMR (CDCl$_3$) δ 1.42 (3H, t, J=7.2 Hz), 4.06 (3H, s), 4.39 (2H, q, J=7.1 Hz), 6.98 (1H, dd, J=8.7 Hz, 2.1 Hz), 7.23 (1H, d, J=2.1 Hz), 7.34 (1H, d, J=0.8 Hz), 7.74 (1H, d, J=8.7 Hz), 9.34 (2H, s).

Reference Example 25

6-(5-Nitropyridin-2-yloxy)-1H-indole-2-carboxylic acid ethyl ester $^1$H NMR (CDCl$_3$) δ 1.42 (3H, t, J=7.1 Hz), 4.42 (2H, q, J=7.1 Hz), 6.96 (1H, dd, J=8.6 Hz, 2.0 Hz), 7.06 (1H, d, J=9.2 Hz), 7.24-7.26 (2H, m), 7.73 (1H, d, J=8.6 Hz), 8.49 (1H, dd, J=9.1 Hz, 2.8 Hz), 8.96 (1H, s), 9.05 (1H, d, J=2.6 Hz).

Reference Example 26

1-Methoxymethyl-6-(5-nitropyridin-2-yloxy)-1H-indole-2-carboxylic acid ethyl ester $^1$H NMR (CDCl$_3$) δ 1.42 (3H, t, J=7.3 Hz), 3.31 (3H, s), 4.40 (2H, q, J=7.1 Hz), 5.95 (2H, s), 7.00 (1H, dd, J=8.6 Hz, 2.0 Hz), 7.07 (1H, d, J=8.6 Hz), 7.37 (1H, d, J=2.0 Hz), 7.39 (1H, s), 7.73 (1H, d, J=8.6 Hz), 8.49 (1H, dd, J=8.9 Hz, 3.0 Hz), 9.05 (1H, d, J=3.0 Hz).

Reference Example 27

6-(5-Nitropyridin-2-yloxy)-2,3-dihydroindole-1,2-dicarboxylic acid 1-tert-butyl ester 2-ethyl ester $^1$H NMR (CDCl$_3$) δ 1.30 (3H, t, J=7.1 Hz), 1.48 (9H, s), 3.13 (1H, dd, J=17.0 Hz, 4.8 Hz), 3.53 (1H, dd, J=16.2 Hz, 11.5 Hz), 4.23 (2H, m), 4.90 (1H, d, J=10.9 Hz), 6.74 (1H, d, J=6.3 Hz), 7.01 (1H, d, J=8.9 Hz), 7.15 (1H, d, J=7.9 Hz), 7.72 (1H, s), 8.46 (1H, dd, J=8.9 Hz, 2.6 Hz), 9.06 (1H, d, J=3.0 Hz).

Reference Example 28

1-Methyl-6-{5-[methyl(4-trifluoromethoxybenzoyl)amino]pyridin-2-yloxy}-1H-indole-2-carboxylic acid $^1$H NMR (CDCl$_3$) δ 3.48 (3H, s), 4.05 (3H, s), 6.87-6.91 (2H, m), 7.09-7.11 (3H, m), 7.36-7.38 (3H, m), 7.46 (1H, dd, J=8.7 Hz, 2.8 Hz), 7.68 (1H, d, J=8.6 Hz), 7.90 (1H, d, J=3.0 Hz).

Reference Example 29

1,3-Dimethyl-6-(5-nitropyridin-2-yloxy)-1H-indole-2-carboxylic acid ethyl ester $^1$H NMR (CDCl$_3$) δ 1.45 (3H, t, J=7.2 Hz), 2.60 (3H, s), 3.97 (3H, s), 4.42 (2H, q, J=7.1 Hz), 6.92 (1H, dd, J=8.6 Hz, 2.0 Hz), 7.05 (1H, d, J=9.1 Hz), 7.14 (1H, d, J=1.8 Hz), 7.71 (1H, d, J=8.6 Hz), 8.48 (1H, dd, J=9.1 Hz, 2.8 Hz), 9.05 (1H, d, J=2.5 Hz).

Reference Example 30

4-[1-Methyl-6-(5-nitropyrimidin-2-yloxy)-1H-indole-2-carbonyl]-piperazine-1-carboxylic acid tert-butyl ester $^1$H NMR (CDCl$_3$) δ 1.49 (9H, s), 3.51 (4H, t, J=4.7 Hz), 3.76 (4H, t, J=5.1 Hz), 3.82 (3H, s), 6.64 (1H, d, J=0.7 Hz), 6.98 (1H, dd, J=8.6 Hz, 2.0 Hz), 7.21 (1H, d, J=2.1 Hz), 7.69 (1H, d, J=8.6 Hz), 9.33 (2H, s).

Reference Example 31

1-Methyl-6-(4-methyl-5-nitropyridin-2-yloxy)-1H-indole-2-carboxylic acid ethyl ester $^1$H NMR (DMSO-d$_6$) δ 1.34 (3H, t, J=7.1 Hz), 2.61 (3H, s), 3.99 (3H, s), 4.33 (2H, q, J=7.1 Hz), 6.97 (1H, dd, J=8.6 Hz, 2.0 Hz), 7.19 (1H, s), 7.31 (1H, d, J=0.7 Hz), 7.50 (1H, d, J=2.0 Hz), 7.74 (1H, d, J=8.9 Hz), 8.84 (1H, s).

Reference Example 32

Production of 4-[1-methyl-6-(5-nitropyridin-2-yloxy)-1H-indole-2-carbonyl]piperazine-1-carboxylic acid tert-butyl ester To a mixture of 6-hydroxy-1-methyl-1H-indole-2-carboxylic acid (12.27 g, 64.2 mmol) and piperazine-1-carboxylic acid tert-butyl ester (14.34 g, 77.0 mmol) in DMF (80 mL) were added 1-ethyl-3-(3-dimethylaminopropyl)carbodiimide hydrochloride (18.4 g, 96.0 mmol) and 1-hydroxybenzotriazole monohydrate (11.6 g, 75.7 mmol) under ice cooling, and the mixture was stirred at room temperature overnight. The mixture was evaporated under reduced pressure, and then water and AcOEt were added to the residue. The organic layer was separated and washed with 1M HCl, saturated aqueous NaHCO$_3$ and brine, dried over anhydrous magnesium sulfate and evaporated. To a mixture of the residue and 2-chloro-5-nitropyridine (10.05 g, 63.4 mmol) in DMF (80 mL) was added K$_2$CO$_3$ (11.92 g, 86.2 mmol) and the mixture was stirred overnight at room temperature. The mixture was evaporated under reduced pressure, and then water and Et$_2$O were added to the residual mixture. After the mixture was stirred for 1 hour, the precipitate was collected by filtration and dried to afford 23.2 g of the title compound as a yellow powder.

$^1$H NMR (CDCl$_3$) δ 1.49 (9H, s), 3.51 (4H, brs), 3.76 (4H, t, J=5.1 Hz), 3.82 (3H, s), 6.63 (1H, s), 6.94 (1H, dd, J=8.6 Hz, 2.0 Hz), 7.05 (1H, d, J=9.2 Hz), 7.17 (1H, d, J=2.0 Hz), 7.67 (1H, d, J=8.6 Hz), 8.48 (1H, dd, J=9.1 Hz, 2.8 Hz), 9.05 (1H, d, (7=3.0 Hz).

Reference Example 33

Production of [4-(5-aminopyridin-2-yloxy)indol-1-yl]acetic acid ethyl ester

[4-(5-Nitropyridin-2-yloxy)indol-1-yl]acetic acid ethyl ester (1.49 g, 4.35 mmol) was dissolved in THF (15 mL). To the solution was added 5% Pd/C (0.15 g) and the resulting solution was subjected to catalytic reduction for 18 hours at room temperature under atmospheric pressure. The catalyst was removed by filtration, and the filtrate was concentrated to yield 1.43 g of the title compound as a pale yellow oil.

$^1$H NMR (CDCl$_3$) δ 1.26 (3H, t, J=7.1 Hz), 3.49 (2H, brs), 4.22 (2H, q, J=7.1 Hz), 4.82 (2H, s), 6.38 (1H, d, J=3.3 Hz), 6.75-6.80 (2H, m), 7.00-7.08 (3H, m), 7.14-7.20 (1H, m), 7.73 (1H, d, J=3.0 Hz).

The following compounds were produced in the same manner as in Reference Example 33 using appropriate starting materials.

Reference Example 34

2-[4-(5-Aminopyridin-2-yloxy)indol-1-yl]-1-(4-benzo[1,3]dioxol-5-ylmethylpiperazin-1-yl)ethanone $^1$H NMR (CDCl$_3$) δ 2.27-2.42 (4H, m), 3.39-3.66 (8H, m), 4.88 (2H, s), 5.94 (2H, s), 6.38 (1H, d, J=3.3 Hz), 6.71-6.82 (5H, m), 6.99 (1H, d, J=3.3 Hz), 7.04 (1H, d, J=3.0 Hz), 7.06-7.07 (1H, m), 7.13-7.19 (1H, m), 7.72-7.74 (1H, m).

Reference Example 35

2-[5-(5-Aminopyridin-2-yloxy)-2,3-dihydroindol-1-yl]-1-(4-benzo[1,3]dioxol-5-ylmethylpiperazin-1-yl)ethanone $^1$H NMR (CDCl$_3$) δ 2.43 (4H, brs), 2.97 (2H, t, J=8.2 Hz), 3.39-3.52 (6H, m), 3.55 (2H, t, J=4.9 Hz), 3.65 (2H, t, J=4.9 Hz), 3.82 (2H, s), 5.95 (2H, s), 6.41 (1H, d, J=8.4 Hz), 6.68 (1H, d, J=8.7 Hz), 6.73-6.80 (3H, m), 6.85-6.86 (2H, m), 7.04 (1H, dd, J=8.7 Hz, 3.1 Hz), 7.69 (1H, d, J=3.1 Hz).

Reference Example 36

2-[4-(5-Aminopyridin-2-yloxy)-2,3-dihydroindol-1-yl]-1-(4-benzo[1,3]dioxol-5-ylmethylpiperazin-1-yl)ethanone $^1$H NMR (CDCl$_3$) δ 2.42 (4H, brs), 2.85 (2H, t, J=8.2 Hz), 3.42 (2H, s), 3.43 (2H, t, J=8.3 Hz), 3.51-3.55 (4H, m), 3.64 (2H, t, J=4.9 Hz), 3.86 (2H, s), 5.95 (2H, s), 6.24 (1H, d, J=7.8 Hz), 6.37 (1H, d, J=7.8 Hz), 6.70-6.77 (3H, m), 6.85 (1H, s), 7.00-7.08 (2H, m), 7.71 (1H, d, J=3.0 Hz).

Reference Example 37

4-[5-(5-Aminopyridin-2-yloxy)-1H-indole-2-carbonyl]piperazine-1-carboxylic acid tert-butyl ester $^1$H NMR (CDCl$_3$) δ 1.49 (9H, s), 3.48 (2H, s), 3.55 (4H, t, J=5.8 Hz), 3.90 (4H, brs), 6.72 (1H, d, J=3.0 Hz), 6.76 (1H, s), 7.03-7.12 (2H, m), 7.33 (1H, d, J=2.3 Hz), 7.40 (1H, d, J=8.9 Hz), 7.70 (1H, d, J=2.9 Hz), 9.19 (1H, brs).

Reference Example 38

[5-(5-Aminopyridin-2-yloxy)-1-methyl-1H-indol-2-yl](4-benzo[1,3]dioxol-5-ylmethylpiperazin-1-yl)methanone $^1$H NMR (CDCl$_3$) δ 2.47 (4H, brs), 3.45 (4H, s), 3.76 (4H, brs), 3.82 (3H, s), 5.95 (2H, s), 6.51 (1H, d, J=0.6 Hz), 6.72 (1H, dd, J=8.6 Hz, 0.6 Hz), 6.75 (2H, s), 6.86 (1H, s), 7.05 (1H, d, J=9.0 Hz), 7.06 (1H, d, J=8.6 Hz), 7.29 (1H, d, J=2.3 Hz), 7.32 (1H, d, J=9.0 Hz), 7.68 (1H, dd, J=2.3 Hz, 0.6 Hz).

Reference Example 39

[5-(5-Aminopyridin-2-yloxy)-1-methyl-1H-indol-2-yl](4-benzyl-piperazin-1-yl)methanone $^1$H NMR (CDCl$_3$) δ 2.50 (4H, brs), 3.44 (2H, brs), 3.55 (2H, s), 3.77 (4H, brs), 3.82 (3H, s), 6.51 (1H, d, J=0.7 Hz), 6.72 (1H, d, J=8.5 Hz), 7.04 (1H, d, J=8.8 Hz), 7.06 (1H, dd, J=8.8 Hz, 0.7 Hz), 7.22-7.39 (7H, m), 7.68 (1H, d, J=3.0 Hz).

Reference Example 40

4-[5-(5-Aminopyridin-2-yloxy)-1-methyl-1H-indole-2-carbonyl]-piperazine-1-carboxylic acid tert-butyl ester $^1$H NMR (CDCl$_3$) δ 1.48 (9H, s), 3.49 (6H, brs), 3.75 (4H, t, J=5.0 Hz), 3.83 (3H, s), 6.53 (1H, s), 6.73 (1H, d, J=8.7 Hz), 7.06 (1H, d, J=8.7 Hz), 7.07 (1H, dd, J=8.7 Hz, 2.3 Hz), 7.31 (1H, d, J=2.3 Hz), 7.33 (1H, d, J=8.7 Hz), 7.69 (1H, d, J=2.9 Hz).

Reference Example 41

[5-(5-Aminopyridin-2-yloxy)-1-methyl-1H-indol-2-yl][4-(4-methoxy-benzyl)piperazin-1-yl]methanone $^1$H NMR (CDCl$_3$) δ 2.47 (4H, brs), 3.45 (2H, brs), 3.49 (4H, s), 3.76-3.79 (4H, m), 3.80 (3H, s), 3.82 (3H, s), 6.52 (1H, s), 6.72 (1H, d, J=8.4 Hz), 6.88 (2H, d, J=8.4 Hz), 7.05 (1H, d, J=8.4 Hz), 7.06 (1H, dd, J=1.1 Hz, 8.6 Hz), 7.21-7.34 (4H, m), 7.69 (1H, d, J=3.0 Hz).

Reference Example 42

[5-(5-Aminopyridin-2-yloxy)-1-methyl-1H-indol-2-yl][4-(4-di-fluoromethoxybenzyl)piperazin-1-yl]methanone $^1$H NMR (CDCl$_3$) δ 2.48 (4H, brs), 3.46 (2H, brs), 3.52 (2H, s), 3.77 (4H, brs), 3.82 (3H, s), 6.50 (1H, t, J=74 Hz), 6.52 (1H, s), 6.72 (1H, d, J=8.6 Hz), 7.05 (2H, d, J=8.0 Hz), 7.02-7.15 (2H, m), 7.27-7.34 (2H, m), 7.32 (2H, d, J=8.0 Hz), 7.69 (1H, d, J=2.5 Hz).

Reference Example 43

[6-(5-Aminopyridin-2-yloxy)-1-methyl-1H-indol-2-yl]{4-[4-(2,2,2-trifluoroethoxy)benzyl]piperazin-1-yl}methanone $^1$H NMR (CDCl$_3$) δ 2.47 (4H, brs), 3.50 (4H, s), 3.76 (7H, s), 4.35 (2H, q, J=8.1 Hz), 6.55 (1H, s), 6.76 (1H, d, J=8.6 Hz), 6.88 (1H, dd, J=8.3 Hz, 2.0 Hz), 6.91 (2H, d, J=8.3 Hz), 7.05 (1H, d, J=2.0 Hz), 7.07 (1H, dd, J=8.6 Hz, 2.9 Hz), 7.27 (2H, d, J=8.3 Hz), 7.54 (1H, d, J=8.5 Hz), 7.71 (1H, d, J=2.9 Hz).

Reference Example 44

[5-(5-Aminopyridin-2-yloxy)-1-methyl-1H-indol-2-yl]{4-[4-(2,2,2-trifluoroethoxy)benzyl]piperazin-1-yl}methanone $^1$H NMR (CDCl$_3$) δ 2.47 (4H, brs), 3.45 (2H, s), 3.50 (2H, s), 3.76 (4H, brs), 3.82 (3H, s), 4.34 (2H, q, J=8.2 Hz), 6.52 (1H, s), 6.72 (1H, d, J=8.6 Hz), 6.91 (2H, d, J=8.6 Hz), 7.05 (1H, dd, J=8.6 Hz, 3.0 Hz), 7.02-7.10 (1H, m), 7.27 (2H, d, J=8.6 Hz), 7.24-7.37 (2H, m), 7.68 (1H, d, J=3.0 Hz).

Reference Example 45

4-[6-(5-Aminopyridin-2-yloxy)-1-methyl-1H-indole-2-carbonyl]-piperazine-1-carboxylic acid tert-butyl ester $^1$H NMR (CDCl$_3$) δ 1.49 (9H, s), 3.50 (4H, t, J=5.6 Hz), 3.75 (4H, t, J=5.6 Hz), 3.77 (3H, s), 3.67-3.88 (2H, m), 6.57 (1H, s), 6.77 (1H, d, J=8.6 Hz), 6.90 (1H, dd, J=8.6 Hz, 2.0 Hz), 7.05 (1H, d, J=2.0 Hz), 7.08 (1H, dd, J=8.6 Hz, 3.0 Hz), 7.56 (1H, d, J=8.6 Hz), 7.71 (1H, d, J=3.0 Hz).

Reference Example 46

6-(5-Aminopyridin-2-yloxy)-1H-indole-2-carboxylic acid ethyl ester $^1$H NMR (DMSO-d$_6$) δ 1.33 (3H, t, J=7.1 Hz), 4.32 (2H, q, J=7.1 Hz), 5.12 (2H, s), 6.76-6.79 (2H, m), 6.90 (1H, s), 7.07-7.12 (2H, m), 7.56-7.61 (2H, m), 11.68 (1H, s).

Reference Example 47

6-(5-Aminopyridin-2-yloxy)-1-methoxymethyl-1H-indole-2-carboxylic acid ethyl ester $^1$H NMR (CDCl$_3$) δ 1.41 (3H, t, J=7.2 Hz), 3.28 (3H, s), 3.52 (2H, s), 4.37 (2H, q, J=7.1 Hz), 5.90 (2H, s), 6.81 (1H, d, J=8.6 Hz), 6.95 (1H, dd, J=8.6 Hz, 2.0 Hz), 7.10 (1H, dd, J=8.6 Hz, 3.0 Hz), 7.25 (1H, dd, J=10.8 Hz, 1.9 Hz), 7.33 (1H, d, J=1.0 Hz), 7.62 (1H, d, J=8.9 Hz), 7.73 (1H, d, J=3.0 Hz).

Reference Example 48

6-(5-Aminopyrimidin-2-yloxy)-1-methyl-1H-indole-2-carboxylic acid ethyl ester $^1$H NMR (CDCl$_3$) δ 1.41 (3H, t, J=7.1 Hz), 3.50 (2H, s), 4.03 (3H, s), 4.37 (2H, q, J=7.1 Hz), 6.96 (1H, dd, J=8.7 Hz, 2.0 Hz), 7.19 (1H, d, J=1.6 Hz), 7.29 (1H, s), 7.66 (1H, d, J=8.6 Hz), 8.08 (2H, s).

Reference Example 49

6-(5-Aminopyridin-2-yloxy)indole-1,2-dicarboxylic acid 1-tert-butyl ester 2-ethyl ester $^1$H NMR (CDCl$_3$) δ 1.39 (3H, t, J=7.3 Hz), 1.59 (9H, s), 3.53 (2H, brs), 4.36 (2H, q, J=7.1 Hz), 6.81 (1H, d, J=8.6 Hz), 7.02 (1H, dd, J=8.6 Hz, 2.3 Hz), 7.08-7.12 (2H, m), 7.54 (1H, d, J=8.2 Hz), 7.75 (2H, dd, J=10.7 Hz, 2.5 Hz).

Reference Example 50

6-(5-Amino-4-methylpyridin-2-yloxy)-1-methyl-1H-indole-2-carboxylic acid ethyl ester $^1$H NMR (CDCl$_3$) δ 1.39-1.42 (3H, m), 2.20 (3H, s), 3.45 (2H, brs), 3.99 (3H, s), 4.34-4.38 (2H, m), 6.70 (1H, s), 6.89 (1H, dd, J=8.7 Hz, 2.1 Hz), 7.04 (1H, d, J=2.0 Hz), 7.27-7.27 (1H, m), 7.61 (1H, d, J=8.6 Hz), 7.67 (1H, s).

Reference Example 51

Production of 5-[5-(3,4-dichlorobenzoylamino)pyridin-2-yloxy]-1H-indole-2-carboxylic acid methyl ester 5-(5-Nitropyridin-2-yloxy)-1H-indole-2-carboxylic acid methyl ester (0.750 g, 2.39 mmol) was dissolved in THF (20 mL). To the solution was added 5% Pd/C (0.10 g), and the resulting mixture was subjected to catalytic reduction for 2 hours at room temperature under atmospheric pressure. The catalyst was removed by filtration, and the filtrate was concentrated to yield of a pale yellow oil (0.677 g). This product was dissolved in THF (30 mL). To the solution were added triethylamine (0.333 mL, 2.39 mmol), subsequently 3,4-Dichlorobenzoyl chloride (0.501 g, 2.39 mmol) and the resulting solution was stirred for 1 hour at room temperature. Water (30 mL) was added to the reaction solution, and the mixture was extracted with ethyl acetate (30 mL). After the organic layer was washed with brine, then dried over anhydrous sodium sulfate, the solvent was evaporated. The obtained residue was recrystallized from ethyl acetate to yield 1.00 g of the title compound as a white powder.

$^1$H NMR (DMSO-d$_6$) δ 3.89 (3H, s), 7.02 (1H, d, J=8.9 Hz), 7.07 (1H, dd, J=8.9 Hz, 2.3 Hz), 7.15 (1H, d, J=1.2 Hz), 7.39 (1H, d, J=2.1 Hz), 7.48 (1H, d, J=8.7 Hz), 7.84 (1H, d, J=8.4 Hz), 7.95 (1H, dd, J=8.4 Hz, 2.0 Hz), 8.16 (1H, dd, J=8.8 Hz, 2.7 Hz), 8.22 (1H, d, J=2.0 Hz), 8.45 (1H, d, J=2.5 Hz), 10.52 (1H, s), 12.00 (1H, brs).

The following compounds were produced in the same manner as in Reference Example 51 using appropriate starting materials.

Reference Example 52

4-{1-Methyl-5-[5-(4-trifluoromethylbenzoylamino)pyridin-2-yloxy]-1H-indole-2-carbonyl}piperazine-1-carboxylic acid tert-butyl ester $^1$H NMR (CDCl$_3$) δ 1.48 (9H, s), 3.49 (4H, brs), 3.76-3.73 (4H, m), 3.84 (3H, s), 6.56 (1H, s), 6.93 (1H, d, J=8.9 Hz), 7.11 (1H, dd, J=8.9 Hz, 2.2 Hz), 7.39-7.36 (1H, m), 7.75 (2H, d, J=8.1 Hz), 7.99 (3H, d, J=8.1 Hz), 8.17 (1H, dd, J=8.9 Hz, 2.7 Hz), 8.25 (1H, d, J=2.2 Hz).

Reference Example 53

4-{5-[5-(3,4-Dichlorobenzoylamino)pyridin-2-yloxy]-1-methyl-1H-indole-2-carbonyl}piperazine-1-carboxylic acid tert-butyl ester $^1$H NMR (CDCl$_3$) δ 1.48 (9H, s), 3.49 (4H, brs), 3.74 (4H, brs), 3.82 (3H, d, J=1.4 Hz), 6.88 (1H, dd, J=1.6 Hz, 8.9 Hz), 7.09 (1H, dd, J=1.6 Hz, 8.6 Hz), 7.34-7.37 (2H, m), 7.53 (1H, dd, J=2.2 Hz, 8.6 Hz), 7.70 (1H, dd, J=2.2 Hz, 8.4 Hz), 7.98 (1H, d, J=2.2 Hz), 8.10 (2H, dd, J=1.9 Hz, 8.9 Hz), 8.23 (1H, d, J=2.7 Hz).

Reference Example 54

4-{1-Methyl-5-[4-methyl-5-(4-trifluoromethylbenzoylamino)pyridin-2-yloxy]-1H-indole-2-carbonyl}piperazine-1-carboxylic acid tert-butyl ester $^1$H NMR (CDCl$_3$) δ 1.49 (9H, s), 2.78 (3H, s), 3.50 (4H, brs), 3.75 (4H, brs), 3.83 (3H, s), 6.55 (1H, s), 6.77 (1H, s), 7.10 (1H, dd, J=1.1 Hz, 8.9 Hz), 7.35-7.38 (2H, m), 7.71 (1H, s), 7.76 (2H, d, J=8.1 Hz), 8.02 (2H, d, J=8.1 Hz), 8.25 (1H, s).

Reference Example 55

4-{1-Methyl-5-[6-methyl-5-(4-trifluoromethylbenzoylamino)pyridin-2-yloxy]-1H-indole-2-carbonyl}piperazine-1-carboxylic acid tert-butyl ester $^1$H NMR (CDCl$_3$) δ 1.48 (9H, s), 2.44 (3H, s), 3.50 (4H, brs), 3.75 (4H, brs), 3.83 (3H, s), 6.54 (1H, s), 6.57 (1H, d, J=8.6 Hz), 7.34 (1H, d, J=9.2 Hz), 7.36 (1H, s), 7.77 (3H, d, J=8.1 Hz), 7.90-7.96 (1H, m), 8.02 (2H, d, J=8.1 Hz).

Reference Example 56

4-{5-[5-(3,4-Dichlorobenzoylamino)-4-methylpyridin-2-yloxy]-1-methyl-1H-indole-2-carbonyl}piperazine-1-carboxylic acid tert-butyl ester $^1$H NMR (CDCl$_3$) δ 1.48 (9H, s), 2.26 (3H, s), 3.49-3.52 (4H, m), 3.73-3.77 (4H, m), 3.83 (3H, s), 6.55 (1H, s), 6.76 (1H, s), 7.10 (1H, dd, J=2.2 Hz, 8.9 Hz), 7.35 (1H, d, J=3.5 Hz), 7.37 (1H, d, J=3.5 Hz), 7.58 (1H, d, J=8.1 Hz), 7.59 (1H, s), 7.73 (1H, dd, J=1.9 Hz, 8.4 Hz), 8.01 (1H, d, J=1.6 Hz), 8.12 (1H, s).

Reference Example 57

4-{5-[5-(3,4-Dichlorobenzoylamino)-6-methylpyridin-2-yloxy]-1-methyl-1H-indole-2-carbonyl}piperazine-1-carboxylic acid tert-butyl ester $^1$H NMR (CDCl$_3$) δ 1.48 (9H, s), 2.84 (3H, s), 3.49-3.52 (4H, m), 3.74-3.76 (4H, m), 3.79 (3H, s), 6.49-6.52 (2H, m), 7.10 (1H, dd, J=2.2 Hz, 8.9 Hz), 7.30-7.34 (2H, m), 7.57 (1H, d, J=8.4 Hz), 7.74 (1H, d, J=8.6 Hz), 7.75 (1H, dd, J=2.2 Hz, 8.4 Hz), 7.98 (1H, s), 8.04 (1H, d, J=2.2 Hz).

Reference Example 58

4-{1-Methyl-5-[5-(4-trifluoromethylbenzoylamino)pyrimidin-2-yl-oxy]-1H-indole-2-carbonyl}piperazine-1-carboxylic acid tert-butyl ester $^1$H NMR (CDCl$_3$) δ 1.48 (9H, s), 3.49 (4H, brs), 3.72-3.76 (4H, m), 3.83 (3H, s), 6.58 (1H, s), 7.15 (1H, dd, J=2.4 Hz, 8.9 Hz), 7.39 (1H, d, J=9.2 Hz), 7.43 (1H, d, J=2.2 Hz), 7.75 (2H, d, J=8.4 Hz), 8.00 (2H, d, J=8.1 Hz), 8.11 (1H, s), 8.85 (2H, s).

Reference Example 59

4-{5-[5-(3,4-Dichlorobenzoylamino)pyrimidin-2-yloxy]-1-methyl-1H-indole-2-carbonyl}piperazine-1-carboxylic acid tert-butyl ester $^1$H NMR (CDCl$_3$) δ 1.48 (9H, s), 3.44-3.49 (4H, m), 3.74 (4H, brs), 3.82 (3H, s), 6.57 (1H, s), 7.13 (1H, dd, J=2.4 Hz, 8.9 Hz), 7.37 (1H, d, J=8.6 Hz), 7.41 (1H, d, J=2.2 Hz), 7.53 (1H, d, J=8.6 Hz), 7.72 (1H, dd, J=2.2 Hz, 8.4 Hz), 8.00 (1H, d, J=2.2 Hz), 8.37 (1H, s), 8.82 (2H, s).

Reference Example 60

1-Methyl-5-[5-(4-trifluoromethylbenzoylamino)pyridin-2-yloxy]-1H-indole-2-carboxylic acid methyl ester $^1$H NMR (CDCl$_3$) δ 3.92 (3H, s), 4.09 (3H, s), 6.95 (1H, d, J=4.1 Hz), 7.16 (1H, dd, J=2.4 Hz, 8.9 Hz), 7.39-7.43 (3H, m), 7.75 (2H, d, J=8.4 Hz), 7.92 (1H, s), 7.98 (2H, d, J=8.1 Hz), 8.19 (1H, dd, J=2.7 Hz, 8.9 Hz), 8.24 (1H, d, J=1.9 Hz).

Reference Example 61

(S)-3-Methyl-4-{1-methyl-5-[5-(4-trifluoromethylbenzoylamino)-pyridin-2-yloxy]-1H-indole-2-carbonyl}piperazine-1-carboxylic acid tert-butyl ester $^1$H NMR (CDCl$_3$) δ 1.29 (3H, d, J=6.8 Hz), 1.48 (9H, s), 2.86 (1H, brs), 3.04 (1H, brs), 3.21-3.30 (1H, m), 3.80 (3H, s), 3.92 (1H, d, J=12.2 Hz), 4.20 (2H, brs), 4.69 (1H, brs), 6.52 (1H, s), 6.90 (1H, d, J=8.9 Hz), 7.09 (1H, dd, J=2.2 Hz, 8.9 Hz), 7.34-7.37 (2H, m), 7.73 (2H, d, J=8.4 Hz), 7.98 (2H, d, J=7.8 Hz), 8.12-8.16 (2H, m), 8.25 (1H, d, J=2.4 Hz).

Reference Example 62

1-Methyl-6-[5-(4-trifluoromethylbenzoylamino)pyridin-2-yloxy]-1H-indole-2-carboxylic acid ethyl ester $^1$H NMR (CDCl$_3$) δ 1.41 (3H, t, J=7.0 Hz), 4.03 (3H, s), 4.37 (2H, q, J=7.0 Hz), 6.94 (1H, dd, J=2.2 Hz, 8.4 Hz), 7.00 (1H, d, J=8.9 Hz), 7.15 (1H, d, J=1.9 Hz), 7.30 (1H, d, J=0.8

Hz), 7.66 (1H, d, J=8.6 Hz), 7.77 (2H, d, J=8.4 Hz), 7.83 (1H, s), 7.99 (2H, d, J=8.1 Hz), 8.22 (1H, dd, J=2.7 Hz, 8.4 Hz), 8.27 (2H, d, J=2.7 Hz).

Reference Example 63

1-Methyl-7-[5-(4-trifluoromethylbenzoylamino)pyridin-2-yloxy]-1H-indole-2-carboxylic acid ethyl ester $^1$H NMR (CDCl$_3$) δ 1.40 (3H, t, J=7.0 Hz), 4.16 (3H, s), 4.35 (2H, q, J=7.0 Hz), 6.97-7.01 (2H, m), 7.11 (1H, t, J=7.8 Hz), 7.33 (1H, s), 7.53 (1H, dd, J=1.1 Hz, 7.8 Hz), 7.77 (3H, d, J=8.4 Hz), 7.99 (2H, d, J=8.4 Hz), 8.25-8.28 (2H, m).

Reference Example 64

1-Methyl-4-[5-(4-trifluoromethylbenzoylamino)pyridin-2-yloxy]-1H-indole-2-carboxylic acid ethyl ester $^1$H NMR (CDCl$_3$) δ 1.36 (3H, t, J=7.0 Hz), 4.09 (3H, s), 4.33 (2H, q, J=7.0 Hz), 6.89 (1H, dd, J=1.1 Hz, 7.6 Hz), 7.00 (2H, d, J=9.7 Hz), 7.12 (1H, d, J=0.8 Hz), 7.23-7.37 (2H, m), 7.74 (1H, d, J=8.1 Hz,), 7.92 (1H, s), 7.97 (2H, d, J=8.1 Hz), 8.20-8.25 (2H, m).

Reference Example 65

1,4-Dimethyl-5-[5-(4-trifluoromethylbenzoylamino)pyridin-2-yl-oxy]-1H-indole-2-carboxylic acid ethyl ester $^1$H NMR (CDCl$_3$) δ 1.43 (3H, t, J=7.0 Hz), 2.38 (3H, s), 4.08 (3H, s), 4.39 (2H, q, J=7.0 Hz), 6.91 (1H, dd, J=1.6 Hz, 7.8 Hz), 7.11 (1H, d, J=8.9 Hz), 7.26 (1H, d, J=8.9 Hz), 7.34 (1H, s), 7.76 (3H, d, J=8.4 Hz), 7.99 (2H, d, J=8.1 Hz), 8.17-8.21 (2H, m).

Reference Example 66

1-Methyl-6-[5-(4-trifluoromethoxybenzoylamino)pyridin-2-yloxy]-1H-indole-2-carboxylic acid ethyl ester $^1$H NMR (CDCl$_3$) δ 1.41 (3H, t, J=7.1 Hz), 4.02 (3H, s), 4.37 (2H, q, J=7.0 Hz), 6.94 (1H, dd, J=8.6 Hz, 2.0 Hz), 6.99 (1H, d, J=8.9 Hz), 7.15 (1H, d, J=2.0 Hz), 7.26-7.35 (3H, m), 7.66 (1H, d, J=8.9 Hz), 7.80 (1H, s), 7.93 (2H, dd, J=6.6 Hz, 2.0 Hz), 8.20-8.26 (2H, R).

Reference Example 67

6-[5-(2-Chloro-4-trifluoromethylbenzoylamino)pyridin-2-yloxy]-1-methyl-1H-indole-2-carboxylic acid ethyl ester $^1$H NMR (CDCl$_3$) δ 1.41 (3H, t, J=7.1 Hz), 4.03 (3H, s), 4.37 (2H, q, J=7.1 Hz), 6.94 (1H, dd, J=8.6 Hz, 2.0 Hz), 7.00 (1H, d, J=9.2 Hz), 7.16 (1H, d, J=2.0 Hz), 7.26-7.31 (1H, m), 7.67 (2H, dd, J=8.2, 2.3 Hz), 7.75 (1H, s), 7.85 (1H, s), 7.89 (1H, d, J=8.2 Hz), 8.22-8.27 (2H, m).

Reference Example 68

6-[5-(3,4-Dichlorobenzoylamino)pyridin-2-yloxy]-1-methyl-1H-indole-2-carboxylic acid methyl ester $^1$H NMR (CDCl$_3$) δ 3.91 (3H, s), 4.03 (3H, s), 6.94 (1H, dd, J=8.7 Hz, 2.1 Hz), 6.99 (1H, d, J=8.7 Hz), 7.16 (1H, d, J=1.9 Hz), 7.29 (1H, d, J=0.5 Hz), 7.58 (1H, d, J=8.4 Hz), 7.67 (1H, d, J=9.1 Hz), 7.71 (1H, dd, J=8.4 Hz, 1.9 Hz), 7.82 (1H, brs), 7.98 (1H, d, J=2.1 Hz), 8.20 (1H, dd, J=8.9 Hz, 2.8 Hz), 8.26 (1H, d, J=2.6 Hz).

Reference Example 69

1-Methyl-6-[5-(4-trifluoromethylbenzoylamino)pyrimidin-2-yloxy]-1H-indole-2-carboxylic acid ethyl ester $^1$H NMR (CDCl$_3$) δ 1.42 (3H, t, J=7.1 Hz), 4.05 (3H, s), 4.38 (2H, q, J=7.1 Hz), 7.00 (1H, dd, J=8.6 Hz, 2.1 Hz), 7.24 (1H, dd, J=1.4 Hz, 0.7 Hz), 7.32 (1H, d, J=0.8 Hz), 7.71 (1H, d, J=8.7 Hz), 7.78 (1H, s), 7.79 (2H, d, J=8.4 Hz), 8.01 (2H, d, J=8.1 Hz), 8.88 (2H, s).

Reference Example 70

6-(5-Acetylaminopyridin-2-yloxy)-1-methyl-1H-indole-2-carboxylic acid ethyl ester $^1$H NMR (CDCl$_3$) δ 1.34 (3H, t, J=7.1 Hz), 2.05 (3H, s), 3.79 (3H, s), 4.32 (2H, q, J=7.0 Hz), 6.88 (1H, dd, J=8.6 Hz, 2.0 Hz), 7.00 (1H, d, J=8.6 Hz), 7.28 (1H, d, J=0.7 Hz), 7.34 (1H, d, J=2.3 Hz), 7.68 (1H, d, J=8.6 Hz), 8.05 (1H, dd, J=8.9 Hz, 2.6 Hz), 8.29 (1H, d, J=2.3 Hz), 10.07 (1H, s).

Reference Example 71

6-[5-(4-Nitrobenzoylamino)pyridin-2-yloxy]-2,3-dihydroindole-1,2-dicarboxylic acid 1-tert-butyl ester 2-ethyl ester $^1$H NMR (CDCl$_3$) δ 1.22-1.32 (3H, m), 1.56 (9H, s), 3.10 (1H, dd, J=16.3 Hz, 4.8 Hz), 3.50 (1H, dd, J=16.5 Hz, 10.9 Hz), 4.23 (2H, d, J=7.3 Hz), 4.88 (1H, s), 6.73 (1H, d, J=6.9 Hz), 6.95 (1H, d, J=8.2 Hz), 7.10 (1H, d, J=7.9 Hz), 7.68 (1H, s), 7.97 (1H, s), 8.05 (2H, d, J=8.9 Hz), 8.18 (1H, s), 8.28 (1H, s), 8.34 (1H, d, J=8.9 Hz).

Reference Example 72

6-[5-(2-Methoxy-4-trifluoromethylbenzoylamino)pyridin-2-yloxy]-1-methyl-1H-indole-2-carboxylic acid methyl ester $^1$H NMR (CDCl$_3$) δ 3.91 (3H, s), 4.03 (3H, s), 4.13 (3H, s), 6.95 (1H, d, J=8.1 Hz), 6.99 (1H, dd, J=8.6 Hz, 1.9 Hz), 7.16 (1H, d, J=2.0 Hz), 7.27 (1H, s), 7.29 (1H, d, J=0.8 Hz), 7.41 (1H, dd, J=8.1 Hz, 0.8 Hz), 7.67 (1H, d, J=8.6 Hz), 8.26-8.32 (2H, m), 8.40 (1H, dd, J=8.2 Hz, 0.7 Hz), 9.65 (1H, brs).

Reference Example 73

6-[5-(2,4-Bistrifluoromethylbenzoylamino)pyridin-2-yloxy]-1-methyl-1H-indole-2-carboxylic acid methyl ester $^1$H NMR (CDCl$_3$) δ 3.91 (3H, s), 4.04 (3H, s), 6.95 (1H, dd, J=8.7 Hz, 2.1 Hz), 7.01 (1H, d, J=9.7 Hz), 7.17 (1H, d, J=2.0

Hz), 7.30 (1H, d, J=0.8 Hz), 7.44 (1H, brs), 7.68 (1H, d, J=8.6 Hz), 7.83 (1H, d, J=7.9 Hz), 7.95 (1H, d, J=7.4 Hz), 8.02 (1H, s), 8.16-8.22 (2H, m).

Reference Example 74

4-{1-Methyl-6-[5-(2-methyl-4-trifluoromethylbenzoylamino)-pyrimidin-2-yloxy]-1H-indole-2-carbonyl}piperazine-1-carboxylic acid tert-butyl ester $^1$H NMR (CDCl$_3$) δ 1.48 (9H, s), 2.52 (3H, s), 3.48 (4H, t, J=4.2 Hz), 3.72 (4H, t, J=4.8 Hz), 3.77 (3H, s), 6.58 (1H, d, J=0.8 Hz), 6.98 (1H, dd, J=8.6 Hz, 2.0 Hz), 7.19 (1H, d, J=1.0 Hz), 7.50 (1H, d, J=10.2 Hz), 7.52 (1H, s), 7.58 (1H, d, J=7.7 Hz), 7.64 (1H, d, J=8.6 Hz), 8.08 (1H, brs), 8.87 (2H, s).

Reference Example 75

Production of {4-[5-(3,4-dichlorobenzoylamino) pyridin-2-yloxy]-indol-1-yl}acetic acid ethyl ester

[4-(5-Aminopyridin-2-yloxy)indole-1-yl]acetic acid ethyl ester (0.715 g, 2.30 mmol) was dissolved in THF (10 mL). To the solution were added triethylamine (0.320 mL, 2.30 mmol), then 3,4-Dichlorobenzoyl chloride (0.481 g, 2.30 mmol), and the resulting solution was stirred for 30 minutes at room temperature. Water (50 mL) was added to the reaction solution, and the mixture was extracted with ethyl acetate (50 mL). After the organic layer was washed with brine, then dried over anhydrous sodium sulfate, the solvent was evaporated. The obtained residue was recrystallized from ethyl acetate and n-hexane to yield 0.972 g of the title compound as a white powder.

$^1$H NMR (CDCl$_3$) δ 1.27 (3H, t, J=7.1 Hz), 4.23 (2H, q, J=7.1 Hz), 4.84 (2H, s), 6.33-6.35 (1H, m), 6.88-6.96 (2H, m), 7.02 (1H, d, J=3.1 Hz), 7.12 (1H, d, J=8.4 Hz), 7.21 (1H, d, J=7.8 Hz), 7.56 (1H, d, J=8.2 Hz), 7.69 (1H, dd, J=8.4 Hz, 2.1 Hz), 7.83 (1H, brs), 7.97 (1H, d, J=2.0 Hz), 8.15 (1H, dd, J=8.7 Hz, 2.8 Hz), 8.24 (1H, d, J=2.6 Hz).

The following compounds were produced in the same manner as in Reference Example 75 using appropriate starting materials.

Reference Example 76

{4-[5-(4-Trifluoromethylbenzoylamino)pyridin-2-yloxy]indol-1-yl}-acetic acid ethyl ester $^1$H NMR (CDCl$_3$) δ 1.27 (3H, t, J=7.1 Hz), 4.23 (2H, q, J=7.1 Hz), 4.84 (2H, s), 6.35 (1H, dd, J=3.3 Hz, 0.7 Hz), 6.91 (1H, dd, J=7.6 Hz, 0.7 Hz), 6.96 (1H, d, J=8.9 Hz), 7.04 (1H, d, J=3.1 Hz), 7.13 (1H, d, J=8.2 Hz), 7.22 (1H, d, J=7.8 Hz), 7.75-7.81 (3H, m), 7.99 (2H, d, J=8.1 Hz), 8.20 (1H, dd, J=8.8 Hz, 2.7 Hz), 8.26 (1H, d, J=2.3 Hz).

Reference Example 77

4-{5-[5-(4-Trifluoromethylbenzoylamino)pyridin-2-yloxy]-1H-indole-2-carbonyl}piperazine-1-carboxylic acid tert-butyl ester $^1$H NMR (DMSO-d$_6$) δ 1.43 (9H, s), 3.44 (4H, brs), 3.75 (4H, brs), 6.82 (1H, d, J=1.5 Hz), 6.98 (1H, d, J=8.7 Hz), 7.00 (1H, d, J=8.9 Hz), 7.34 (1H, d, J=2.2 Hz), 7.45 (1H, d, J=8.9 Hz), 7.93 (2H, d, J=8.1 Hz), 8.16 (2H, d, J=8.1 Hz), 8.18 (1H, dd, J=8.7 Hz, 2.5 Hz), 8.47 (1H, d, J=2.5 Hz), 10.58 (1H, s), 11.66 (1H, s).

Reference Example 78

4-{5-[5-(3,4-Dichlorobenzoylamino)pyridin-2-yloxy]-1H-indole-2-carbonyl}piperazine-1-carboxylic acid tert-butyl ester $^1$H NMR (CDCl$_3$) δ 1.42 (9H, s), 3.36-3.55 (4H, m), 3.75-3.89 (4H, m), 6.82 (1H, d, J=2.0 Hz), 6.98 (1H, d, J=8.9 Hz), 6.99 (1H, d, J=8.6 Hz), 7.34 (1H, d, J=2.5 Hz), 7.45 (1H, d, J=8.6 Hz), 7.84 (1H, d, J=8.3 Hz), 7.94 (1H, dd, J=8.3 Hz, 2.1 Hz), 8.15 (1H, dd, J=8.9 Hz, 2.8 Hz), 8.22 (1H, d, J=2.1 Hz), 8.45 (1H, d, J=2.8 Hz), 10.52 (1H, s), 11.68 (1H, s).

Reference Example 79

4-{1-Methyl-6-[5-(2-methyl-4-trifluoromethylbenzoylamino)pyridin-2-yloxy]-1H-indole-2-carbonyl}piperazine-1-carboxylic acid tert-butyl ester $^1$H NMR (CDCl$_3$) δ 1.49 (9H, s), 2.56 (3H, s), 3.50 (4H, t, J=4.9 Hz), 3.75 (4H, t, J=5.2 Hz), 3.79 (3H, s), 6.59 (1H, s), 6.94 (1H, dd, J=8.6 Hz, 1.9 Hz), 6.98 (1H, d, J=9.7 Hz), 7.14 (1H, d, J=1.6 Hz), 7.52-7.63 (5H, m), 8.23-8.25 (2H, m).

Reference Example 80

4-{6-[5-(2-Fluoro-4-trifluoromethylbenzoylamino) pyridin-2-yloxy]-1-methyl-1H-indole-2-carbonyl}piperazine-1-carboxylic acid tert-butyl ester $^1$H NMR (CDCl$_3$) δ 1.48 (9H, d, J=2.0 Hz), 3.50 (4H, s), 3.76 (4H, s), 3.80 (3H, d, J=2.0 Hz), 6.60 (1H, s), 6.96 (2H, t, J=8.4 Hz), 7.15 (1H, s), 7.49 (1H, d, J=11.9 Hz), 7.60-7.64 (2H, m), 8.18 (1H, d, J=9.2 Hz), 8.28-8.36 (3H, m).

Reference Example 81

1-Methoxymethyl-6-[5-(4-nitrobenzoylamino)pyridin-2-yloxy]-1H-indole-2-carboxylic acid ethyl ester $^1$H NMR (CDCl$_3$) δ 1.42 (3H, t, J=7.1 Hz), 3.29 (3H, s), 4.38 (2H, q, J=7.1 Hz), 5.92 (2H, s), 7.00 (1H, dd, J=8.6 Hz, 1.9 Hz), 7.01 (1H, d, J=8.9 Hz), 7.33 (1H, d, J=2.0 Hz), 7.36 (1H, d, J=0.7 Hz), 7.68 (1H, d, J=8.6 Hz), 7.91 (1H, s), 8.03-8.07 (2H, m), 8.21 (1H, dd, J=8.9 Hz, 2.6 Hz), 8.28 (1H, d, J=2.3 Hz), 8.35 (2H, dt, J=9.1 Hz, 2.1 Hz).

Reference Example 82

1-Methyl-6-{5-[methyl(4-methylbenzoyl)amino] pyridin-2-yloxy}-1H-indole-2-carboxylic acid $^1$H NMR (DMSO-d$_6$) δ 2.26 (3H, s), 3.32 (3H, s), 3.95 (3H, s), 6.82 (1H, dd, J=8.6 Hz, 2.0 Hz), 6.97 (1H, d, J=8.9 Hz), 7.09 (2H, d, J=8.2 Hz), 7.18 (2H, d, J=7.9 Hz), 7.23 (1H, d, J=0.7 Hz), 7.32 (1H, s), 7.66 (1H, d, J=8.6 Hz), 7.76 (1H, dd, J=8.7 Hz, 2.8 Hz), 7.90 (1H, d, J=2.6 Hz), 12.89 (1H, s).

Reference Example 83

4-(1-Methyl-6-{5-[methyl(4-trifluoromethylbenzoyl) amino]-pyrimidin-2-yloxy}-1H-indole-2-carbonyl) piperazine-1-carboxylic acid tert-butyl ester $^1$H NMR (CDCl$_3$) δ 1.49 (9H, s), 3.50 (3H, s), 3.51 (4H, s), 3.75 (4H, t, J=4.9 Hz), 3.79 (3H, s), 6.60 (1H, s), 6.92 (1H, dd, J=8.6 Hz, 2.0 Hz), 7.15 (1H, d, J=1.6 Hz), 7.44 (2H, d, J=7.4 Hz), 7.57 (2H, d, J=7.7 Hz), 7.63 (1H, d, J=8.6 Hz), 8.31 (2H, brs).

Reference Example 84

4-(1-Methyl-6-{5-[methyl(toluene-4-sulfonyl)amino] pyridin-2-yl-oxy}-1H-indole-2-carbonyl)piperazine-1-carboxylic acid tert-butyl ester $^1$H NMR (CDCl$_3$) δ 1.49 (9H, s), 2.42 (3H, s), 3.16 (3H, s), 3.49-3.52 (4H, m), 3.74-3.78 (4H, m), 3.81 (3H, s), 6.60 (1H, s), 6.87 (1H, d, J=8.9 Hz), 6.93 (1H, dd, J=8.6 Hz, 2.0 Hz), 7.15 (1H, d, J=1.6 Hz), 7.28 (2H, d, J=8.1 Hz), 7.49 (2H, d, J=8.2 Hz), 7.54 (1H, dd, J=8.7 Hz, 2.8 Hz), 7.62 (1H, d, J=8.6 Hz), 7.77 (1H, d, J=2.6 Hz).

Reference Example 85

6-{5-[(4-Difluoromethoxybenzoyl)methylamino] pyridin-2-yloxy}-1-methyl-1H-indole-2-carboxylic acid $^1$H NMR (CDCl$_3$) δ 3.48 (3H, s), 4.01 (3H, s), 6.50 (1H, t, J=73.2 Hz), 6.90 (2H, dd, J=8.6 Hz, 2.0 Hz), 6.98 (2H, d, J=8.9 Hz), 7.13 (1H, d, J=2.0 Hz), 7.33-7.37 (3H, m), 7.45 (1H, dd, J=8.6 Hz, 2.6 Hz), 7.68 (1H, d, J=8.6 Hz), 7.89 (1H, d, J=2.6 Hz).

Reference Example 86

1,3-Dimethyl-6-{5-[methyl(4-trifluoromethylbenzoyl)amino]pyridin-2-yloxy}-1H-indole-2-carboxylic acid $^1$H NMR (DMSO-d$_6$) δ 2.50 (3H, s), 3.37 (3H, s), 3.87 (3H, s), 6.77 (1H, dd, J=8.7 Hz, 1.3 Hz), 6.98 (1H, d, J=8.7 Hz), 7.24 (1H, d, J=1.3 Hz), 7.51 (2H, d, J=6.9 Hz), 7.65 (1H, d, J=8.9 Hz), 7.68 (2H, d, J=8.1 Hz), 7.83 (1H, dd, J=8.6 Hz, 2.5 Hz), 7.96 (1H, brs), 13.01 (1H, brs).

Reference Example 87

Production of 4-{5-[5-(3,4-dichlorobenzenesulfonylamino)pyridin-2-yloxy]-1-methyl-1H-indole-2-carbonyl}piperazine-1-carboxylic acid tert-butyl ester A stirred solution of 4-[5-(5-aminopyridin-2-yloxy)-1-methyl-1H-indole-2-carbonyl]piperazine-1-carboxylic acid tert-butyl ester (4.69 g, 10.4 mmol) in THF (250 mL) was ice cooled, then 3,4-dichlorobenzenesulfonyl chloride (3.7 g, 15.1 mmol) and pyridine (1.51 mL, 18.7 mmol) were added to the solution. The resulting mixture was stirred for 17 hours while gradually warming up to room temperature. Water was added to the mixture, and the aqueous layer was extracted with AcOEt. The extract was washed with saturated aqueous NaHCO$_3$ and brine. The organic layer was dried over anhydrous magnesium sulfate and evaporated. The residue was purified by silica gel column chromatography (CH$_2$Cl$_2$: MeOH=40:1) to afford 5.26 g of the title compound as a pale yellow powder.

$^1$H NMR (CDCl$_3$) δ 1.48 (9H, s), 3.50 (4H, brs), 3.74 (4H, brs), 3.82 (3H, s), 6.53 (1H, s), 6.81 (1H, d, J=8.7 Hz), 7.04 (1H, dd, J=9.1 Hz, 2.3 Hz), 7.21 (1H, brs), 7.31 (1H, d, J=2.3 Hz), 7.35 (1H, d, J=9.1 Hz), 7.49 (2H, d, J=1.0 Hz), 7.51 (1H, dd, J=8.7 Hz, 2.8 Hz), 7.70 (1H, d, J=2.8 Hz), 7.81 (1H, t, J=1.2 Hz).

The following compounds were produced in the same manner as in Reference Example 87 using appropriate starting materials.

Reference Example 88

4-{1-Methyl-5-[5-(4-trifluoromethylbenzenesulfonylamino)pyridin-2-yloxy]-1H-indole-2-carbonyl}piperazine-1-carboxylic acid tert-butyl ester $^1$H NMR (CDCl$_3$) δ 1.48 (9H, s), 3.50 (4H, brs), 3.74 (4H, brs), 3.82 (3H, s), 6.53 (1H, s), 6.80 (1H, d, J=8.8 Hz), 7.03 (1H, dd, J=8.9 Hz, 2.1 Hz), 7.27-7.33 (1H, m), 7.31 (1H, d, J=2.1 Hz), 7.34 (1H, d, J=8.9 Hz), 7.51 (1H, dd, J=8.8 Hz, 2.7 Hz), 7.68 (1H, d, J=2.7 Hz), 7.69 (2H, d, J=8.1 Hz), 7.82 (2H, d, J=8.1 Hz).

Reference Example 89

4-{6-[5-(3,4-Dichlorobenzenesulfonylamino)pyridin-2-yloxy]-1-methyl-1H-indole-2-carbonyl}piperazine-1-carboxylic acid tert-butyl ester $^1$H NMR (CDCl$_3$) δ 1.49 (9H, s), 3.50 (4H, brs), 3.74-3.77 (7H, m), 6.59 (1H, d, J=0.7 Hz), 6.86-6.91 (2H, m), 6.99 (1H, s), 7.10 (1H, d, J=2.0 Hz), 7.52-7.62 (4H, m), 7.75 (1H, d, J=2.3 Hz), 7.83 (1H, t, J=1.2 Hz).

Reference Example 90

4-{1-Methyl-6-[5-(4-trifluoromethylbenzenesulfonylamino)pyridin-2-yloxy]-1H-indole-2-carbonyl}piperazine-1-carboxylic acid tert-butyl ester $^1$H NMR (CDCl$_3$) δ 1.49 (9H, s), 3.48-3.52 (4H, m), 3.73-3.77 (7H, m), 6.58 (1H, s), 6.85-6.90 (2H, m), 7.10 (1H, d, J=2.0 Hz), 7.55-7.61 (2H, m), 7.70-7.74 (3H, m), 7.85 (2H, d, J=8.2 Hz).

Reference Example 91

4-{1-Methyl-5-[5-(toluene-4-sulfonylamino)pyridin-2-yloxy]-1H-indole-2-carbonyl}piperazine-1-carboxylic acid tert-butyl ester $^1$H NMR (CDCl$_3$) δ 1.48 (9H, s), 2.39 (3H, s), 3.50 (4H, brs), 3.75 (4H, brs), 3.83 (3H, s), 6.55 (1H, s), 6.80-6.84 (2H, m), 7.04 (1H, dd, J=8.9 Hz, 2.3 Hz), 7.22 (2H, d, J=7.9 Hz), 7.33-7.36 (2H, m), 7.53-7.60 (3H, m), 7.68 (1H, d, J=2.6 Hz).

Reference Example 92

6-(5-Methanesulfonylaminopyridin-2-yloxy) indole-1,2-dicarboxylic acid 1-tert-butyl ester 2-ethyl ester $^1$H NMR (CDCl$_3$) δ 1.40 (3H, t, J=7.1 Hz), 1.61 (9H, s), 3.01 (3H, s), 4.38 (2H, q, J=7.1 Hz), 6.33 (1H, brs), 6.98 (1H, d, J=8.6 Hz), 7.07 (1H, dd, J=8.6 Hz, 2.0 Hz), 7.11 (1H, s), 7.61 (1H, d, J=8.6 Hz), 7.75 (1H, dd, J=8.7 Hz, 2.8 Hz), 7.90 (1H, d, J=2.0 Hz), 8.04 (1H, d, J=3.0 Hz).

Reference Example 93

6-[5-(3,4-Dichlorobenzenesulfonylamino)-4-methylpyridin-2-yloxy]-1-methyl-1H-indole-2-carboxylic acid ethyl ester $^1$H NMR (CDCl$_3$) δ 1.41 (3H, t, J=7.1 Hz), 2.26 (3H, s), 4.02 (3H, s), 4.37 (2H, q, J=7.1 Hz), 6.33 (1H, s), 6.78 (1H, s), 6.88 (1H, dd, J=8.9 Hz, 2.0 Hz), 7.12 (1H, d, J=1.6 Hz), 7.29 (1H, s), 7.56 (2H, d, J=0.7 Hz), 7.66 (2H, t, J=4.3 Hz), 7.86 (1H, d, J=0.7 Hz).

Reference Example 94

Production of 6-(5-acetylaminopyridin-2-yloxy)-1H-indole-2-carboxylic acid ethyl ester To a solution of 6-(5-aminopyridin-2-yloxy)-1H-indole-2-carboxylic acid ethyl ester (2.6 g, 8.6 mmol) in pyridine (13 mL) was added acetic anhydride (2.2 g, 21 mmol) under ice cooling and the mixture was stirred for 2 hours. Water (30 mL) was added to the reaction mixture and extracted with AcOEt, the organic layer was washed with 2 M HCl, saturated aqueous NaHCO$_3$ and brine, dried over anhydrous sodium sulfate and evaporated. The residue was crystallized with 2-propyl alcohol and filtrated to give 0.85 g of the title compound. The filtrate was evaporated and the residue was purified by silica gel column chromatography (n-hexane:AcOEt=1:3) to give 1.26 g (total of 2.11 g) of the title compound as pale yellow crystals.

$^1$H NMR (DMSO-d$_6$) δ 1.34 (3H, t, J=7.1 Hz), 2.05 (3H, s), 4.34 (2H, q, J=7.0 Hz), 6.85 (1H, dd, J=8.7 Hz, 2.1 Hz), 7.00 (1H, d, J=8.9 Hz), 7.08 (1H, d, J=2.0 Hz), 7.16 (1H, d, J=1.3 Hz), 7.66 (1H, d, J=8.9 Hz), 8.05 (1H, dd, J=8.7 Hz, 2.8 Hz), 8.30 (1H, d, J=2.3 Hz), 10.08 (1H, s), 11.81 (1H, s).

Reference Example 95

Production of 5-[5-(3,4-dichlorobenzoylamino)pyridin-2-yloxy]-1H-indole-2-carboxylic acid 5-[5-(3,4-Dichlorobenzoylamino)pyridin-2-yloxy]-1H-indole-2-carboxylic acid methyl ester (1.00 g, 2.19 mmol) was dissolved in THF (30 mL). To the solution were added 1 M sodium hydroxide (3.50 mL, 3.50 mmol) and water (15 ml), and the resulting solution was refluxed for 3 hours. After cooling with ice, 1 M hydrochloric acid (3.50 mL, 3.50 mmol) and brine (50 mL) was added to the reaction solution, and the mixture was extracted with ethyl acetate (30 ml). After the organic layer was washed with brine, then dried over anhydrous sodium sulfate, the solvent was evaporated. The obtained residue was crystallized from n-hexane to yield 0.875 g of the title compound as a pale yellow powder.

$^1$H NMR (DMSO-d$_6$) δ 6.99-7.08 (3H, m), 7.38 (1H, d, J=2.1 Hz), 7.47 (1H, d, J=8.9 Hz), 7.83 (1H, d, J=8.4 Hz), 7.95 (1H, dd, J=8.4 Hz, 2.0 Hz), 8.16 (1H, dd, J=8.8 Hz, 2.7 Hz), 8.22 (1H, d, J=2.0 Hz), 8.45 (1H, d, J=2.5 Hz), 10.52 (1H, s), 11.83 (1H, s), 13.00 (1H, brs).

The following compounds were produced in the same manner as in Reference Example 95 using appropriate starting materials.

Reference Example 96

[4-(5-Nitropyridin-2-yloxy)indol-1-yl]acetic acid $^1$H NMR (CDCl$_3$+DMSO-d$_6$) δ 4.85 (2H, s), 6.29 (1H, d, J=3.3 Hz), 6.92-6.95 (1H, m), 7.01 (1H, d, J=9.1 Hz), 7.10 (1H, d, J=3.3 Hz), 7.25-7.27 (2H, m), 8.45 (1H, dd, J=9.1 Hz, 2.8 Hz), 9.06 (1H, d, J=2.8 Hz).

Reference Example 97

{4-[5-(3,4-Dichlorobenzoylamino)pyridin-2-yloxy]indol-1-yl}acetic acid $^1$H NMR (DMSO-d$_6$) δ 5.03 (2H, s), 6.11 (1H, d, J=2.6 Hz), 6.78 (1H, d, j=6.9 Hz), 7.06 (1H, d, J=8.9 Hz), 7.11-7.17 (1H, m), 7.25-7.29 (2H, m), 7.83 (1H, d, J=8.4 Hz), 7.95 (1H, dd, J=8.4 Hz, 2.0 Hz), 8.19 (1H, dd, J=8.9 Hz, 2.8 Hz), 8.22 (1H, d, J=2.0 Hz), 8.45 (1H, d, J=2.5 Hz), 10.55 (1H, s).

Reference Example 98

{4-[5-(4-Trifluoromethylbenzoylamino)pyridin-2-yloxy]indol-1-yl}-acetic acid $^1$H NMR (DMSO-d$_6$) δ 5.03 (2H, s), 6.11 (1H, d, J=3.3 Hz), 6.78 (1H, d, j=7.4 Hz), 7.06 (1H, d, J=8.9 Hz), 7.11-7.17 (1H, m), 7.25-7.29 (2H, m), 7.93 (2H, d, J=8.4 Hz), 8.16 (2H, d, J=8.1 Hz), 8.21 (1H, dd, J=8.9 Hz, 2.6 Hz), 8.47 (1H, d, J=2.6 Hz), 10.63 (1H, s).

Reference Example 99

[5-(5-Nitropyridin-2-yloxy)-2,3-dihydroindol-1-yl]acetic acid $^1$H NMR (CDCl$_3$) δ 3.10 (2H, t, J=8.3 Hz), 3.62 (2H, t, J=8.3 Hz), 3.92 (2H, s), 6.47 (1H, d, J=8.4 Hz), 6.87 (1H, dd, J=8.4 Hz, 2.3 Hz), 6.93 (1H, t, J=2.1 Hz), 6.98 (1H, d, J=9.1 Hz), 8.45 (1H, dd, J=9.1 Hz, 2.8 Hz), 9.06 (1H, d, J=2.8 Hz).

Reference Example 100

[4-(5-Nitropyridin-2-yloxy)-2,3-dihydroindol-1-yl]acetic acid $^1$H NMR (DMSO-d$_6$) δ 2.71 (2H, t, J=8.5 Hz), 3.49 (2H, t, J=8.5 Hz), 3.96 (2H, s), 6.35-6.40 (2H, m), 7.02-7.08 (1H, m), 7.20 (1H, d, J=9.1 Hz), 8.61 (1H, dd, J=9.1 Hz, 3.0 Hz), 9.05 (1H, d, J=3.0 Hz), 12.63 (1H, brs).

Reference Example 101

1-Methyl-5-(5-methylaminopyridin-2-yloxy)-1H-indole-2-carboxylic acid $^1$H NMR (CDCl$_3$) δ 2.67 (3H, s), 3.43 (2H, brs), 4.02 (3H, s), 6.78 (1H, d, J=8.7 Hz), 7.03 (1H, dd, J=8.9 Hz, 2.3 Hz), 7.06 (1H, dd, J=8.7 Hz, 2.8 Hz), 7.15 (1H, s), 7.22 (1H, d, J=2.3 Hz), 7.48 (1H, d, J=2.8 Hz), 7.55 (1H, d, J=8.9 Hz).

Reference Example 102

[5-(5-Bromopyridin-2-yloxy)indol-1-yl]acetic acid $^1$H NMR (DMSO-d$_6$) δ 5.03 (2H, s), 6.43 (1H, d, J=3.1 Hz), 6.91 (1H, dd, J=8.8 Hz, 2.3 Hz), 6.95 (1H, d, J=8.8 Hz), 7.30 (1H, d, J=2.3 Hz), 7.34-7.47 (2H, m), 7.99 (1H, dd, J=8.8 Hz, 2.6 Hz), 8.23 (1H, d, J=2.6 Hz), 12.60-13.30 (1H, m).

Reference Example 103

6-{1-[2-(4-Benzo[1,3]dioxol-5-ylmethylpiperazin-1-yl)-2-oxo-ethyl]-2,3-dihydro-1H-indol-4-yloxy}nicotinic acid $^1$H NMR (DMSO-d$_6$) δ 2.34-2.41 (4H, m), 2.66 (2H, t, J=8.2 Hz), 3.40-3.46 (8H, m), 4.05 (2H, s), 5.99 (2H, s), 6.31-6.34 (2H, m), 6.75-6.78 (1H, m), 6.84-6.88 (2H, m), 6.97-7.06 (2H, m), 8.26 (1H, dd, J=8.6 Hz, 2.3 Hz), 8.68 (1H, d, J=2.0 Hz).

Reference Example 104

1-Methyl-5-[5-(4-trifluoromethylbenzoylamino)pyridin-2-yloxy]-1H-indole-2-carboxylic acid $^1$H NMR (DMSO-d$_6$) δ 4.05 (3H, s), 7.02 (1H, d, J=8.1 Hz), 7.13 (1H, dd, J=2.2 Hz, 8.9 Hz), 7.20 (1H, s), 7.40 (1H, d, J=2.4 Hz), 7.61 (1H, d, J=9.2 Hz), 7.93 (2H, d, J=8.1 Hz), 8.16 (2H, d, J=8.9 Hz), 8.21 (1H, d, J=2.7 Hz), 8.47 (1H, d, J=2.7 Hz), 10.59 (1H, s), 12.96 (1H, s).

Reference Example 105

1-Methyl-6-[5-(4-trifluoromethylbenzoylamino)pyridin-2-yloxy]-1H-indole-2-carboxylic acid $^1$HNMR (DMSO-d$_6$) δ 3.98 (3H, s), 6.90 (1H, dd, J=2.2 Hz, 8.6 Hz), 7.08 (1H, d, J=8.9 Hz), 7.24 (1H, s), 7.36 (1H, d, J=1.9 Hz), 7.69 (1H, d, J=8.6 Hz), 7.93 (2H, d, J=8.4 Hz), 8.17 (2H, d, J=8.4 Hz), 8.23 (1H, dd, J=2.7 Hz, 8.9 Hz), 8.51 (1H, d, J=2.7 Hz), 10.65 (1H, s).

Reference Example 106

1-Methyl-7-[5-(4-trifluoromethylbenzoylamino)pyridin-2-yloxy]-1H-indole-2-carboxylic acid $^1$H NMR (DMSO-d$_6$) δ 4.04 (3H, s), 6.80 (1H, d, J=7.6 Hz), 6.83 (1H, s), 6.98 (1H, t, J=8.1 Hz), 7.07 (1H, d, J=8.6 Hz), 7.40 (1H, d, J=7.6 Hz), 7.92 (2H, d, J=8.1 Hz), 8.16 (1H, d, J=8.1 Hz), 8.24 (1H, dd, J=2.7 Hz, 8.9 Hz), 8.46 (1H, d, J=2.4 Hz), 10.66 (1H, s).

Reference Example 107

1-Methyl-4-[5-(4-trifluoromethylbenzoylamino)pyridin-2-yloxy]-1H-indole-2-carboxylic acid $^1$H NMR (DMSO-d$_6$) δ 4.05 (3H, s), 6.79 (1H, s), 6.87 (1H, d, J=7.6 Hz), 7.13 (1H, d, J=8.6 Hz), 7.35 (1H, t, J=7.6 Hz), 7.45 (1H, d, J=8.4 Hz), 8.16 (2H, d, J=8.4 Hz), 8.24 (1H, dd, J=2.7 Hz, 8.9 Hz), 8.47 (1H, d, J=2.4 Hz), 10.63 (1H, s).

Reference Example 108

1,4-Dimethyl-5-[5-(4-trifluoromethylbenzoylamino)pyridin-2-yl-oxy]-1H-indole-2-carboxylic acid $^1$H NMR (DMSO-d$_6$) δ 2.27 (3H, s), 4.04 (3H, s), 6.98 (1H, d, J=8.9 Hz), 7.07 (1H, d, J=8.9 Hz), 7.29 (1H, s), 7.45 (1H, d, J=8.9 Hz), 7.93 (2H, d, J=8.1 Hz), 8.14-8.20 (3H, m), 8.41 (1H, d, J=2.7 Hz), 10.59 (1H, s), 12.96 (1H, brs).

Reference Example 109

1-Methyl-6-[5-(4-trifluoromethoxybenzoylamino)pyridin-2-yloxy]-1H-indole-2-carboxylic acid $^1$H NMR (DMSO-d$_6$) δ 3.98 (3H, s), 6.90 (1H, dd, J=8.6 Hz, 2.0 Hz), 7.07 (1H, d, J=8.9 Hz), 7.25 (1H, s), 7.36 (1H, s), 7.54 (2H, d, J=8.2 Hz), 7.69 (1H, d, J=8.6 Hz), 8.10 (2H, d, J=8.9 Hz), 8.21 (1H, dd, J=8.9 Hz, 2.6 Hz), 8.49 (1H, d, J=2.6 Hz), 10.51 (1H, s).

Reference Example 110

6-[5-(2-Chloro-4-trifluoromethylbenzoylamino)pyridin-2-yloxy]-1-methyl-1H-indole-2-carboxylic acid $^1$H NMR (DMSO-d$_6$) δ 3.98 (3H, s), 6.90 (1H, dd, J=8.6 Hz, 1.3 Hz), 7.08 (1H, d, J=8.9 Hz), 7.24 (1H, s), 7.36 (1H, s), 7.69 (1H, d, J=8.6 Hz), 7.87 (2H, s), 8.05 (1H, s), 8.18 (1H, dd, J=8.9 Hz, 2.6 Hz), 8.43 (1H, d, J=2.6 Hz), 10.80 (1H, s), 12.86 (1H, s).

Reference Example 111

6-[5-(3,4-Dichlorobenzoylamino)pyridin-2-yloxy]-1-methyl-1H-indole-2-carboxylic acid $^1$H NMR (DMSO-d$_6$) δ 3.98 (3H, s), 6.90 (1H, dd, J=8.7 Hz, 2.1 Hz), 7.07 (1H, d, J=8.9 Hz), 7.25 (1H, d, J=0.7 Hz), 7.36 (1H, d, J=2.1 Hz), 7.69 (1H, d, J=8.6 Hz), 7.84 (1H, d, J=8.4 Hz), 7.95 (1H, dd, J=8.4 Hz, 2.1 Hz), 8.20 (1H, dd, J=8.9 Hz, 2.6 Hz), 8.23 (1H, d, J=2.1 Hz), 8.48 (1H, d, J=2.6 Hz), 10.55 (1H, s), 12.85 (1H, brs).

Reference Example 112

1-Methyl-6-[5-(4-trifluoromethylbenzoylamino)pyrimidin-2-yloxy]-1H-indole-2-carboxylic acid $^1$H NMR (DMSO-d$_6$) δ 3.99 (3H, s), 6.97 (1H, dd, J=8.6 Hz, 2.0 Hz), 7.24 (1H, s), 7.47 (1H, d, J=2.0 Hz), 7.70 (1H, d, J=8.6 Hz), 7.96 (2H, d, J=8.2 Hz), 8.19 (2H, d, J=8.1 Hz), 8.96 (2H, s), 10.80 (1H, s), 13.04 (1H, brs).

Reference Example 113

1-Methyl-6-(5-methylaminopyridin-2-yloxy)-1H-indole-2-carboxylic acid $^1$H NMR (DMSO-d$_6$) δ 2.68 (3H, s), 3.93 (3H, s), 5.67 (1H, s), 6.78 (1H, dd, J=8.7 Hz, 1.5 Hz), 6.84 (1H, d, J=8.9 Hz), 7.07 (1H, dd, J=8.9 Hz, 3.0 Hz), 7.13 (1H, s), 7.19 (1H, s), 7.51 (1H, d, J=3.0 Hz), 7.61 (1H, d, J=8.9 Hz), 12.78 (1H, s).

Reference Example 114

6-(5-Aminopyridin-2-yloxy)-1H-indole-2-carboxylic acid $^1$H NMR (CDCl$_3$) δ 5.20 (1H, s), 6.77 (2H, d, J=8.6 Hz), 6.89 (1H, d, J=1.0 Hz), 7.07 (1H, s), 7.09 (1H, dd, J=8.6 Hz, 1.4 Hz), 7.55-7.56 (2H, m), 11.56 (1H, s).

Reference Example 115

6-(5-Methylaminopyridin-2-yloxy)-1H-indole-2-carboxylic acid $^1$H NMR (DMSO-d$_6$) δ 2.69 (3H, s), 5.70 (1H, s), 6.77 (1H, dd, J=8.6 Hz, 2.3 Hz), 6.84 (1H, d, J=8.9 Hz), 6.90 (1H, d, J=2.3 Hz), 7.06 (1H, d, J=2.6 Hz), 7.08 (1H, dd, J=8.9 Hz, 3.0 Hz), 7.53 (1H, d, J=3.0 Hz), 7.59 (1H, d, J=8.6 Hz), 11.56 (1H, s).

Reference Example 116

1-Methyl-6-(5-methylaminopyrimidin-2-yloxy)-1H-indole-2-carboxylic acid $^1$H NMR (DMSO-d$_6$) δ 2.70 (3H, s), 3.96 (3H, s), 5.81 (1H, s), 6.85 (1H, dd, J=8.7 Hz, 2.1 Hz), 7.22 (1H, s), 7.30 (1H, d, J=2.0 Hz), 7.64 (1H, d, J=8.6 Hz), 7.97 (2H, s), 12.86 (1H, brs).

Reference Example 117

1-Methoxymethyl-6-(5-methylaminopyridin-2-yloxy)-1H-indole-2-carboxylic acid $^1$H NMR (DMSO-d$_6$) δ 2.69 (3H, s), 3.14 (3H, s), 5.87 (2H, s), 6.83 (1H, dd, J=8.4 Hz, 2.2 Hz), 6.86 (1H, d, J=8.6 Hz), 7.08 (1H, dd, J=8.7 Hz, 3.1 Hz), 7.23 (1H, d, J=1.6 Hz), 7.29 (1H, s), 7.51 (1H, d, J=3.0 Hz), 7.64 (1H, d, J=8.6 Hz).

Reference Example 118

6-[5-(Methanesulfonylmethylamino)pyridin-2-yloxy]-1H-indole-2-carboxylic acid $^1$H NMR (DMSO-d$_6$) δ 3.00 (3H, s), 3.25 (3H, s), 6.87 (1H, dd, J=8.7 Hz, 2.1 Hz), 7.06 (1H, d, J=8.9 Hz), 7.12-7.13 (2H, m), 7.67 (1H, d, J=8.6 Hz), 7.91 (1H, dd, J=8.7 Hz, 2.8 Hz), 8.17 (1H, d, J=3.0 Hz), 11.77 (1H, s), 12.94 (1H, s).

Reference Example 119

6-[5-(2-Methoxy-4-trifluoromethylbenzoylamino)pyridin-2-yloxy]-1-methyl-1H-indole-2-carboxylic acid $^1$H NMR (DMSO-d$_6$) δ 3.96 (3H, s), 3.98 (3H, s), 6.89 (1H, dd, J=8.6 Hz, 2.0 Hz), 7.06 (1H, d, J=8.7 Hz), 7.25 (1H, s), 7.35 (1H, d, J=2.0 Hz), 7.43 (1H, d, J=7.9 Hz), 7.46 (1H, s), 7.69 (1H, d, J=8.6 Hz), 7.77 (1H, d, J=7.6 Hz), 8.19 (1H, dd, J=8.9 Hz, 2.8 Hz), 8.45 (1H, d, J=2.6 Hz), 10.42 (1H, s), 12.85 (1H, brs).

Reference Example 120

6-[5-(2,4-Bistrifluoromethylbenzoylamino)pyridin-2-yloxy]-1-methyl-1H-indole-2-carboxylic acid $^1$H NMR (DMSO-d$_6$) δ 3.99 (3H, s), 6.89 (1H, dd, J=8.6 Hz, 2.0 Hz), 7.08 (1H, d, J=8.9 Hz), 7.21 (1H, s), 7.36 (1H, d, J=1.5 Hz), 7.68 (1H, d, J=8.7 Hz), 8.02 (1H, d, J=7.9 Hz), 8.15 (1H, dd, J=8.9 Hz, 2.6 Hz), 8.23-8.26 (2H, m), 8.39 (1H, d, J=2.6 Hz), 10.87 (1H, s), 12.87 (1H, brs).

Reference Example 121

1-Methyl-6-(5-methylaminopyridin-2-yloxy)-2,3-dihydro-1H-indole-2-carboxylic acid $^1$H NMR (DMSO-d$_6$) δ 2.66-2.67 (6H, m), 2.84 (1H, dd, J=15.7 Hz, 9.4 Hz), 2.99 (1H, dd, J=15.8 Hz, 9.6 Hz), 3.66 (1H, t, J=9.6 Hz), 5.61 (1H, q, J=4.9 Hz), 5.90 (1H, d, J=2.0 Hz), 5.97 (1H, dd, J=7.6 Hz, 2.0 Hz), 6.71 (1H, d, J=8.6 Hz), 6.79 (1H, d, J=7.9 Hz), 7.02 (1H, dd, J=8.7 Hz, 3.1 Hz), 7.50 (1H, d, J=3.0 Hz).

Reference Example 122

6-[5-(3,4-Dichlorobenzenesulfonylamino)-4-methylpyridin-2-yloxy]-1-methyl-1H-indole-2-carboxylic acid $^1$H NMR (CDCl$_3$) δ 2.08 (3H, s), 3.96 (3H, s), 6.85 (1H, dd, J=8.9 Hz, 2.0 Hz), 6.90 (1H, s), 7.23 (1H, s), 7.35 (1H, s), 7.54 (1H, s), 7.62 (1H, dd, J=8.6 Hz, 2.0 Hz), 7.67 (1H, d, J=8.6 Hz), 7.85 (1H, d, J=2.0 Hz), 7.88 (1H, d, J=8.2 Hz), 10.01 (1H, s).

Reference Example 123

6-(5-tert-Butoxycarbonylamino-4-methylpyridin-2-yloxy)-1-methyl-1H-indole-2-carboxylic acid $^1$H NMR (DMSO-d$_6$) δ 1.45 (9H, s), 2.21 (3H, s), 3.97 (3H, s), 6.84-6.88 (2H, m), 7.23 (1H, d, J=0.7 Hz), 7.33 (1H, d, J=2.0 Hz), 7.67 (1H, d, J=8.6 Hz), 7.94 (1H, s), 8.67 (1H, s), 12.86 (1H, brs).

Reference Example 124

Production of 1-(4-benzo[1,3]dioxol-5-ylmethylpiperazin-1-yl)-2-[4-(5-nitropyridin-2-yloxy)indol-1-yl]ethanone

[4-(5-Nitropyridin-2-yloxy)indol-1-yl]acetic acid (0.210 g, 0.670 mmol) was dissolved in a mixture of THF (10 mL)-DMF (2 mL). To the solution were added 1-benzo[1,3]dioxol-5-yl-methylpiperazine (0.148 g, 0.670 mmol), then 1-ethyl-3-(3-di-methylaminopropyl)carbodiimide hydrochloride (0.129 g, 0.670 mmol), and the resulting solution was stirred for 3 hours at room temperature. Brine (50 mL) was added to the reaction solution, and the mixture was extracted with ethyl acetate (30 mL). After the organic layer was washed with brine, then dried over anhydrous sodium sulfate, the solvent was evaporated. The obtained residue was recrystallized from ethyl acetate to yield 0.258 g of the title compound as pale brown powder.

$^1$H NMR (CDCl$_3$) δ 2.37 (2H, t, J=4.9 Hz), 2.43 (2H, t, J=4.9 Hz), 3.42 (2H, s), 3.48 (2H, t, J=4.9 Hz), 3.66 (2H, t, J=4.9 Hz), 4.93 (2H, s), 5.95 (2H, s), 6.29-6.30 (1H, m), 6.70-6.77 (2H, m), 6.83 (1H, d, J=1.2 Hz), 6.93 (1H, dd, J=7.0 Hz, 1.3 Hz), 7.00 (1H, d, J=9.1 Hz), 7.06 (1H, d, J=3.3 Hz), 7.19-7.29 (2H, m), 8.44 (1H, dd, J=9.1 Hz, 3.0 Hz), 9.06 (1H, d, J=2.8 Hz).

The following compounds were produced in the same manner as in Reference Example 124 using appropriate starting materials.

Reference Example 125

1-(4-Benzo[1,3]dioxol-5-ylmethylpiperazin-1-yl)-2-[5-(5-nitro-pyridin-2-yloxy)-2,3-dihydroindol-1-yl]ethanone $^1$H NMR (CDCl$_3$) δ 2.44 (4H, t, J=4.8 Hz), 3.03 (2H, t, J=8.2 Hz), 3.44 (2H, s), 3.49-3.55 (4H, m), 3.65 (2H, t, J=4.8 Hz), 3.88 (2H, s), 5.95 (2H, s), 6.44 (1H, d, J=8.2 Hz), 6.74-6.75 (2H, m), 6.80-6.89 (3H, m), 6.96 (1H, d, J=9.1 Hz), 8.43 (1H, dd, J=9.1 Hz, 2.8 Hz), 9.06 (1H, d, J=2.8 Hz).

Reference Example 126

1-(4-Benzo[1,3]dioxol-5-ylmethylpiperazin-1-yl)-2-[4-(5-nitro-pyridin-2-yloxy)-2,3-dihydroindol-1-yl]ethanone $^1$H NMR (CDCl$_3$) δ 2.44 (4H, t, J=4.9 Hz), 2.83 (2H, t, J=8.2 Hz), 3.44 (2H, s), 3.51 (2H, t, J=8.2 Hz), 3.52 (2H, t, J=4.8 Hz), 3.65 (2H, t, J=4.8 Hz), 3.92 (2H, s), 5.95 (2H, s), 6.35 (1H, d, J=7.6 Hz), 6.45 (1H, d, J=8.1 Hz), 6.74-6.75 (2H, m), 6.85 (1H, s), 6.99 (1H, d, J=9.1 Hz), 7.10-7.16 (1H, m), 8.45 (1H, dd, J=9.1 Hz, 2.8 Hz), 9.07 (1H, d, J=2.8 Hz).

Reference Example 127

(4-Benzo[1,3]dioxol-5-ylmethylpiperazin-1-yl)[1-methyl-5-(5-methylaminopyridin-2-yloxy)-1H-indol-2-yl]methanone $^1$H NMR (CDCl$_3$) δ 2.20 (1H, brs), 2.47 (4H, brs), 2.81 (3H, s), 3.45 (2H, s), 3.76 (4H, brs), 3.81 (3H, s), 5.95 (2H, s), 6.51 (1H, s), 6.75 (2H, s), 6.75 (1H, d, J=8.8 Hz), 6.86 (1H, s), 6.98 (1H, dd, J=8.8 Hz, 3.0 Hz), 7.05 (1H, dd, J=8.8 Hz, 2.3 Hz), 7.28 (1H, d, J=2.3 Hz), 7.32 (1H, d, J=8.8 Hz), 7.61 (1H, d, J=3.0 Hz).

Reference Example 128

1-(4-Benzo[1,3]dioxol-5-ylmethylpiperazin-1-yl)-2-[5-(5-bromo-pyridin-2-yloxy)indol-1-yl]ethanone $^1$H NMR (CDCl$_3$) δ 2.25-2.50 (4H, m), 3.41 (2H, s), 3.40-3.54 (2H, m), 3.57-3.72 (2H, m), 4.90 (2H, s), 5.95 (2H, s), 6.50-6.55 (1H, m), 6.68-6.79 (3H, m), 6.40-6.46 (1H, m), 6.98 (1H, dd, J=8.8 Hz, 2.3 Hz), 7.12 (1H, d, J=3.2 Hz), 7.22-7.30 (1H, m), 7.36 (1H, d, J=2.3 Hz), 7.70 (1H, dd, J=8.7 Hz, 2.6 Hz), 8.18-8.23 (1H, m).

Reference Example 129

6-{1-[2-(4-Benzo[1,3]dioxol-5-ylmethylpiperazin-1-yl)-2-oxo-ethyl]-2,3-dihydro-1H-indol-4-yloxy}nicotinic acid ethyl ester $^1$H NMR (CDCl$_3$) δ 1.38 (3H, t, J=7.1 Hz), 2.41-2.45 (4H, m), 2.82 (2H, t, J=8.2 Hz), 3.41-3.50 (2H, m), 3.43 (2H, s), 3.51-3.55 (2H, m), 3.63-3.66 (2H, m), 3.90 (2H, s), 4.38 (2H, q, J=7.1 Hz), 5.95 (2H, s), 6.33 (1H, d, J=7.8 Hz), 6.47 (1H, d, J=7.9 Hz), 6.73-6.74 (2H, m), 6.85-6.91 (2H, m), 7.08-7.14 (1H, m), 8.25 (1H, dd, J=8.6 Hz, 2.5 Hz), 8.84 (1H, d, J=2.5 Hz).

Reference Example 130

(R)-3-Methyl-4-{1-methyl-5-[5-(4-trifluoromethylbenzoylamino)-pyridin-2-yloxy]-1H-indole-2-carbonyl}piperazine-1-carboxylic acid tert-butyl ester $^1$H NMR (CDCl$_3$) δ 1.30 (3H, d, J=6.5 Hz), 1.48 (9H, s), 2.88 (1H, brs), 3.05 (1H, brs), 3.27 (1H, brs), 3.82 (3H, s), 3.91 (1H, brs), 4.22 (2H, brs), 4.69 (1H, brs), 6.54 (1H, s), 6.94 (1H, d, J=8.9 Hz), 7.10 (1H, dd, J=2.4 Hz, 8.9 Hz), 7.36-7.39 (2H, m), 7.76 (2H, d, J=8.4 Hz), 7.85 (1H, s), 7.99 (2H, d, J=8.4 Hz), 8.17 (1H, dd, J=2.7 Hz, 8.6 Hz), 8.24 (1H, d, J=2.4 Hz).

Reference Example 131

4-{1-Methyl-6-[5-(4-trifluoromethylbenzoylamino)pyridin-2-yloxy]-1H-indole-2-carbonyl}piperazine-1-carboxylic acid tert-butyl ester $^1$H NMR (CDCl$_3$) δ 1.48 (9H, s), 3.50 (4H, brs), 3.76 (4H, t, J=4.9 Hz), 3.80 (3H, s), 6.60 (1H, s), 6.95 (1H, dd, J=2.2 Hz, 8.6 Hz), 6.99 (1H, d, J=8.6 Hz), 7.15 (1H, d, J=1.9 Hz), 7.62 (1H, d, J=8.4 Hz), 7.77 (2H, d, J=8.4 Hz), 7.83 (1H, s), 8.00 (2H, d, J=8.1 Hz), 8.21 (1H, dd, J=2.7 Hz, 8.9 Hz), 8.27 (1H, d, J=2.4 Hz).

Reference Example 132

4-{1,4-Dimethyl-5-[5-(4-trifluoromethylbenzoylamino)pyridin-2-yl-oxy]-1H-indole-2-carbonyl}piperazine-1-carboxylic acid tert-butyl ester $^1$H NMR (CDCl$_3$) δ 1.49 (9H, s), 2.35 (3H, s), 3.51-3.52 (4H, m), 3.75-3.78 (4H, m), 3.83 (3H, s), 6.62 (1H, s), 6.91 (1H, d, J=8.9 Hz), 7.06 (1H, d, J=8.9 Hz), 7.24 (1H, d, J=10.8 Hz), 7.76 (2H, d, J=8.1 Hz), 7.83 (1H, s), 7.99 (1H, d, J=8.4 Hz), 8.18 (1H, dd, J=2.7 Hz, 8.6 Hz), 8.22 (1H, d, J=2.2 Hz).

Reference Example 133

4-{1-Methyl-6-[5-(4-trifluoromethoxybenzoylamino)pyridin-2-yl-oxy]-1H-indole-2-carbonyl}piperazine-1-carboxylic acid tert-butyl ester $^1$H NMR (CDCl$_3$) δ 1.49 (9H, s), 3.51 (4H, d, J=5.3 Hz), 3.75 (4H, t, J=5.1 Hz), 3.79 (3H, s), 6.60 (1H, d, J=0.7 Hz), 6.93-6.99 (2H, m), 7.14 (1H, d, J=2.0 Hz), 7.33 (2H, d, J=7.9 Hz), 7.62 (1H, d, J=8.6 Hz), 7.82 (1H, s), 7.94 (2H, dt, J=9.2 Hz, 2.5 Hz), 8.18-8.26 (2H, m).

Reference Example 134

4-{6-[5-(2-Chloro-4-trifluoramethylbenzoylamino)pyridin-2-yloxy]-1-methyl-1H-indole-2-carbonyl}piperazine-1-carboxylic acid tert-butyl ester $^1$H NMR (CDCl$_3$) δ 1.49 (9H, s), 3.34-3.50 (4H, m), 3.76 (4H, t, J=5.1 Hz), 3.80 (3H, s), 6.60 (1H, s), 6.93-7.01 (2H, m), 7.15 (1H, s), 7.61-7.67 (2H, m), 7.75 (1H, s), 7.89 (1H, d, J=7.9 Hz), 7.92 (1H, s), 8.23 (1H, dd, J=8.9 Hz, 2.6 Hz), 8.27 (1H, d, J=2.6 Hz).

Reference Example 135

4-{6-[5-(3,4-Dichlorobenzoylamino)pyridin-2-yloxy]-1-methyl-1H-indole-2-carbonyl}piperazine-1-carboxylic acid tert-butyl ester $^1$H NMR (CDCl$_3$) δ 1.49 (9H, s), 3.50 (4H, t, J=4.9 Hz), 3.74 (4H, t, J=5.6 Hz), 3.78 (3H, s), 6.59 (1H, s), 6.68 (1H, dd, J=8.6 Hz, 1.9 Hz), 6.95 (1H, d, J=8.9 Hz), 7.13 (1H, d, J=2.0 Hz), 7.55 (1H, d, J=8.1 Hz), 7.61 (1H, d, J=8.6 Hz), 7.71 (1H, dd, J=8.4 Hz, 2.1 Hz), 7.92 (1H, brs), 7.98 (1H, d, J=2.0 Hz), 8.15 (1H, dd, J=8.7 Hz, 2.8 Hz), 8.26 (1H, d, J=2.6 Hz).

Reference Example 136

4-[1-Methyl-6-(5-methylaminopyrimidin-2-yloxy)-1H-indole-2-carbonyl]piperazine-1-carboxylic acid tert-butyl ester $^1$H NMR (CDCl$_3$) δ 1.49 (9H, s), 2.87 (3H, d, J=4.9 Hz), 3.50 (4H, t, J=5.1 Hz), 3.56-3.58 (1H, m), 3.75 (4H, t, J=4.9 Hz), 3.80 (3H, s), 6.59 (1H, d, J=0.7 Hz), 6.97 (1H, dd, J=8.6 Hz, 2.0 Hz), 7.17 (1H, d, J=2.0 Hz), 7.61 (1H, d, J=8.6 Hz), 7.98 (2H, s).

Reference Example 137

4-[1-Methyl-6-(5-methylaminopyridin-2-yloxy)-1H-indole-2-carbonyl]piperazine-1-carboxylic acid tert-butyl ester $^1$H NMR (CDCl$_3$) δ 1.49 (9H, s), 2.83 (3H, s), 3.45-3.60 (4H, m), 3.76 (7H, s), 6.57 (1H, s), 6.80 (1H, d, J=8.9 Hz), 6.90 (1H, dd, J=8.6 Hz, 2.0 Hz), 7.00 (1H, dd, J=8.6 Hz, 3.2 Hz), 7.04 (1H, d, J=1.9 Hz), 7.56 (1H, d, J=8.6 Hz), 7.64 (1H, d, J=3.0 Hz).

Reference Example 138

[1-Methyl-6-(5-methylaminopyridin-2-yloxy)-1H-indol-2-yl][4-(4-propoxybenzyl)piperazin-1-yl]methanone $^1$H NMR (CDCl$_3$) δ 1.04 (3H, t, J=7.6 Hz), 1.74-1.87 (2H, m), 2.47 (4H, s), 2.87 (3H, s), 3.49 (2H, s), 3.53 (1H, s), 3.75 (7H, s), 3.92 (2H, t, J=6.5 Hz), 6.55 (1H, d, J=0.7 Hz), 6.80 (1H, d, J=8.2 Hz), 6.85-6.91 (3H, m), 6.99-7.04 (2H, m), 7.22 (1H, d, J=8.4 Hz), 7.54 (1H, d, J=8.6 Hz), 7.64 (1H, d, J=3.0 Hz).

Reference Example 139

[1-Methoxymethyl-6-(5-methylaminopyridin-2-yloxy)-1H-indol-2-yl]-{4-[4-(2,2,2-trifluoroethoxy)benzyl]piperazin-1-yl}methanone $^1$H NMR (CDCl$_3$) δ 2.45 (4H, s), 2.79 (3H, s), 3.20 (3H, s), 3.48 (2H, s), 3.76 (5H, s), 4.34 (2H, q, J=8.2 Hz), 5.56 (2H, s), 6.60 (1H, s), 6.77 (1H, d, J=8.6 Hz), 6.88-6.99 (4H, m), 7.19 (1H, d, J=8.2 Hz), 7.26 (2H, d, J=8.2 Hz), 7.56 (1H, t, J=7.1 Hz), 7.61 (1H, d, J=3.0 Hz).

Reference Example 140

[6-(5-Methylaminopyridin-2-yloxy)-1H-indol-2-yl]{4-[4-(2,2,2-tri-fluoroethoxy)benzyl]piperazin-1-yl}methanone $^1$H NMR (CDCl$_3$) δ 2.51 (4H, t, J=5.1 Hz), 2.85 (3H, s), 3.51 (2H, s), 3.57 (1H, s), 3.91 (4H, s), 4.35 (2H, q, J=8.1 Hz), 6.72 (1H, dd, J=2.0 Hz, 1.0 Hz), 6.81 (1H, dd, J=8.6 Hz, 0.7 Hz), 6.88-6.95 (3H, m), 7.01 (1H, dd, J=8.9 Hz, 3.0 Hz), 7.07 (1H, d, J=1.9 Hz), 7.29 (2H, d, J=8.4 Hz), 7.57 (1H, d, J=8.9 Hz), 7.65 (1H, d, J=3.0 Hz), 9.00 (1H, s).

Reference Example 141

[6-(5-Aminopyridin-2-yloxy)-1H-indol-2-yl]{4-[4-(2,2,2-trifluoro-ethoxy)benzyl]piperazin-1-yl}methanone $^1$H NMR (CDCl$_3$) δ 2.51 (4H, t, J=4.9 Hz), 3.51 (4H, s), 3.91 (4H, s), 4.35 (2H, q, J=8.1 Hz), 6.72 (1H, d, J=2.0 Hz), 6.77 (1H, d, J=8.6 Hz), 6.88-6.93 (3H, m), 7.06-7.10 (2H, m), 7.29 (2H, d, J=8.6 Hz), 7.57 (1H, d, J=8.6 Hz), 7.72 (1H, d, J=3.0 Hz), 9.03 (1H, s).

Reference Example 142

[1-Methyl-6-(5-methylaminopyridin-2-yloxy)-2,3-dihydro-1H-indol-2-yl]{4-[4-(2,2,2-trifluoroethoxy)benzyl]piperazin-1-yl}methanone $^1$H NMR (CDCl$_3$) δ 2.40 (2H, s), 2.47 (2H, s), 2.70 (3H, s), 2.77 (3H, s), 2.93 (1H, dd, J=15.8 Hz, 9.9 Hz), 3.24 (1H, dd, J=15.5 Hz, 9.9 Hz), 3.48 (2H, s), 4.29 (1H, t, J=9.7 Hz), 4.34 (2H, q, J=7.8 Hz), 4.53 (1H, s), 6.14 (1H, d, J=2.0 Hz), 6.28 (1H, dd, J=7.9 Hz, 2.0 Hz), 6.71 (1H, d, J=8.9 Hz), 6.87-6.96 (4H, m), 7.26 (2H, d, J=8.6 Hz), 7.60 (1H, d, J=3.0 Hz).

Reference Example 143

[4-(4-Isopropoxybenzyl)piperazin-1-yl][1-methyl-6-(5-methylamino-pyrimidin-2-yloxy)-1H-indol-2-yl]methanone $^1$H NMR (CDCl$_3$) δ 1.34 (6H, d, J=6.3 Hz), 2.48 (4H, brs), 2.86 (3H, d, J=5.3 Hz), 3.48 (2H, s), 3.55-3.57 (1H, m), 3.78 (7H, s), 4.49-4.58 (1H, m), 6.57 (1H, s), 6.85 (2H, d, J=8.6 Hz), 6.95 (1H, dd, J=8.6 Hz, 2.0 Hz), 7.17-7.21 (3H, m), 7.59 (1H, d, J=8.6 Hz), 7.98 (2H, s).

Reference Example 144

[4-Methyl-6-(1-methyl-2-{4-[4-(2,2,2-trifluoroethoxy)benzyl]-piperazine-1-carbonyl}-1H-indol-6-yloxy)pyridin-3-yl]carbamic acid tert-butyl ester $^1$H NMR (CDCl$_3$) δ 1.50 (9H, s), 2.26 (3H, s), 2.48 (4H, brs), 3.51 (2H, s), 3.77 (7H, s), 4.35 (2H, q, J=8.1 Hz), 6.05 (1H, brs), 6.57 (1H, s), 6.72 (1H, s), 6.88-6.95 (3H, m), 7.10 (1H, d, J=1.6 Hz), 7.28-7.32 (2H, m), 7.57 (1H, d, J=8.6 Hz), 8.25 (1H, brs).

Reference Example 145

Production of 5-(5-nitropyridin-2-yloxy)-2,3-dihydro-1H-indole 5-(5-Nitropyridin-2-yloxy)-1H-indole (3.00 g, 11.8 mmol) was dissolved in 1,4-dioxane (30 mL). To the solution were added boran-trimethylamine complex (3.43 g, 47.0 mmol) and hydrochloric acid (1.96 mL, 23.5 mmol) and the resulting solution was refluxed for 1 hour. After cooling for 30 minutes, 6 M hydrochloric acid (9.40 mL, 56.4 mmol) was added to the solution, and the mixture was refluxed again. Thirty minutes later, the reaction mixture was cooled with ice and the pH of the solution was adjusted to 8 by dropwise addition of concentrated aqueous sodium hydroxide. Water (150 mL) was added to the solution, and the mixture was extracted with ethyl acetate (150 mL). After the organic layer was washed with brine, then dried over anhydrous sodium sulfate, the solvent was evaporated to yield 2.82 g of the title compound as reddish orange oil.

$^1$H NMR (CDCl$_3$) δ 3.07 (2H, t, J=8.4 Hz), 3.62 (2H, t, J=8.4 Hz), 3.78 (1H, brs), 6.65 (1H, d, J=8.4 Hz), 6.78 (1H, dd, J=8.4 Hz, 2.3 Hz), 6.90 (1H, d, J=2.0 Hz), 6.97 (1H, d, J=9.1 Hz), 8.43 (1H, dd, J=9.1 Hz, 2.8 Hz), 9.07 (1H, d, J=2.8 Hz).

The following compounds were produced in the same manner as in Reference Example 145 using appropriate starting materials.

Reference Example 146

4-(5-Nitropyridin-2-yloxy)-2,3-dihydro-1H-indole $^1$H NMR (CDCl$_3$) δ 2.85 (2H, t, J=8.4 Hz), 3.59 (2H, t, J=8.4 Hz), 6.47 (1H, d, J=7.9 Hz), 6.57 (1H, d, J=7.8 Hz), 7.00 (1H, d, J=9.1 Hz), 7.06-7.12 (1H, m), 8.46 (1H, dd, J=9.1 Hz, 2.8 Hz), 9.07 (1H, d, J=2.8 Hz).

Reference Example 147

6-(2,3-Dihydro-1H-indol-4-yloxy)nicotinic acid ethyl ester $^1$H NMR (CDCl$_3$) δ 1.38 (3H, t, J=7.1 Hz), 2.84 (2H, t, J=8.4 Hz), 3.56 (2H, t, J=8.4 Hz), 3.88 (1H, brs), 4.38 (2H, q, J=7.1 Hz), 6.48 (1H, d, J=8.1 Hz), 6.54 (1H, d, J=7.8 Hz), 6.89 (1H, d, J=8.6 Hz), 7.04-7.10 (1H, m), 8.26 (1H, dd, J=8.6 Hz, 2.3 Hz), 8.85 (1H, d, J=2.3 Hz).

Reference Example 148

Production of
[4-(5-nitropyridin-2-yloxy)indol-1-yl]acetic acid ethyl ester 4-(5-Nitropyridin-2-yloxy)-1H-indole (3.34 g, 13.1 mmol) was dissolved in DMF (20 mL). To the solution were added 60% sodium hydride (0.523 g, 13.1 mmol) and ethyl bromoacetate (1.45 mL, 13.1 mmol) under cooling with ice, and the resulting solution was stirred for 1 hour. Ice water (150 mL) was added to the solution, and the mixture was extracted with ethyl acetate (150 mL). After the organic layer was washed with brine, then dried over anhydrous sodium sulfate, the solvent was evaporated. Thus obtained residue was purified by silica gel column chromatography (AcOEt:n-hexane=1:3), and then the obtained solid was recrystallized from ethyl acetate and n-hexane to yield 1.84 g of the title compound as a yellow powder.

$^1$H NMR (CDCl$_3$) δ 1.28 (3H, t, J=7.1 Hz), 4.24 (2H, q, J=7.1 Hz), 4.86 (2H, s), 6.30 (1H, d, J=3.3 Hz), 6.95 (1H, dd, J=7.3 Hz, 1.2 Hz), 7.02 (1H, d, J=9.1 Hz), 7.08 (1H, d, J=3.3 Hz), 7.21 (1H, d, J=8.2 Hz), 7.25-7.31 (1H, m), 8.47 (1H, dd, J=9.1 Hz, 3.0 Hz), 9.06 (1H, d, J=2.8 Hz).

The following compounds were produced in the same manner as in Reference Example 148 using appropriate starting materials.

Reference Example 149

[5-(5-Nitropyridin-2-yloxy)-2,3-dihydroindol-1-yl] acetic acid ethyl ester $^1$H NMR (CDCl$_3$) δ 1.29 (3H, t, J=7.1 Hz), 3.06 (2H, t, J=8.4 Hz), 3.62 (2H, t, J=8.4 Hz), 3.90 (2H, s), 4.22 (2H, q, J=7.1 Hz), 6.39 (1H, d, J=8.4 Hz), 6.82 (1H, dd, J=8.4 Hz, 2.5 Hz), 6.88 (1H, d, J=2.1 Hz), 6.95 (1H, d, J=9.1 Hz), 8.43 (1H, dd, J=9.1 Hz, 2.8 Hz), 9.07 (1H, d, J=2.8 Hz).

Reference Example 150

[4-(5-Nitropyridin-2-yloxy)-2,3-dihydroindol-1-yl] acetic acid ethyl ester $^1$H NMR (CDCl$_3$) δ 1.29 (3H, t, J=7.1 Hz), 2.86 (2H, t, J=8.4 Hz), 3.59 (2H, t, J=8.4 Hz), 3.90 (2H, s), 4.22 (2H, q, J=7.1 Hz), 6.32 (1H, d, J=7.8 Hz), 6.45 (1H, d, J=8.1 Hz), 6.98 (1H, d, J=9.1 Hz), 7.09-7.15 (1H, m), 8.45 (1H, dd, J=9.1 Hz, 2.8 Hz), 9.07 (1H, d, J=2.8 Hz).

Reference Example 151

5-{5-[(3,4-Dichlorobenzoyl)methylamino]pyridin-2-yloxy}-1-methyl-1H-indole-2-carboxylic acid methyl ester $^1$H NMR (CDCl$_3$) δ 3.45 (3H, s), 3.92 (3H, s), 4.08 (3H, s), 6.85 (1H, d, J=8.7 Hz), 7.03-7.14 (2H, m), 7.23-7.27 (1H, m), 7.29 (1H, d, J=8.2 Hz), 7.36-7.46 (4H, m), 7.84 (1H, d, J=2.6 Hz).

Reference Example 152

4-(1-Methyl-5-{5-[methyl(4-trifluoromethylbenzoyl) amino]pyridin-2-yloxy}-1H-indole-2-carbonyl)piperazine-1-carboxylic acid tert-butyl ester $^1$H NMR (CDCl$_3$) δ 1.49 (9H, s), 3.47 (3H, s), 3.48 (4H, brs), 3.74 (4H, brs), 3.84 (3H, s), 6.55 (1H, s), 6.83 (1H, d, J=8.7 Hz), 7.03 (1H, dd, J=8.9 Hz, 2.1 Hz), 7.31 (1H, d, J=2.1 Hz), 7.35 (1H, d, J=8.9 Hz), 7.35-7.46 (1H, m), 7.40 (2H, d, J=8.0 Hz), 7.50 (2H, d, J=8.0 Hz), 7.82 (1H, brs).

Reference Example 153

4-(5-{5-[(3,4-Dichlorobenzoyl)methylamino]pyridin-2-yloxy}-1-methyl-1H-indole-2-carbonyl)piperazine-1-carboxylic acid tert-butyl ester $^1$H NMR (CDCl$_3$) δ 1.49 (9H, s), 3.45 (3H, s), 3.50 (4H, brs), 3.75 (4H, brs), 3.84 (3H, s), 6.56 (1H, s), 6.86 (1H, d, J=8.7 Hz), 7.05 (1H, dd, J=9.0 Hz, 2.3 Hz), 7.08 (1H, dd, J=8.2 Hz, 1.8 Hz), 7.29 (1H, d, J=8.2 Hz), 7.33 (1H, d, J=2.3 Hz), 7.37 (1H, d, J=9.0 Hz), 7.42 (1H, dd, J=8.7 Hz, 2.5 Hz), 7.42 (1H, d, J=1.8 Hz), 7.83 (1H, d, J=2.5 Hz).

Reference Example 154

4-[1-Methyl-5-(5-nitropyridin-2-yloxy)-1H-indole-2-carbonyl]-piperazine-1-carboxylic acid tert-butyl ester $^1$H NMR (CDCl$_3$) δ 1.49 (9H, s), 3.51 (4H, brs), 3.76 (4H, brs), 3.87 (3H, s), 6.59 (1H, s), 7.02 (1H, d, J=9.1 Hz), 7.09

(1H, dd, J=8.9 Hz, 2.2 Hz), 7.39 (1H, d, J=2.2 Hz), 7.42 (1H, d, J=8.9 Hz), 8.45 (1H, dd, J=9.1 Hz, 2.8 Hz), 9.03 (1H, d, J=2.8 Hz).

Reference Example 155

4-(5-{5-[(3,4-Dichlorophenyl)methylamino]pyridin-2-yloxy}-1-methyl-1H-indole-2-carbonyl)piperazine-1-carboxylic acid tert-butyl ester $^1$H NMR (CDCl$_3$) δ 1.48 (9H, s), 3.24 (3H, s), 3.50 (4H, brs), 3.75 (4H, brs), 3.85 (3H, s), 6.58 (1H, dd, J=8.7 Hz, 2.8 Hz), 6.58 (1H, s), 6.83 (1H, d, J=2.8 Hz), 6.90 (1H, d, J=8.7 Hz), 7.13 (1H, dd, J=8.9 Hz, 2.1 Hz), 7.21 (1H, d, J=8.9 Hz), 7.38 (1H, s), 7.40 (1H, d, J=2.1 Hz), 7.46 (1H, dd, J=8.7 Hz, 2.8 Hz), 8.01 (1H, d, J=2.8 Hz).

Reference Example 156

{6-[2-(4-Benzylpiperazine-1-carbonyl)-1-methyl-1H-indol-5-yloxy]-pyridin-3-yl}ethylcarbamic acid tert-butyl ester $^1$H NMR (CDCl$_3$) δ 1.14 (3H, t, J=7.1 Hz), 1.43 (9H, s), 2.65-3.40 (4H, m), 3.62 (2H, q, J=7.1 Hz), 3.82 (3H, s), 3.95-4.50 (6H, m), 6.58 (1H, s), 6.87 (1H, d, J=8.9 Hz), 7.12 (1H, dd, J=8.9 Hz, 2.0 Hz), 7.33-7.69 (8H, m), 7.98 (1H, d, J=2.6 Hz).

Reference Example 157

4-(1-Methyl-5-{5-[methyl(4-trifluoromethylphenyl)amino]pyridin-2-yloxy}-1H-indole-2-carbonyl)piperazine-1-carboxylic acid tert-butyl ester $^1$H NMR (CDCl$_3$) δ 1.48 (9H, s), 3.31 (3H, s), 3.50 (4H, brs), 3.75 (4H, t, J=5.0 Hz), 3.85 (3H, s), 6.57 (1H, s), 6.76 (2H, d, J=8.6 Hz), 6.93 (1H, dd, J=8.7 Hz, 0.6 Hz), 7.14 (1H, dd, J=8.8 Hz, 2.2 Hz), 7.38 (1H, d, J=8.8 Hz), 7.41 (1H, d, J=2.2 Hz), 7.42 (2H, d, J=8.6 Hz), 7.50 (1H, dd, J=8.7 Hz, 3.0 Hz), 8.05 (1H, d, J=3.0 Hz).

Reference Example 158

{6-[2-(4-Benzo[1,3]dioxol-5-ylmethylpiperazine-1-carbonyl)-1-methyl-1H-indol-5-yloxy]pyridin-3-yl}ethylcarbamic acid tert-butyl ester $^1$H NMR (CDCl$_3$) δ 1.13 (3H, t, J=7.1 Hz), 1.42 (9H, s), 2.59 (4H, brs), 3.57 (2H, s), 3.62 (2H, q, J=7.1 Hz), 3.83 (3H, s), 3.87 (4H, brs), 5.96 (2H, s), 6.55 (1H, s), 6.74-6.80 (2H, m), 6.85 (1H, d, J=8.8 Hz), 6.91 (1H, s), 7.09 (1H, dd, J=8.9 Hz, 2.3 Hz), 7.36 (1H, d, J=2.3 Hz), 7.36 (1H, d, J=2.3 Hz), 7.49 (1H, d, J=8.8 Hz), 7.99 (1H, d, J=2.5 Hz).

Reference Example 159

4-(1-Ethyl-5-{5-[methyl(4-trifluoromethylbenzoyl)amino]pyridin-2-yloxy}-1H-indole-2-carbonyl)piperazine-1-carboxylic acid tert-butyl ester $^1$H NMR (CDCl$_3$) δ 1.40 (3H, t, J=7.0 Hz), 1.48 (9H, s), 3.47 (7H, s), 3.74 (4H, brs), 4.31 (2H, q, J=7.0 Hz), 6.52 (1H, s), 6.83 (1H, d, J=8.9 Hz), 7.01 (1H, dd, J=8.6 Hz, 2.2 Hz), 7.52-7.30 (7H, m), 7.83 (1H, s).

Reference Example 160

4-(1-Methyl-5-{4-methyl-5-[methyl(4-trifluoromethylbenzoyl)-amino]pyridin-2-yloxy}-1H-indole-2-carbonyl)piperazine-1-carboxylic acid tert-butyl ester $^1$H NMR (CDCl$_3$) δ 1.49 (9H, s), 2.24 (3H, s), 3.38 (3H, s), 3.49 (4H, brs), 3.74 (4H, brs), 3.83 (3H, s), 6.54 (1H, s), 6.68 (1H, s), 7.00 (1H, dd, J=2.2 Hz, 8.9 Hz), 7.26-7.37 (5H, m), 7.47 (2H, d, J=8.4 Hz), 7.98 (1H, s).

Reference Example 161

4-(1-Methyl-5-{6-methyl-5-[methyl(4-trifluoromethylbenzoyl)-amino]pyridin-2-yloxy}-1H-indole-2-carbonyl)piperazine-1-carboxylic acid tert-butyl ester $^1$H NMR (CDCl$_3$) δ 1.48 (9H, s), 2.32 (3H, s), 3.38 (3H, s), 3.50 (4H, brs), 3.75 (4H, brs), 3.85 (3H, s), 6.46 (1H, d, J=8.4 Hz), 6.55 (1H, s), 7.02 (1H, dd, J=2.2 Hz, 8.6 Hz), 7.25-7.39 (5H, m), 7.48 (2H, d, J=8.1 Hz).

Reference Example 162

4-(5-{5-[(3,4-Dichlorobenzoyl)methylamino]-4-methylpyridin-2-yl-oxy}-1-methyl-1H-indole-2-carbonyl)piperazine-1-carboxylic acid tert-butyl ester $^1$H NMR (CDCl$_3$) δ 1.48 (9H, s), 2.23 (3H, s), 3.35 (3H, s), 3.49 (4H, brs), 3.74 (4H, brs), 3.84 (3H, s), 6.56 (1H, s), 6.70 (1H, s), 7.03 (2H, d, J=8.6 Hz), 7.24-7.38 (4H, m), 7.80 (1H, s).

Reference Example 163

4-(5-{5-[(3,4-Dichlorobenzoyl)methylamino]-6-methylpyridin-2-yl-oxy}-1-methyl-1H-indole-2-carbonyl)piperazine-1-carboxylic acid tert-butyl ester $^1$H NMR (CDCl$_3$) δ 1.48 (9H, s), 2.30 (3H, s), 3.35 (3H, s), 3.50 (4H, brs), 3.76 (4H, brs), 3.85 (3H, s), 6.51 (1H, d, J=8.4 Hz), 6.56 (1H, s), 7.05 (2H, d, J=8.6 Hz), 7.26-7.41 (5H, m).

Reference Example 164

[4-(4-Methoxybenzyl)piperazin-1-yl][1-methyl-5-(5-methylamino-pyridin-2-yloxy)-1H-indol-2-yl]methanone $^1$H NMR (CDCl$_3$) δ 2.47 (4H, brs), 2.83 (3H, s), 3.49 (2H, s), 3.76 (4H, brs), 3.80 (3H, s), 3.81 (3H, s), 6.51 (1H, s), 6.75 (1H, d, J=8.6 Hz), 6.86 (2H, d, J=8.9 Hz), 6.98 (1H, dd, J=3.2 Hz, 8.9 Hz), 7.06 (1H, dd, J=2.4 Hz, 8.9 Hz), 7.21-7.33 (4H, m), 7.61 (1H, d, J=3.0 Hz).

Reference Example 165

(R)-3-Methyl-4-(1-methyl-5-{5-[methyl(4-trifluoromethylbenzoyl)-amino]pyridin-2-yloxy}-1H-indole-2-carbonyl)piperazine-1-carboxylic acid tert-butyl ester $^1$H NMR (CDCl$_3$) δ 1.29 (3H, d, J=6.8 Hz), 1.48 (9H, s), 2.88 (1H, brs), 3.05 (1H, brs), 3.25 (1H, t, J=12.2 Hz), 3.47

(3H, s), 3.81 (3H, s), 3.91 (1H, brs), 4.20 (2H, brs), 4.68 (1H, brs), 6.52 (1H, d, J=0.5 Hz), 6.83 (1H, d, J=8.6 Hz), 7.02 (1H, dd, J=2.2 Hz, 8.6 Hz), 7.30-7.41 (5H, m), 7.50 (2H, d, J=8.4 Hz), 8.01 (1H, s).

Reference Example 166

(S)-3-Methyl-4-(1-methyl-5-{5-[methyl(4-trifluoromethylbenzoyl)-amino]pyridin-2-yloxy}-1H-indole-2-carbonyl)piperazine-1-carboxylic acid tert-butyl ester $^1$H NMR (CDCl$_3$) δ 1.29 (3H, d, J=6.8 Hz), 1.48 (9H, s), 2.88 (1H, brs), 3.05 (1H, brs), 3.25 (1H, t, J=12.2 Hz), 3.47 (3H, s), 3.81 (3H, s), 3.91 (1H, brs), 4.20 (2H, brs), 4.68 (1H, brs), 6.52 (1H, d, J=0.5 Hz), 6.83 (1H, d, J=8.6 Hz), 7.02 (1H, dd, J=2.2 Hz, 8.6 Hz), 7.30-7.41 (5H, m), 7.50 (2H, d, J=8.4 Hz), 8.01 (1H, s).

Reference Example 167

4-(1-Methyl-6-{5-[methyl(4-trifluoromethylbenzoyl)amino]pyridin-2-yloxy}-1H-indole-2-carbonyl)piperazine-1-carboxylic acid tert-butyl ester $^1$H NMR (CDCl$_3$) δ 1.49 (9H, s), 3.48 (3H, s), 3.52 (4H, brs), 3.73-3.75 (4H, m), 3.77 (3H, s), 6.59 (1H, s), 6.86 (1H, d, J=8.6 Hz), 6.87 (1H, d, J=8.4 Hz), 7.08 (1H, d, J=1.6 Hz), 7.40-7.42 (3H, m), 7.51 (2H, d, J=8.1 Hz), 7.60 (1H, d, J=8.4 Hz), 7.85 (1H, s).

Reference Example 168

4-(1,4-Dimethyl-5-{5-[methyl(4-trifluoromethylbenzoyl)amino]-pyridin-2-yloxy}-1H-indole-2-carbonyl)piperazine-1-carboxylic acid tert-butyl ester $^1$H NMR (CDCl$_3$) δ 1.49 (9H, s), 2.19 (3H, s), 3.48 (3H, s), 3.50 (4H, brs), 3.73-3.77 (4H, m), 3.81 (3H, s), 6.58 (1H, s), 6.83 (1H, d, J=8.6 Hz), 6.98 (1H, d, J=8.9 Hz), 7.21 (1H, d, J=8.9 Hz), 7.37 (3H, d, J=8.1 Hz), 7.48 (2H, d, J=8.1 Hz), 7.75 (1H, s).

Reference Example 169

4-(6-{5-[(2-Chloro-4-trifluoromethylbenzoyl)methylamino]pyridin-2-yloxy}-1-methyl-1H-indole-2-carbonyl)piperazine-1-carboxylic acid tert-butyl ester $^1$H NMR (CDCl$_3$) δ 1.49 (9H, s), 3.49 (7H, s), 3.74-3.79 (7H, m), 6.58 (1H, s), 6.79-6.84 (2H, m), 7.00-7.05 (1H, m), 7.32 (1H, d, J=8.2 Hz), 7.42 (1H, d, J=7.9 Hz), 7.49-7.75 (3H, m), 7.92 (1H, d, J=2.6 Hz).

Reference Example 170

4-(1-Methyl-6-{5-[methyl(4-trifluoromethoxybenzoyl)amino]pyridin-2-yloxy}-1H-indole-2-carbonyl)piperazine-1-carboxylic acid tert-butyl ester $^1$H NMR (CDCl$_3$) δ 1.49 (9H, s), 3.47-3.52 (7H, s), 3.74-3.77 (7H, m), 6.59 (1H, s), 6.84-6.89 (2H, m), 7.06 (1H, s), 7.10 (2H, s), 7.35 (2H, d, J=8.9 Hz), 7.42 (1H, dd, J=8.7 Hz, 2.8 Hz), 7.60 (1H, d, J=8.6 Hz), 7.86 (1H, d, J=2.6 Hz).

Reference Example 171

Methyl-[6-(1-methyl-2-{4-[4-(2,2,2-trifluoroethoxy)benzoyl]-piperazine-1-carbonyl}-1H-indol-6-yloxy)pyridin-3-yl]carbamic acid tert-butyl ester $^1$H NMR (CDCl$_3$) δ 1.45 (9H, s), 2.48 (4H, brs), 3.24 (3H, s), 3.51 (2H, s), 3.78 (7H, s), 4.35 (2H, q, J=8.0 Hz), 6.58 (1H, s), 6.87 (1H, d, J=8.9 Hz), 6.87-7.00 (1H, m), 6.91 (1H, d, J=8.6 Hz), 6.92 (1H, dd, J=8.6 Hz, 2.0 Hz), 7.13 (1H, d, J=2.0 Hz), 7.28 (2H, d, J=8.6 Hz), 7.59 (2H, d, J=8.6 Hz), 8.06 (1H, d, J=2.9 Hz).

Reference Example 172

4-(6-{5-[(3,4-Dichlorobenzoyl)methylamino]pyridin-2-yloxy}-1-methyl-1H-indole-2-carbonyl)piperazine-1-carboxylic acid tert-butyl ester $^1$H NMR (CDCl$_3$) δ 1.49 (9H, s), 3.46 (3H, s), 3.50 (4H, t, J=4.9 Hz), 3.75 (4H, t, J=5.1 Hz), 3.79 (3H, s), 6.59 (1H, s), 6.89 (2H, dd, J=8.7 Hz, 1.6 Hz), 7.09 (1H, dd, J=8.1 Hz, 4.1 Hz), 7.10 (1H, s), 7.30 (1H, d, J=8.2 Hz), 7.41 (1H, d, J=1.9 Hz), 7.44 (1H, dd, J=8.9 Hz, 2.7 Hz), 7.61 (1H, d, J=8.6 Hz), 7.85 (1H, d, J=2.6 Hz).

Reference Example 173

6-[5-(Acetylmethylamino)pyridin-2-yloxy]-1-methyl-1H-indole-2-carboxylic acid ethyl ester $^1$H NMR (CDCl$_3$) δ 1.42 (3H, t, J=7.1 Hz), 1.90 (3H, s), 3.25 (3H, s), 4.04 (3H, s), 4.38 (2H, q, J=7.1 Hz), 6.96 (1H, dd, J=8.6 Hz, 2.0 Hz), 7.00 (1H, d, J=8.6 Hz), 7.19 (1H, s), 7.31 (1H, s), 7.54 (1H, dd, J=8.7 Hz, 2.8 Hz), 7.69 (1H, d, J=8.6 Hz), 8.05 (1H, d, J=2.3 Hz).

Reference Example 174

6-[5-(Acetylmethylamino)pyridin-2-yloxy]indole-1,2-dicarboxylic acid 1-tert-butyl ester 2-ethyl ester $^1$H NMR (CDCl$_3$) δ 1.40 (3H, t, J=7.3 Hz), 1.59 (9H, s), 1.90 (3H, s), 3.25 (3H, s), 4.38 (2H, q, J=7.1 Hz), 7.02 (1H, d, J=8.6 Hz), 7.09 (1H, dd, J=8.9 Hz, 2.1 Hz), 7.12 (1H, s), 7.56 (1H, dd, J=8.6 Hz, 2.6 Hz), 7.63 (1H, d, J=8.6 Hz), 7.94 (1H, d, J=1.6 Hz), 8.05 (1H, d, J=2.6 Hz).

Reference Example 175

4-(6-{5-[(2-Fluoro-4-trifluoromethylbenzoyl)methylamino]pyridin-2-yloxy}-1-methyl-1H-indole-2-carbonyl)piperazine-1-carboxylic acid tert-butyl ester $^1$H NMR (CDCl$_3$) δ 1.49 (9H, s), 3.48-3.52 (7H, m), 3.72-3.76 (7H, m), 6.58 (1H, s), 6.83 (2H, dd, J=8.7 Hz, 2.5 Hz), 7.06 (1H, s), 7.14 (1H, d, J=8.9 Hz), 7.35 (1H, d, J=7.9 Hz), 7.47 (2H, t, J=7.4 Hz), 7.59 (1H, d, J=8.6 Hz), 7.84 (1H, d, J=2.6 Hz).

Reference Example 176

4-(6-{5-[(3,4-Dichlorobenzenesulfonyl)methylamino]pyridin-2-yl-oxy}-1-methyl-1H-indole-2-carbonyl)piperazine-1-carboxylic acid tert-butyl ester $^1$H NMR (CDCl$_3$) δ 1.49 (9H, s), 3.21 (3H, s), 3.51-3.52 (4H, m), 3.74-3.78 (4H, m), 3.81 (3H, s), 6.60 (1H, s), 6.92

(1H, d, J=8.1 Hz), 6.93 (1H, dd, J=8.4 Hz, 1.9 Hz), 7.15 (1H, d, J=2.0 Hz), 7.41 (1H, dd, J=8.4 Hz, 2.1 Hz), 7.55 (1H, dd, J=8.9 Hz, 3.0 Hz), 7.57 (1H, d, J=8.6 Hz), 7.63 (1H, d, J=8.6 Hz), 7.72 (1H, d, J=2.0 Hz), 7.82 (1H, d, J=2.3 Hz).

Reference Example 177

4-(1-Methyl-5-{5-[methyl(4-trifluoromethylbenzenesulfonyl)amino]-pyridin-2-yloxy}-1H-indole-2-carbonyl)piperazine-1-carboxylic acid tert-butyl ester $^1$H NMR (CDCl$_3$) δ 1.49 (9H, s), 3.20 (3H, s), 3.50 (4H, brs), 3.75 (4H, t, J=4.9 Hz), 3.85 (3H, s), 6.57 (1H, s), 6.87-6.89 (1H, m), 7.09 (1H, dd, J=8.7 Hz, 2.5 Hz), 7.38-7.40 (2H, m), 7.51 (1H, dd, J=8.9 Hz, 2.6 Hz), 7.76-7.77 (5H, m).

Reference Example 178

4-(5-{5-[(3,4-Dichlorobenzenesulfonyl)methylamino]pyridin-2-yl-oxy}-1-methyl-1H-indole-2-carbonyl)piperazine-1-carboxylic acid tert-butyl ester $^1$H NMR (CDCl$_3$) δ 1.49 (9H, s), 3.20 (3H, s), 3.50 (4H, brs), 3.75 (4H, t, J=4.9 Hz), 3.85 (3H, s), 6.57 (1H, s), 6.89 (1H, d, J=8.9 Hz), 7.09 (1H, dd, J=8.6 Hz, 2.3 Hz), 7.37-7.38 (2H, m), 7.41 (1H, d, J=2.3 Hz), 7.51 (1H, dd, J=8.7 Hz, 2.8 Hz), 7.56 (1H, d, J=8.6 Hz), 7.71 (1H, d, J=2.3 Hz), 7.80 (1H, d, J=3.0 Hz).

Reference Example 179

4-(1-Methyl-5-{5-[methyl(toluene-4-sulfonyl)amino]pyridin-2-yl-oxy}-1H-indole-2-carbonyl)piperazine-1-carboxylic acid tert-butyl ester $^1$H NMR (CDCl$_3$) δ 1.49 (9H, s), 2.42 (3H, s), 3.15 (3H, s), 3.50 (4H, brs), 3.75 (4H, t, J=4.9 Hz), 3.85 (3H, s), 6.57 (1H, s), 6.84 (1H, d, J=8.9 Hz), 7.09 (1H, dd, J=9.1 Hz, 2.1 Hz), 7.26-7.28 (2H, m), 7.38-7.39 (2H, m), 7.48-7.52 (3H, m), 7.75 (1H, d, J=2.6 Hz).

Reference Example 180

6-[5-(tert-Butoxycarbonylmethylamino) pyrimidin-2-yloxy]-1-methyl-1H-indole-2-carboxylic acid ethyl ester $^1$H NMR (CDCl$_3$) δ 1.41 (3H, t, J=7.1 Hz), 1.46 (9H, s), 3.27 (3H, s), 4.04 (3H, s), 4.38 (2H, q, J=7.1 Hz), 6.99 (1H, dd, J=8.6 Hz, 2.0 Hz), 7.22 (1H, d, J=2.0 Hz), 7.31 (1H, d, J=0.8 Hz), 7.69 (1H, d, J=8.7 Hz), 8.48 (2H, s).

Reference Example 181

1-Methoxymethyl-6-{5-[methyl(4-nitrobenzoyl)amino]pyridin-2-yl-oxy}-1H-indole-2-carboxylic acid ethyl ester $^1$H NMR (CDCl$_3$) δ 1.41 (3H, t, J=7.3 Hz), 3.28 (3H, s), 3.50 (3H, s), 4.38 (2H, q, J=7.1 Hz), 5.91 (2H, s), 6.89 (1H, d, J=9.7 Hz), 6.93 (1H, dd, J=8.9 Hz, 1.9 Hz), 7.27 (1H, d, J=0.7 Hz), 7.34 (1H, d, J=0.7 Hz), 7.46 (3H, d, J=8.2 Hz), 7.66 (1H, d, J=8.6 Hz), 7.84 (1H, s), 8.11 (2H, d, J=8.6 Hz).

Reference Example 182

6-[5-(Methanesulfonylmethylamino)pyridin-2-yloxy]indole-1,2-dicarboxylic acid 1-tert-butyl ester 2-ethyl ester $^1$H NMR (CDCl$_3$) δ 1.40 (3H, t, J=7.1 Hz), 1.59 (9H, s), 2.88 (3H, s), 3.32 (3H, s), 4.38 (2H, q, J=7.1 Hz), 6.97 (1H, d, J=8.9 Hz), 7.07 (1H, dd, J=8.6 Hz, 2.3 Hz), 7.11 (1H, d, J=0.7 Hz), 7.61 (1H, d, J=8.6 Hz), 7.76 (1H, dd, J=8.9 Hz, 3.0 Hz), 7.91 (1H, d, J=2.0 Hz), 8.15 (1H, d, J=2.6 Hz).

Reference Example 183

1-Methyl-6-{5-[methyl(4-nitrobenzoyl)amino]pyridin-2-yloxy}-2,3-dihydro-1H-indole-2-carboxylic acid ethyl ester $^1$H NMR (CDCl$_3$) δ 1.30 (3H, t, J=7.3 Hz), 2.79 (3H, s), 3.09 (1H, dd, J=16.8 Hz, 9.2 Hz), 3.32 (1H, dd, J=16.2 Hz, 10.2 Hz), 3.48 (3H, s), 4.13 (1H, dd, J=9.5 Hz, 8.1 Hz), 4.21-4.29 (2H, m), 6.15 (1H, d, J=2.0 Hz), 6.33 (1H, dd, J=7.9 Hz, 2.0 Hz), 6.79 (1H, d, J=8.9 Hz), 6.98 (1H, d, J=7.9 Hz), 7.40 (1H, s), 7.45 (2H, d, J=8.6 Hz), 7.85 (1H, s), 8.08 (2H, d, J=8.6 Hz).

Reference Example 184

Methyl[4-methyl-6-(1-methyl-2-{4-[4-(2,2,2-trifluoroethoxy)-benzyl]piperazine-1-carbonyl}-1H-indol-6-yloxy)pyridin-3-yl]-carbamic acid tert-butyl ester $^1$H NMR (CDCl$_3$) δ 1.35 (5H, s), 1.61 (4H, s), 2.21 (3H, s), 2.48 (4H, brs), 3.15 (3H, s), 3.51 (2H, s), 3.78 (7H, s), 4.35 (2H, q, J=8.1 Hz), 6.58 (1H, s), 6.75 (1H, s), 6.91-6.92 (3H, m), 7.13 (1H, s), 7.27-7.29 (2H, m), 7.60 (1H, d, J=8.6 Hz), 7.91 (1H, s).

Reference Example 185

Production of 6-{5-[(3,4-dichlorobenzenesulfonyl)methylamino]-4-methylpyridin-2-yloxy}-1-methyl-1H-indole-2-carboxylic acid To a solution of 6-[5-(3,4-dichlorobenzenesulfonylamino)-4-methylpyridin-2-yloxy]-1-methyl-1H-indole-2-carboxylic acid ethyl ester (3.1 g, 5.80 mmol) in DMF (30 mL) was added 60% sodium hydride in oil (0.302 g, 7.54 mmol) under ice cooling. After the mixture was stirred for several minutes, iodomethane (0.399 mL, 6.38 mmol) was added under ice cooling and the mixture was stirred for 1 hour. Water and AcOEt were added to the reaction mixture under ice cooling and the organic layer was separated and washed with 1 M HCl and brine and evaporated. To the residue in EtOH (30 mL) was added 5 M NaOH (3.48 mL, 17.40 mmol) and the mixture was refluxed for 1 hour. After the evaporation of the reaction mixture, water and 6 M HCl were added to the mixture. Resulting precipitate was collected by filtration and dried to afford 3.03 g of the title compound as a white powder.

$^1$H NMR (DMSO-d$_6$) δ 2.29 (3H, s), 3.17 (3H, s), 4.01 (3H, s), 6.73-6.77 (2H, m), 6.91 (1H, s), 7.18 (1H, d, J=1.3 Hz), 7.51 (2H, d, J=8.9 Hz), 7.64 (1H, dd, J=8.4 Hz, 2.1 Hz), 7.90-7.92 (2H, m).

Reference Example 186

Production of N-{6-[1-methyl-2-(piperazine-1-carbonyl)-1H-indol-5-yloxy]pyridin-3-yl}-4-trifluoromethylbenzamide To 4-{1-methyl-5-[5-(4-trifluoromethylbenzoylamino)-pyridin-2-yloxy]-1H-indol-2-carbonyl}piperazine-1-carboxylic acid tert-butyl ester (2.75 g, 4.41 mmol) was added trifluoroacetic acid (16 mL) under ice cooling. The reaction mixture was stirred for 1 hour at room temperature. The reaction mixture was evaporated under reduced pressure. The residue was made alkaline with 5 M NaOH, and extracted with dichloromethane. The organic layer was washed with brine, dried over anhydrous magnesium sulfate. The solvent was evaporated under reduced pressure to afford 2.03 g of the title compound as a yellow amorphous powder.

$^1$H NMR (CDCl$_3$) δ 2.92 (4H, brs), 3.75 (4H, brs), 3.81 (3H, s), 6.54 (1H, s), 6.89 (1H, d, J=8.9 Hz), 7.08 (1H, dd, J=8.9 Hz, 2.2 Hz), 7.37-7.34 (2H, m), 7.73 (2H, d, J=8.1 Hz), 7.99 (2H, d, J=8.1 Hz), 8.14 (1H, dd, J=8.6 Hz, 2.7 Hz), 8.23 (1H, s), 8.26 (1H, d, J=2.7 Hz).

The following compounds were produced in the same manner as in Reference Example 186 using appropriate starting materials.

Reference Example 187

N-{6-[1-Ethyl-2-(piperazine-1-carbonyl)-1H-indol-5-yloxy]pyridin-3-yl}-N-methyl-4-trifluoromethylbenzamide $^1$H NMR (CDCl$_3$) δ 1.38 (3H, t, J=7.0 Hz), 2.96 (4H, brs), 3.45 (3H, s), 3.80 (4H, brs), 4.29 (2H, q, J=7.0 Hz), 6.50 (1H, s), 6.81 (1H, d, J=8.9 Hz), 6.99 (1H, dd, J=8.9 Hz, 2.4 Hz), 7.50-7.28 (7H, m), 7.82 (1H, s).

Reference Example 188

3,4-Dichloro-N-{6-[1-methyl-2-(piperazine-1-carbonyl)-1H-indol-5-yloxy}pyridin-3-yl]benzamide $^1$H NMR (CDCl$_3$) δ 2.76 (4H, brs), 3.57 (4H, brs), 3.77 (3H, s), 6.61 (1H, s), 6.99 (1H, d, J=9.7 Hz), 7.03 (1H, dd, J=8.9 Hz, 2.2 Hz), 7.33 (1H, d, J=2.4 Hz), 7.55 (1H, d, J=8.9 Hz), 7.83 (1H, d, J=8.4 Hz), 7.94 (1H, dd, J=8.4 Hz, 1.9 Hz), 8.15 (1H, dd, J=8.9 Hz, 2.4 Hz), 8.22 (1H, d, J=1.9 Hz), 8.44 (1H, d, J=2.4 Hz).

Reference Example 189

N-{4-Methyl-6-[1-methyl-2-(piperazine-1-carbonyl)-1H-indol-5-yl-oxy]pyridin-3-yl}-4-trifluoromethylbenzamide $^1$H NMR (CDCl$_3$) δ 2.26 (3H, s), 2.92 (4H, brs), 3.74 (4H, brs), 3.82 (3H, s), 6.54 (1H, s), 6.74 (1H, s), 7.09 (1H, dd, J=2.2 Hz, 8.9 Hz), 7.35 (1H, d, J=5.1 Hz), 7.36 (1H, s), 7.75 (1H, s), 7.76 (2H, d, J=8.1 Hz), 8.03 (2H, d, J=8.1 Hz), 8.25 (1H, s).

Reference Example 190

N-Methyl-N-{4-methyl-6-[1-methyl-2-(piperazine-1-carbonyl)-1H-indol-5-yloxy]pyridin-3-yl}-4-trifluoromethylbenzamide $^1$H NMR (CDCl$_3$) δ 2.23 (3H, s), 2.91 (4H, brs), 3.37 (3H, s), 3.73 (4H, brs), 3.83 (3H, s), 6.53 (1H, s), 6.67 (1H, s), 6.99 (1H, dd, J=1.9 Hz, 8.9 Hz), 7.24-7.28 (1H, m), 7.32-7.37 (3H, m), 7.46 (2H, d, J=8.6 Hz), 7.80 (1H, s).

Reference Example 191

3,4-Dichloro-N-{4-methyl-6-[1-methyl-2-(piperazine-1-carbonyl)-1H-indol-5-yloxy]pyridin-3-yl}benzamide $^1$H NMR (CDCl$_3$) δ 2.16 (3H, s), 2.94 (4H, brs), 3.77 (7H, brs), 6.49 (1H, s), 6.65 (1H, s), 7.07 (1H, dd, J=2.4 Hz, 8.9 Hz), 7.29 (1H, s), 7.32 (1H, d, J=2.2 Hz), 7.55 (1H, d, J=8.4 Hz), 7.76 (1H, dd, J=1.6 Hz, 8.1 Hz), 8.05-8.10 (3H, m).

Reference Example 192

N-{2-Methyl-6-[1-methyl-2-(piperazine-1-carbonyl)-1H-indol-5-yl-oxy]pyridin-3-yl}-4-trifluoromethylbenzamide $^1$H NMR (DMSO-d$_6$) δ 2.59 (3H, s), 2.74 (4H, brs), 3.57 (4H, brs), 3.77 (3H, s), 6.61 (1H, s), 6.75 (1H, d, J=8.4 Hz), 7.05 (1H, dd, J=2.2 Hz, 8.9 Hz), 7.34 (1H, d, J=2.2 Hz), 7.56 (1H, d, J=8.9 Hz), 7.73 (1H, d, J=8.6 Hz), 7.92 (2H, d, J=8.1 Hz), 8.17 (2H, d, J=8.1 Hz), 10.21 (1H, s).

Reference Example 193

N-Methyl-N-{2-methyl-6-[1-methyl-2-(piperazine-1-carbonyl)-1H-indol-5-yloxy]pyridin-3-yl}-4-trifluoromethylbenzamide $^1$H NMR (CDCl$_3$) δ 2.32 (3H, s), 2.92 (4H, brs), 3.38 (3H, s), 3.75 (4H, brs), 3.84 (3H, s), 6.45 (1H, d, J=8.6 Hz), 6.54 (1H, s), 7.01 (1H, dd, J=2.2 Hz, 8.6 Hz), 7.24-7.39 (5H, m), 7.46 (2H, d, J=8.4 Hz).

Reference Example 194

3,4-Dichloro-N-methyl-N-{4-methyl-6-[1-methyl-2-(piperazine-1-carbonyl)-1H-indol-5-yloxy]pyridin-3-yl}benzamide $^1$H NMR (CDCl$_3$) δ 2.22 (3H, s), 2.92 (4H, brs), 3.35 (3H, s), 3.74 (4H, brs), 3.83 (3H, s), 6.55 (1H, s), 6.69 (1H, s), 7.01 (1H, t, J=1.9 Hz), 7.04 (1H, t, J=1.9 Hz), 7.24-7.39 (4H, m), 7.81 (1H, s).

Reference Example 195

3,4-Dichloro-N-{2-methyl-6-[1-methyl-2-(piperazine-1-carbonyl)-1H-indol-5-yloxy]pyridin-3-yl}benzamide $^1$H NMR (CDCl$_3$) δ 2.38 (3H, s), 2.93 (4H, brs), 3.77 (7H, s), 6.47-6.49 (2H, m), 7.08 (1H, dd, J=2.2 Hz, 8.9 Hz), 7.25-7.33 (2H, m), 7.57 (1H, d, J=8.4 Hz), 7.70 (1H, d, J=7.6 Hz), 7.76 (1H, dd, J=1.6 Hz, 8.4 Hz), 8.02 (1H, s), 8.06 (1H, d, J=1.9 Hz).

Reference Example 196

3,4-Dichloro-N-methyl-N-{2-methyl-6-[1-methyl-2-(piperazine-1-carbonyl)-1H-indol-5-yloxy]pyridin-3-yl}benzamide $^1$H NMR (CDCl$_3$) δ 2.30 (3H, s), 2.88-2.95 (4H, m), 3.35 (3H, s), 3.75 (4H, brs), 3.85 (3H, s), 6.50 (1H, d, J=8.4 Hz), 6.55 (1H, s), 7.04 (2H, d, J=8.4 Hz), 7.25-7.42 (5H, m).

Reference Example 197

N-{2-[1-Methyl-2-(piperazine-1-carbonyl)-1H-indol-5-yloxy]-pyrimidin-5-yl}-4-trifluoromethylbenzamide $^1$H NMR (CDCl$_3$+CD$_3$OD) δ 3.00 (4H, brs), 3.84 (7H, s), 6.61 (1H, s), 7.15 (1H, dd, J=2.4 Hz, 8.9 Hz), 7.40-7.43 (2H, m), 7.75 (2H, d, J=8.4 Hz), 8.07 (2H, d, J=8.1 Hz), 8.92 (2H, s).

Reference Example 198

3,4-Dichloro-N-{2-[1-methyl-2-(piperazine-1-carbonyl)-1H-indol-5-yloxy]pyrimidin-5-yl}benzamide $^1$H NMR (CDCl$_3$) δ 2.91 (4H, brs), 3.73 (4H, brs), 3.80 (2H, s), 6.55 (1H, s), 7.12 (1H, dd, J=2.4 Hz, 8.9 Hz), 7.36 (1H, d, J=8.9 Hz), 7.40 (1H, d, J=2.2 Hz), 7.53 (1H, d, J=8.4 Hz), 7.71 (1H, dd, J=2.2 Hz, 8.4 Hz), 8.00 (1H, d, J'=2.2 Hz), 8.39 (1H, brs), 8.82 (2H, s).

Reference Example 199

N-{6-[1-Methyl-2-((R)-2-methylpiperazine-1-carbonyl)-1H-indol-5-yloxy]pyridin-3-yl}-4-trifluoromethylbenzamide $^1$H NMR (CDCl$_3$) δ 1.38 (3H, d, J=7.0 Hz), 2.75 (1H, dt, J=3.2 Hz, 12.2 Hz), 2.85 (1H, d, J=11.6 Hz), 2.96 (1H, dd, J=3.8 Hz, 12.4 Hz), 3.04 (1H, d, J=11.6 Hz), 3.23 (1H, t, J=12.2 Hz), 3.79 (3H, s), 4.18 (1H, d, J=12.7 Hz), 4.60 (1H, brs), 6.51 (1H, d, J=0.5 Hz), 6.89 (1H, d, J=8.9 Hz), 7.07 (1H, dd, J=2.2 Hz, 8.9 Hz), 7.33-7.36 (2H, m), 7.73 (2H, d, J=8.1 Hz), 7.98 (2H, d, J=8.1 Hz), 8.11-8.15 (2H, m), 8.25 (1H, d, J=2.4 Hz).

Reference Example 200

N-Methyl-N-{6-[1-methyl-2-((R)-2-methylpiperazine-1-carbonyl)-1H-indol-5-yloxy]pyridin-3-yl}-4-trifluoromethylbenzamide $^1$H NMR (CDCl$_3$) δ 1.38 (3H, d, J=6.8 Hz), 2.70-3.06 (4H, m), 3.23 (1H, t, J=12.1 Hz), 3.47 (3H, s), 3.80 (3H, s), 4.18 (1H, d, J=12.1 Hz), 4.59 (1H, brs), 6.51 (1H, s), 6.82 (1H, d, J=8.6 Hz), 7.00 (1H, dd, J=2.2 Hz, 8.9 Hz), 7.29-7.41 (5H, m), 7.50 (2H, d, J=8.1 Hz), 7.82 (1H, s).

Reference Example 201

N-{6-[1-Methyl-2-((S)-2-methylpiperazine-1-carbonyl)-1H-indol-5-yloxy]pyridin-3-yl}-4-trifluoromethylbenzamide $^1$H NMR (CDCl$_3$) δ 1.37 (3H, d, J=6.8 Hz), 2.68-3.05 (4H, m), 3.18-3.26 (1H, m), 3.76 (3H, s), 4.13 (1H, brs), 4.56 (1H, brs), 6.49 (1H, s), 6.84 (1H, d, J=8.9 Hz), 7.05 (1H, dd, J=1.6 Hz, 8.6 Hz), 7.30-7.33 (2H, m), 7.68 (2H, d, J=7.8 Hz), 7.97 (2H, d, J=8.1 Hz), 8.07 (1H, d, J=8.9 Hz), 8.26 (1H, d, J=2.7 Hz), 8.43 (1H, brs).

Reference Example 202

N-Methyl-N-{6-[1-methyl-2-((S)-2-methylpiperazine-1-carbonyl)-1H-indol-5-yloxy]pyridin-3-yl}-4-trifluoromethylbenzamide $^1$H NMR (CDCl$_3$) δ 1.38 (3H, d, J=7.0 Hz), 2.70-3.06 (5H, m), 3.23 (1H, t, J=12.4 Hz), 3.47 (3H, s), 3.80 (3H, s), 4.18 (1H, d, J=11.3 Hz), 4.58 (1H, brs), 6.51 (1H, s), 6.82 (1H, d, J=8.6 Hz), 7.00 (1H, dd, J=2.2 Hz, 8.9 Hz), 7.29-7.41 (5H, m), 7.50 (2H, d, J=8.1 Hz), 7.82 (1H, s).

Reference Example 203

N-Methyl-N-{6-[1-methyl-2-(piperazine-1-carbonyl)-1H-indol-6-yl-oxy]pyridin-3-yl}-4-trifluoromethylbenzamide $^1$H NMR (CDCl$_3$) δ 2.92 (4H, brs), 3.48 (3H, s), 3.74 (4H, brs), 3.77 (3H, s), 6.57 (1H, d, J=0.8 Hz), 6.85 (1H, d, J=8.4 Hz), 6.86 (1H, d, J=8.6 Hz), 7.07 (1H, d, J=1.9 Hz), 7.40-7.42 (3H, m), 7.50 (2H, d, J=8.4 Hz), 7.59 (1H, d, J=8.6 Hz), 7.85 (1H, s).

Reference Example 204

N-{6-[1,4-Dimethyl-2-(piperazine-1-carbonyl)-1H-indol-5-yloxy]-pyridin-3-yl}-hr-methyl-4-trifluoromethylbenzamide $^1$H NMR (CDCl$_3$) δ 2.19 (3H, s), 2.92 (4H, brs), 3.48 (3H, s), 3.74 (4H, brs), 3.81 (3H, s), 6.56 (1H, s), 6.81 (1H, d, J=8.6 Hz), 6.97 (1H, d, J=8.6 Hz), 7.20 (1H, d, J=8.9 Hz), 7.36-7.49 (5H, m), 7.75 (1H, s).

Reference Example 205

N-Methyl-N-{6-[1-methyl-2-(piperazine-1-carbonyl)-1H-indol-6-yl-oxy]pyridin-3-yl}-4-trifluoromethoxybenzamide $^1$H NMR (CDCl$_3$) δ 2.92 (4H, s), 3.47 (3H, s), 3.73-3.77 (7H, m), 6.58 (1H, s), 6.86 (2H, dd, J=8.9 Hz, 2.6 Hz), 7.06-7.09 (3H, m), 7.35 (2H, d, J=8.6 Hz), 7.41 (1H, dd, J=8.6 Hz, 2.6 Hz), 7.59 (1H, d, J=8.6 Hz), 7.86 (1H, d, J=2.6 Hz).

Reference Example 206

N-{6-[1-Methyl-2-(piperazine-1-carbonyl)-1H-indol-6-yloxy]-pyridin-3-yl}-4-trifluoromethylbenzamide $^1$H NMR (CDCl$_3$) δ 1.26 (1H, brs), 2.90 (4H, brs), 3.71 (7H, s), 6.54 (1H, s), 6.88 (1H, d, J=8.6 Hz), 6.90 (1H, dd, J=8.5 Hz, 2.1 Hz), 7.08 (1H, d, J=1.5 Hz), 7.57 (1H, d, J=8.6 Hz), 7.66 (2H, d, J=8.1 Hz), 7.96 (2H, d, J=8.2 Hz), 8.12 (1H, dd, J=8.8 Hz, 2.6 Hz), 8.30 (1H, d, J=2.6 Hz), 8.69 (1H, s).

Reference Example 207

N-Methyl-N-{6-[1-methyl-2-(piperazine-1-carbonyl)-1H-indol-5-yl-oxy]pyridin-3-yl}-4-trifluoromethylbenzamide $^1$H NMR (CDCl$_3$) δ 1.59 (1H, brs), 2.92 (4H, brs), 3.47 (3H, s), 3.74 (4H, brs), 3.83 (3H, s), 6.54 (1H, s), 6.82 (1H, d, J=8.7 Hz), 7.01 (1H, dd, J=8.7 Hz, 2.2 Hz), 7.30 (1H, d, J=2.2 Hz), 7.35 (1H, d, J=8.9 Hz), 7.36-7.46 (1H, m), 7.40 (2H, d, J=8.1 Hz), 7.50 (2H, d, J=8.1 Hz), 7.83 (1H, brs).

Reference Example 208

3,4-Dichloro-N-methyl-N-{6-[1-methyl-2-(piperazine-1-carbonyl)-1H-indol-5-yloxy]pyridin-3-yl}benzamide $^1$H NMR (CDCl$_3$) δ 1.66 (1H, s), 2.92 (4H, brs), 3.45 (3H, s), 3.74 (4H, brs), 3.84 (3H, s), 6.56 (1H, s), 6.85 (1H, d, J=8.8

Hz), 7.03 (1H, dd, J=8.9 Hz, 2.2 Hz), 7.07 (1H, dd, J=8.3 Hz, 2.0 Hz), 7.29 (1H, d, J=8.3 Hz), 7.33 (1H, d, J=2.2 Hz), 7.37 (1H, d, J=8.9 Hz), 7.41 (1H, dd, J=8.8 Hz, 2.0 Hz), 7.42 (1H, d, J=2.0 Hz), 7.83 (1H, d, J=2.5 Hz).

Reference Example 209

[1-Methyl-5-(5-nitropyridin-2-yloxy)-1H-indol-2-yl]piperazin-1-ylmethanone $^1$H NMR (CDCl$_3$) δ 1.64 (1H, brs), 2.93 (4H, brs), 3.75 (4H, brs), 3.86 (3H, s), 6.58 (1H, s), 7.02 (1H, d, J=9.0 Hz), 7.07 (1H, dd, J=8.9 Hz, 2.3 Hz), 7.39 (1H, d, J=2.3 Hz), 7.42 (1H, d, (J=8.9 Hz), 8.45 (1H, dd, J=9.0 Hz, 2.8 Hz), 9.04 (1H, d, J=2.8 Hz).

Reference Example 210

3,4-Dichloro-N-{6-[1-methyl-2-(piperazine-1-carbonyl)-1H-indol-5-yloxy]pyridin-3-yl}benzenesulfonamide trifluoroacetate $^1$H NMR (DMSO-d$_6$) δ 3.21 (4H, brs), 3.79 (3H, s), 3.85 (4H, brs), 6.74 (1H, s), 6.91 (1H, d, J=8.8 Hz), 7.01 (1H, dd, J=8.8 Hz, 2.2 Hz), 7.31 (1H, d, J=2.2 Hz), 7.51 (1H, dd, J=8.8 Hz, 2.8 Hz), 7.52 (1H, d, J=8.8 Hz), 7.63 (1H, dd, J=8.6 Hz, 2.2 Hz), 7.76 (1H, d, J=2.8 Hz), 7.87 (1H, d, J=8.6 Hz), 7.89 (1H, d, J=2.2 Hz), 8.93 (1H, brs), 10.41 (1H, s).

Reference Example 211

N-{6-[1-Methyl-2-(piperazine-1-carbonyl)-1H-indol-5-yloxy]-pyridin-3-yl}-4-trifluoromethylbenzenesulfonamide tri-fluoroacetate $^1$H NMR (DMSO-d$_6$) δ 3.21 (4H, brs), 3.79 (3H, s), 3.85 (4H, brs), 6.73 (1H, s), 6.90 (1H, d, J=8.7 Hz), 7.00 (1H, dd, J=8.9 Hz, 2.3 Hz), 7.30 (1H, d, J=2.3 Hz), 7.51 (1H, dd, J=8.7 Hz, 2.8 Hz), 7.54 (1H, d, J=8.9 Hz), 7.76 (1H, d, J=2.8 Hz), 7.92 (2H, d, J=8.4 Hz), 7.98 (2H, d, J=8.4 Hz), 8.90 (1H, brs), 10.49 (1H, s).

Reference Example 212

(5-{5-[(3,4-Dichlorophenyl)methylamino]pyridin-2-yloxy}-1-methyl-1H-indol-2-yl)piperazin-1-ylmethanone $^1$H NMR (CDCl$_3$) δ 1.73 (1H, brs), 2.92 (4H, brs), 3.24 (3H, s), 3.75 (4H, brs), 3.85 (3H, s), 6.57 (1H, s), 6.58 (1H, dd, J=8.9 Hz, 2.8 Hz), 6.83 (1H, d, J=2.8 Hz), 6.90 (1H, d, J=8.7 Hz), 7.12 (1H, dd, J=8.7 Hz, 2.3 Hz), 7.21 (1H, d, J=8.9 Hz), 7.38 (1H, d, J=8.7 Hz), 7.40 (1H, s), 7.45 (1H, dd, J=8.7 Hz, 2.5 Hz), 8.00 (1H, d, J=2.5 Hz).

Reference Example 213

(4-Benzylpiperazin-1-yl)[5-(5-ethylaminopyridin-2-yloxy)-1-methyl-1H-indol-2-yl]methanone $^1$H NMR (CDCl$_3$) δ 1.30 (3H, t, J=7.1 Hz), 3.21 (5H, brs), 3.22 (2H, q, J=7.1 Hz), 3.81 (3H, s), 4.23 (4H, brs), 4.24 (2H, s), 6.55 (1H, s), 6.84 (1H, d, J=8.9 Hz), 7.06 (1H, dd, J=8.9 Hz, 2.3 Hz), 7.31 (1H, d, J=8.1 Hz), 7.35 (1H, d, J=8.9 Hz), 7.35-7.50 (6H, m), 7.95 (1H, d, J=3.0 Hz).

Reference Example 214

(1-Methyl-5-{5-[methyl(4-trifluoromethylphenyl)amino]pyridin-2-yloxy}-1H-indol-2-yl)piperazin-1-ylmethanone $^1$H NMR (CDCl$_3$) δ 1.80 (1H, brs), 2.93 (4H, brs), 3.31 (3H, s), 3.76 (4H, brs), 3.85 (3H, s), 6.57 (1H, s), 6.75 (2H, d, J=8.7 Hz), 6.92 (1H, d, J=8.7 Hz), 7.12 (1H, dd, J=8.7 Hz, 2.1 Hz), 7.39 (1H, d, J=8.7 Hz), 7.40 (1H, d, J=2.1 Hz), 7.42 (2H, d, J=8.7 Hz), 7.50 (1H, dd, J=8.7 Hz, 2.8 Hz), 8.05 (1H, d, J=2.8 Hz).

Reference Example 215

(4-Benzo[1,3]dioxol-5-ylmethylpiperazin-1-yl)[5-(5-ethylamino-pyridin-2-yloxy)-1-methyl-1H-indol-2-yl]methanone $^1$H NMR (CDCl$_3$) δ 1.25 (3H, t, J=7.1 Hz), 2.47 (4H, brs), 3.12 (2H, q, J=7.1 Hz), 3.35 (1H, brs), 3.45 (2H, s), 3.76 (4H, brs), 3.82 (3H, s), 5.95 (2H, s), 6.51 (1H, s), 6.74 (1H, d, J=8.8 Hz), 6.74 (2H, s), 6.86 (1H, s), 6.97 (1H, dd, J=8.8 Hz, 2.8 Hz), 7.05 (1H, dd, J=8.9 Hz, 2.3 Hz), 7.28 (1H, d, J=2.3 Hz), 7.31 (1H, d, J=8.9 Hz), 7.61 (1H, d, J=2.8 Hz).

Reference Example 216

2-Chloro-N-methyl-N-{6-[1-methyl-2-(piperazine-1-carbonyl)-1H-indol-6-yloxy]pyridin-3-yl}-4-trifluoromethylbenzamide $^1$H NMR (CDCl$_3$) δ 2.92 (4H, s), 3.49 (3H, s), 3.75-3.80 (7H, m), 6.58 (1H, d, J=7.9 Hz), 6.78-6.83 (2H, m), 7.04 (1H, s), 7.31 (1H, d, J=7.9 Hz), 7.41 (1H, d, J=8.2 Hz), 7.48-7.83 (3H, m), 7.92 (1H, d, J=2.6 Hz).

Reference Example 217

2-Chloro-N-{6-[1-methyl-2-(piperazine-1-carbonyl)-1H-indol-6-yl-oxy]pyridin-3-yl}-4-trifluoromethylbenzamide $^1$H NMR (CDCl$_3$) δ 2.91 (4H, brs), 3.73 (4H, brs), 3.76 (3H, s), 6.56 (1H, s), 6.92 (1H, dd, J=8.6 Hz, 2.0 Hz), 6.93 (1H, d, J=8.8 Hz), 7.12 (1H, d, J=2.0 Hz), 7.61 (1H, d, J=8.6 Hz), 7.63 (1H, d, J=8.2 Hz), 7.71 (1H, s), 7.82 (1H, d, J=8.2 Hz), 8.18 (1H, dd, J=8.8 Hz, 2.7 Hz), 8.20 (1H, s), 8.28 (1H, d, J=2.7 Hz).

Reference Example 218

[1-Methyl-6-(5-nitropyridin-2-yloxy)-1H-indol-2-yl]piperazin-1-ylmethanone $^1$H NMR (CDCl$_3$) δ 2.95 (4H, t, J=4.8 Hz), 3.79 (4H, t, J=4.8 Hz), 3.81 (3H, s), 6.62 (1H, s), 6.93 (1H, dd, J=8.6 Hz, 2.0 Hz), 7.04 (1H, d, J=8.9 Hz), 7.16 (1H, d, J=2.0 Hz), 7.66 (1H, d, J=8.6 Hz), 8.47 (1H, dd, J=8.9 Hz, 2.6 Hz), 9.05 (1H, d, J=2.6 Hz).

Reference Example 219

[1-Methyl-6-(5-methylaminopyridin-2-yloxy)-1H-indol-2-yl]{4-[4-(2,2,2-trifluoroethoxy)benzyl]piperazin-1-yl}methanone $^1$H NMR (CDCl$_3$) δ 2.47 (4H, brs), 2.84 (3H, s), 3.50 (2H, s), 3.57 (1H, brs), 3.75 (7H, s), 4.35 (2H, q, J=8.1 Hz), 6.55

(1H, s), 6.80 (1H, d, J=8.5 Hz), 6.88 (1H, dd, J=8.5 Hz, 1.9 Hz), 6.91 (2H, d, J=8.3 Hz), 7.00 (1H, dd, J=8.5 Hz, 3.0 Hz), 7.04 (1H, d, J=1.9 Hz), 7.28 (2H, d, J=8.3 Hz), 7.54 (1H, d, J=8.5 Hz), 7.64 (1H, d, J=3.0 Hz).

Reference Example 220

3,4-Dichloro-N-methyl-N-{6-[1-methyl-2-(piperazine-1-carbonyl)-1H-indol-6-yloxy]pyridin-3-yl}benzamide $^1$H NMR (CDCl$_3$) δ 1.27 (1H, s), 2.92 (4H, t, J=5.1 Hz), 3.46 (3H, s), 3.74 (4H, t, J=4.9 Hz), 3.78 (3H, s), 6.58 (1H, d, J=0.8 Hz), 6.876 (1H, dd, J=8.4 Hz, 1.4 Hz), 6.879 (1H, dd, J=8.9 Hz, 1.6 Hz), 7.086 (1H, dd, J=8.1 Hz, 2.2 Hz), 7.090 (1H, d, J=2.2 Hz), 7.30 (1H, d, J=8.2 Hz), 7.42 (1H, d, J=1.9 Hz), 7.43 (1H, dd, J=8.6 Hz, 2.7 Hz), 7.60 (1H, dd, J=8.6 Hz, 0.5 Hz), 7.85 (1H, d, J=2.8 Hz).

Reference Example 221

2-Methyl-N-{6-[1-methyl-2-(piperazine-1-carbonyl)-1H-indol-6-yl-oxy]pyridin-3-yl}-4-trifluoromethylbenzamide $^1$H NMR (CDCl$_3$) δ 1.59 (1H, s), 2.56 (3H, s), 2.92 (4H, t, J=4.5 Hz), 3.75 (4H, t, J=4.9 Hz), 3.79 (3H, s), 6.58 (1H, d, J=0.7 Hz), 6.94 (1H, dd, J=8.6 Hz, 1.9 Hz), 6.95 (1H, d, J=9.7 Hz), 7.14 (1H, d, J=2.0 Hz), 7.48-7.63 (5H, m), 8.21-8.25 (2H, m).

Reference Example 222

3,4-Dichloro-N-{6-[1-methyl-2-(piperazine-1-carbonyl)-1H-indol-6-yloxy]pyridin-3-yl}benzamide $^1$H NMR (DMSO-d$_6$) δ 2.77 (4H, t, J=4.5 Hz), 3.38 (1H, brs), 3.59 (4H, t, J=4.5 Hz), 3.71 (3H, s), 6.66 (1H, d, J=0.5 Hz), 6.88 (1H, dd, J=8.6 Hz, 2.0 Hz), 7.03 (1H, d, J=8.9 Hz), 7.32 (1H, d, J=2.0 Hz), 7.61 (1H, d, J=8.6 Hz), 7.83 (1H, d, J=8.4 Hz), 7.95 (1H, dd, J=8.5 Hz, 2.1 Hz), 8.18 (1H, dd, J=8.9 Hz, 2.6 Hz), 8.22 (1H, d, J=2.0 Hz), 8.47 (1H, d, J=2.5 Hz), 10.53 (1H, brs).

Reference Example 223

3,4-Dichloro-N-{6-[1-methyl-2-(piperazine-1-carbonyl)-1H-indol-6-yloxy]pyridin-3-yl}benzenesulfonamide hydrochloride $^1$H NMR (DMSO-d$_6$) δ 3.21 (4H, s), 3.72 (3H, s), 3.88 (4H, s), 6.80 (1H, s), 6.84 (1H, dd, J=8.6 Hz, 2.0 Hz), 6.95 (1H, d, J=8.6 Hz), 7.31 (1H, d, J=2.0 Hz), 7.53-7.67 (3H, m), 7.80 (1H, d, J=2.3 Hz), 7.87 (1H, d, J=8.6 Hz), 7.91 (1H, d, J=2.3 Hz), 9.15 (2H, brs), 10.48 (1H, s).

Reference Example 224

3,4-Dichloro-N-methyl-N-{6-[1-methyl-2-(piperazine-1-carbonyl)-1H-indol-6-yloxy]pyridin-3-yl}benzenesulfonamide hydrochloride $^1$H NMR (DMSO-d$_6$) δ 3.18 (3H, s), 3.18-3.25 (4H, m), 3.75 (3H, s), 3.85-3.89 (4H, m), 6.82 (1H, s), 6.90 (1H, dd, J=8.6 Hz, 2.0 Hz), 7.01 (1H, d, J=8.9 Hz), 7.39 (1H, d, J=1.6 Hz), 7.48 (1H, dd, J=8.6 Hz, 2.0 Hz), 7.64 (2H, dd, J=8.9 Hz, 2.6 Hz), 7.77 (1H, d, J=2.0 Hz), 7.90 (1H, d, J=8.2 Hz), 7.95 (1H, d, J=2.6 Hz), 9.20 (2H, s).

Reference Example 225

2-Fluoro-N-methyl-N-{6-[1-methyl-2-(piperazine-1-carbonyl)-1H-indol-6-yloxy]pyridin-3-yl}-4-trifluoromethylbenzamide hydrochloride $^1$H NMR (CDCl$_3$) δ 3.32 (4H, brs), 3.48 (3H, s), 3.78 (3H, s), 4.19 (4H, brs), 6.63 (1H, s), 6.86 (2H, d, J=8.9 Hz), 7.08 (1H, s), 7.14 (1H, d, J=8.9 Hz), 7.35 (1H, d, J=7.3 Hz), 7.45-7.52 (2H, m), 7.61 (1H, d, J=8.6 Hz), 7.82 (1H, s), 10.28 (2H, brs).

Reference Example 226

N-{6-[1-Methyl-2-(piperazine-1-carbonyl)-1H-indol-6-yloxy]-pyridin-3-yl}-4-trifluoramethylbenzenesulfonamide hydrochloride $^1$H NMR (DMSO-d$_6$) δ 3.19 (4H, s), 3.72 (3H, s), 3.90 (4H, s), 6.80-6.85 (2H, m), 6.94 (1H, d, J=8.9 Hz), 7.30 (1H, d, J=2.0 Hz), 7.53-7.62 (2H, m), 7.81 (1H, d, J=3.0 Hz), 7.97 (4H, dd, J=12.5 Hz, 8.9 Hz), 9.48 (2H, brs), 10.63 (1H, s).

Reference Example 227

N-Methyl-N-{6-[1-methyl-2-(piperazine-1-carbonyl)-1H-indol-5-yl-oxy]pyridin-3-yl}-4-trifluoromethylbenzenesulfonamide hydrochloride $^1$H NMR (DMSO-d$_6$) δ 3.17-3.19 (7H, m), 3.32 (1H, s), 3.80 (3H, s), 3.88 (4H, brs), 6.76 (1H, s), 6.96 (1H, d, J=8.9 Hz), 7.07 (1H, dd, J=8.9 Hz, 2.3 Hz), 7.38 (1H, d, J=2.3 Hz), 7.58 (2H, dt, J=8.9 Hz, 1.2 Hz), 7.79 (2H, d, J=8.2 Hz), 7.91 (1H, d, J=2.6 Hz), 8.01 (2H, d, J=8.2 Hz), 9.30 (2H, brs).

Reference Example 228

3,4-Dichloro-N-methyl-N-{6-[1-methyl-2-(piperazine-1-carbonyl)-1H-indol-5-yloxy]pyridin-3-yl}benzenesulfonamide hydrochloride $^1$H NMR (DMSO-d$_6$) δ 3.17-3.19 (7H, m), 3.32 (1H, s), 3.80 (3H, s), 3.88 (4H, brs), 6.76 (1H, s), 6.96 (1H, d, J=8.9 Hz), 7.06 (1H, dd, J=8.9 Hz, 2.3 Hz), 7.37 (1H, d, J=2.0 Hz), 7.48 (1H, dd, J=8.4 Hz, 2.1 Hz), 7.56-7.64 (2H, m), 7.76 (1H, d, J=2.3 Hz), 7.90 (1H, d, J=8.6 Hz), 7.93 (1H, d, J=2.3 Hz), 9.29 (2H, brs).

Reference Example 229

4,N-Dimethyl-N-{6-[1-methyl-2-(piperazine-1-carbonyl)-1H-indol-5-yloxy]pyridin-3-yl}benzenesulfonamide hydrochloride $^1$H NMR (CDCl$_3$) δ 2.42 (3H, s), 3.15 (3H, s), 3.31 (4H, brs), 3.86 (3H, s), 4.19 (4H, brs), 6.61 (1H, s), 6.87 (1H, d, J=8.9 Hz), 7.13 (1H, dd, J=8.9 Hz, 2.0 Hz), 7.26-7.29 (2H, m), 7.41 (2H, d, J=8.9 Hz), 7.48 (2H, d, J=8.2 Hz), 7.53 (1H, dd, J=8.7 Hz, 2.8 Hz), 7.75 (1H, d, J=2.6 Hz), 10.29 (2H, brs).

Reference Example 230

1-Methyl-6-(5-methylaminopyrimidin-2-yloxy)-1H-indole-2-carboxylic acid ethyl ester $^1$H NMR (CDCl$_3$) δ 1.41 (3H, t, J=7.1 Hz), 2.87 (3H, d, J=5.4 Hz), 3.54-3.56 (1H, m), 4.01 (3H, s), 4.37 (2H, q, J=7.1

Hz), 6.96 (1H, dd, J=8.8 Hz, 1.9 Hz), 7.18 (1H, d, J=1.6 Hz), 7.29 (1H, d, J=0.8 Hz), 7.65 (1H, d, J=8.7 Hz), 7.99 (2H, s).

Reference Example 231

N-Methyl-N-{2-[1-methyl-2-(piperazine-1-carbonyl)-1H-indol-6-yl-oxy]pyrimidin-5-yl}-4-trifluoromethylbenzamide $^1$H NMR (CDCl$_3$) δ 1.60 (1H, s), 2.92 (4H, brs), 3.50 (3H, s), 3.75 (4H, brs), 3.78 (3H, s), 6.59 (1H, s), 6.91 (1H, dd, J=8.4 Hz, 2.0 Hz), 7.14 (1H, d, J=1.8 Hz), 7.44 (2H, d, J=7.3 Hz), 7.57 (2H, d, J=7.7 Hz), 7.62 (1H, d, J=8.6 Hz), 8.31 (2H, brs).

Reference Example 232

6-[5-(4-Nitrobenzoylamino)pyridin-2-yloxy]-2,3-dihydro-1H-indole-2-carboxylic acid ethyl ester $^1$H NMR (CDCl$_3$) δ 1.29 (3H, t, J=7.3 Hz), 3.20-3.40 (2H, m), 4.20 (2H, q, J=7.0 Hz), 4.40 (1H, dd, J=10.3 Hz, 5.9 Hz), 4.53 (1H, s), 6.37-6.42 (2H, m), 6.87 (1H, d, J=8.9 Hz), 7.00 (1H, d, J=7.6 Hz), 8.02 (2H, d, J=8.9 Hz), 8.13 (1H, dd, J=8.9 Hz, 2.7 Hz), 8.23-8.27 (3H, m), 8.69 (1H, s).

Reference Example 233

4,N-Dimethyl-N-{6-[1-methyl-2-(piperazine-1-carbonyl)-1H-indol-6-yloxy]pyridin-3-yl}benzenesulfonamide hydrochloride $^1$H NMR (DMSO-d$_6$) δ 2.40 (3H, s), 3.11 (3H, s), 3.20 (4H, s), 3.75 (3H, s), 3.89 (4H, s), 6.82 (1H, s), 6.89 (1H, dd, J=8.6 Hz, 2.0 Hz), 6.97 (1H, d, J=8.9 Hz), 7.38 (1H, d, J=1.9 Hz), 7.40-7.47 (4H, m), 7.53 (1H, dd, J=8.7 Hz, 2.8 Hz), 7.64 (1H, d, J=8.6 Hz), 7.86 (1H, d, J=2.6 Hz), 9.23 (2H, s).

Reference Example 234

2-Methyl-N-{2-[1-methyl-2-(piperazine-1-carbonyl)-1H-indol-6-yl-oxy]pyrimidin-5-yl}-4-trifluoromethylbenzamide $^1$H NMR (CDCl$_3$) δ 1.65 (1H, brs), 2.52 (3H, s), 2.90 (4H, brs), 3.72 (4H, t, J=4.9 Hz), 3.76 (3H, s), 6.56 (1H, d, J=0.8 Hz), 6.97 (1H, dd, J=8.6 Hz, 2.0 Hz), 7.18 (1H, d, J=2.0 Hz), 7.50 (1H, d, J=8.9 Hz), 7.52 (1H, s), 7.58 (1H, d, J=7.9 Hz), 7.63 (1H, d, J=8.6 Hz), 8.00 (1H, brs), 8.85 (2H, s).

Reference Example 235

2-Fluoro-N-{6-[1-methyl-2-(piperazine-1-carbonyl)-1H-indol-6-yl-oxy]pyridin-3-yl}-4-trifluoromethylbenzamide hydrochloride $^1$H NMR (DMSO-d$_6$) δ 3.20 (4H, brs), 3.74 (3H, s), 3.89 (4H, brs), 6.82 (1H, s), 6.89 (1H, dd, J=8.6 Hz, 2.0 Hz), 7.06 (1H, d, J=8.9 Hz), 7.34 (1H, d, J=1.6 Hz), 7.63 (1H, d, J=8.6 Hz), 7.75 (1H, d, J=8.2 Hz), 7.91-7.93 (2H, m), 8.17 (1H, dd, J=8.9 Hz, 2.6 Hz), 8.44 (1H, d, J=2.6 Hz), 9.31 (2H, brs), 10.78 (1H, s).

Reference Example 236

[6-(5-Amino-4-methylpyridin-2-yloxy)-1-methyl-1H-indol-2-yl]{4-[4-(2,2,2-trifluoroethoxy)benzyl]piperazin-1-yl}methanone $^1$H NMR (CDCl$_3$) δ 2.18 (3H, s), 2.48 (4H, brs), 3.42 (2H, brs), 3.51 (2H, s), 3.75-3.77 (7H, m), 4.35 (2H, q, J=8.1 Hz), 6.55 (1H, s), 6.66 (1H, s), 6.87-6.92 (3H, m), 7.04 (1H, d, J=1.6 Hz), 7.27-7.29 (2H, m), 7.54 (1H, d, J=8.6 Hz), 7.65 (1H, s).

Reference Example 237

[1-Methyl-6-(4-methyl-5-methylaminopyridin-2-yloxy)-1H-indol-2-yl]{4-[4-(2,2,2-trifluoroethoxy)benzyl]piperazin-1-yl}methanone $^1$H NMR (CDCl$_3$) δ 2.14 (3H, s), 2.47 (4H, brs), 2.89 (3H, s), 3.30 (1H, brs), 3.50 (2H, s), 3.76-3.78 (7H, m), 4.35 (2H, q, J=8.1 Hz), 6.55 (1H, s), 6.68 (1H, s), 6.89-6.92 (3H, m), 7.04 (1H, d, J=2.3 Hz), 7.27-7.29 (2H, m), 7.53-7.55 (2H, m).

Reference Example 238

Production of (4-benzylpiperazin-1-yl)[1-methyl-5-(5-nitro-pyridin-2-yloxy)-1H-indol-2-yl]methanone To a solution of [1-methyl-5-(5-nitropyridin-2-yloxy)-1H-indol-2-yl]piperazin-1-ylmethanone (2.09 g, 5.5 mmol) in 1,2-dichloroethane (45 mL) were added benzaldehyde (1.16 g, 10 mmol), sodium triacetoxyborohydride (2.33 g, 11 mmol) and acetic acid (0.7 mL, 11 mmol) under ice cooling. The reaction mixture was stirred for 14 hours at room temperature under a nitrogen atomoshere. The solvent was removed under reduced pressure, and to the residue was added water. The mixture was neutralized with saturated aqueous NaHCO$_3$ and extracted with AcOEt. The organic layer was washed with brine, dried over anhydrous sodium sulfate, and evaporated under reduced pressure. The residue was purified by silica gel column chromatography (CH$_2$Cl$_2$:MeOH=60:1) to give 2.66 g of the title compound as a pale brown oil.

$^1$H NMR (CDCl$_3$) δ 2.51 (4H, brs), 3.56 (2H, s), 3.78 (4H, brs), 3.85 (3H, s), 6.58 (1H, s), 7.01 (1H, d, J=9.1 Hz), 7.06 (1H, dd, J=8.7 Hz, 2.3 Hz), 7.23-7.39 (6H, m), 7.41 (1H, d, J=8.9 Hz), 8.45 (1H, dd, J=9.1 Hz, 2.8 Hz), 9.03 (1H, d, J=2.8 Hz).

The following compounds were produced in the same manner as in Reference Example 238 using appropriate starting materials.

Reference Example 239

[4-(4-Methoxybenzyl)piperazin-1-yl][1-methyl-5-(5-nitropyridin-2-yloxy)-1H-indol-2-yl]methanone $^1$H NMR (CDCl$_3$) δ 2.48 (4H, brs), 3.50 (2H, s), 3.77 (4H, brs), 3.80 (3H, s), 3.85 (3H, s), 6.57 (1H, s), 6.86 (2H, d, J=8.1 Hz), 7.00 (1H, d, J=9.2 Hz), 7.06 (1H, ddd, J=0.8 Hz, 2.2 Hz, 8.9 Hz), 7.23 (2H, d, J=8.4 Hz), 7.37 (1H, d, J=2.4 Hz), 7.40 (1H, d, J=8.9 Hz), 8.45 (1H, ddd, J=0.5 Hz, 2.7 Hz, 8.9 Hz), 9.03 (1H, d, J=3.0 Hz).

Reference Example 240

[4-(4-Difluoromethoxybenzyl)piperazin-1-yl][1-methyl-5-(5-nitro-pyridin-2-yloxy)-1H-indol-2-yl]methanone $^1$H NMR (CDCl$_3$) δ 2.49 (4H, brs), 3.53 (2H, s), 3.78 (4H, brs), 3.86 (3H, s), 6.50 (1H, t, J=73.5 Hz), 6.58 (1H, s), 7.02 (1H, d, J=8.9 Hz), 7.03-7.18 (1H, m), 7.09 (2H, d, J=8.5 Hz), 7.33 (2H, d, J=8.5 Hz), 7.30-7.50 (2H, m), 8.45 (1H, dd, J=8.9 Hz, 2.8 Hz), 9.03 (1H, d, J=2.8 Hz).

Reference Example 241

(4-Benzo[1,3]dioxol-5-ylmethylpiperazin-1-yl)[1-methyl-5-(5-nitropyridin-2-yloxy)-1H-indol-2-yl]methanone $^1$H NMR (CDCl$_3$) δ 2.48 (4H, brs), 3.46 (2H, s), 3.77 (4H, brs), 3.85 (3H, s), 5.95 (2H, s), 6.57 (1H, s), 6.75 (2H, s), 6.86 (1H, s), 7.01 (1H, d, J=9.0 Hz), 7.06 (1H, dd, J=8.9 Hz, 2.2 Hz), 7.38 (1H, d, J=2.2 Hz), 7.40 (1H, d, J=8.9 Hz), 8.44 (1H, dd, J=9.0 Hz, 2.8 Hz), 9.03 (1H, d, J=2.8 Hz).

Reference Example 242

[1-Methyl-5-(5-nitropyridin-2-yloxy)-1H-indol-2-yl]{4-[4-(2,2,2-trifluoroethoxy)benzyl]piperazin-1-yl}methanone $^1$H NMR (CDCl$_3$) δ 2.48 (4H, brs), 3.51 (2H, s), 3.77 (4H, brs), 3.85 (3H, s), 4.35 (2H, q, J=8.2 Hz), 6.58 (1H, s), 6.91 (2H, d, J=8.6 Hz), 7.01 (1H, d, J=8.9 Hz), 7.07 (1H, dd, J=8.9 Hz, 2.3 Hz), 7.27 (2H, d, J=8.6 Hz), 7.38 (1H, d, J=2.3 Hz), 7.41 (1H, d, J=8.9 Hz), 8.45 (1H, dd, J=8.9 Hz, 2.9 Hz), 9.03 (1H, d, J=2.9 Hz).

Reference Example 243

[1-Methyl-6-(5-nitropyridin-2-yloxy)-1H-indol-2-yl]{4-[4-(2,2,2-trifluoroethoxy)benzyl]piperazin-1-yl}methanone $^1$H NMR (CDCl$_3$) δ 2.49 (4H, brs), 3.51 (2H, s), 3.80 (7H, s), 4.35 (2H, q, J=8.1 Hz), 6.61 (1H, s), 6.91 (2H, d, J=8.6 Hz), 6.93 (1H, d, J=8.6 Hz), 7.03 (1H, d, J=8.9 Hz), 7.16 (1H, s), 7.28 (2H, d, J=8.6 Hz), 7.65 (1H, d, J=8.5 Hz), 8.47 (1H, dd, J=8.9 Hz, 3.0 Hz), 9.05 (1H, d, J=3.0 Hz).

Reference Example 244

Production of 1-(4-benzo[1,3]dioxol-5-ylmethylpiperazin-1-yl)-2-[4-(5-hydroxymethylpyridin-2-yloxy)-2,3-dihydroindol-1-yl]-ethanone 6-{1-[2-(4-Benzo[1,3]dioxol-5-ylmethylpiperazin-1-yl)-2-oxoethyl]-2,3-dihydro-1H-indol-4-yloxy}nicotinic acid (0.789 g, 1.53 mmol) was suspended in THF (15 mL). To the suspension were added triethylamine 0.234 mL, 1.68 mmol), then ethyl chloroformate (0.161 g, 1.68 mmol) under cooling in an ice-salt bath, and the resulting mixture was stirred for 30 minutes at the same temperature. The reaction mixture was filtered, and to the filtrate was added 80% solution of sodium borohydride (0.289 g, 7.64 mmol) in methanol (20 mL) under cooling with ice, and then the solution was stirred for 30 minutes at the same temperature. The reaction mixture was concentrated and the residue was extracted with ethyl acetate (50 mL). After the organic layer was washed with brine, then dried over anhydrous sodium sulfate, the solvent was evaporated to yield 0.671 g of the title compound as a pale brown amorphous powder.

$^1$H NMR (CDCl$_3$) δ 2.43 (4H, t, J=5.0 Hz), 2.83 (2H, t, J=8.4 Hz), 3.40-3.48 (5H, m), 3.53 (2H, t, J=4.6 Hz), 3.64 (2H, t, J=4.6 Hz), 3.88 (2H, s), 4.65 (2H, s), 5.95 (2H, s), 6.30 (1H, d, J=7.8 Hz), 6.45 (1H, d, J=8.1 Hz), 6.71-6.78 (2H, m), 6.85-6.89 (2H, m), 7.05-7.11 (1H, m), 7.71 (1H, dd, J=8.6 Hz, 2.5 Hz), 8.16 (1H, d, J=2.5 Hz).

Reference Example 245

Production of 4-{5-[5-(3,4-dichlorophenylamino)pyridin-2-yloxy]-1-methyl-1H-indole-2-carbonyl}piperazine-1-carboxylic acid tert-butyl ester To a solution of 4-[5-(5-aminopyridin-2-yloxy)-1-methyl-1 hr-indole-2-carbonyl]piperazine-1-carboxylic acid tert-butyl ester (1.67 g, 3.70 mmol) in dichloromethane (30 mL) were added 3,4-dichlorophenylboronic acid (1.41 g, 7.39 mmol), copper(II) acetate (0.68 g, 3.74 mmol), molecular sieves 4A (4.4 g) and triethylamine (1.03 ml, 7.33 mmol). The reaction mixture was stirred for 17 hours at room temperature. The reaction mixture was filtered with celite and the filtrate was evaporated under reduced pressure. The residue was purified by silica gel column chromatography (CH$_2$Cl$_2$:MeOH=60:1) to give 1.41 g of the title compound as a dark brown powder.

$^1$H NMR (CDCl$_3$) δ 1.48 (9H, s), 3.50 (4H, brs), 3.75 (4H, brs), 3.84 (3H, s), 5.57 (1H, s), 6.57 (1H, s), 6.69 (1H, dd, J=8.8 Hz, 2.7 Hz), 6.88 (1H, d, J=8.8 Hz), 6.94 (1H, d, J=2.7 Hz), 7.11 (1H, dd, J=8.8 Hz, 2.2 Hz), 7.23 (1H, d, J=8.9 Hz), 7.38 (1H, d, J=2.5 Hz), 7.38 (1H, d, J=8.8 Hz), 7.47 (1H, dd, J=8.8 Hz, 2.7 Hz), 7.99 (1H, d, J=2.7 Hz).

The following compound was produced in the same manner as in Reference Example 245 using appropriate starting materials.

Reference Example 246

4-{1-Methyl-5-[5-(4-trifluoromethylphenylamino)pyridin-2-yloxy]-1H-indole-2-carbonyl}piperazine-1-carboxylic acid tert-butyl ester $^1$H NMR (CDCl$_3$) δ 1.48 (9H, s), 3.50 (4H, brs), 3.77 (4H, brs), 3.85 (3H, s), 5.76 (1H, s), 6.56 (1H, s), 6.87 (2H, d, J=8.4 Hz), 6.90 (1H, d, J=8.8 Hz), 7.12 (1H, dd, J=8.9 Hz, 2.1 Hz), 7.39 (1H, d, J=2.1 Hz), 7.39 (1H, d, J=8.9 Hz), 7.44 (2H, d, J=8.4 Hz), 7.53 (1H, dd, J=8.8 Hz, 2.6 Hz), 8.04 (1H, d, J=2.6 Hz).

Reference Example 247

Production of 4-{1-ethyl-5-[5-(4-trifluoromethylbenzoylamino)-pyridin-2-yloxy]-1H-indole-2-carbonyl}piperazine-1-carboxylic acid tert-butyl ester To a solution of 4-[5-(5-nitropyridin-2-yloxy)-1H-indole-2-carbonyl]piperazine-1-carboxylic acid tert-butyl ester (2.73 g, 5.84 mmol) and iodoethane (0.6 mL, 7.50 mmol) in dry DMF (25 mL) was added 60% sodium hydride in oil (300 mg, 7.50 mmol) under ice cooling and the mixture was stirred for 1.5 hours. Water was added to the reaction mixture and extracted with AcOEt, the organic layer was washed with saturated aqueous NaHCO$_3$ and brine, dried over anhydrous magnesium sulfate and evaporated. The residue was purified by silica gel column chromatography (CH$_2$Cl$_2$:MeOH=50:1 to 40:1 to 30:1) to give a pale yellow amorphous powder (1.82 g). This amorphous powder was dissolved in ethanol (20 mL) and 10% Pd/C (200 mg) in EtOH (20 mL) was added. The reaction mixture was stirred under a hydrogen atmosphere at 40° C. for 3 hours. The reaction mixture was filtered with celite and the filtrate was evaporated. The residue was dissolved in CH$_2$Cl$_2$ (20 mL) and cooled to 0° C. To the solution were added trietylamine (0.70 mL, 5.02 mmol), subsequently 4-(trifluoromethyl)benzoyl chloride (0.60 mL, 4.04 mmol) dropwise and the resulting solution was stirred at room temperature for 2 hours. Water was added to the reaction mixture. The organic layer was washed with saturated aqueous NaHCO$_3$ and brine, dried over anhydrous magnesium sulfate and evaporated. The residue was purified by silica gel column chromatography (CH$_2$Cl$_2$:MeOH=50:1 to 30:1) to give 800 mg of the title compound as a pale brown amorphous powder.

$^1$H NMR (CDCl$_3$) δ 1.41 (3H, t, J=7.0 Hz), 1.48 (9H, s), 3.49 (4H, brs), 3.75 (4H, brs), 4.32 (2H, q, J=7.0 Hz), 6.94 (1H, d, J=8.9 Hz), 7.09 (1H, dd, J=8.6 Hz, 1.9 Hz), 7.38-7.41 (2H, m), 7.75 (2H, d, J=8.1 Hz), 7.97-8.00 (3H, m), 8.17 (1H, dd, J=8.9 Hz, 2.7 Hz), 8.26 (1H, d, J=2.7 Hz).

Reference Example 248

Production of {6-[2-(4-benzylpiperazine-1-carbonyl)-1-methyl-1H-indol-5-yloxy]pyridin-3-yl}carbamic acid tert-butyl ester To a solution of [5-(5-aminopyridin-2-yloxy)-1-methyl-1H-indol-2-yl](4-benzylpiperazin-1-yl)methanone (1.23 g, 2.79 mmol) in dichloromethane (15 mL) were added di-tert-butyl dicarbonate (0.91 g, 4.17 mmol) and triethylamine (0.78 mL, 5.6 mmol), and the reaction mixture was stirred for 3 days at room temperature. The solvent was removed under reduced pressure and the residue was extracted with AcOEt. The organic layer was washed with water, saturated aqueous NaHCO$_3$ and brine, dried over anhydrous magnesium sulfate and evaporated. The residue was purified by silica gel column chromatography (CH$_2$Cl$_2$:MeOH=60:1) to give 870 mg of the title compound as a white powder.

$^1$H NMR (CDCl$_3$) δ 1.51 (9H, s), 2.50 (4H, brs), 3.56 (2H, s), 3.78 (4H, brs), 3.83 (3H, s), 6.38 (1H, brs), 6.54 (1H, s), 6.83 (1H, d, J=8.9 Hz), 7.05 (1H, dd, J=8.9 Hz, 2.5 Hz), 7.24-7.38 (8H, m), 7.97 (1H, d, J=2.5 Hz).

The following compounds were produced in the same manner as in Reference Example 248 using appropriate starting materials.

Reference Example 249

{6-[2-(4-Benzo[1,3]dioxol-5-ylmethylpiperazine-1-carbonyl)-1-methyl-1H-indol-5-yloxy]pyridin-3-yl}carbamic acid tert-butyl ester $^1$H NMR (CDCl$_3$) δ 1.50 (9H, s), 2.47 (4H, brs), 3.45 (2H, s), 3.76 (4H, brs), 3.82 (3H, s), 5.95 (2H, s), 6.42 (1H, brs), 6.53 (1H, s), 6.75 (2H, s), 6.83 (1H, d, J=8.9 Hz), 6.86 (1H, s), 7.05 (1H, dd, J=8.6 Hz, 2.3 Hz), 7.32 (1H, s), 7.34 (1H, d, J=8.6 Hz), 7.88-7.98 (1H, m), 7.97 (1H, d, J=2.7 Hz).

Reference Example 250

[6-(1-Methyl-2-{4-[4-(2,2,2-trifluoroethoxy)benzyl]piperazine-1-carbonyl}-1H-indol-6-yloxy)pyridin-3-yl]carbamic acid tert-butyl ester $^1$H NMR (CDCl$_3$) δ 1.51 (9H, s), 2.48 (4H, brs), 3.51 (2H, s), 3.77 (7H, s), 4.35 (2H, q, J=8.1 Hz), 6.43 (1H, brs), 6.57 (1H, s), 6.86-6.98 (1H, m), 6.90 (1H, dd, J=8.9 Hz, 2.0 Hz), 6.91 (2H, d, J=8.9 Hz), 7.09 (1H, d, J=2.0 Hz), 7.27 (2H, d, J=8.9 Hz), 7.57 (1H, d, J=8.6 Hz), 7.95 (1H, d, J=8.2 Hz), 8.01 (1H, d, J=2.7 Hz).

Reference Example 251

6-(5-Acetylaminopyridin-2-yloxy)indole-1,2-dicarboxylic acid 1-tert-butyl ester 2-ethyl ester $^1$H NMR (CDCl$_3$) δ 1.39 (3H, t, J=7.1 Hz), 1.57 (9H, s), 2.12 (3H, s), 4.37 (2H, q, J=7.1 Hz), 6.89 (1H, d, J=8.9 Hz), 7.02 (1H, dd, J=8.6 Hz, 2.3 Hz), 7.09 (1H, d, J=0.7 Hz), 7.56 (1H, d, J=8.6 Hz), 7.83 (1H, d, J=2.0 Hz), 8.05 (1H, dd, J=8.7 Hz, 2.8 Hz), 8.15 (1H, d, J=2.2 Hz), 8.18 (1H, s).

Reference Example 252

6-(5-tert-Butoxycarbonylaminopyrimidin-2-yloxy)-1-methyl-1H-indole-2-carboxylic acid ethyl ester $^1$H NMR (CDCl$_3$) δ 1.41 (3H, t, J=7.1 Hz), 1.52 (9H, s), 4.03 (3H, s), 4.37 (2H, q, J=7.1 Hz), 6.50 (1H, s), 6.97 (1H, dd, J=8.7 Hz, 2.1 Hz), 7.20 (1H, d, J=1.8 Hz), 7.30 (1H, d, J=0.7 Hz), 7.67 (1H, d, J=8.6 Hz), 8.62 (2H, s).

Reference Example 253

6-(5-Nitropyridin-2-yloxy)indole-1,2-dicarboxylic acid 1-tert-butyl ester 2-ethyl ester $^1$H NMR (CDCl$_3$) δ 1.40 (3H, t, J=7.3 Hz), 1.61 (9H, s), 4.39 (2H, q, J=7.1 Hz), 7.07-7.11 (3H, m), 7.65 (1H, d, J=8.6 Hz), 7.95 (1H, d, J=2.0 Hz), 8.49 (1H, dd, J=9.1 Hz, 2.8 Hz), 9.04 (1H, d, J=2.6 Hz).

Reference Example 254

6-(5-tert-Butoxycarbonylamino-4-methylpyridin-2-yloxy)-1-methyl-1H-indole-2-carboxylic acid ethyl ester $^1$H NMR (CDCl$_3$) δ 1.41 (3H, t, J=7.1 Hz), 1.52 (9H, s), 2.27 (3H, s), 4.01 (3H, s), 4.37 (2H, q, J=7.0 Hz), 6.04 (1H, brs), 6.75 (1H, s), 6.91 (1H, dd, J=8.7 Hz, 2.1 Hz), 7.12 (1H, t, J=1.0 Hz), 7.29 (1H, d, J=1.0 Hz), 7.64 (1H, d, J=8.2 Hz), 8.27 (1H, s).

Reference Example 255

Production of 6-(1-carboxymethyl-2,3-dihydro-1H-indol-4-yloxy)-nicotinic acid ethyl ester 6-(2,3-Dihydro-1H-indol-4-yloxy)nicotinic acid ethyl ester (1.13 g, 3.97 mmol) was dissolved in DMF (5 mL). To the solution were added triethylamine (0.665 mL, 4.77 mmol) and tert-butyl bromoacetate (0.704 g, 4.77 mmol), and the resulting solution was stirred for 16 hours at room temperature, followed by stirring for 4 hours at 50° C. Water (100 mL) was added and the resulting solution was extracted with ethyl acetate (100 mL). After the organic layer was washed with brine, then dried over anhydrous sodium sulfate, the solvent was evaporated to give a pale brown oil (1.58 g). This oil was dissolved in trifluoroacetic acid (10 mL) and the solution was stirred for 1 hour at room temperature. The solution was concentrated, and the pH of the solution was adjusted to 5 using saturated sodium bicarbonate solution. The resulting solution was extracted with a mixture of ethyl acetate (50 mL)-THF (25 mL). After the organic layer was washed with brine, then dried over anhydrous sodium sulfate, the solvent was evaporated. The obtained residue was recrystallized from a mixed solution of ethyl acetate and n-hexane to yield 0.220 g of the title compound as a pale brown powder.

$^1$H NMR (DMSO-$d_6$) δ 1.31 (3H, t, J=7.1 Hz), 2.67 (2H, t, J=8.6 Hz), 3.48 (2H, t, J=8.6 Hz), 3.94 (2H, s), 4.32 (2H, q, J=7.1 Hz), 6.33-6.36 (2H, m), 7.00-7.09 (2H, m), 8.29 (1H, dd, J=8.7 Hz, 2.5 Hz), 8.71 (1H, d, J=2.5 Hz).

The following compounds were produced in the same manner as in Reference Example 255 using appropriate starting materials.

Reference Example 256

N-Methyl-N-{2-[1-methyl-2-(piperazine-1-carbonyl)-1H-indol-5-yl-oxy]pyrimidin-5-yl}-4-trifluoromethylbenzamide $^1$H NMR (CDCl$_3$) δ 2.91 (4H, brs), 3.48 (3H, s), 3.74 (4H, brs), 3.83 (3H, s), 6.56 (1H, s), 7.06 (1H, dd, J=2.2 Hz, 8.9 Hz), 7.36-7.44 (4H, m), 7.56 (2H, d, J=8.1 Hz), 8.29 (2H, s).

Reference Example 257

[6-(5-Ethylaminopyridin-2-yloxy)-1-methyl-1H-indol-2-yl]{4-[4-(2,2,2-trifluoroethoxy)benzyl]piperazin-1-yl}methanone $^1$H NMR (CDCl$_3$) δ 1.27 (3H, t, J=7.1 Hz), 2.47 (4H, s), 3.14 (2H, q, J=7.1 Hz), 3.40 (1H, s), 3.50 (2H, s), 3.75 (7H, s), 4.35 (2H, q, J=8.1 Hz), 6.55 (1H, s), 6.79 (1H, d, J=8.6 Hz), 6.87-6.93 (3H, m), 7.00 (1H, dd, J=8.7 Hz, 3.1 Hz), 7.04 (1H, d, J=1.6 Hz), 7.26-7.30 (2H, m), 7.54 (1H, d, J=8.6 Hz), 7.64 (1H, d, J=3.0 Hz).

Reference Example 258

[6-(5-Isopropylaminopyridin-2-yloxy)-1-methyl-1H-indol-2-yl]{4-[4-(2,2,2-trifluoroethoxy)benzyl]piperazin-1-yl}methanone $^1$H NMR (CDCl$_3$) δ 1.21 (6H, d, J=6.3 Hz), 2.48 (4H, s), 3.28 (1H, s), 3.51-3.61 (3H, m), 3.76 (7H, s), 4.35 (2H, q, J=8.1 Hz), 6.55 (1H, s), 6.79 (1H, d, J=8.9 Hz), 6.87-6.93 (3H, m), 6.99 (1H, dd, J=8.7 Hz, 3.1 Hz), 7.04 (1H, d, J=1.6 Hz), 7.26-7.30 (2H, m), 7.54 (1H, d, J=8.6 Hz), 7.62 (1H, d, J=3.0 Hz).

Reference Example 259

Production of (6-{2-[4-(4-methoxybenzyl)piperazine-1-carbonyl]-1-methyl-1H-indol-5-yloxy}pyridin-3-yl)carbamic acid tert-butyl ester To a suspension of [4-(4-methoxybenzyl)piperazin-1-yl]-[1-methyl-5-(5-nitropyridin-2-yloxy)-1H-indol-2-yl]methanone (6.3 g, 12.56 mmol) and di-tert-butyl dicarbonate (4.11 g, 18.8 mmol) in AcOEt (50 mL) was added 5% platinum/Carbon (630 mg) in AcOEt (50 mL), and the reaction mixture was stirred for 4 hours at 40° C. under a hydrogen atmosphere. The reaction mixture was filtered with celite and the filtrate was evaporated in vacuo. The residue was solidified with n-hexane, diethyl ether and acetone. The precipitate was collected by filtration and dried to give 6.33 g of the title compound as a pale yellow powder.

$^1$H NMR (CDCl$_3$) δ 1.50 (9H, s), 2.47 (4H, brs), 3.49 (2H, s), 3.76 (4H, brs), 3.80 (3H, s), 3.82 (3H, s), 6.45 (1H, s), 6.53 (1H, s), 6.81-6.89 (3H, m), 7.05 (1H, dd, J=2.7 Hz, 8.9 Hz), 7.21-7.35 (4H, m), 7.92 (1H, d, J=7.6 Hz), 7.97 (1H, d, J=2.2 Hz).

Reference Example 260

Production of 1,3-dimethyl-6-(5-methylaminopyridin-2-yloxy)-1H-indole-2-carboxylic acid A solution of 1,3-dimethyl-6-(5-nitropyridin-2-yloxy)-1H-indole-2-carboxylic acid ethyl ester (383 mg, 1.08 mmol) in ethanol (8 mL) and dioxane (4 mL) was hydrogenated over 10% Pd/C (40 mg) for 3 hours at 40° C. under atmospheric pressure. The catalyst was removed by filtration, and the filtrate was evaporated in vacuo to give a colorless oil (358 mg). This oil was dissolved in AcOEt (6 mL), and to this solution were added triethylamine (196 µL, 1.41 mmol) and acetyl chloride (98 µL, 1.38 mmol) under ice cooling. The reaction mixture was stirred for 30 minutes under ice cooling, and then washed with water and brine, dried over anhydrous sodium sulfate, and evaporated in vacuo. The residue was purified by silica gel column chromatography (AcOEt:n-hexane=1:1 to 10:1) to give a white powder (309 mg). This powder was dissolved in DMF (6 mL), and to this solution was added sodium hydride (34 mg, 0.85 mmol) under ice cooling. The mixture was stirred 10 minutes under ice cooling, and then iodomethane (58 µL, 0.91 mmol) was added under ice cooling. The reaction mixture was stirred for 1 hour under ice cooling, and then water was added, and extracted with AcOEt. The organic layer was washed with water and brine, dried over anhydrous sodium sulfate, and evaporated in vacuo to give a white powder (319 mg). This powder was dissolved in ethanol (6 mL), and to this solution was added 5 M NaOH (0.84 mL, 4.2 mmol) at room temperature. The reaction mixture was stirred overnight under reflux. The solvent was evaporated in vacuo, and the residue was diluted with water. The aqueous mixture was extracted with AcOEt after being acidified with 5 M HCl. The organic layer was washed with brine, dried over anhydrous sodium sulfate, and evaporated in vacuo to give 292 mg of the title compound as a brown powder.

$^1$H NMR (DMSO-$d_6$) δ 2.50 (3H, s), 2.68 (3H, s), 3.86 (3H, s), 5.67 (1H, s), 6.76 (1H, dd, J=8.7 Hz, 2.1 Hz), 6.83 (1H, d, J=8.6 Hz), 7.05-7.09 (2H, m), 7.51 (1H, d, J=3.1 Hz), 7.62 (1H, d, J=8.7 Hz), 12.84 (1H, s).

Example 1

Production of N-(6-{1-[2-(4-benzo[1,3]dioxol-5-ylmethylpiperazin-1-yl)-2-oxoethyl]-2,3-dihydro-1H-indol-5-yloxy}pyridin-3-yl)-3,4-dichlorobenzamide 2-[5-(5-Aminopyridin-2-yloxy)-2,3-dihydroindol-1-yl]-1-(4-benzo[1,3]dioxol-5-ylmethylpiperazin-1-yl)ethanone (0.240 g, 0.492 mmol) was dissolved in THF (10 mL). To the solution were added triethylamine (0.0686 mL, 0.492 mmol), then 3,4-dichlorobenzoyl chloride (0.103 g, 0.492 mmol), and the resulting solution was stirred for 30 minutes at room temperature. Brine (50 ml) was added to the reaction solution, and the mixture was extracted with ethyl acetate (50 mL). After the organic layer was washed with brine, then dried over anhydrous sodium sulfate, the solvent was evaporated. The obtained residue was purified by silica gel column chromatography (CH$_2$Cl$_2$:MeOH=40:1), to yield 0.143 g of the title compound as a grayish white powder.

¹H NMR (CDCl₃) δ 2.42-2.43 (4H, m), 2.92 (2H, t, J=8.2 Hz), 3.40 (2H, t, J=8.2 Hz), 3.44 (2H, s), 3.54-3.63 (4H, m), 3.82 (2H, s), 5.30 (2H, s), 6.35 (1H, d, J=8.4 Hz), 6.74-6.85 (6H, m), 7.52 (1H, d, J=8.4 Hz), 7.71 (1H, dd, J=8.4 Hz, 2.0 Hz), 7.99 (1H, d, J=2.0 Hz), 8.08 (1H, dd, J=8.8 Hz, 2.6 Hz), 8.24 (1H, d, J=2.6 Hz), 8.51 (1H, s).

The following compounds were produced in the same manner as in Example 1 using appropriate starting materials.

Example 2

N-(6-{1-[2-(4-Benzo[1,3]dioxol-5-ylmethylpiperazin-1-yl)-2-oxo-ethyl]-1,1-indol-4-yloxy}pyridin-3-yl)-3,4-dichlorobenzamide ¹H NMR (DMSO-d₆) δ 2.34 (2H, brs), 2.45 (2H, brs), 3.44 (4H, s), 3.58 (2H, brs), 5.18 (2H, s), 6.00 (2H, s), 6.08 (1H, d, J=3.1 Hz), 6.74-6.79 (2H, m), 6.85-6.89 (2H, m), 7.03-7.13 (2H, m), 7.19-7.22 (2H, m), 7.84 (1H, d, J=8.4 Hz), 7.93-7.97 (1H, m), 8.16-8.22 (2H, m), 8.45 (1H, d, J=2.6 Hz), 10.55 (1H, s).

Example 3

N-(6-{1-[2-(4-Benzo[1,3]dioxol-5-ylmethylpiperazin-1-yl)-2-oxo-ethyl]-1H-indol-4-yloxy}pyridin-3-yl)-4-trifluoromethylbenzamide ¹H NMR (DMSO-d₆) δ 2.34-2.50 (4H, m), 3.44-3.63 (6H, m), 5.18 (2H, s), 6.00 (2H, s), 6.09 (1H, d, J=3.1 Hz), 6.74-6.79 (2H, m), 6.85-6.90 (2H, m), 7.04-7.14 (2H, m), 7.20-7.22 (2H, m), 7.93 (2H, d, J=8.4 Hz), 8.15-8.23 (3H, m), 8.47 (1H, d, J=2.5 Hz), 10.63 (1H, s).

Example 4

N-(6-{1-[2-(4-Benzo[1,3]dioxol-5-ylmethylpiperazin-1-yl)-2-oxo-ethyl]-2,3-dihydro-1H-indol-4-yloxy}pyridin-3-yl)-3,4-dichloro-benzamide ¹H NMR (DMSO-d₆) δ 2.31-2.38 (4H, m), 2.68 (2H, t, J=8.5 Hz), 3.41-3.46 (8H, m), 4.03 (2H, s), 5.99 (2H, s), 6.26-6.30 (2H, m), 6.75 (1H, dd, J=7.8 Hz, 1.4 Hz), 6.84-6.88 (2H, m), 6.95-7.02 (2H, m), 7.84 (1H, d, J=8.4 Hz), 7.95 (1H, dd, J=8.4 Hz, 2.0 Hz), 8.17 (1H, dd, J=8.9 Hz, 2.8 Hz), 8.22 (1H, d, J=2.0 Hz), 8.47 (1H, d, J=2.3 Hz), 10.54 (1H, brs).

Example 5

N-(6-{1-[2-(4-Benzo[1,3]dioxol-5-ylmethylpiperazin-1-yl)-2-oxo-ethyl]-2,3-dihydro-1H-indol-4-yloxy}pyridin-3-yl)-4-trifluoro-methylbenzamide ¹H NMR (DMSO-d₆) δ 2.31-2.38 (4H, m), 2.68 (2H, t, J=8.4 Hz), 3.41-3.46 (8H, m), 4.03 (2H, s), 5.99 (2H, s), 6.26-6.30 (2H, m), 6.76 (1H, dd, J=7.9 Hz, 1.5 Hz), 6.84-6.88 (2H, m), 6.95-7.03 (2H, m), 7.93 (2H, d, J=8.2 Hz), 8.16 (2H, d, J=7.9 Hz), 8.20 (1H, dd, J=8.9 Hz, 2.6 Hz), 8.50 (1H, d, J=2.5 Hz), 10.61 (1H, brs).

Example 6

N-{6-[2-(4-Benzo[1,3]dioxol-5-ylmethylpiperazine-1-carbonyl)-1-methyl-1H-indol-5-yloxy]pyridin-3-yl}-3,4-dichloro-N-methyl-benzamide hydrobromide Melting point: 222-226° C.

Example 7

N-{6-[2-(4-Benzo[1,3]dioxol-5-ylmethylpiperazine-1-carbonyl)-1-methyl-1H-indol-5-yloxy]pyridin-3-yl}-3,4-dichlorobenzamide hydrobromide Melting point: 264-269° C.

Example 8

N-{6-[2-(4-Benzo[1,3]dioxol-5-ylmethylpiperazine-1-carbonyl)-1-methyl-1H-indol-5-yloxy]pyridin-3-yl}-4-trifluoromethylbenzamide hydrobromide Melting point: 240-244° C.

Example 9

N-{6-[2-(4-Benzo[1,3]dioxol-5-ylmethylpiperazine-1-carbonyl)-1-methyl-1H-indol-5-yloxy]pyridin-3-yl}-2,4-bistrifluoromethyl-benzamide hydrobromide Melting point: 258-261° C. (decomposition)

Example 10

N-{6-[2-(4-Benzo[1,3]dioxol-5-ylmethylpiperazine-1-carbonyl)-1-methyl-1H-indol-5-yloxy]pyridin-3-yl}-2-methoxy-4-trifluoro-methylbenzamide hydrobromide Melting point: 228-231° C. (decomposition)

Example 11

N-{6-[2-(4-Benzo[1,3]dioxol-5-ylmethylpiperazine-1-carbonyl)-1-methyl-1H-indol-5-yloxy]pyridin-3-yl}-4-pyrrol-1-ylbenzamide hydrobromide Melting point: 227-232° C. (decomposition)

Example 12

(E)-N-{6-[2-(4-Benzo[1,3]dioxol-5-ylmethylpiperazine-1-carbonyl)-1-methyl-1H-indol-5-yloxy]pyridin-3-yl}-3-(3,5-difluorophenyl)-N-methylacrylamide hydrobromide Melting point: 176-178° C.

Example 13

N-{6-[2-(4-Benzo[1,3]dioxol-5-ylmethylpiperazine-1-carbonyl)-1-methyl-1H-indol-5-yloxy]pyridin-3-yl]-N-methyl-4-trifluoro-methoxybenzamide hydrobromide Melting point: 220-222° C.

Example 14

N-(6-{2-[4-(4-Methoxybenzyl)piperazine-1-carbonyl]-1-methyl-1H-indol-5-yloxy}pyridin-3-yl)-2-methyl-4-trifluoromethylbenzamide hydrobromide Melting point: 249-251° C.

Example 15

N-(6-{2-[4-(4-Methoxybenzyl)piperazine-1-carbonyl]-1-methyl-1H-indol-5-yloxy}pyridin-3-yl)-2,N-dimethyl-4-trifluoromethyl-benzamide hydrobromide $^1$H NMR (CDCl$_3$) δ 2.36 (3H, s), 2.47 (4H, brs), 3.49 (3H, s), 3.76 (4H, brs), 3.81 (6H, s), 6.52 (1H, s), 6.75 (1H, d, J=8.9 Hz), 6.87 (2H, d, J=8.4 Hz), 6.95 (1H, d, J=8.4 Hz), 7.10 (1H, d, J=7.3 Hz), 7.22-7.32 (8H, m), 7.80 (1H, s).

Example 16

2-Chloro-N-(6-{2-[4-(4-methoxybenzyl)piperazine-1-carbonyl]-1-methyl-1H-indol-5-yloxy}pyridin-3-yl)-N-methyl-4-trifluoromethyl-benzamide oxalate Melting point: 163-165° C.

Example 17

N-(6-{2-[4-(4-Methoxybenzyl)piperazine-1-carbonyl]-1-methyl-1H-indol-5-yloxy}pyridin-3-yl)-4-trifluoromethoxybenzamide hydrobromide Melting point: 226-227° C.

Example 18

N-(6-{2-[4-(4-Methoxybenzyl)piperazine-1-carbonyl]-1-methyl-1H-indol-5-yloxy}pyridin-3-yl)-N-methyl-4-trifluoromethoxybenzamide maleate Melting point: 147-148° C.

Example 19

N-(6-{2-[4-(4-Methoxybenzyl)piperazine-1-carbonyl]-1-methyl-1H-indol-5-yloxy}pyridin-3-yl)-3-methyl-4-trifluoromethylbenzamide hydrobromide Melting point: 188-191° C.

Example 20

N-(6-{2-[4-(4-Methoxybenzyl)piperazine-1-carbonyl]-1-methyl-1H-indol-5-yloxy}pyridin-3-yl)-3,N-dimethyl-4-trifluoromethyl-benzamide hydrobromide Melting point: 199-202° C.

Example 21

5-Trifluoromethylpyridine-2-carboxylic acid (6-{2-[4-(4-methoxy-benzyl)piperazine-1-carbonyl]-1-methyl-1H-indol-5-yloxy}pyridin-3-yl)methylamide dioxalate Melting point: 152-154° C.

Example 22

2-Fluoro-N-methyl-N-[6-(1-methyl-2-{4-[4-(2,2,2-trifluoroethoxy)-benzyl]piperazine-1-carbonyl}-1H-indol-6-yloxy)pyridin-3-yl]-4-trifluoromethylbenzamide hydrochloride Melting point: 234.5-235.8° C.

Example 23

4,N-Dimethyl-N-[6-(1-methyl-2-{4-[4-(2,2,2-trifluoroethoxy)-benzyl]piperazine-1-carbonyl}-1H-indol-6-yloxy)pyridin-3-yl]-benzamide hydrobromide Melting point: 226.1-227.3° C.

Example 24

N-[6-(1-Methyl-2-{4-[4-(2,2,2-trifluoroethoxy)benzyl]piperazine-1-carbonyl}-1H-indol-6-yloxy)pyridin-3-yl]-6-trifluoromethyl-nicotinamide hydrochloride Melting point: 195.4° C.

Example 25

3-Fluoro-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzamide hydrochloride Melting point: 259.0-263.2° C.

Example 26

N-Ethyl-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzamide hydrobromide Melting point: 189.8-192.8° C.

Example 27

N-Isopropyl-N-[6-(1-methyl-2-{4-[4-(2,2,2-trifluoroethoxy)-benzyl]piperazine-1-carbonyl}-1H-indol-6-yloxy)pyridin-3-yl]-4-trifluoromethylbenzamide $^1$H NMR (CDCl$_3$) δ 1.20 (6H, d, J=6.9 Hz), 2.48 (4H, s), 3.51 (2H, s), 3.76 (7H, s), 4.35 (2H, q, J=8.1 Hz), 5.12 (1H, brs), 6.57 (1H, d, J=0.7 Hz), 6.82-6.84 (2H, m), 6.91-6.92 (2H, m), 7.06 (1H, s), 7.24-7.33 (5H, m), 7.47 (2H, d, J=7.3 Hz), 7.58 (1H, d, J=8.6 Hz), 7.81 (1H, s).

Example 28

3,4-Dichloro-N-isopropyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide hydrochloride Melting point: 232.8-235.6° C.

Example 29

N-Methyl-N-[6-(1-methyl-2-{4-[4-(2,2,2-trifluoroethoxy)benzyl]-piperazine-1-carbonyl}-1H-indol-6-yloxy)pyridin-3-yl]-methanesulfonamide hydrochloride Melting point: 252.7-253.6° C.

Example 30

N-Methyl-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide hydrobromide Melting point: 234.6-235.2° C.

Example 31

Butane-1-sulfonic acid methyl-[6-(1-methyl-2-{4-[4-(2,2,2-tri-fluoroethoxy)benzyl]piperazine-1-carbonyl}-1H-indol-6-yloxy)-pyridin-3-yl]amide hydrochloride Melting point: 253.6-254.4° C.

Example 32

4,N-Dimethyl-N-(6-{1-methyl-2-[4-(4-propoxybenzyl)piperazine-1-carbonyl]-1H-indol-6-yloxy}pyridin-3-yl)benzenesulfonamide Melting point: 135.9-136.8° C.

Example 33

3,4-Dichloro-N-methyl-N-(6-{1-methyl-2-[4-(4-propoxybenzyl)-piperazine-1-carbonyl]-1H-indol-6-yloxy}pyridin-3-yl)-benzenesulfonamide Melting point: 231.7-235° C. (decomposition)

Example 34

2,2,2-Trifluoroethanesulfonic acid methyl-[6-(1-methyl-2-{4-[4-(2,2,2-trifluoroethoxy)benzyl]piperazine-1-carbonyl}-1H-indol-6-yloxy)pyridin-3-yl] amide hydrochloride Melting point: 243.4-244.4° C.

Example 35

N-[6-(1-Methoxymethyl-2-{4-[4-(2,2,2-trifluoroethoxy)benzyl]-piperazine-1-carbonyl}-1H-indol-6-yloxy)pyridin-3-yl]-N-methyl-4-trifluoromethylbenzamide $^1$H NMR (CDCl$_3$) δ 2.47 (4H, s), 3.22 (3H, s), 3.48 (3H, s), 3.15 (2H, s), 3.77 (4H, s), 4.35 (2H, q, J=8.1 Hz), 5.56 (2H, s), 6.60 (1H, s), 6.83-6.92 (4H, m), 7.25-7.30 (2H, m), 7.39-7.52 (5H, m), 7.59 (1H, d, J=8.6 Hz), 7.80-7.83 (1.5H, m), 8.27 (0.5H, d, J=7.9 Hz).

Example 36

N-[6-(2-{4-[4-(2,2,2-Trifluoroethoxy)benzyl]piperazine-1-carbonyl}-1H-indol-6-yloxy)pyridin-3-yl]-4-trifluoramethyl-benzamide Melting point: 281.3-282.3° C.

Example 37

2,4,6-Trimethyl-N-[6-(1-methyl-2-{4-[4-(2,2,2-trifluoroethoxy)-benzyl]piperazine-1-carbonyl}-1H-indol-6-yloxy)pyridin-3-yl]-benzamide hydrochloride $^1$H NMR (DMSO-d$_6$) δ 2.24 (6H, s), 2.27 (3H, s), 3.16 (2H, brs), 3.39-3.65 (4H, m), 3.74 (3H, s), 4.33 (2H, s), 4.43-4.47 (2H, m), 4.81 (2H, q, J=9.1 Hz), 6.80 (1H, s), 6.88 (1H, dd, J=8.7 Hz, 1.7 Hz), 6.93 (2H, s), 7.02 (1H, d, J=8.7 Hz), 7.16 (2H, d, J=8.2 Hz), 7.33 (1H, s), 7.58 (2H, d, J=8.4 Hz), 7.63 (1H, d, J=8.4 Hz), 8.18 (1H, dd, J=8.9 Hz, 2.6 Hz), 8.44 (1H, d, J=2.6 Hz), 10.44 (1H, s), 11.10 (1H, brs).

Example 38

N-Methyl-N-[6-(1-methyl-2-{4-[4-(2,2,2-trifluoroethoxy)benzyl]-piperazine-1-carbonyl}-2,3-dihydro-1H-indol-6-yloxy)pyridin-3-yl]-4-trifluoromethyl-benzamide $^1$H NMR (CDCl$_3$) δ 2.40 (2H, s), 2.46 (2H, s), 2.73 (3H, s), 2.97 (1H, dd, J=15.8 Hz, 9.9 Hz), 3.28 (1H, dd, J=15.7 Hz, 10.1 Hz), 3.46 (3H, s), 3.48 (2H, s), 3.55-3.62 (2H, m), 3.72-3.76 (2H, m), 4.30-4.39 (3H, m), 6.13 (1H, d, J=2.0 Hz), 6.31 (1H, dd, J=7.9 Hz, 2.0 Hz), 6.78 (1H, d, J=8.9 Hz), 6.90 (2H, d, J=11.1 Hz), 6.95 (1H, d, J=7.9 Hz), 7.27 (2H, d, J=8.6 Hz), 7.44 (5H, dd, J=24.1 Hz, 8.2 Hz), 7.86 (1H, s).

Example 39

N-Methyl-N-[6-(2-{4-[4-(2,2,2-trifluoroethoxy)benzyl]piperazine-1-carbonyl}-1H-indol-6-yloxy)pyridin-3-yl]-4-trifluoromethyl-benzenesulfonamide Melting point: 200.1-200.2° C.

Example 40

3,4-Dichloro-N-methyl-N-[6-(2-{4-[4-(2,2,2-trifluoroethoxy)-benzyl]piperazine-1-carbonyl}-1H-indol-6-yloxy)pyridin-3-yl]-benzenesulfonamide hydrochloride Melting point: 225.2-229.3° C.

Example 41

4,N-Dimethyl-N-[6-(2-{4-[4-(2,2,2-trifluoroethoxy)benzyl]-piperazine-1-carbonyl}-1H-indol-6-yloxy)pyridin-3-yl]benzene-sulfonamide Melting point: 184.0-184.2° C.

Example 42

N-(2-{2-[4-(4-Isopropoxybenzyl)piperazine-1-carbonyl]-1-methyl-1H-indol-6-yloxy}pyrimidin-5-yl)-N-methyl-4-trifluoromethyl-benzenesulfonamide Melting point: 186.6-187.3° C.

Example 43

3,4-Dichloro-N-(2-{2-[4-(4-isopropoxybenzyl)piperazine-1-carbonyl]-1-methyl-1H-indol-6-yloxy}pyrimidin-5-yl)-N-methyl-benzenesulfonamide Melting point: 191.2-193.0° C.

Example 44

N-(2-{2-[4-(4-Isopropoxybenzyl)piperazine-1-carbonyl]-1-methyl-1H-indol-6-yloxy}pyrimidin-5-yl)-4,N-dimethylbenzenesulfonamide Melting point: 154.3-155.1° C.

Example 45

N-(2-{2-[4-(4-Isopropoxybenzyl)piperazine-1-carbonyl]-1-methyl-1H-indol-6-yloxy}pyrimidin-5-yl)-N-methylmethanesulfonamide Melting point: 134.3-135.6° C.

Example 46

N-[4-Methyl-6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzamide hydrobromide Melting point: 222.4-224.6° C.

Example 47

N-Methyl-N-[4-methyl-6-(1-methyl-2-{4-[4-(2,2,2-trifluoroethoxy)-benzyl]piperazine-1-carbonyl}-1H-indol-6-yloxy)pyridin-3-yl]-4-trifluoromethylbenzamide hydrobromide Melting point: 220.0-222.5° C.

Example 48

Production of acetic acid 2-{methyl[6-(1-methyl-2-{4-[4-(2,2,2-trifluoroethoxy)benzyl]piperazine-1-carbonyl}-1H-indol-6-yloxy)-pyridin-3-yl]carbamoyl}-5-trifluoromethylphenyl ester To a stirred solution of 2-acetoxy-4-trifluoromethyl-benzoic acid (180 mg, 0.73 mmol) in $CH_2Cl_2$ (6 mL) were added oxalyl chloride (0.08 mL, 0.91 mmol) and DMF (1 drop). The reaction mixture was stirred at room temperature for 1 hour. $CH_2Cl_2$ and excess oxalyl chloride were removed in vacuo. Acetic acid 2-chlorocarbonyl-5-trifluoromethylphenyl ester was obtained as a colorless oil (190 mg) and used in the following step without further purification. To a stirred solution of [1-Methyl-6-(5-methylaminopyridin-2-yloxy)-1H-indol-2-yl]{4-[4-(2,2,2-tri-fluoroethoxy)benzyl]piperazin-1-yl}methanone (340 mg, 0.6 mmol) in AcOEt (4 mL) were added triethylamine (0.13 mL, 0.91 mmol) and acetic acid 2-chlorocarbonyl-5-trifluoromethyl-phenyl ester (190 mg, 0.73 mmol) in AcOEt (3 mL) under ice cooling. The reaction mixture was stirred for 10 minutes at 0° C. Water was added to the reaction mixture, and the aqueous layer was extracted with AcOEt. The organic layer was washed with saturated aqueous $NaHCO_3$ and brine, dried over anhydrous magnesium sulfate, and evaporated. The residue was purified by silica gel column chromatography ($CH_2Cl_2$:MeOH=50:1) to afford 0.46 g of the title compound as a white powder.

$^1$H NMR (CDCl$_3$) δ 2.32 (3H, s), 2.48 (4H, brs), 3.47 (2H, s), 3.51 (3H, s), 3.76 (7H, s), 4.35 (2H, q, J=7.3 Hz), 6.57 (1H, s), 6.72-6.89 (2H, m), 6.92 (2H, d, J=8.2 Hz), 7.07 (1H, brs), 7.28 (2H, d, J=8.2 Hz), 7.18-7.53 (4H, m), 7.58 (1H, d, J=8.6 Hz), 7.99 (1H, brs).

The following compounds were produced in the same manner as in Example 48 using appropriate starting materials.

Example 49

4-Chloro-3-methyl-N-[6-(1-methyl-2-{4-[4-(2,2,2-trifluoroethoxy)-benzyl]piperazine-1-carbonyl}-1H-indol-6-yloxy)pyridin-3-yl]-benzamide hydrochloride Melting point: 182.9° C.

Example 50

4-Chloro-N-[6-(1-methyl-2-{4-[4-(2,2,2-trifluoroethoxy)benzyl]-piperazine-1-carbonyl}-1H-indol-6-yloxy)pyridin-3-yl]-3-tri-fluoromethylbenzamide hydrochloride $^1$H NMR (DMSO-d$_6$) δ 3.17 (2H, brs), 3.35-3.48 (4H, brs), 3.64 (2H, brs), 3.75 (3H, brs), 4.34-4.46 (2H, m), 4.72-4.80 (2H, m), 6.67-6.81 (1H, m), 6.88-6.92 (1H, m), 7.01 (1H, s), 7.05 (1H, d, J=8.9 Hz), 7.16-7.19 (1H, m), 7.28-7.32 (1H, m), 7.35 (1H, brs), 7.54-7.64 (2H, m), 7.95 (1H, d, J=8.4 Hz), 8.18 (1H, dd, J=8.9 Hz, 2.7 Hz), 8.28 (1H, dd, J=8.4 Hz, 2.2 Hz), 8.40 (1H, d, J=2.2 Hz), 8.47 (1H, d, J=2.7 Hz), 10.49 (1H, brs), 10.68 (1H, s).

Example 51

3-Methyl-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzamide hydrochloride $^1$H NMR (DMSO-d$_6$) δ 2.54 (3H, d, J=1.9 Hz), 3.15 (2H, brs), 3.35-3.48 (4H, m), 3.65 (2H, brs), 3.75 (3H, brs), 4.33-4.49 (2H, m), 4.72-4.85 (2H, m), 6.66-6.81 (1H, m), 6.90 (1H, d, J=8.1 Hz), 7.01 (1H, brs), 7.05 (1H, d, J=8.9 Hz), 7.17 (1H, d, J=7.6 Hz), 7.27-7.34 (2H, m), 7.54-7.65 (2H, m), 7.85 (1H, d, J=8.4 Hz), 7.95 (1H, d, J=8.1 Hz), 8.01 (1H, s), 8.21 (1H, dd, J=8.6 Hz, 2.7 Hz), 8.49 (1H, d, J=2.4 Hz), 10.58 (1H, s), 10.71 (1H, s).

Example 52

4-Chloro-3-fluoro-N-[6-(1-methyl-2-{4-[4-(2,2,2-trifluoroethoxy)-benzyl]piperazine-1-carbonyl}-1H-indol-6-yloxy)pyridin-3-yl]-benzamide hydrochloride $^1$H NMR (DMSO-d$_6$) δ 3.16 (2H, brs), 3.35-3.48 (4H, s), 3.65 (2H, brs), 3.72 (3H, brs), 4.34-4.46 (2H, m), 4.72-4.83

(2H, m), 6.66-6.81 (1H, m), 6.89 (1H, d, J=7.8 Hz), 7.00 (1H, s), 7.04 (1H, d, J=8.9 Hz), 7.18 (1H, d, J=8.9 Hz), 7.27-7.33 (2H, m), 7.52-7.64 (2H, m), 7.77-7.88 (2H, m), 8.00 (1H, dd, J=10.0 Hz, 1.6 Hz), 8.18 (1H, dd, J=8.6 Hz, 2.7 Hz), 8.47 (1H, d, J=2.4 Hz), 10.47 (1H, brs), 10.52 (1H, s).

Example 53

3,N-Dimethyl-N-[6-(1-methyl-2-{4-[4-(2,2,2-trifluoroethoxy)-benzyl]piperazine-1-carbonyl}-1H-indol-6-yloxy)pyridin-3-yl]-4-trifluoromethylbenzamide hydrobromide $^1$H NMR (DMSO-d$_6$) δ 2.38 (3H, s), 3.19 (2H, brs), 3.32-3.48 (4H, m), 3.48 (3H, s), 3.72 (3H, s), 4.36 (2H, brs), 4.42-4.47 (2H, m), 4.82 (2H, q, J=8.8 Hz), 6.78 (1H, brs), 6.80 (1H, s), 6.99 (1H, d, J=8.6 Hz), 7.18 (1H, d, J=8.6 Hz), 7.20 (2H, brs), 7.29 (1H, s), 7.43-7.62 (5H, m), 7.84 (1H, dd, J=8.6 Hz, 2.1 Hz), 7.92 (1H, s), 9.86 (1H, brs).

Example 54

4-Chloro-3,N-dimethyl-N-[6-(1-methyl-2-{4-[4-(2,2,2-trifluoro-ethoxy)benzyl]piperazine-1-carbonyl}-1H-indol-6-yloxy)pyridin-3-yl]benzamide hydrochloride $^1$H NMR (DMSO-d$_6$) δ 2.26 (3H, s), 3.15 (2H, brs), 3.36 (3H, s), 3.36-3.50 (4H, m), 3.72 (3H, s), 4.34 (2H, s), 4.42-4.46 (2H, m), 4.82 (2H, q, J=8.7 Hz), 6.79 (1H, s), 6.81 (1H, dd, J=8.6 Hz, 1.6 Hz), 6.98 (1H, d, J=8.7 Hz), 7.05 (1H, d, J=8.6 Hz), 7.17 (2H, d, J=8.6 Hz), 7.30-7.35 (3H, m), 7.54 (2H, d, J=8.1 Hz), 7.61 (1H, d, J=8.6 Hz), 7.80 (1H, dd, J=8.6 Hz, 2.8 Hz), 7.90 (1H, d, J=1.6 Hz), 10.66 (1H, brs).

Example 55

4-Chloro-3-fluoro-N-methyl-N-[6-(1-methyl-2-{4-[4-(2,2,2-tri-fluoroethoxy)benzyl]piperazine-1-carbonyl}-1H-indol-6-yloxy)-pyridin-3-yl]benzamide hydrochloride $^1$H NMR (DMSO-d$_6$) δ 3.11-3.19 (2H, m), 3.35 (3H, s), 3.38-3.47 (4H, m), 3.63 (2H, brs), 3.72 (3H, s), 4.34 (2H, s), 4.42-4.46 (2H, m), 4.82 (2H, q, J=8.8 Hz), 6.79 (1H, s), 6.80 (1H, d, J=8.6 Hz), 6.99 (1H, d, J=8.4 Hz), 7.01-7.15 (2H, m), 7.17 (1H, d, J=8.4 Hz), 7.29 (1H, s), 7.39 (1H, d, J=9.7 Hz), 7.51-7.63 (4H, m), 7.83 (1H, dd, J=8.7 Hz, 2.1 Hz), 7.96 (1H, s), 10.80 (1H, brs).

Example 56

4-Chloro-N-methyl-N-[6-(1-methyl-2-{4-[4-(2,2,2-trifluoroethoxy)-benzyl]piperazine-1-carbonyl}-1H-indol-6-yloxy)pyridin-3-yl]-3-trifluoromethylbenzamide oxalate $^1$H NMR (DMSO-d$_6$) δ 2.65 (4H, brs), 3.37 (3H, s), 3.69 (3H, s), 3.72 (6H, brs), 4.76 (2H, q, J=8.9 Hz), 6.69 (1H, s), 6.76 (1H, d, J=8.9 Hz), 7.00 (1H, d, J=8.7 Hz), 7.06 (2H, d, J=8.7 Hz), 7.24 (1H, s), 7.34 (2H, d, J=8.4 Hz), 7.59 (2H, d, J=8.6 Hz), 7.68 (1H, d, J=8.1 Hz), 7.74 (1H, brs), 7.86 (1H, dd, J=8.7 Hz, 2.8 Hz), 7.96 (1H, brs).

Example 57

2-Fluoro-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoramethylbenzamide hydrochloride $^1$H NMR (DMSO-d$_6$) δ 3.13-3.20 (2H, m), 3.39-3.49 (4H, m), 3.75 (3H, s), 4.34 (2H, brs), 4.43-4.77 (2H, m), 4.82 (2H, q, J=8.9 Hz), 6.81 (1H, s), 6.90 (1H, dd, J=8.7 Hz, 1.9 Hz), 7.06 (1H, d, J=8.9 Hz), 7.17 (2H, d, J=8.2 Hz), 7.35 (1H, d, J=1.5 Hz), 7.57 (2H, d, J=8.2 Hz), 7.64 (1H, d, J=8.6 Hz), 7.75 (1H, d, J=8.1 Hz), 7.90-7.96 (2H, m), 8.17 (1H, dd, J=8.9 Hz, 2.6 Hz), 8.44 (1H, d, J=2.6 Hz), 10.78 (1H, s), 10.96 (1H, brs).

Example 58

2-Chloro-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzamide hydrochloride $^1$H NMR (DMSO-d$_6$) δ 3.11 (2H, brs), 3.56-3.65 (6H, m), 3.73 (3H, s), 4.33 (2H, brs), 4.78 (2H, q, J=8.3 Hz), 6.73 (1H, s), 6.89 (1H, dd, J=8.7 Hz, 1.9 Hz), 7.06 (1H, d, J=8.6 Hz), 7.10 (2H, brs), 7.34 (1H, d, J=1.9 Hz), 7.42 (2H, brs), 7.63 (1H, d, J=8.6 Hz), 7.87 (2H, s), 8.05 (1H, s), 8.16 (1H, dd, J=8.9 Hz, 2.6 Hz), 8.43 (1H, d, J=2.8 Hz), 10.83 (1H, s), 10.97 (1H, brs).

Example 59

2-Methoxy-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoramethylbenzamide $^1$H NMR (CDCl$_3$) δ 2.48 (4H, brs), 3.51 (2H, s), 3.78 (4H, brs), 3.79 (3H, s), 4.12 (3H, s), 4.35 (2H, q, J=8.2 Hz), 6.58 (1H, d, J=0.7 Hz), 6.89-6.97 (4H, m), 7.14 (1H, d, J=2.0 Hz), 7.26-7.30 (3H, m), 7.41 (1H, d, J=8.1 Hz), 7.60 (1H, d, J=8.6 Hz), 8.24-8.28 (2H, m), 8.40 (1H, d, J=8.1 Hz), 9.64 (1H, brs).

Example 60

2,N-Dimethyl-N-[6-(1-methyl-2-{4-[4-(2,2,2-trifluoroethoxy)-benzyl]piperazine-1-carbonyl}-1H-indol-6-yloxy)pyridin-3-yl]-4-trifluoromethylbenzamide hydrobromide $^1$H NMR (DMSO-d$_6$) δ 2.31 (3H, s), 3.10-3.22 (4H, m), 3.40 (3H, s), 3.70 (3H, s), 3.76 (2H, brs), 4.36 (2H, s), 4.42-4.48 (2H, m), 4.82 (2H, q, J=8.9 Hz), 6.73 (1H, dd, J=8.4 Hz, 1.6 Hz), 6.80 (1H, s), 6.92 (1H, d, J=8.7 Hz), 7.18 (2H, d, J=8.6 Hz), 7.25 (1H, s), 7.37 (1H, d, J=8.4 Hz), 7.42 (1H, d, J=7.6 Hz), 7.50 (1H, d, J=8.2 Hz), 7.52 (2H, s), 7.58 (1H, d, J=8.6 Hz), 7.82 (1H, dd, J=9.0 Hz, 2.6 Hz), 7.92 (1H, d, J=2.3 Hz), 9.88 (1H, brs).

Example 61

N-[6-(1-Methyl-2-{4-[4-(2,2,2-trifluoroethoxy)benzyl]piperazine-1-carbonyl}-1H-indol-6-yloxy)pyridin-3-yl]-2,4-bistrifluoro-methylbenzamide hydrochloride $^1$H NMR (DMSO-d$_6$) δ 2.89 (4H, brs), 3.42-4.16 (6H, m), 3.73 (3H, s), 4.78 (2H, q, J=8.8 Hz), 6.73 (1H, brs), 6.89 (1H, dd, J=8.6 Hz, 2.0 Hz), 7.06 (1H, d, J=8.9 Hz), 7.10 (2H, s), 7.34 (1H, d, J=1.6 Hz), 7.41 (2H, brs), 7.63 (1H, d, J=8.6 Hz), 8.02 (1H, d, J=7.9 Hz), 8.13 (1H, dd, J=8.9 Hz, 2.6 Hz), 8.23-8.27 (2H, m), 8.38 (1H, d, J=2.6 Hz), 10.88 (1H, s), 11.00 (1H, brs).

Example 62

Production of N-{6-[2-(4-benzo[1,3]dioxol-5-ylmethylpiperazine-1-carbonyl)-1-methyl-1H-indol-5-yloxy]pyridin-3-yl}-3,4-dichloro-benzenesulfonamide hydrochloride A stirred solution of [5-(5-aminopyridin-2-yloxy)-1-methyl-1H-indol-2-yl](4-benzo[1,3]dioxol-5-ylmethylpiperazin-1-yl)methanone (0.26 g, 0.54 mmol) in THF (7 mL) was cooled to 0° C., then 3,4-dichlorobenzenesulfonyl chloride (0.14 g, 0.54 mmol) and pyridine (0.07 mL, 0.81 mmol) were added to the solution. The resulting mixture was allowed to warm to room temperature and stirred for 3 hours. Water was added to the mixture, and the aqueous layer was extracted with AcOEt. The extract was washed with saturated aqueous NaHCO$_3$ and brine. The organic layer was dried over anhydrous magnesium sulfate and evaporated. The residue was purified by silica gel column chromatography (CH$_2$Cl$_2$: MeOH=50:1) to give a pale yellow powder (190 mg). This powder was dissolved in AcOEt and 6 M HCl (0.046 mL, 0.276 mmol) was added to the solution. The resulting precipitate was collected by filtration, and then dried in vacuo to give 0.18 g of the title compound as a white powder.

Melting point: 167-177° C.

The following compounds were produced in the same manner as in Example 62 using appropriate starting materials.

Example 63

N-(6-{1-[2-(4-Benzo[1,3]dioxol-5-ylmethylpiperazin-1-yl)-2-oxo-ethyl]-2,3-dihydro-1H-indol-5-yloxy}pyridin-3-yl)-4-trifluoro-methylbenzenesulfonamide Melting point: 182.0-183.0° C.

Example 64

N-(6-{1-[2-(4-Benzo[1,3]dioxol-5-ylmethylpiperazin-1-yl)-2-oxo-ethyl]-2,3-dihydro-1H-indol-5-yloxy}pyridin-3-yl)-3,4-dichloro-benzenesulfonamide Melting point: 152.0-153.0° C.

Example 65

N-{6-[2-(4-Benzo[1,3]dioxol-5-ylmethylpiperazine-1-carbonyl)-1-methyl-1H-indol-5-yloxy]pyridin-3-yl}-4-trifluoromethylbenzene-sulfonamide hydrobromide Melting point: 210-212° C.

Example 66

N-{6-[2-(4-Benzylpiperazine-1-carbonyl)-1-methyl-1H-indol-5-yl-oxy]pyridin-3-yl}-3,4-dichlorobenzenesulfonamide $^1$H NMR (CDCl$_3$) δ 1.59 (1H, brs), 2.50 (4H, brs), 3.55 (2H, s), 3.77 (4H, brs), 3.81 (3H, s), 6.51 (1H, s), 6.80 (1H, d, J=8.9 Hz), 7.02 (1H, dd, J=8.9 Hz, 2.3 Hz), 7.25-7.37 (7H, m), 7.45-7.52 (2H, m), 7.50 (1H, dd, J=6.0 Hz, 2.6 Hz), 7.69 (1H, d, J=2.6 Hz), 7.81 (1H, t, J=1.0 Hz).

Example 67

N-{6-[2-(4-Benzylpiperazine-1-carbonyl)-1-methyl-1H-indol-5-yl-oxy]pyridin-3-yl}-4-trifluoromethyl-benzenesulfonamide $^1$H NMR (CDCl$_3$) δ 1.59 (1H, brs), 2.49 (4H, brs), 3.55 (2H, s), 3.77 (4H, brs), 3.81 (3H, s), 6.50 (1H, s), 6.79 (1H, d, J=8.8 Hz), 7.01 (1H, dd, J=8.8 Hz, 2.3 Hz), 7.20-7.37 (7H, m), 7.49 (1H, dd, J=8.8 Hz, 2.6 Hz), 7.66 (1H, d, J=2.6 Hz), 7.70 (2H, d, J=8.2 Hz), 7.83 (2H, d, J=8.2 Hz).

Example 68

3,4-Dichloro-N-methyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide Melting point: 165.9-167.2° C.

Example 69

N-Methyl-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzene-sulfonamide hydrochloride Melting point: 256.9-257.7° C.

Example 70

4,N-Dimethyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide hydrochloride Melting point: 246.4-247.2° C.

Example 71

4-Methyl-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide Melting point: 198.3-200.3° C.

Example 72

3,4-Dichloro-N-ethyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide hydrochloride Melting point: 226.9-227.2° C.

Example 73

4-Methoxy-N-methyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide hydrochloride Melting point: 213.4-214.1° C.

Example 74

Propane-2-sulfonic acid [6-(1-methyl-2-{4-[4-(2,2,2-trifluoro-ethoxy)benzyl]piperazine-1-carbonyl}-1H-indol-6-yloxy)pyridin-3-yl]amide $^1$H NMR (CDCl$_3$) δ 1.41 (6H, d, J=6.9 Hz), 2.48 (4H, brs), 3.18-3.29 (1H, m), 3.51 (2H, s), 3.78 (7H, s), 4.35 (2H, q, J=8.2 Hz), 6.38 (1H, s), 6.58 (1H, s), 6.89 (2H, d, J=2.6 Hz), 6.92 (2H, d, J=2.3 Hz), 7.12 (1H, d, J=1.6 Hz), 7.30 (1H, s), 7.60 (1H, d, J=8.6 Hz), 7.72 (1H, dd, J=8.9 Hz, 2.6 Hz), 8.02 (1H, d, J=3.0 Hz).

Example 75

2,4,6-Trimethyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide hydrochloride Melting point: 191.3-192.5° C.

Example 76

N-[6-(1-Methyl-2-{4-[4-(2,2,2-trifluoroethoxy)benzyl]piperazine-1-carbonyl}-1H-indol-6-yloxy)pyridin-3-yl]methanesulfonamide hydrobromide Melting point: 237.8-240.1° C.

Example 77

N-[4-Methyl-6-(1-methyl-2-{4-[4-(2,2,2-trifluoroethoxy)benzyl]-piperazine-1-carbonyll}-1H-indol-6-yloxy)pyridin-3-yl]-methanesulfonamide hydrobromide Melting point: 229.3-231.2° C.

Example 78

N-Methyl-N-[4-methyl-6-(1-methyl-2-{4-[4-(2,2,2-trifluoroethoxy)-benzyl]piperazine-1-carbonyl}-1H-indol-6-yloxy)pyridin-3-yl]-methanesulfonamide hydrobromide Melting point: 235.8-237.8° C.

Example 79

4-Methoxy-N-[6-(1-methyl-2-{4-[4-(2,2,2-trifluoro-ethoxy)benzyl]-piperazine-1-carbonyl}-1H-indol-6-yloxy)pyridin-3-yl]benzene-sulfonamide

MS: 710 [M+H]$^+$

Example 80

4-Chloro-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 714 [M+H]$^+$

Example 81

Naphthalene-1-sulfonic acid [6-(1-methyl-2-{4-[4-(2,2,2-tri-fluoroethoxy)benzyl]piperazine-1-carbonyl}-1H-indol-6-yloxy)-pyridin-3-yl]amide

MS: 730 [M+H]$^+$

Example 82

Naphthalene-2-sulfonic acid [6-(1-methyl-2-{4-[4-(2,2,2-tri-fluoroethoxy)benzyl]piperazine-1-carbonyl}-1H-indol-6-yloxy)-pyridin-3-yl]amide

MS: 730 [M+H]$^+$

Example 83

2-Methyl-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 694 [M+H]$^+$

Example 84

4-Fluoro-M-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 698 [M+H]$^+$

Example 85

5-Chloro-2-methoxy-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 744 [M+H]$^+$

Example 86

N-[6-(1-Methyl-2-{4-[4-(2,2,2-trifluoroethoxy)benzyl]piperazine-1-carbonyl}-1H-indol-6-yloxy)pyridin-3-yl]-2-trifluoromethyl-benzenesulfonamide

MS: 748 [M+H]$^+$

Example 87

Thiophene-2-sulfonic acid [6-(1-methyl-2-{4-[4-(2,2,2-trifluoro-ethoxy)benzyl]piperazine-1-carbonyl}-1H-indol-6-yloxy)pyridin-3-yl]amide

MS: 686 [M+H]$^+$

Example 88

2-Chloro-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 714 [M+H]$^+$

Example 89

N-[6-(1-Methyl-2-{4-[4-(2,2,2-trifluoroethoxy)benzyl]piperazine-1-carbonyl}-1H-indol-6-yloxy)pyridin-3-yl]-2-trifluoromethoxy-benzenesulfonamide

MS: 764 [M+H]$^+$

Example 90

2-[6-(1-Methyl-2-{4-[4-(2,2,2-trifluoroethoxy)benzyl]piperazine-1-carbonyl}-1H-indol-6-yloxy)pyridin-3-ylsulfamoyl]benzoic acid methyl ester

MS: 738 [M+H]$^+$

Example 91

2-Cyano-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 705 [M+H]$^+$

Example 92

3-Methoxy-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 710 [M+H]$^+$

Example 93

3-Fluoro-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 698 [M+H]$^+$

Example 94

2-Fluoro-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 698 [M+H]$^+$

Example 95

N-[6-(1-Methyl-2-{4-[4-(2,2,2-trifluoroethoxy)benzyl]piperazine-1-carbonyl}-1H-indol-6-yloxy)pyridin-3-yl]-3-trifluoromethyl-benzenesulfonamide

MS: 748 [M+H]$^+$

Example 96

N-[6-(1-Methyl-2-{4-[4-(2,2,2-trifluoroethoxy)benzyl]piperazine-1-carbonyl}-1H-indol-6-yloxy)pyridin-3-yl]-4-trifluoromethoxy-benzenesulfonamide

MS: 764 [M+H]$^+$

Example 97

Biphenyl-4-sulfonic acid [6-(1-methyl-2-{4-[4-(2,2,2-trifluoro-ethoxy)benzyl]piperazine-1-carbonyl}-1H-indol-6-yloxy)pyridin-3-yl]amide

MS: 756 [M+H]$^+$

Example 98

3,4-Dimethoxy-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 740 [M+H]$^+$

Example 99

2,5-Dimethoxy-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 740 [M+H]$^+$

Example 100

3-Methyl-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 694 [M+H]$^+$

Example 101

N-[6-(1-Methyl-2-{4-[4-(2,2,2-trifluoroethoxy)benzyl]piperazine-1-carbonyl}-1H-indol-6-yloxy)pyridin-3-yl]-2-nitrobenzene-sulfonamide

MS: 725 [M+H]$^+$

Example 102

N-[6-(1-Methyl-2-{4-[4-(2,2,2-trifluoroethoxy)benzyl]piperazine-1-carbonyl}-1H-indol-6-yloxy)pyridin-3-yl]-3-nitrobenzene-sulfonamide

MS: 725 [M+H]$^+$

Example 103

3-Chloro-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 714 [M+H]$^+$

Example 104

N-[6-(1-Methyl-2-{4-[4-(2,2,2-trifluoroethoxy)benzyl]piperazine-1-carbonyl}-1H-indol-6-yloxy)pyridin-3-yl]benzenesulfonamide

MS: 680 [M+H]$^+$

Example 105

2-Methoxy-5-methyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 724 [M+H]$^+$

Example 106

2,6-Dichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 748 [M+H]$^+$

Example 107

N-[6-(1-Methyl-2-{4-[4-(2,2,2-trifluoroethoxy)benzyl]piperazine-1-carbonyl}-1H-indol-6-yloxy)pyridin-3-yl]-3-trifluoromethoxy-benzenesulfonamide

MS: 764 [M+H]$^+$

Example 108

Quinoline-8-sulfonic acid [6-(1-methyl-2-{4-[4-(2,2,2-trifluoro-ethoxy)benzyl]piperazine-1-carbonyl}-1H-indol-6-yloxy)pyridin-3-yl]amide

MS: 731 [M+H]$^+$

Example 109

5-Dimethylaminonaphthalene-1-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 773 [M+H]$^+$

Example 110

1-Methyl-1H-imidazole-4-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 684 [M+H]$^+$

Example 111

2,3-Dichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 748 [M+H]$^+$

Example 112

2,5-Dichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 748 [M+H]$^+$

Example 113

2,4-Dichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 748 [M+H]$^+$

Example 114

2,3,4-Trichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 782 [M+H]$^+$

Example 115

4-Methyl-N-[6-(1-methyl-2-{4-[4-(2,2,2-trifluoroethoxy)benzyl]-piperazine-1-carbonyl}-1H-indol-6-yloxy)pyridin-3-yl]-3-nitro-benzenesulfonamide

MS: 739 [M+H]$^+$

Example 116

2-Chloro-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzenesulfonamide

MS: 782 [M+H]$^+$

Example 117

4-Chloro-N-[6-(1-methyl-2-{4-[4-(2,2,2-trifluoroethoxy)benzyl]-piperazine-1-carbonyl}-1H-indol-6-yloxy)pyridin-3-yl]-3-nitro-benzenesulfonamide

MS: 759 [M+H]$^+$

Example 118

2,4,6-Trichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 782 [M+H]$^+$

Example 119

2-Chloro-4-fluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 732 [M+H]$^+$

Example 120

2,4-Dichloro-5-methyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 762 [M+H]$^+$

Example 121

2-Chloro-M-[6-(1-methyl-2-{4-[4-(2,2,2-trifluoroethoxy)benzyl]-piperazine-1-carbonyl}-1H-indol-6-yloxy)pyridin-3-yl]-5-tri-fluoromethylbenzene-sulfonamide

MS: 782 [M+H]+

Example 122

2,4,5-Trichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 782 [M+H]+

Example 123

2-Methyl-N-[6-(1-methyl-2-{4-[4-(2,2,2-trifluoroethoxy)benzyl]-piperazine-1-carbonyl}-1H-indol-6-yloxy)pyridin-3-yl]-5-nitro-benzenesulfonamide

MS: 739 [M+H]+

Example 124

2-Chloro-N-[6-(1-methyl-2-{4-[4-(2,2,2-trifluoroethoxy)benzyl]-piperazine-1-carbonyl}-1H-indol-6-yloxy)pyridin-3-yl]-3-nitro-benzenesulfonamide

MS: 759 [M+H]+

Example 125

2-Chloro-N-[6-(1-methyl-2-{4-[4-(2,2,2-trifluoroethoxy)benzyl]-piperazine-1-carbonyl}-1H-indol-6-yloxy)pyridin-3-yl]-5-nitro-benzenesulfonamide

MS: 759 [M+H]+

Example 126

2-Chloro-4-cyano-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 739 [M+H]+

Example 127

2-Chloro-4,5-difluoro-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 750 [M+H]+

Example 128

N-{4-[6-(1-Methyl-2-{4-[4-(2,2,2-trifluoroethoxy)benzyl]-piperazine-1-carbonyl}-1H-indol-6-yloxy)pyridin-3-ylsulfamoyl]-phenyl}acetamide

MS: 737 [M+H]+

Example 129

N-[6-(1-Methyl-2-{4-[4-(2,2,2-trifluoroethoxy)benzyl]piperazine-1-carbonyl}-1H-indol-6-yloxy)pyridin-3-yl]-4-nitrobenzene-sulfonamide

MS: 725 [M+H]+

Example 130

3,5-Dichloro-2-hydroxy-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 764 [M+H]+

Example 131

4-Methoxy-N-[6-(1-methyl-2-{4-[4-(2,2,2-trifluoroethoxy)benzyl]-piperazine-1-carbonyl}-1H-indol-6-yloxy)pyridin-3-yl]-2-nitro-benzenesulfonamide

MS: 755 [M+H]+

Example 132

4-tert-Butyl-N-[6-(1-methyl-2-{4-[4-(2,2,2-trifluoro-ethoxy)-benzyl]piperazine-1-carbonyl}-1H-indol-6-yloxy)pyridin-3-yl]-benzenesulfonamide

MS: 736 [M+H]+

Example 133

4-Iodo-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 806 [M+H]+

Example 134

3-[6-(1-Methyl-2-{4-[4-(2,2,2-trifluoroethoxy)benzyl]piperazine-1-carbonyl}-1H-indol-6-yloxy)pyridin-3-ylsulfamoyl]benzoic acid

MS: 724 [M+H]+

Example 135

2-Bromo-5-chloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 792 [M+H]+

Example 136

2,5-Dimethyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 708 [M+H]+

Example 137

2,5-Difluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 716 [M+H]+

Example 138

3-Cyano-M-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 705 [M+H]+

Example 139

4-Methyl-N-[6-(1-methyl-2-{4-[4-(2,2,2-trifluoroethoxy)benzyl]-piperazine-1-carbonyl}-1H-indol-6-yloxy)pyridin-3-yl]naphthalene-1-sulfonamide

MS: 744 [M+H]+

Example 140

N-[6-(1-Methyl-2-{4-[4-(2,2,2-trifluoroethoxy)benzyl]piperazine-1-carbonyl}-1H-indol-6-yloxy)pyridin-3-yl]-2,3-Dihydrobenzo[1,4]dioxine-6-sulfonamide

MS: 738 [M+H]+

Example 141

2,4-Dichloro-6-methyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 762 [M+H]+

Example 142

3-Chloro-5-fluoro-2-methyl-N-[6-(1-methyl-2-{4-[4-(2,2,2-tri-fluoroethoxy)benzyl]piperazine-1-carbonyl}-1H-indol-6-yloxy)-pyridin-3-yl]benzene-sulfonamide

MS: 746 [M+H]+

Example 143

4-Bromo-2-methyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 772 [M+H]+

Example 144

N-[6-(1-Methyl-2-{4-[4-(2,2,2-trifluoroethoxy)benzyl]piperazine-1-carbonyl}-1H-indol-6-yloxy)pyridin-3-yl]-4-phenoxybenzene-sulfonamide

MS: 772 [M+H]+

Example 145

3-Bromo-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 758 [M+H]+

Example 146

4-Cyano-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 705 [M+H]+

Example 147

N-{2-Chloro-4-[6-(1-methyl-2-{4-[4-(2,2,2-trifluoroethoxy)-benzyl]piperazine-1-carbonyl}-1H-indol-6-yloxy)pyridin-3-yl-sulfamoyl]phenyl}acetamide

MS: 771 [M+H]+

Example 148

2,4-Difluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 716 [M+H]+

Example 149

2-Methoxy-4-methyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 724 [M+11]+

Example 150

3-Chloro-2-methyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 728 [M+H]+

Example 151

2,6-Difluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 716 [M+H]+

Example 152

5-Fluoro-2-methyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 712 [M+H]+

Example 153

4-Chloro-2,5-dimethyl-N-[6-(1-methyl-2-{4-[4-(2,2,2-trifluoro-ethoxy)benzyl]piperazine-1-carbonyl}-1H-indol-6-yloxy)pyridin-3-yl]benzenesulfonamide

MS: 742 [M+H]$^+$

Example 154

2-Chloro-6-methyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 728 [M+H]$^+$

Example 155

4-Isopropyl-N-[6-(1-methyl-2-{4-[4-(2,2,2-trifluoro-ethoxy)-benzyl]piperazine-1-carbonyl}-1H-indol-6-yloxy)pyridin-3-yl]-benzenesulfonamide

MS: 722 [M+H]$^+$

Example 156

3-Chloro-4-fluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 732 [M+H]$^+$

Example 157

4-Bromo-2-fluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 776 [M+H]$^+$

Example 158

3-Chloro-4-methyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 728 [M+H]$^+$

Example 159

3,4-Difluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 716 [M+H]$^+$

Example 160

5-Chloronaphthalene-1-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 764 [M+H]$^+$

Example 161

5-Chloronaphthalene-2-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 764 [M+H]$^+$

Example 162

2-Bromo-N-[6-(1-methyl-2-{4-[4-(2,2,2-trifluoroethoxy)benzyl]-piperazine-1-carbonyl}-1H-indol-6-yloxy)pyridin-3-yl]benzene-sulfonamide

MS: 758 [M+H]$^+$

Example 163

5-Chlorothiophene-2-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 720 [M+H]$^+$

Example 164

3,5-Dichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 748 [M+H]$^+$

Example 165

N-[6-(1-Methyl-2-{4-[4-(2,2,2-trifluoroethoxy)benzyl]piperazine-1-carbonyl}-1H-indol-6-yloxy)pyridin-3-yl]-4-oxazol-5-ylbenzene-sulfonamide

MS: 747 [M+H]$^+$

Example 166

3-{4-[6-(1-Methyl-2-{4-[4-(2,2,2-trifluoroethoxy)benzyl]-piperazine-1-carbonyl}-1H-indol-6-yloxy)pyridin-3-ylsulfamoyl]-phenyl}propionic acid methyl ester

MS: 766 [M+H]$^+$

Example 167

4-Methyl-3,4-dihydro-2H-benzo[1,4]oxazine-7-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 751 [M+H]$^+$

Example 168

3-Methylquinoline-8-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 745 [M+H]$^+$

Example 169

N-{5-[6-(1-Methyl-2-{4-[4-(2,2,2-trifluoroethoxy)benzyl]-piperazine-1-carbonyl}-1H-indol-6-yloxy)pyridin-3-ylsulfamoyl]-naphthalen-1-yl}acetamide

MS: 787 [M+H]$^+$

Example 170

Isoquinoline-5-sulfonic acid [6-(1-methyl-2-{4-[4-(2,2,2-tri-fluoroethoxy)benzyl]piperazine-1-carbonyl}-1H-indol-6-yloxy)-pyridin-3-yl]amide

MS: 731 [M+H]$^+$

Example 171

2,2,2-Trifluoroethanesulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 686 [M+H]$^+$

Example 172

4-Methoxy-2,3,6-trimethyl-N-[6-(1-methyl-2-{4-[4-(2,2,2-tri-fluoroethoxy)benzyl]piperazine-1-carbonyl}-1H-indol-6-yloxy)-pyridin-3-yl]benzenesulfonamide

MS: 752 [M+H]$^+$

Example 173

N-[6-(1-Methyl-2-{4-[4-(2,2,2-trifluoroethoxy)benzyl]piperazine-1-carbonyl}-1H-indol-6-yloxy)pyridin-3-yl]-trifluoromethanesulfonamide

MS: 672 [M+H]$^+$

Example 174

5-Chloro-1,3-dimethyl-1H-pyrazole-4-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 732 [M+H]$^+$

Example 175

3,5-Dimethylisoxazole-4-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 699 [M+H]$^+$

Example 176

2-Hydroxy-5-[6-(1-methyl-2-{4-[4-(2,2,2-trifluoroethoxy)benzyl]-piperazine-1-carbonyl}-1H-indol-6-yloxy)pyridin-3-ylsulfamoyl]-benzoic acid

MS: 740 [M+H]$^+$

Example 177

4,5-Dichlorothiophene-2-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 754 [M+H]$^+$

Example 178

2,5-Dichlorothiophene-3-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 754 [M+H]$^+$

Example 179

5-Bromothiophene-2-sulfonic acid [6-(1-methyl-2-{4-[4-(2,2,2-tri-fluoroethoxy)benzyl]piperazine-1-carbonyl}-1H-indol-6-yloxy)-pyridin-3-yl]amide

MS: 764 [M+H]$^+$

Example 180

4-[6-(1-Methyl-2-{4-[4-(2,2,2-trifluoroethoxy)benzyl]piperazine-1-carbonyl}-1H-indol-6-yloxy)pyridin-3-ylsulfamoyl]benzoic acid

MS: 724 [M+H]$^+$

Example 181

N-{4-Methyl-5-[6-(1-methyl-2-{4-[4-(2,2,2-trifluoroethoxy)-benzyl]piperazine-1-carbonyl}-1H-indol-6-yloxy)pyridin-3-yl-sulfamoyl]thiazol-2-yl}acetamide

MS: 758 [M+H]$^+$

Example 182

3-[6-(1-Methyl-2-{4-[4-(2,2,2-trifluoroethoxy)benzyl]piperazine-1-carbonyl}-1H-indol-6-yloxy)pyridin-3-ylsulfamoyl]thiophene-2-carboxylic acid methyl ester

MS: 744 [M+H]$^+$

Example 183

5-Bromo-2-methoxy-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 788 [M+H]$^+$

Example 184

N-[6-(1-Methyl-2-{4-[4-(2,2,2-trifluoroethoxy)benzyl]piperazine-1-carbonyl}-1H-indol-6-yloxy)pyridin-3-yl]benzylsulfonamide

MS: 694 [M+H]$^+$

Example 185

(E)-2-Phenylethenesulfonic acid [6-(1-methyl-2-{4-[4-(2,2,2-tri-fluoroethoxy)benzyl]piperazine-1-carbonyl}-1H-indol-6-yloxy)-pyridin-3-yl]amide

MS: 706 [M+H]$^+$

Example 186

2,3,4-Trifluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 734 [M+H]$^+$

Example 187

2,4,5-Trifluoro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 734 [M+H]$^+$

Example 188

Benzo[b]thiophene-2-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 736 [M+H]$^+$

Example 189

3-(4-Methoxyphenoxy)propane-1-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 768 [M+H]$^+$

Example 190

2-Naphthalen-1-ylethanesulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 758 [M+H]$^+$

Example 191

Cyclopropanesulfonic acid [6-(1-methyl-2-{4-[4-(2,2,2-trifluoro-ethoxy)benzyl]piperazine-1-carbonyl}-1H-indol-6-yloxy)pyridin-3-yl]amide

MS: 644 [M+H]$^+$

Example 192

4-(1-Methyl-1H-pyrazol-3-yl)-N-[6-(1-methyl-2-{4-[4-(2,2,2-tri-fluoroethoxy)benzyl]piperazine-1-carbonyl}-1H-indol-6-yloxy)-pyridin-3-yl]benzenesulfonamide

MS: 760 [M+H]$^+$

Example 193

1-Methyl-1H-indole-7-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 733 [M+H]$^+$

Example 194

3-[1,3]Dioxolan-2-ylthiophene-2-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 758 [M+H]$^+$

Example 195

2,5-Dimethylthiophene-3-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 714 [M+H]$^+$

Example 196

2-Cyano-5-methyl-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide

MS: 719 [M+H]$^+$

Example 197

5-Methylthiophene-2-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 700 [M+H]$^+$

Example 198

2-Methyl-5-[6-(1-methyl-2-{4-[4-(2,2,2-trifluoroethoxy)benzyl]-piperazine-1-carbonyl}-1H-indol-6-yloxy)pyridin-3-ylsulfamoyl]-furan-3-carboxylic acid methyl ester

MS: 742 [M+H]$^+$

Example 199

1-Methyl-5-[6-(1-methyl-2-{4-[4-(2,2,2-trifluoroethoxy)benzyl]-piperazine-1-carbonyl}-1H-indol-6-yloxy)pyridin-3-ylsulfamoyl]-1H-pyrrole-2-carboxylic acid methyl ester

MS: 741 [M+H]$^+$

Example 200

5-Pyridin-2-ylthiophene-2-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 763 [M+H]$^+$

Example 201

5-Chloro-3-methylbenzo[b]thiophene-2-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 784 [M+H]$^+$

Example 202

Benzofuran-2-sulfonic acid [6-(1-methyl-2-{4-[4-(2,2,2-trifluoro-ethoxy)benzyl]piperazine-1-carbonyl}-1H-indol-6-yloxy)pyridin-3-yl]amide

MS: 720 [M+H]$^+$

Example 203

5-Methyl-1-phenyl-1H-pyrazole-4-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 760 [M+H]$^+$

Example 204

2,5-Dimethylfuran-3-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 698 [M+H]$^+$

Example 205

5-Phenylthiophene-2-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 762 [M+H]$^+$

Example 206

4-Methoxy-5-[6-(1-methyl-2-{4-[4-(2,2,2-trifluoro-ethoxy)benzyl]-piperazine-1-carbonyl}-1H-indol-6-yloxy)pyridin-3-ylsulfamoyl]-thiophene-3-carboxylic acid methyl ester

MS: 774 [M+H]$^+$

Example 207

4-Phenyl-5-trifluoromethylthiophene-3-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 830 [M+H]$^+$

Example 208

5-Methylbenzo[b]thiophene-2-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 750 [M+H]$^+$

Example 209

5-Methyl-3-phenylisoxazole-4-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 761 [M+H]$^+$

Example 210

1,3,5-Trimethyl-1H-pyrazole-4-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 712 [M+H]$^+$

Example 211

2-Chloro-N-[6-(1-methyl-2-{4-[4-(2,2,2-trifluoroethoxy)benzyl]-piperazine-1-carbonyl}-1H-indol-6-yloxy)pyridin-3-yl]-benzylsulfonamide

MS: 728 [M+H]$^+$

Example 212

Benzo[b]thiophene-3-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 736 [M+H]$^+$

Example 213

6-Chloroimidazo[2,1-b]thiazole-5-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 760 [M+H]$^+$

Example 214

3,5-Dimethyl-1-phenyl-1H-pyrazole-4-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 774 [M+H]$^+$

Example 215

3-Bromothiophene-2-sulfonic acid [6-(1-methyl-2-{4-[4-(2,2,2-tri-fluoroethoxy)benzyl]piperazine-1-carbonyl}-1H-indol-6-yloxy)-pyridin-3-yl]amide

MS: 764 [M+H]$^+$

Example 216

5-Methyl-2-trifluoromethylfuran-3-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 752 [M+H]$^+$

Example 217

1-Methyl-1H-pyrazole-3-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 684 [M+H]$^+$

Example 218

1-Methyl-3-trifluoromethyl-1H-pyrazole-4-sulfonic acid [6-(1-methyl-2-{4-[4-(2,2,2-trifluoroethoxy)benzyl]piperazine-1-carbonyl}-1H-indol-6-yloxy)pyridin-3-yl]amide

MS: 752 [M+H]$^+$

Example 219

2-Methyl-2H-pyrazole-3-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 684 [M+H]$^+$

Example 220

1-Methyl-1H-indole-4-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 733 [M+H]$^+$

Example 221

2,4-Dimethylthiazole-5-sulfonic acid [6-(1-methyl-2-{4-[4-(2,2,2-trifluoroethoxy)benzyl]piperazine-1-carbonyl}-1H-indol-6-yloxy)-pyridin-3-yl]amide

MS: 715 [M+H]$^+$

Example 222

Production of N-{6-[2-(4-benzo[1,3]dioxol-5-ylmethylpiperazine-1-carbonyl)-1H-indol-5-yloxy]pyridin-3-yl}-3,4-dichlorobenzamide 5-[5-(3,4-Dichlorobenzoylamino)pyridin-2-yloxy]-1H-indole-2-carboxylic acid (0.250 g, 0.565 mmol) was dissolved in THF (20 mL). To the solution were added 1-benzo[1,3]dioxol-5-ylmethylpiperadine (0.125 g, 0.565 mmol) and 1-ethyl-3-(3-dimethylaminopropyl)carbodiimide hydrochloride (0.119 g, 0.622 mmol), and the resulting solution was stirred for 15 hours at room temperature. Water (50 mL) was added to the reaction solution, and the mixture was extracted with ethyl acetate (40 mL). After the organic layer was washed with brine, then dried over anhydrous sodium sulfate, the solvent was evaporated. The obtained residue was purified by silica gel column chromatography ($CH_2Cl_2$:MeOH=30:1) to yield 0.360 g of the title compound as a pale yellow powder.

$^1$H NMR (DMSO-$d_6$) δ 2.43 (4H, brs), 3.44 (2H, s), 3.75 (4H, brs), 5.99 (2H, s), 6.76-6.79 (2H, m), 6.84-6.90 (2H, m), 6.95-6.99 (2H, m), 7.32 (1H, d, J=2.1 Hz), 7.44 (1H, d, J=8.7 Hz), 7.83 (1H, d, J=8.4 Hz), 7.94 (1H, dd, J=8.4 Hz, 2.0 Hz), 8.15 (1H, dd, J=8.9 Hz, 2.6 Hz), 8.22 (1H, d, J=2.0 Hz), 8.44 (1H, d, J=2.3 Hz), 10.50 (1H, s), 11.64 (1H, s).

The following compounds were produced in the same manner as in Example 222 using appropriate starting materials.

Example 223

N-(6-{1-[2-(4-Benzylpiperazin-1-yl)-2-oxoethyl]-1H-indol-4-yl-oxy}pyridin-3-yl)-3,4-dichlorobenzamide $^1$H NMR (DMSO-$d_6$) δ 2.36 (2H, brs), 2.47 (2H, brs), 3.47 (2H, brs), 3.53 (2H, s), 3.59 (2H, brs), 5.19 (2H, s), 6.08 (1H, d, J=3.1 Hz), 6.75 (1H, d, J=7.6 Hz), 7.05 (1H, d, J=8.9 Hz), 7.07-7.13 (2H, m), 7.20-7.36 (5H, m), 7.84 (2H, d, J=8.4 Hz), 7.95 (1H, dd, J=8.4 Hz, 2.1 Hz), 8.19 (1H, dd, J=8.9 Hz, 2.8 Hz), 8.22-8.23 (1H, m), 8.45 (1H, d, J=2.8 Hz), 10.56 (1H, s).

Example 224

N-(6-{1-[2-(4-Benzylpiperazin-1-yl)-2-oxoethyl]-1H-indol-4-yl-oxy}pyridin-3-yl)-4-trifluoromethylbenzamide $^1$H NMR (DMSO-$d_6$) δ 2.36 (2H, brs), 2.49 (2H, brs), 3.47 (2H, brs), 3.54 (2H, s), 3.59 (2H, brs), 5.19 (2H, s), 6.09 (1H, d, J=3.1 Hz), 6.76 (1H, d, J=7.1 Hz), 7.06 (1H, d, J=8.9 Hz), 7.08-7.14 (1H, m), 7.20-7.23 (2H, m), 7.27-7.36 (5H, m), 7.93 (2H, d, J=8.4 Hz), 8.17 (2H, d, J=8.1 Hz), 8.21 (1H, dd, J=8.9 Hz, 2.6 Hz), 8.47 (1H, d, J=2.6 Hz), 10.64 (1H, s).

Example 225

N-{6-[2-(4-Benzo[1,3]dioxol-5-ylmethylpiperazine-1-carbonyl)-1-methyl-1H-indol-5-yloxy]pyridin-3-yl}-6-pyrrol-1-ylnicotinamide Melting point: 155-158° C.

Example 226

N-(6-{2-[4-(4-Methoxybenzyl)piperazine-1-carbonyl]-1-methyl-1H-indol-5-yloxy}pyridin-3-yl)-6-pyrrol-1-ylnicotinamide Melting point: 194-195° C.

Example 227

N-(6-{2-[4-(4-Methoxybenzyl)piperazine-1-carbonyl]-1-methyl-1H-indol-5-yloxy}pyridin-3-yl)-N-methyl-6-pyrrol-1-ylnicotinamide dioxalate Melting point: 185-187° C.

Example 228

5-Bromo-1H-indole-2-carboxylic acid (6-{2-[4-(4-methoxybenzyl)-piperazine-1-carbonyl]-1-methyl-1H-indol-5-yloxy}pyridin-3-yl)-amide hydrobromide Melting point: 263-265° C.

Example 229

5-Bromo-1H-indole-2-carboxylic acid (6-{2-[4-(4-methoxybenzyl)-piperazine-1-carbonyl]-1-methyl-1H-indol-5-yloxy}pyridin-3-yl)-methylamide maleate Melting point: 205-207° C.

Example 230

5-Trifluoromethylpyridine-2-carboxylic acid (6-{2-[4-(4-methoxy-benzyl)piperazine-1-carbonyl]-1-methyl-1H-indol-5-yloxy}pyridin-3-yl)amide dihydrobromide Melting point: 241-243° C.

Example 231

2-Chloro-N-(6-{2-[4-(4-methoxybenzyl)piperazine-1-carbonyl]-1-methyl-1H-indol-5-yloxy}pyridin-3-yl)-4-trifluoromethylbenzamide hydrobromide Melting point: 239-241° C.

Example 232

N-[6-(2-{4-[(4-Methoxybenzyl)methylamino]piperidine-1-carbonyl}-1-methyl-1H-indol-5-yloxy)pyridin-3-yl]-4-trifluoromethyl-benzamide oxalate $^1$H NMR (DMSO-$d_6$) δ 1.72-1.79 (2H, m), 2.07 (2H, brs), 2.49-2.51 (3H, brs), 3.01 (2H, brs), 3.37 (1H, brs), 3.777 (3H, s), 3.783 (3H, s), 4.10 (4H, brs), 6.69 (1H, s), 6.97-7.07 (4H, m), 7.35 (1H, d, J=2.4 Hz), 7.42 (2H, d, J=8.6 Hz), 7.56 (1H, d, J=8.9 Hz), 7.93 (2H, d, J=8.1 Hz), 8.15-8.20 (3H, m), 8.47 (1H, d, J=2.4 Hz), 10.61 (1H, s).

Example 233

N-[6-(2-{4-[(4-Methoxyphenyl)methylamino]piperidine-1-carbonyl}-1-methyl-1H-indol-5-yloxy)pyridin-3-yl]-4-trifluoromethyl-benzamide Melting point: 139-142° C.

Example 234

N-{6-[1,4-Dimethyl-2-(4-pyridin-2-ylmethylpiperazine-1-carbonyl)-1H-indol-5-yloxy]pyridin-3-yl}-4-trifluoromethylbenzamide bismethanesulfonate Melting point: 149-150° C.

Example 235

N-(6-{2-[4-(4-Methoxybenzyl)piperazine-1-carbonyl]-1,4-dimethyl-1H-indol-5-yloxy}pyridin-3-yl)-4-trifluoromethylbenzamide Melting point: 219-221° C.

Example 236

N-{6-[1-Methyl-2-(4-pyridin-2-ylmethylpiperazine-1-carbonyl)-1H-indol-6-yloxy]pyridin-3-yl}-4-trifluoromethylbenzamide dioxalate Melting point: 176-178° C.

Example 237

N-(6-{2-[4-(4-Cyanobenzyl)piperazine-1-carbonyl]-1-methyl-1H-indol-6-yloxy}pyridin-3-yl)-4-trifluoromethylbenzamide $^1$H NMR (CDCl$_3$) δ 2.50 (4H, s), 3.60 (2H, s), 3.70-3.79 (7H, m), 6.57 (1H, s), 6.94 (2H, t, J=7.3 Hz), 7.12 (1H, s), 7.47 (2H, d, J=8.1 Hz), 7.58-7.68 (3H, m), 7.74 (2H, d, J=7.3 Hz), 7.99 (2H, d, J=8.2 Hz), 8.11 (1H, brs), 8.18 (1H, d, J=8.9 Hz), 8.28 (1H, d, J=2.6 Hz).

Example 238

N-(6-{2-[4-(4-Methoxybenzyl)piperazine-1-carbonyl]-1-methyl-1H-indol-6-yloxy}pyridin-3-yl)-4-trifluoromethylbenzamide $^1$H NMR (CDCl$_3$) δ 2.48 (4H, s), 3.50 (2H, s), 3.77 (7H, s), 3.81 (3H, s), 6.57 (1H, s), 6.84-6.97 (4H, m), 7.12 (1H, d, J=1.5 Hz), 7.19-7.23 (2H, m), 7.59 (1H, d, J=8.6 Hz), 7.75 (2H, d, J=7.9 Hz), 7.99 (3H, d, J=8.2 Hz), 8.18 (1H, d, J=8.7 Hz), 8.27 (1H, d, J=2.5 Hz).

Example 239

N-(6-{1-Methyl-2-[4-(pyridine-2-carbonyl)piperazine-1-carbonyl]-1H-indol-5-yloxy}pyridin-3-yl)-4-trifluoromethylbenzamide Melting point: 162-164° C.

Example 240

N-(6-{2-[4-(4-Methoxybenzoyl)piperazine-1-carbonyl]-1-methyl-1H-indol-5-yloxy}pyridin-3-yl)-4-trifluoromethylbenzamide Melting point: 195-196° C.

Example 241

N-(6-{2-[4-(4-Methoxybenzoyl)piperazine-1-carbonyl]-1-methyl-1H-indol-5-yloxy}pyridin-3-yl)-N-methyl-4-trifluoromethylbenzamide Melting point: 126-128° C.

Example 242

N-(6-{2-[4-(4-Cyanobenzoyl)piperazine-1-carbonyl]-1-methyl-1H-indol-5-yloxy}pyridin-3-yl)-N-methyl-4-trifluoromethylbenzamide Melting point: 135-137° C.

Example 243

N-{6-[1-Methyl-2-(4-pyridin-2-ylmethylpiperazine-1-carbonyl)-1H-indol-7-yloxy]pyridin-3-yl}-4-trifluoromethylbenzamide dioxalate Melting point: 121-123° C.

Example 244

N-(6-{2-[4-(4-Methoxybenzyl)piperazine-1-carbonyl]-1-methyl-1H-indol-7-yloxy}pyridin-3-yl)-4-trifluoromethylbenzamide $^1$H NMR (CDCl$_3$) δ 2.45 (4H, brs), 3.47 (2H, s), 3.71 (4H, brs), 3.79 (3H, s), 3.80 (3H, s), 6.52 (1H, s), 6.85 (3H, d, J=8.7 Hz), 6.90 (1H, dd, J=7.7 Hz, 0.7 Hz), 7.07 (1H, t, J=7.7 Hz), 7.19-7.24 (2H, m), 7.43 (1H, dd, J=8.0 Hz, 0.7 Hz), 7.69 (2H, d, J=8.4 Hz), 7.95 (2H, d, J=8.1 Hz), 8.13 (1H, dd, J=8.8 Hz, 2.7 Hz), 8.28 (1H, d, J=2.6 Hz), 8.46 (1H, s).

Example 245

N-(6-{2-[4-(4-Cyanobenzyl)piperazine-1-carbonyl]-1-methyl-1H-indol-7-yloxy}pyridin-3-yl)-4-trifluoromethylbenzamide Melting point: 228-229° C.

Example 246

N-{6-[1-Methyl-2-(4-pyridin-2-ylmethylpiperazine-1-carbonyl)-1H-indol-4-yloxy]pyridin-3-yl}-4-trifluoromethylbenzamide hydrobromide Melting point: 186-189° C.

Example 247

N-(6-{2-[4-(4-Methoxybenzyl)piperazine-1-carbonyl]-1-methyl-1H indol-4-yloxy}pyridin-3-yl)-4-trifluoromethylbenzamide $^1$H NMR (CDCl$_3$) δ 2.43 (4H, brs), 3.46 (2H, s), 3.71 (4H, brs), 3.79 (6H, s), 6.33 (1H, s), 6.82-6.89 (4H, m), 7.16-7.31 (4H, m), 7.73 (2H, d, J=8.1 Hz), 8.00 (2H, d, J=8.2 Hz), 8.05 (1H, d, J=9.1 Hz), 8.23 (1H, d, J=2.6 Hz), 8.28 (1H, s).

Example 248

N-(6-{2-[4-(4-Cyanobenzyl)piperazine-1-carbonyl]-1-methyl-1H-indol-4-yloxy}pyridin-3-yl)-4-trifluoromethylbenzamide $^1$H NMR (CDCl$_3$) δ 2.45 (4H, brs), 3.57 (2H, s), 3.73 (4H, brs), 3.80 (3H, s), 6.36 (1H, s), 6.82-6.89 (2H, m), 7.19 (1H, d, J=8.2 Hz), 7.30 (1H, d, J=8.2 Hz), 7.44 (2H, d, J=8.2 Hz), 7.60 (2H, d, J=8.4 Hz), 7.74 (2H, d, J=8.2 Hz), 8.00 (2H, d, J=8.1 Hz), 8.06 (1H, dd, J=8.8 Hz, 2.7 Hz), 8.24 (2H, d, J=2.6 Hz).

Example 249

N-(6-{2-[4-(4-Difluoromethoxybenzyl)piperazine-1-carbonyl]-1-methyl-1H-indol-5-yloxy}pyridin-3-yl)-2-methoxymethoxy-4-tri-fluoromethylbenzamide $^1$H NMR (CDCl$_3$) δ 2.49 (4H, brs), 3.53 (2H, s), 3.58 (3H, s), 3.78 (4H, brs), 3.84 (3H, s), 5.44 (2H, s), 6.50 (1H, t, J=74 Hz), 6.55 (1H, s), 6.92 (1H, d, J=8.9 Hz), 7.09 (2H, d, J=8.3 Hz), 7.03-7.18 (1H, m), 7.32 (2H, d, J=8.3 Hz), 7.30-7.55 (4H, m), 8.22 (1H, d, J=2.5 Hz), 8.27 (1H, dd, J=8.9 Hz, 2.5 Hz), 8.36 (1H, d, J=7.9 Hz), 9.61 (1H, s).

Example 250

N-[6-(1-Methyl-2-{4-[4-(1,1,2,2-tetrafluoroethoxy)benzyl]-piperazine-1-carbonyl}-1H-indol-6-yloxy)pyridin-3-yl]-4-tri-fluoromethylbenzamide hydrobromide Melting point: 279-282° C. (decomposition)

Example 251

N-(6-{2-[4-(4-Isopropoxybenzyl)piperazine-1-carbonyl]-1-methyl-1H-indol-6-yloxy}pyridin-3-yl)-4-trifluoromethoxybenzamide hydrobromide Melting point: 265-267° C. (decomposition)

Example 252

N-(6-{2-[4-(4-tert-Butylbenzyl)piperazine-1-carbonyl]-1-methyl-1H-indol-6-yloxy}pyridin-3-yl)-4-trifluoromethylbenzamide hydrobromide $^1$H NMR (DMSO-d$_6$) δ 1.30 (9H, s), 3.10-3.60 (6H, m), 3.76 (3H, s), 4.37 (2H, s), 4.35-4.60 (2H, m), 6.82 (1H, s), 6.90 (1H, d, J=8.7 Hz), 7.06 (1H, d, J=8.5 Hz), 7.35 (1H, s), 7.48 (2H, d, J=8.2 Hz), 7.52 (2H, d, J=8.2 Hz), 7.65 (1H, d, J=8.7 Hz), 7.93 (2H, d, J=8.2 Hz), 8.17 (2H, d, J=8.2 Hz), 8.21 (1H, dd, J=8.5 Hz, 2.6 Hz), 8.50 (1H, d, J=2.6 Hz), 10.61 (1H, s).

Example 253

2-Chloro-N-(6-{2-[4-(4-isopropoxybenzyl)piperazine-1-carbonyl]-1-methyl-1H-indol-6-yloxy}pyridin-3-yl)-4-trifluoromethylbenzamide hydrobromide Melting point: 237.2-238.2° C.

Example 254

3,4-Dichloro-N-(6-{2-[4-(4-difluoromethoxybenzyl)piperazine-1-carbonyl]-1-methyl-1H-indol-6-yloxy}pyridin-3-yl)benzamide hydrobromide Melting point: 249.0-253.7° C.

Example 255

3,4-Dichloro-N-(6-{2-[4-(4-isopropoxybenzyl)piperazine-1-carbonyl]-1-methyl-1H-indol-6-yloxy}pyridin-3-yl)benzamide hydrobromide Melting point: 239.7-243.5° C.

Example 256

3,4-Dichloro-N-(6-{1-methyl-2-[4-(4-propoxybenzyl)piperazine-1-carbonyl]-1H-indol-6-yloxy}pyridin-3-yl)benzamide hydrobromide Melting point: 239.2-240.4° C.

Example 257

N-{6-[2-(4-Benzo[1,3]dioxol-5-ylmethylpiperazine-1-carbonyl)-1-methyl-1H-indol-6-yloxy]pyridin-3-yl}-3,4-dichlorobenzamide hydrobromide Melting point: 241.3-243.9° C.

Example 258

3,4-Dichloro-N-(6-{2-[4-(4-methoxybenzyl)piperazine-1-carbonyl]-1-methyl-1H-indol-6-yloxy}pyridin-3-yl)benzamide hydrobromide Melting point: 234.6-237.2° C.

Example 259

3,4-Dichloro-N-(6-{2-[4-(4-methoxymethylbenzyl)piperazine-1-carbonyl]-1-methyl-1H-indol-6-yloxy}pyridin-3-yl)benzamide hydrobromide Melting point: 243.6-247.7° C.

Example 260

3,4-Dichloro-N-(6-{2-[4-(4-isobutylbenzyl)piperazine-1-carbonyl]-1-methyl-1H-indol-6-yloxy}pyridin-3-yl)benzamide hydrobromide Melting point: 255.8-257.4° C.

Example 261

3,4-Dichloro-N-[6-(2-{4-[4-(2,2-difluoroethoxy)-3-methoxybenzyl]-piperazine-1-carbonyl}-1-methyl-1H-indol-6-yloxy)pyridin-3-yl]-benzamide hydrobromide $^1$H NMR (DMSO-$d_6$) δ 3.19-3.48 (8H, m), 3.76 (3H, s), 3.84 (3H, s), 4.34-4.42 (4H, m), 6.40 (1H, tt, J=54.5 Hz, 3.7 Hz), 6.82 (1H, s), 6.91 (1H, dd, J=8.5 Hz, 1.9 Hz), 7.05 (2H, d, J=8.9 Hz), 7.15-7.18 (2H, m), 7.36 (1H, d, J=1.5 Hz), 7.65 (1H, d, J=8.6 Hz), 7.84 (1H, d, J=8.4 Hz), 7.95 (1H, dd, J=8.3 Hz, 1.6 Hz), 8.18 (1H, dd, J=8.8 Hz, 2.7 Hz), 8.22 (1H, d, J=2.0 Hz), 8.47 (1H, d, J=2.8 Hz), 9.86 (1H, brs), 10.53 (1H, s).

Example 262

3,4-Dichloro-N-(6-{1-methyl-2-[4-(4-trifluoromethylbenzyl)-piperazine-1-carbonyl]-1H-indol-6-yloxy}pyridin-3-yl)benzamide hydrobromide Melting point: 259.4-260.7° C.

Example 263

3,4-Dichloro-N-(6-{2-[4-(4-cyanobenzyl)piperazine-1-carbonyl]-1-methyl-1H-indol-6-yloxy}pyridin-3-yl)benzamide hydrobromide Melting point: 263.9-267.4° C.

Example 264

3,4-Dichloro-N-(6-{1-methyl-2-[4-(4-trifluoromethoxybenzyl)-piperazine-1-carbonyl]-1H-indol-6-yloxy}pyridin-3-yl)benzamide hydrobromide Melting point: 261.6-264.7° C.

Example 265

3,4-Dichloro-N-(6-{2-[4-(2-fluoro-4-isopropoxybenzyl)piperazine-1-carbonyl]-1-methyl-1H-indol-6-yloxy}pyridin-3-yl)benzamide hydrobromide Melting point: 242.5-246.7° C.

Example 266

3,4-Dichloro-N-(6-{2-[4-(3-fluoro-4-isopropoxybenzyl)piperazine-1-carbonyl]-1-methyl-1H-indol-6-yloxy}pyridin-3-yl)benzamide hydrobromide Melting point: 244.3-247.0° C.

Example 267

2-Hydroxy-N-[6-(1-methyl-2-{4-[4-(2,2,2-trifluoroethoxy)benzyl]-piperazine-1-carbonyl}-1H-indol-5-yloxy)pyridin-3-yl]-4-tri-fluoromethylbenzamide hydrobromide Melting point: 214-219° C. (decomposition)

Example 268

3,4-Dichloro-N-[6-(2-{4-[4-(2,2-difluoroethoxy)benzyl]piperazine-1-carbonyl}-1-methyl-1H-indol-6-yloxy)pyridin-3-yl]benzamide hydrobromide Melting point: 221.5-222.3° C.

Example 269

3,4-Dichloro-N-{6-[1-methyl-2-(4-pyridin-2-ylmethylpiperazine-1-carbonyl)-1H-indol-6-yloxy]pyridin-3-yl}benzamide dihydrobromide $^1$H NMR (DMSO-$d_6$) δ 3.40 (4H, brs), 3.98 (3H, s), 4.25 (4H, brs), 4.57 (2H, brs), 6.82 (1H, s), 6.91 (1H, dd, J=8.1 Hz, 2.7 Hz), 7.05 (1H, d, J=8.1 Hz), 7.36 (1H, d, J=2.7 Hz), 7.49-7.61 (2H, m), 7.64 (1H, d, J=8.1 Hz), 7.85 (1H, d, J=8.1 Hz), 7.91-8.02 (2H, m), 8.18 (1H, dd, J=8.1 Hz, 2.7 Hz), 8.23 (1H, d, J=2.7 Hz), 8.48 (1H, d, J=2.7 Hz), 8.73 (1H, d, J=5.4 Hz), 10.53 (1H, brs).

Example 270

2-Hydroxy-N-[6-(1-methyl-2-{4-[4-(2,2,2-trifluoro-ethoxy)benzyl]-piperazine-1-carbonyl}-1H-indol-6-yloxy)pyridin-3-yl]-4-tri-fluoromethylbenzamide hydrobromide $^1$H NMR (DMSO-d$_6$) δ 3.21 (2H, brs), 3.39 (4H, brs), 3.75 (3H, s), 4.37 (2H, s), 4.46 (2H, brs), 4.82 (2H, q, J=8.6 Hz), 6.81 (1H, s), 6.90 (1H, dd, J=8.6 Hz, 1.7 Hz), 7.05 (1H, d, J=8.6 Hz), 7.18 (2H, d, J=8.6 Hz), 7.29 (1H, s), 7.30 (1H, d, J=8.6 Hz), 7.35 (1H, d, J=1.7 Hz), 7.52 (2H, d, J=8.6 Hz), 7.65 (1H, d, J=8.6 Hz), 8.01 (1H, d, J=8.6 Hz), 8.17 (1H, dd, J=8.6 Hz, 2.7 Hz), 8.45 (1H, d, J=2.7 Hz), 9.91 (1H, s), 10.53 (1H, s).

Example 271

N-[2-(1-Methyl-2-{4-[4-(2,2,2-trifluoroethoxy)ben-zyl]piperazine-1-carbonyl}-1H-indol-6-yloxy)pyri-midin-5-yl]-4-trifluoromethyl-benzamide hydrochloride Melting point: 250.8-254.2° C.

Example 272

N-[2-(2-{4-[4-(2,2-Difluoroethoxy)benzyl]pipera-zine-1-carbonyl}-1-methyl-1H-indol-6-yloxy)pyri-midin-5-yl]-4-trifluoromethyl-benzamide hydrochloride Melting point: 251.4-253.5° C.

Example 273

N-(2-{2-[4-(4-Isopropoxybenzyl)piperazine-1-carbo-nyl]-1-methyl-1H-indol-6-yloxy}pyrimidin-5-yl)-4-trifluoromethylbenzamide hydrochloride Melting point: 249.8-251.0° C.

Example 274

N-(2-{2-[4-(4-Difluoromethoxybenzyl)piperazine-1-carbonyl]-1-methyl-1H-indol-6-yloxy}pyrimidin-5-yl)-4-trifluoromethyl-benzamide hydrochloride Melting point: 247.7-249.8° C.

Example 275

N-[6-(2-{4-[4-(2,2-Difluoroethoxy)benzyl]pipera-zine-1-carbonyl}-1-methyl-1H-indol-6-yloxy)pyri-din-3-yl]-4,N-dimethylbenzamide hydrochloride Melting point: 207.8-209.3° C.

Example 276

N-(6-{2-[4-(4-Difluoromethoxybenzyl)piperazine-1-carbonyl]-1-methyl-1H-indol-6-yloxy}pyridin-3-yl)-4,N-dimethylbenzamide Melting point: 140.1-141.3° C.

Example 277

N-(6-{2-[4-(4-Isopropoxybenzyl)piperazine-1-carbo-nyl]-1-methyl-1H-indol-6-yloxy}pyridin-3-yl)-4,N-dimethylbenzamide hydrochloride Melting point: 230.1-232.0° C.

Example 278

4,N-Dimethyl-N-(6-{1-methyl-2-[4-(4-propoxyben-zyl)piperazine-1-carbonyl]-1H-indol-6-yloxy}pyridin-3-yl)benzamide hydrochloride Melting point: 231.2-231.8° C.

Example 279

N-[6-(2-{4-[4-(2-Fluoro-1-fluoromethylethoxy)ben-zyl]piperazine-1-carbonyl}-1-methyl-1H-indol-6-yloxy)pyridin-3-yl]-N-methyl-4-tri-fluoromethoxy-benzamide hydrobromide Melting point: 227.5-230.3° C.

Example 280

4-Difluoromethoxy-N-methyl-N-(6-{1-methyl-2-[4-(4-propoxybenzyl)-piperazine-1-carbonyl]-1H-indol-6-yloxy}pyridin-3-yl)benzamide hydrochloride Melting point: 226.9-229.0° C.

Example 281

4-Difluoromethoxy-N-(6-{2-[4-(4-isopropoxyben-zyl)piperazine-1-carbonyl]-1-methyl-1H-indol-6-yloxy}pyridin-3-yl)-N-methyl-benzamide hydrochloride Melting point: 229.7-230.4° C.

Example 282

4-Difluoromethoxy-N-(6-{2-[4-(4-difluoromethoxy-benzyl)piperazine-1-carbonyl]-1-methyl-1H-indol-6-yloxy}pyridin-3-yl)-N-methyl-benzamide hydrobromide Melting point: 198.7-200.5° C.

Example 283

N-[6-(2-{4-[4-(2,2-Difluoroethoxy)benzyl]pipera-zine-1-carbonyl}-1-methyl-1H-indol-6-yloxy)pyri-din-3-yl]-4-difluoromethoxy-N-methylbenzamide hydrobromide Melting point: 196.9-198.6° C.

Example 284

4-Difluoromethoxy-N-methyl-N-[6-(1-methyl-2-{4-[4-(2,2,2-tri-fluoroethoxy)benzyl]piperazine-1-carbonyl}-1H-indol-6-yloxy)-pyridin-3-yl]benzamide hydrobromide
Melting point: 203.8-205.6° C.

Example 285

N-Methyl-N-[6-(2-{4-[4-(2,2,2-trifluoroethoxy)benzyl]piperazine-1-carbonyl}-1H-indol-6-yloxy)pyridin-3-yl]methanesulfonamide Melting point: 167.0-168.1° C.

Example 286

N-[6-(2-{4-[4-(2-Fluoro-1-fluoromethylethoxy)benzyl]piperazine-1-carbonyl}-1-methyl-1H-indol-6-yloxy)pyridin-3-yl]-2-methoxy-4-trifluoromethyl-benzamide $^1$H NMR (CDCl$_3$) δ 2.49 (4H, brs), 3.50 (2H, s), 3.78 (4H, brs), 3.79 (3H, s), 4.12 (3H, s), 4.58-4.77 (5H, m), 6.58 (1H, d, J=0.7 Hz), 6.92-6.96 (4H, m), 7.14 (1H, d, J=2.0 Hz), 7.25-7.28 (3H, m), 7.41 (1H, dd, J=8.2 Hz, 0.8 Hz), 7.60 (1H, d, J=8.7 Hz), 8.26 (2H, m), 8.40 (1H, dd, J=8.2 Hz, 0.7 Hz), 9.63 (1H, s).

Example 287

N-[6-(2-{4-[4-(2,2-Difluoroethoxy)benzyl]piperazine-1-carbonyl}-1-methyl-1H-indol-6-yloxy)pyridin-3-yl]-2-methoxy-4-trifluoro-methylbenzamide $^1$H NMR (CDCl$_3$) δ 2.51 (4H, brs), 3.53 (2H, s), 3.78 (3H, s), 3.80 (4H, s), 4.12 (3H, s), 4.18 (2H, td, J=13.3 Hz, 4.3 Hz), 6.09 (1H, tt, J=55.1 Hz, 4.2 Hz), 6.58 (1H, s), 6.89 (2H, d, J=8.6 Hz), 6.92-6.97 (3H, m), 7.14 (1H, d, J=1.6 Hz), 7.26-7.29 (3H, m), 7.41 (1H, d, J=7.9 Hz), 7.60 (1H, d, J=8.6 Hz), 8.24-8.29 (2H, m), 8.40 (1H, d, J=7.9 Hz), 9.63 (1H, s).

Example 288

N-(6-{2-[4-(4-Isopropoxybenzyl)piperazine-1-carbonyl]-1-methyl-1H-indol-6-yloxy}pyridin-3-yl)-2-methoxy-4-trifluoromethyl-benzamide $^1$H NMR (CDCl$_3$) δ 1.33 (3H, s), 1.36 (3H, s), 2.49 (4H, brs), 3.49 (2H, s), 3.77 (4H, brs), 3.78 (3H, s), 4.12 (3H, s), 4.49-4.58 (1H, m), 6.58 (1H, d, J=0.7 Hz), 6.85 (2H, dt, J=9.2 Hz, 2.4 Hz), 6.91-6.97 (2H, m), 7.13 (1H, d, J=2.0 Hz), 7.22 (2H, d, J=8.6 Hz), 7.26-7.27 (1H, m), 7.41 (1H, d, J=8.1 Hz), 7.60 (1H, d, J=8.6 Hz), 8.23-8.28 (2H, m), 8.40 (1H, d, J=8.1 Hz), 9.64 (1H, s).

Example 289

2-Methoxy-N-(6-{1-methyl-2-[4-(4-propoxybenzyl)piperazine-1-carbonyl]-1H-indol-6-yloxy}pyridin-3-yl)-4-trifluoromethyl-benzamide $^1$H NMR (CDCl$_3$) δ 1.04 (3H, t, J=7.4 Hz), 1.81 (2H, td, J=14.1 Hz, 7.3 Hz), 2.49 (4H, brs), 3.50 (2H, brs), 3.78 (7H, brs), 3.92 (2H, t, J=6.6 Hz), 4.12 (3H, s), 6.58 (1H, d, J=0.5 Hz), 6.87 (2H, dt, J=9.0 Hz, 2.2 Hz), 6.92-6.97 (2H, m), 7.14 (1H, d, J=2.0 Hz), 7.24-7.27 (3H, m), 7.41 (1H, d, J=8.4 Hz), 7.60 (1H, d, J=8.6 Hz), 8.24-8.27 (2H, m), 8.40 (1H, d, J=8.1 Hz), 9.64 (1H, s).

Example 290

N-(6-{2-[4-(4-Difluoramethoxybenzyl)piperazine-1-carbonyl]-1-methyl-1H-indol-6-yloxy}pyridin-3-yl)-2-methoxy-4-trifluoro-methylbenzamide $^1$H NMR (CDCl$_3$) δ 2.49 (4H, brs), 3.54 (2H, s), 3.79 (7H, brs), 4.12 (3H, s), 6.51 (1H, t, J=74.0 Hz), 6.59 (1H, d, J=0.7 Hz), 6.93-6.96 (2H, m), 7.07-7.14 (3H, m), 7.27 (1H, s), 7.34 (2H, d, J=8.4 Hz), 7.41 (1H, d, J=8.2 Hz), 7.60 (1H, d, J=8.6 Hz), 8.24-8.28 (2H, m), 8.39 (1H, d, J=8.1 Hz), 9.64 (1H, s).

Example 291

N-(6-{2-[4-(4-Difluoromethoxybenzyl)piperazine-1-carbonyl]-1-methyl-1H-indol-6-yloxy}pyridin-3-yl)-4-trifluoromethoxybenzamide hydrochloride Melting point: 256.2-256.5° C.

Example 292

N-(6-{2-[(S)-4-(4-Difluoromethoxybenzyl)-3-methylpiperazine-1-carbonyl]-1-methyl-1H-indol-6-yloxy}pyridin-3-yl)-4-trifluoro-methoxybenzamide hydrobromide Melting point: 199.4-202.1° C.

Example 293

N-[6-(1-Methyl-2-{(S)-3-methyl-4-[4-(2,2,2-trifluoroethoxy)-benzyl]piperazine-1-carbonyl}-1H-indol-6-yloxy)pyridin-3-yl]-4-trifluoromethoxybenzamide hydrobromide Melting point: 199.4-203.1° C.

Example 294

N-(6-{2-[(S)-4-(4-Difluoromethoxybenzyl)-3-methylpiperazine-1-carbonyl]-1-methyl-1H-indol-6-yloxy}pyridin-3-yl)-N-methyl-4-tri-fluoramethoxy-benzamide $^1$H NMR (CDCl$_3$) δ 1.21 (3H, brs), 2.17 (1H, brs), 2.55 (1H, brs), 2.71 (1H, brs), 3.22 (2H, d, J=13.5 Hz), 3.38-3.50 (4H, m), 3.76 (3H, s), 3.99-4.12 (3H, m), 6.50 (1H, t, J=72.9 Hz), 6.56 (1H, s), 6.83-6.87 (2H, m), 7.07-7.10 (5H, m), 7.32-7.36 (4H, m), 7.42 (1H, dd, J=8.6 Hz, 3.0 Hz), 7.58 (1H, d, J=8.6 Hz), 7.85 (1H, d, J=2.6 Hz).

Example 295

N-Methyl-N-[6-(1-methyl-2-{(S)-3-methyl-4-[4-(2,2,2-trifluoro-ethoxy)benzyl]piperazine-1-carbonyl}-1H-indol-6-yloxy)pyridin-3-yl]-4-trifluoromethoxy-benzamide $^1$H NMR (CDCl$_3$) δ 1.17 (3H, brs), 2.17 (1H, brs), 2.52 (1H, brs), 2.71 (1H, brs), 3.19 (2H, d, J=13.5 Hz), 3.31 (1H, brs), 3.49 (3H, s), 3.76 (3H, s), 3.98 (3H, d, J=12.9 Hz), 4.35 (2H, q, J=8.2 Hz), 6.56 (1H, s), 6.85 (2H, d, J=8.6 Hz), 6.91

(2H, d, J=8.6 Hz), 7.06-7.08 (3H, m), 7.28 (2H, d, J=8.6 Hz), 7.34 (2H, d, J=8.9 Hz), 7.42 (1H, d, J=6.3 Hz), 7.58 (1H, d, J=8.6 Hz), 7.85 (1H, d, J=2.6 Hz).

Example 296

2-Methoxy-N-[6-(1-methyl-2-{(S)-3-methyl-4-[4-(2,2,2-trifluoro-ethoxy)benzyl]piperazine-1-carbonyl}-1H-indol-6-yloxy)pyridin-3-yl]-4-trifluoromethyl-benzamide hydrochloride $^1$H NMR (DMSO-d$_6$) δ 1.09-1.59 (3H, m), 2.11-2.19 (1H, m), 2.64-2.68 (1H, m), 3.10-3.26 (2H, m), 3.44 (1H, s), 3.70-3.74 (3H, m), 3.86-3.91 (1H, m), 3.96 (3H, s), 4.02-4.10 (1H, m), 4.30-4.39 (2H, m), 4.68-4.86 (2H, m), 6.65-6.80 (1H, m), 6.85-6.90 (1H, m), 7.00-7.05 (2H, m), 7.17 (1H, d, J=8.1 Hz), 7.28-7.31 (2H, m), 7.42 (1H, d, J=8.1 Hz), 7.46 (1H, s), 7.57-7.64 (2H, m), 7.76 (1H, d, J=7.6 Hz), 8.17 (1H, dd, J=8.8 Hz, 2.7 Hz), 8.44 (1H, d, J=2.5 Hz), 10.40 (1H, s), 10.86 (1H, brs).

Example 297

N-[6-(1,3-Dimethyl-2-{4-[4-(2,2,2-trifluoroethoxy)benzyl]-piperazine-1-carbonyl}-1H-indol-6-yloxy)pyridin-3-yl]-N-methyl-4-trifluoromethylbenzamide hydrobromide $^1$H NMR (DMSO-d$_6$) δ 2.23-2.28 (3H, m), 3.17-3.27 (4H, m), 3.37 (3H, s), 3.41-3.50 (2H, m), 3.58-3.65 (3H, m), 4.36-4.64 (4H, m), 4.82 (2H, q, J=8.8 Hz), 6.77 (1H, d, J=7.4 Hz), 6.96 (1H, d, J=8.6 Hz), 7.16-7.23 (3H, m), 7.48-7.57 (5H, m), 7.68 (2H, d, J=8.1 Hz), 7.83 (1H, dd, J=8.7 Hz, 2.3 Hz), 7.93 (1H, brs), 9.89 (1H, brs).

Example 298

N-(6-{2-[4-(4-Difluoromethoxybenzyl)piperazine-1-carbonyl]-1,3-dimethyl-1H-indol-6-yloxy}pyridin-3-yl)-N-methyl-4-trifluoro-methylbenzamide hydrobromide $^1$H NMR (DMSO-d$_6$) δ 2.21-2.31 (3H, m), 3.05-3.24 (4H, m), 3.37 (3H, s), 3.43-3.46 (2H, m), 3.56-3.65 (3H, m), 3.94 (2H, brs), 4.40-4.45 (2H, m), 6.76 (1H, d, J=7.4 Hz), 6.96 (1H, d, J=8.7 Hz), 7.23 (1H, s), 7.29-7.31 (2H, m), 7.32 (1H, t, J=73.7 Hz), 7.50-7.70 (7H, m), 7.83 (1H, dd, J=8.7 Hz, 2.2 Hz), 7.93 (1H, brs), 9.94 (1H, brs).

Example 299

N-(6-{2-[(S)-4-(4-Difluoromethoxybenzyl)-3-methylpiperazine-1-carbonyl]-1-methyl-1H-indol-6-yloxy}pyridin-3-yl)-2-methoxy-4-trifluoromethyl-benzamide hydrobromide $^1$H NMR (DMSO-d$_6$) δ 1.36-1.52 (3H, m), 3.17-3.52 (3H, m), 3.75 (3H, s), 3.96 (3H, s), 4.11 (3H, brs), 4.37-4.51 (2H, m), 4.79-4.84 (1H, m), 6.82 (1H, t, J=71.8 Hz), 6.89 (1H, dd, J=8.6 Hz, 2.0 Hz), 7.04 (1H, d, J=8.4 Hz), 7.30-7.34 (4H, m), 7.43 (1H, d, J=8.1 Hz), 7.47 (1H, s), 7.60-7.69 (3H, m), 7.76 (1H, d, J=7.7 Hz), 8.17 (1H, dd, J=8.9 Hz, 2.6 Hz), 8.45 (1H, d, J=2.6 Hz), 9.96 (1H, brs), 10.41 (1H, s).

Example 300

N-[6-(1-Methyl-2-{(S)-3-methyl-4-[4-(2,2,2-trifluoroethoxy)-benzyl]piperazine-1-carbonyl}-1H-indol-6-yloxy)pyridin-3-yl]-2,4-bistrifluoromethylbenzamide hydrobromide $^1$H NMR (DMSO-d$_6$) δ 1.35-1.53 (3H, m), 3.16-3.51 (3H, m), 3.75 (3H, s), 4.04 (4H, brs), 4.34-4.50 (2H, m), 4.82 (2H, q, J=8.9 Hz), 6.82 (1H, s), 6.90 (1H, dd, J=8.5 Hz, 1.9 Hz), 7.07 (1H, d, J=8.9 Hz), 7.19 (2H, d, J=8.6 Hz), 7.36 (1H, s), 7.54 (1H, d, J=8.6 Hz), 7.60 (1H, d, J=8.4 Hz), 7.65 (1H, d, J=8.7 Hz), 8.02 (1H, d, J=7.9 Hz), 8.13 (1H, dd, J=8.8 Hz, 2.7 Hz), 8.22 (1H, s), 8.25 (1H, d, J=8.9 Hz), 8.39 (1H, d, J=2.6 Hz), 9.96 (1H, brs), 10.86 (1H, s).

Example 301

N-[6-(2-{4-[4-(2-Fluoro-1-fluoromethylethoxy)benzyl]piperazine-1-carbonyl}-1-methyl-1H-indol-6-yloxy)pyridin-3-yl]-2,4-bistri-fluoromethylbenzamide hydrobromide $^1$H NMR (DMSO-d$_6$) δ 3.18-3.25 (2H, m), 3.40-3.45 (4H, m), 3.76 (3H, s), 4.36 (2H, brs), 4.36 (2H, brs), 4.44-4.50 (2H, m), 4.56-5.10 (5H, m), 6.82 (1H, s), 6.91 (1H, dd, J=8.6 Hz, 2.1 Hz), 7.01 (1H, d, J=8.9 Hz), 7.16 (2H, d, J=8.7 Hz), 7.36 (1H, d, J=1.8 Hz), 7.50 (2H, d, J=8.7 Hz), 7.65 (1H, d, J=8.6 Hz), 8.02 (1H, d, J=8.1 Hz), 8.13 (1H, dd, J=8.8 Hz, 2.7 Hz), 8.22 (1H, s), 8.25 (1H, d, J=8.9 Hz), 8.39 (1H, d, J=2.6 Hz), 9.98 (1H, brs), 10.86 (1H, s).

Example 302

N-[6-(2-{4-[4-(2,2-Difluoroethoxy)benzyl]piperazine-1-carbonyl}-1-methyl-1H-indol-6-yloxy)pyridin-3-yl]-2,4-bistrifluoromethyl-benzamide hydrobromide $^1$H NMR (DMSO-d$_6$) δ 3.18-3.25 (2H, m), 3.40-3.46 (4H, m), 3.76 (3H, s), 4.37 (2H, td, J=14.7 Hz, 3.5 Hz), 4.45-4.50 (4H, m), 6.41 (1H, tt, J=54.4 Hz, 3.5 Hz), 6.82 (1H, s), 6.91 (1H, dd, J=8.6 Hz, 2.1 Hz), 7.07 (1H, d, J=8.9 Hz), 7.13 (2H, d, J=8.7 Hz), 7.36 (1H, d, J=2.0 Hz), 7.52 (2H, d, J=8.7 Hz), 7.65 (1H, d, J=8.7 Hz), 8.02 (1H, d, J=8.1 Hz), 8.13 (1H, dd, J=8.9 Hz, 2.8 Hz), 8.22 (1H, s), 8.25 (1H, d, J=8.4 Hz), 8.39 (1H, d, J=2.6 Hz), 10.03 (1H, brs), 10.86 (1H, s).

Example 303

N-(6-{2-[4-(4-Isopropoxybenzyl)piperazine-1-carbonyl]-1-methyl-1H-indol-6-yloxy}pyridin-3-yl)-2,4-bistrifluoramethylbenzamide hydrobromide $^1$H NMR (DMSO-d$_6$) δ 1.27 (3H, s), 1.29 (3H, s), 3.18-3.25 (2H, m), 3.40-3.48 (4H, m), 3.76 (3H, s), 4.33-4.35 (2H, m), 4.45-4.50 (2H, m), 4.56-4.73 (1H, m), 6.82 (1H, s), 6.90 (1H, dd, J=8.6 Hz, 2.0 Hz), 7.01 (2H, d, J=8.7 Hz), 7.07 (1H, d, J=8.9 Hz), 7.36 (1H, d, J=2.0 Hz), 7.46 (2H, d, J=8.6 Hz), 7.65 (1H, d, J=8.6 Hz), 8.02 (1H, d, J=7.9 Hz), 8.13 (1H, dd, J=8.8 Hz, 2.7 Hz), 8.22 (1H, s), 8.25 (1H, d, J=8.4 Hz), 8.40 (1H, d, J=2.6 Hz), 10.00 (1H, brs), 10.87 (1H, s).

Example 304

N-(6-{1-Methyl-2-[4-(4-propoxybenzyl)piperazine-1-carbonyl]-1H-indol-6-yloxy}pyridin-3-yl)-2,4-bistrifluoromethylbenzamide hydrobromide $^1$H NMR (DMSO-d$_6$) δ 0.98 (3H, t, J=7.4 Hz), 1.74 (2H, td, J=13.9 Hz, 7.1 Hz), 3.18-3.25 (2H, m), 3.44 (4H, m), 3.76 (3H, s), 3.96 (2H, t, J=6.4 Hz), 4.35 (2H, d, J=3.5 Hz), 4.45-4.50 (2H, m), 6.82 (1H, s), 6.91 (1H, dd, J=8.6 Hz, 2.0 Hz), 7.02-7.08 (3H, m), 7.36 (1H, d, J=1.8 Hz), 7.48 (2H, d, J=8.6 Hz), 7.65 (1H, d, J=8.7 Hz), 8.02 (1H, d, J=7.7 Hz), 8.14 (1H, dd, J=8.8 Hz, 2.7 Hz), 8.22 (1H, s), 8.25 (1H, d, J=8.7 Hz), 8.40 (1H, d, J=2.5 Hz), 10.02 (1H, brs), 10.87 (1H, s).

Example 305

N-(6-{2-[4-(4-Difluoromethoxybenzyl)piperazine-1-carbonyl]-1-methyl-1H-indol-6-yloxy}pyridin-3-yl)-2,4-bistrifluoromethyl-benzamide hydrobromide $^1$H NMR (DMSO-d$_6$) δ 3.27 (2H, brs), 3.40-3.46 (4H, m), 3.76 (3H, s), 4.45 (2H, brs), 4.50 (2H, brs), 6.82 (1H, s), 6.91 (1H, dd, J=8.6 Hz, 2.0 Hz), 7.07 (1H, d, J=8.9 Hz), 7.31 (2H, d, J=8.6 Hz), 7.34 (1H, t, J=73.7 Hz), 7.36 (1H, d, J=1.8 Hz), 7.63-7.68 (3H, m), 8.02 (1H, d, J=7.9 Hz), 8.14 (1H, dd, J=8.9 Hz, 2.8 Hz), 8.22 (1H, s), 8.25 (1H, d, J=8.2 Hz), 8.40 (1H, d, J=2.6 Hz), 10.25 (1H, brs), 10.88 (1H, s).

Example 306

3,4-Dichloro-N-(6-{2-[4-(4-difluoromethoxybenzyl)piperazine-1-carbonyl]-1-methyl-1H-indol-6-yloxy}-4-methylpyridin-3-yl)-benzenesulfonamide $^1$H NMR (CDCl$_3$) δ 2.22 (3H, s), 2.49 (4H, brs), 3.53 (2H, s), 3.76 (7H, s), 6.42 (1H, s), 6.51 (1H, t, J=72.9 Hz), 6.56 (1H, s), 6.74 (1H, s), 6.87 (1H, dd, J=8.6 Hz, 1.6 Hz), 7.09 (3H, d, J=8.2 Hz), 7.33 (2H, d, J=8.6 Hz), 7.56-7.58 (4H, m), 7.85 (1H, s).

Example 307

3,4-Dichloro-N-[4-methyl-6-(1-methyl-2-{4-[4-(2,2,2-trifluoro-ethoxy)benzyl]piperazine-1-carbonyl}-1H-indol-6-yloxy)pyridin-3-yl]benzenesulfonamide $^1$H NMR (CDCl$_3$) δ 2.22 (3H, s), 2.48 (4H, brs), 3.51 (2H, s), 3.75 (7H, brs), 4.35 (2H, q, J=8.1 Hz), 6.43 (1H, brs), 6.56 (1H, s), 6.73 (1H, s), 6.87 (1H, dd, J=8.6 Hz, 2.0 Hz), 6.91 (2H, d, J=8.6 Hz), 7.07 (1H, s), 7.26-7.30 (4H, m), 7.55-7.58 (4H, m), 7.85 (1H, s).

Example 308

3,4-Dichloro-N-(6-{2-[4-(4-isopropoxybenzyl)piperazine-1-carbonyl]-1-methyl-1H-indol-6-yloxy}-4-methylpyridin-3-yl)-benzenesulfonamide $^1$H NMR (CDCl$_3$) δ 1.34 (6H, d, J=6.3 Hz), 2.20 (3H, s), 2.48 (4H, brs), 3.49 (2H, s), 3.71 (7H, s), 4.49-4.58 (1H, m), 6.55 (2H, s), 6.72 (1H, s), 6.84-6.87 (3H, m), 7.07 (1H, d, J=1.6 Hz), 7.21 (2H, d, J=8.6 Hz), 7.50-7.59 (4H, m), 7.85 (1H, t, J=1.2 Hz).

Example 309

3,4-Dichloro-N-(6-{2-[(R)-4-(4-difluoromethoxybenzyl)-3-methyl-piperazine-1-carbonyl]-1-methyl-1H-indol-6-yloxy}-4-methyl-pyridin-3-yl)benzenesulfonamide $^1$H NMR (CDCl$_3$) δ 1.21 (3H, brs), 2.22 (4H, s), 2.55 (1H, brs), 2.71 (1H, brs), 3.22 (2H, d, J=13.2 Hz), 3.39 (1H, brs), 3.75 (3H, s), 4.00 (4H, d, J=13.5 Hz), 6.45 (1H, brs), 6.51 (1H, t, J=75.6 Hz), 6.55 (1H, s), 6.74 (1H, s), 6.87 (1H, dd, J=8.6 Hz, 2.0 Hz), 7.09 (3H, d, J=7.3 Hz), 7.33 (2H, d, J=8.6 Hz), 7.52-7.58 (4H, m), 7.85 (1H, s).

Example 310

3,4-Dichloro-N-[4-methyl-6-(1-methyl-2-{(R)-3-methyl-4-[4-(2,2,2-trifluoroethoxy)benzyl]piperazine-1-carbonyl}-1H-indol-6-yloxy)-pyridin-3-yl]benzenesulfonamide $^1$H NMR (CDCl$_3$) δ 1.22 (3H, brs), 2.17-2.22 (4H, m), 2.53 (1H, brs), 2.72 (1H, brs), 3.19 (2H, d, J=13.2 Hz), 3.38 (1H, brs), 3.75 (3H, s), 3.98 (4H, d, J=13.2 Hz), 4.35 (2H, q, J=8.1 Hz), 6.44 (1H, brs), 6.55 (1H, s), 6.73 (1H, s), 6.87-6.91 (3H, m), 7.08 (1H, d, J=2.0 Hz), 7.26-7.30 (2H, m), 7.55-7.58 (4H, m), 7.85 (1H, s).

Example 311

3,4-Dichloro-N-(6-{2-[4-(4-difluoromethoxybenzyl)piperazine-1-carbonyl]-1-methyl-1H-indol-6-yloxy}-4-methylpyridin-3-yl)-N-methylbenzenesulfonamide hydrobromide Melting point: 213.5-215.3° C.

Example 312

3,4-Dichloro-N-methyl-N-[4-methyl-6-(1-methyl-2-{4-[4-(2,2,2-tri-fluoroethoxy)benzyl]piperazine-1-carbonyl}-1H-indol-6-yloxy)-pyridin-3-yl]benzenesulfonamide $^1$H NMR (CDCl$_3$) δ 2.41 (3H, s), 2.48 (4H, brs), 3.19 (3H, s), 3.51 (2H, s), 3.79 (7H, s), 4.35 (2H, q, J=8.2 Hz), 6.58 (1H, s), 6.82 (1H, s), 6.89-6.92 (3H, m), 7.12 (1H, d, J=1.6 Hz), 7.28 (2H, d, J=8.6 Hz), 7.41 (1H, s), 7.53 (1H, dd, J=8.2 Hz, 2.0 Hz), 7.59 (2H, dd, J=8.6 Hz, 2.6 Hz), 7.84 (1H, d, J=2.0 Hz).

Example 313

3,4-Dichloro-N-(6-{2-[4-(4-isopropoxybenzyl)piperazine-1-carbonyl]-1-methyl-1H-indol-6-yloxy}-4-methylpyridin-3-yl)-N-methylbenzenesulfonamide Melting point: 151.0-151.6° C.

Example 314

3,4-Dichloro-N-(6-{2-[(R)-4-(4-difluoromethoxybenzyl)-3-methyl-piperazine-1-carbonyl]-1-methyl-1H-indol-6-yloxy}-4-methyl-pyridin-3-yl)-N-methylbenzenesulfonamide $^1$H NMR (CDCl$_3$) δ 1.21 (3H, brs), 2.18 (1H, brs), 2.42 (3H, s), 2.55 (1H, brs), 2.72 (1H, brs), 3.19-3.24 (5H, m), 3.40

(1H, brs), 3.79 (3H, s), 4.01-4.08 (3H, m), 6.50 (1H, t, J=72.9 Hz), 6.57 (1H, s), 6.83 (1H, s), 6.90 (1H, d, J=8.6 Hz), 7.08-7.11 (3H, m), 7.29-7.38 (3H, m), 7.51-7.62 (3H, m), 7.84 (1H, d, J=2.0 Hz).

Example 315

3,4-Dichloro-N-methyl-N-[4-methyl-6-(1-methyl-2-{(R)-3-methyl-4-[4-(2,2,2-trifluoroethoxy)benzyl]piperazine-1-carbonyl}-1hr-indol-6-yloxy)pyridin-3-yl]benzenesulfonamide $^1$H NMR (CDCl$_3$) δ 1.16 (3H, brs), 2.16 (1H, brs), 2.41 (3H, s), 2.52 (1H, brs), 2.71 (1H, brs), 3.17-3.19 (5H, m), 3.38 (1H, brs), 3.78 (3H, s), 3.99-4.10 (3H, m), 4.35 (2H, q, J=8.2 Hz), 6.57 (1H, s), 6.82 (1H, s), 6.88-6.92 (3H, m), 7.11 (1H, d, J=1.6 Hz), 7.26-7.30 (2H, m), 7.41 (1H, s), 7.52-7.57 (2H, m), 7.61 (1H, d, J=3.6 Hz), 7.84 (1H, d, J=2.0 Hz).

Example 316

N-{6-[2-(4-Benzo[1,3]dioxol-5-ylmethylpiperazine-1-carbonyl)-1-methyl-1H-indol-5-yloxy]pyridin-3-yl}-2-fluoro-4-trifluoromethyl-benzamide hydrobromide Melting point: 254-257° C. (decomposition)

Example 317

Production of 6-{1-[2-(4-benzo[1,3]dioxol-5-ylmethylpiperazin-1-yl)-2-oxoethyl]-2,3-dihydro-1H-indol-4-yloxy}-N-(4-trifluoro-methylphenyl)nicotinamide 6-(2,3-Dihydro-1H-indol-4-yloxy]-N-(4-trifluoromethylphenyl)nicotinamide (0.268 g, 0.671 mmol) was dissolved in DMF (3 mL). To the solution were added triethylamine (0.187 mL, 1.34 mmol) and tert-butyl bromoacetate (0.198 g, 1.34 mmol), and the resulting solution was stirred for 3 hours at 50° C. Water (50 mL) was added and the resulting solution was extracted with ethyl acetate (50 ml). After the organic layer was washed with brine, then dried over anhydrous sodium sulfate, the solvent was evaporated to form a brown powder (0.345 g), which was dissolved in trifluoroacetic acid (10 mL) and the solution was stirred for 1 hour at room temperature. The solution was concentrated, and the pH of the solution was adjusted to 5 using saturated sodium bicarbonate solution. The resulting solution was extracted with ethyl acetate. After the organic layer was washed with brine, then dried over anhydrous sodium sulfate, the solvent was evaporated to yield brown oil (0.307 g). This brown oil was dissolved in DMF (3 mL). To the solution were added 1-benzo[1,3]dioxol-5-ylmethylpiperazine (0.163 g, 0.738 mmol) and 1-ethyl-3-(3-dimethylaminopropyl)carbodiimide hydrochloride (0.141 g, 0.738 mmol), and the resulting solution was stirred for 16 hours at room temperature. Brine (100 mL) was added to the reaction solution, and the mixture was extracted with ethyl acetate (100 mL). After the organic layer was washed with saturated brine, then dried over anhydrous sodium sulfate, the solvent was evaporated. The obtained residue was purified by silica gel column chromatography (CH$_2$Cl$_2$:MeOH=10:1) to yield 0.106 g of the title compound as a pale brown oil.
$^1$H NMR (CDCl$_3$) δ 2.44 (4H, brs), 2.83 (2H, t, J=8.6 Hz), 3.44-3.52 (6H, m), 3.65 (2H, brs), 3.92 (2H, s), 5.95 (2H, s), 6.32 (1H, d, J=7.8 Hz), 6.46 (1H, d, J=8.1 Hz), 6.75 (2H, s), 6.85 (1H, s), 6.99 (1H, d, J=8.7 Hz), 7.08-7.14 (1H, m), 7.63 (2H, d, J=8.7 Hz), 7.77 (2H, d, J=8.6 Hz), 8.02 (1H, brs), 8.21 (1H, dd, J=8.7 Hz, 2.5 Hz), 8.69 (1H, d, J=2.5 Hz).

Example 318

Production of 2,4,6,N-tetramethyl-N-[6-(1-methyl-2-{4-[4-(2,2,2-trifluoroethoxy)benzyl]piperazine-1-carbonyl}-1H-indol-6-yloxy)-pyridin-3-yl]benzenesulfonamide To a solution of 2,4,6-trimethyl-N-[6-(1-methyl-2-{4-[4-(2,2,2-trifluoroethoxy)benzyl]piperazine-1-carbonyl}-1H-indol-6-yloxy)pyridin-3-yl]benzenesulfonamide (0.38 g, 0.53 mmol) in DMF (4 mL) was added 60% sodium hydride in oil (0.025 g, 0.63 mmol) under ice cooling and stirred for 10 minutes. Then to the mixture was added iodomethane (0.036 mL, 0.58 mmol) at 0° C. and the mixture was stirred for 2 hours. Water (8 ml) was added to the reaction mixture and extracted with AcOEt, the organic layer was washed with brine, dried over anhydrous sodium sulfate and evaporated. The residue was purified by silica gel column chromatography (AcOEt to AcOEt:MeOH=95:5) to give 0.28 g of the title compound as a colorless amorphous powder.
$^1$H NMR (CDCl$_3$) δ 2.28 (3H, s), 2.51 (10H, s), 3.22 (3H, s), 3.51 (2H, s), 3.78 (7H, s), 4.35 (2H, q, J=8.2 Hz), 6.57 (1H, s), 6.85-6.93 (6H, m), 7.10 (1H, d, J=2.0 Hz), 7.28 (2H, d, J=8.6 Hz), 7.59 (1H, d, J=8.6 Hz), 7.64 (1H, dd, J=8.7 Hz, 2.8 Hz), 7.85 (1H, d, J=2.6 Hz).

The following compounds were produced in the same manner as in Example 318 using appropriate starting materials.

Example 319

N-{6-[2-(4-Benzo[1,3]dioxol-5-ylmethylpiperazine-1-carbonyl)-1-methyl-1H-indol-5-yloxy]pyridin-3-yl}-2-fluoro-N-methyl-4-tri-fluoromethylbenzamide hydrobromide Melting point: 187-190° C.

Example 320

N-[6-(2-{4-[(4-Methoxyphenyl)methylamino]piperidine-1-carbonyl}-1-methyl-1H-indol-5-yloxy)pyridin-3-yl]-N-methyl-4-trifluoro-methylbenzamide methanesulfonate $^1$H NMR (CDCl$_3$) δ 1.76-1.90 (3H, m), 2.36 (1H, d, J=11.9 Hz), 2.87 (3H, s), 3.02 (2H, brs), 3.26 (3H, s), 3.47 (3H, s), 3.65-3.73 (1H, m), 3.80 (3H, s), 3.85 (3H, s), 4.64 (2H, brs), 6.55 (1H, s), 6.81 (1H, d, J=8.6 Hz), 7.30-7.54 (9H, m), 7.95 (1H, s), 12.74 (1H, brs).

Example 321

N-(6-{2-[4-(4-Cyanobenzyl)piperazine-1-carbonyl]-1-methyl-1H-indol-6-yloxy}pyridin-3-yl)-N-methyl-4-trifluoromethylbenzamide hydrobromide Melting point: 267-270° C.

Example 322

N-(6-{2-[4-(4-Methoxybenzyl)piperazine-1-carbonyl]-1-methyl-1H-indol-6-yloxy}pyridin-3-yl)-N-methyl-4-trifluoromethylbenzamide hydrobromide Melting point: 233-235° C.

Example 323

N-(6-{2-[4-(4-Methoxybenzyl)piperazine-1-carbonyl]-1-methyl-1H-indol-7-yloxy}pyridin-3-yl)-N-methyl-4-trifluoromethylbenzamide oxalate Melting point: 134-135° C.

Example 324

N-(6-{2-[4-(4-Cyanobenzyl)piperazine-1-carbonyl]-1-methyl-1H-indol-7-yloxy}pyridin-3-yl)-N-methyl-4-trifluoromethylbenzamide hydrobromide Melting point: 200-201° C.

Example 325

N-(6-{2-[4-(4-Methoxybenzyl)piperazine-1-carbonyl]-1-methyl-1H-indol-4-yloxy}pyridin-3-yl)-N-methyl-4-trifluoromethylbenzamide oxalate Melting point: 139-141° C.

Example 326

N-(6-{2-[4-(4-Cyanobenzyl)piperazine-1-carbonyl]-1-methyl-1H-indol-4-yloxy}pyridin-3-yl)-N-methyl-4-trifluoromethylbenzamide hydrobromide Melting point: 273-276° C.

Example 327

Propane-2-sulfonic acid methyl-[6-(1-methyl-2-{4-[4-(2,2,2-tri-fluoroethoxy)benzyl]piperazine-1-carbonyl}-1H-indol-6-yloxy)-pyridin-3-yl]amide hydrochloride Melting point: 256.5-259.8° C.

Example 328

Production of N-{6-[2-(4-benzo[1,3]dioxol-5-ylmethylpiperazine-1-carbonyl)-1-methyl-1H-indol-5-yloxy]pyridin-3-yl}-N-methyl-4-tri-fluoromethylbenzamide hydrobromide A stirred solution of N-methyl-N-{6-[1-methyl-2-(piperazine-1-carbonyl)-1H-indol-5-yloxy]pyridin-3-yl}-4-tri-fluoromethylbenzamide (0.22 g, 0.41 mmol) in 1,2-dichloroethane (8 mL) was cooled to 0° C., then piperonal (0.13 g, 0.82 mmol), sodium triacetoxyborohydride (0.18 g, 0.82 mmol) and acetic acid (0.05 mL, 0.82 mmol) were added to the solution. The resulting mixture was stirred at room temperature for 17 hours. The solvent was evaporated and water was added to the residue, and the aqueous phase was extracted with AcOEt. The extract was washed with saturated aqueous NaHCO$_3$ and brine. The organic layer was dried over anhydrous magnesium sulfate and concentrated. The residue was purified by silica gel column chromatography (CH$_2$Cl$_2$:MeOH=60:1) to give a white powder (220 mg). This powder was dissolved in EtOH, and 47% hydrobromic acid (0.038 mL, 0.33 mmol) in water (0.2 mL) was added to the solution. The mixture was allowed to stand for 17 hours at room temperature. The resulting precipitate was collected by filtration and dried in vacuo to give 0.18 g of the title compound as a white powder.

Melting point: 228-231° C.

The following compounds were produced in the same manner as in Example 328 using appropriate starting materials.

Example 329

N-{6-[2-(4-Benzylpiperazine-1-carbonyl)-1-methyl-1H-indol-5-yl-oxy]pyridin-3-yl}-N-methyl-4-trifluoromethylbenzamide hydrobromide Melting point: 189-201° C.

Example 330

N-{6-[2-(4-Benzylpiperazine-1-carbonyl)-1-methyl-1H-indol-5-yl-oxy]pyridin-3-yl}-3,4-dichloro-N-methylbenzamide hydrobromide Melting point: 210-213° C.

Example 331

3,4-Dichloro-N-(6-{1-methyl-2-[4-(tetrahydropyran-4-yl)-piperazine-1-carbonyl]-1H-indol-5-yloxy}pyridin-3-yl)-benzenesulfonamide Melting point: 208-210° C.

Example 332

N-(6-{1-Methyl-2-[4-(tetrahydropyran-4-yl)piperazine-1-carbonyl]-1H-indol-5-yloxy}pyridin-3-yl)-4-trifluoromethylbenzene-sulfonamide Melting point: 174-178° C.

Example 333

(4-Benzo[1,3]dioxol-5-ylmethylpiperazin-1-yl)(5-{5-[(3,4-di-chlorophenyl)methylamino]pyridin-2-yloxy}-1-methyl-1H-indol-2-yl)methanone hydrobromide Melting point: 205-214° C.

Example 334

(4-Benzylpiperazin-1-yl)(5-{5-[(3,4-dichlorophenyl)methylamino]-pyridin-2-yloxy}-1-methyl-1H-indol-2-yl)methanone hydrobromide Melting point: 209-217° C.

Example 335

(4-Benzo[1,3]dioxol-5-ylmethylpiperazin-1-yl)(1-methyl-5-{5-[methyl(4-trifluoromethylphenyl)amino]pyridin-2-yloxy}-1H-indol-2-yl)methanone hydrobromide Melting point: 211-215° C.

Example 336

(4-Benzylpiperazin-1-yl)(1-methyl-5-{5-[methyl(4-trifluoromethyl-phenyl)amino]pyridin-2-yloxyl}-1H-indol-2-yl)methanone hydrobromide Melting point: 212-218° C.

Example 337

(1-Methyl-5-{5-[methyl(4-trifluoromethylphenyl)amino]pyridin-2-yloxy}-1H-indol-2-yl)(4-pyridin-4-ylmethylpiperazin-1-yl)-methanone hydrobromide Melting point: 167-174° C.

Example 338

N-(6-{2-[4-(4-Methoxybenzyl)piperazine-1-carbonyl]-1-methyl-1H-indol-5-yloxy}pyridin-3-yl)-N-methyl-4-trifluoromethylbenzamide maleate $^1$H NMR (DMSO-d$_6$) δ 3.07 (4H, brs), 3.22-3.55 (2H, m), 3.40 (3H, s), 3.78 (8H, s), 4.12 (2H, brs), 6.12 (2H, s), 6.68 (1H, s), 6.92 (1H, d, J=8.5 Hz), 6.92-7.05 (1H, m), 7.01 (2H, d, J=8.5 Hz), 7.28 (1H, d, J=2.1 Hz), 7.37 (2H, d, J=8.5 Hz), 7.43-7.57 (1H, m), 7.52 (2H, d, J=8.2 Hz), 7.67 (2H, d, J=8.2 Hz), 7.81 (1H, d, J=8.5 Hz), 7.92 (1H, brs).

Example 339

N-(6-{2-[4-(4-Cyanobenzyl)piperazine-1-carbonyl]-1-methyl-1H-indol-5-yloxy}pyridin-3-yl)-N-methyl-4-trifluoromethylbenzamide hydrobromide Melting point: 251-255° C. (decomposition)

Example 340

N-(6-{2-[4-(3,4-Diethoxybenzyl)piperazine-1-carbonyl]-1-methyl-1H-indol-5-yloxy}pyridin-3-yl)-4-trifluoromethylbenzamide hydrobromide Melting point: 196-198° C.

Example 341

N-(6-{2-[4-(3,4-Diethoxybenzyl)piperazine-1-carbonyl]-1-methyl-1H-indol-5-yloxy}pyridin-3-yl)-N-methyl-4-trifluoramethyl-benzamide hydrobromide Melting point: 215-218° C.

Example 342

N-(6-{2-[4-(4-Ethoxybenzyl)piperazine-1-carbonyl]-1-methyl-1H-indol-5-yloxy}pyridin-3-yl)-N-methyl-4-trifluoromethylbenzamide maleate Melting point: 131-135° C.

Example 343

N-Methyl-N-(6-{1-methyl-2-[4-(4-trifluoromethoxybenzyl)-piperazine-1-carbonyl]-1H-indol-5-yloxy}pyridin-3-yl)-4-tri-fluoromethylbenzamide hydrobromide Melting point: 213-216° C.

Example 344

N-{6-[2-(4-Benzo[1,3]dioxol-5-ylmethylpiperazine-1-carbonyl)-1-ethyl-1H-indol-5-yloxy]pyridin-3-yl}-N-methyl-4-trifluoromethyl-benzamide hydrobromide Melting point: 179-183° C.

Example 345

N-(6-{2-[4-(3,4-Dimethoxybenzyl)piperazine-1-carbonyl]-1-methyl-1H-indol-5-yloxy}pyridin-3-yl)-N-methyl-4-trifluoromethyl-benzamide hydrobromide Melting point: 175-177° C.

Example 346

N-(6-{2-[4-(6-Methoxypyridin-3-ylmethyl)piperazine-1-carbonyl]-1-methyl-1H-indol-5-yloxy}pyridin-3-yl)-hr-methyl-4-trifluoromethyl-benzamide maleate Melting point: 128-130° C.

Example 347

3,4-Dichloro-N-(6-{2-[4-(4-methoxybenzyl)piperazine-1-carbonyl]-1-methyl-1H-indol-5-yloxy}pyridin-3-yl)-N-methylbenzamide maleate Melting point: 171-172° C.

Example 348

N-(6-{2-[4-(6-Methoxypyridin-3-ylmethyl)piperazine-1-carbonyl]-1-methyl-1H-indol-5-yloxy}pyridin-3-yl)-4-trifluoromethylbenzamide maleate Melting point: 135-138° C.

Example 349

3,4-Dichloro-N-(6-{2-[4-(4-methoxybenzyl)piperazine-1-carbonyl]-1-methyl-1H-indol-5-yloxy}pyridin-3-yl)benzamide hydrobromide Melting point: 244-247° C. (decomposition)

Example 350

N-(6-{2-[4-(3,4-Dimethoxybenzyl)piperazine-1-carbonyl]-1-methyl-1H-indol-5-yloxy}pyridin-3-yl)-4-trifluoromethylbenzamide hydrobromide Melting point: 233-235° C.

Example 351

N-(6-{2-[4-(3-Methoxybenzyl)piperazine-1-carbonyl]-1-methyl-1H-indol-5-yloxy}pyridin-3-yl)-N-methyl-4-trifluoromethylbenzamide hydrobromide Melting point: 217-219° C.

Example 352

N-(6-{2-[4-(4-Methoxybenzyl)piperazine-1-carbonyl]-1-methyl-1 hr-indol-5-yloxy}pyridin-3-yl)-4-trifluoromethylbenzamide oxalate Melting point: 181-183° C.

Example 353

N-(6-{2-[4-(3-Methoxybenzyl)piperazine-1-carbonyl]-1-methyl-1H-indol-5-yloxy}pyridin-3-yl)-4-trifluoromethylbenzamide hydrobromide Melting point: 231-233° C.

Example 354

N-(6-{2-[4-(2-Methoxybenzyl)piperazine-1-carbonyl]-1-methyl-1H-indol-5-yloxy}pyridin-3-yl)-4-trifluoromethylbenzamide oxalate Melting point: 142-144° C.

Example 355

N-(6-{2-[4-(2-Methoxybenzyl)piperazine-1-carbonyl]-1-methyl-1H-indol-5-yloxy}pyridin-3-yl)-N-methyl-4-trifluoromethylbenzamide oxalate Melting point: 140-142° C.

Example 356

N-[6-(2-{4-[(E)-3-(4-Methoxyphenyl)allyl]piperazine-1-carbonyl}-1-methyl-1H-indol-5-yloxy)pyridin-3-yl]-N-methyl-4-trifluoro-methylbenzamide methanesulfonate Melting point: 195-197° C.

Example 357

N-[6-(2-{4-[(E)-3-(4-Methoxyphenyl)allyl]piperazine-1-carbonyl}-1-methyl-1H-indol-5-yloxy)pyridin-3-yl]-4-trifluoromethyl-benzamide methanesulfonate Melting point: 246-249° C. (decomposition)

Example 358

N-[6-(2-{4-[(E)-3-(2-Methoxyphenyl)allyl]piperazine-1-carbonyl}-1-methyl-1H-indol-5-yloxy)pyridin-3-yl]-4-trifluoromethyl-benzamide methanesulfonate Melting point: 268-271° C. (decomposition)

Example 359

N-[6-(2-{4-[(E)-3-(2-Methoxyphenyl)allyl]piperazine-1-carbonyl}-1-methyl-1H-indol-5-yloxy)pyridin-3-yl]-N-methyl-4-trifluoro-methylbenzamide hydrobromide Melting point: 187-190° C.

Example 360

3,4-Dichloro-N-(6-{2-[4-(4-ethoxybenzyl)piperazine-1-carbonyl]-1-methyl-1H-indol-5-yloxy}pyridin-3-yl)benzamide hydrobromide Melting point: 235-238° C. (decomposition)

Example 361

3,4-Dichloro-N-(6-{2-[4-(4-ethoxybenzyl)piperazine-1-carbonyl]-1-methyl-1H-indol-5-yloxy}pyridin-3-yl)-N-methylbenzamide methanesulfonate Melting point: 168-170° C.

Example 362

N-{4-Methyl-6-[1-methyl-2-(4-pyridin-4-ylmethylpiperazine-1-carbonyl)-1H-indol-5-yloxy]pyridin-3-yl}-4-trifluoromethyl-benzamide dihydrobromide Melting point: 228-232° C. (decomposition)

Example 363

N-(6-{2-[4-(4-Ethoxybenzyl)piperazine-1-carbonyl]-1-methyl-1H-indol-5-yloxy}pyridin-3-yl)-4-trifluoromethylbenzamide hydrobromide Melting point: 231-234° C.

Example 364

3,4-Dichloro-N-(6-{2-[4-(4-ethoxybenzyl)piperazine-1-carbonyl]-1-methyl-1H-indol-5-yloxy}-4-methylpyridin-3-yl)benzamide hydrobromide Melting point: 197-199° C.

Example 365

N-(6-{2-[4-(4-Ethoxybenzyl)piperazine-1-carbonyl]-1-methyl-1H-indol-5-yloxy}-4-methylpyridin-3-yl)-N-methyl-4-trifluoromethyl-benzamide hydrobromide Melting point: 163-166° C.

Example 366

3,4-Dichloro-N-(6-{2-[4-(4-ethoxybenzyl)piperazine-1-carbonyl]-1-methyl-1H-indol-5-yloxy}-4-methylpyridin-3-yl)-N-methylbenzamide hydrobromide Melting point: 201-204° C.

Example 367

N-(6-{2-[4-(4-Methoxybenzyl)piperazine-1-carbonyl]-1-methyl-1H-indol-5-yloxy}-2-methylpyridin-3-yl)-4-trifluoramethylbenzamide hydrobromide Melting point: 206-208° C.

Example 368

N-(6-{2-[4-(4-Ethoxybenzyl)piperazine-1-carbonyl]-1-methyl-1H-indol-5-yloxy}-2-methylpyridin-3-yl)-h=methyl-4-trifluoromethyl-benzamide hydrobromide Melting point: 188-191° C.

Example 369

3,4-Dichloro-N-(6-{1-methyl-2-[4-(4-propoxybenzyl)piperazine-1-carbonyl]-1H-indol-5-yloxy}pyridin-3-yl)benzamide hydrobromide Melting point: 249-252° C. (decomposition)

Example 370

3,4-Dichloro-N-methyl-N-(6-{1-methyl-2-[4-(4-propoxybenzyl)-piperazine-1-carbonyl]-1H-indol-5-yloxy}pyridin-3-yl)benzamide maleate Melting point: 163-164° C.

Example 371

3,4-Dichloro-N-(6-{2-[4-(4-ethoxybenzyl)piperazine-1-carbonyl]-1-methyl-1H-indol-5-yloxy}-2-methylpyridin-3-yl)benzamide oxalate $^1$H NMR (DMSO-$d_6$) δ 1.31 (3H, t, J=7.0 Hz), 2.25 (3H, s), 2.66 (4H, brs), 3.69 (2H, s), 3.74 (4H, brs), 3.77 (3H, s), 4.02 (2H, q, J=7.0 Hz), 6.64 (1H, s), 6.74 (1H, d, J=8.4 Hz), 6.90 (2H, d, J=8.4 Hz), 7.05 (1H, dd, J=2.2 Hz, 8.9 Hz), 7.26 (2H, d, J=8.4 Hz), 7.34 (1H, d, J=2.2 Hz), 7.53 (1H, d, J=8.9 Hz), 7.70 (1H, d, J=8.6 Hz), 7.79 (1H, d, J=8.4 Hz), 7.93 (1H, dd, J=1.9 Hz, 8.4 Hz), 8.19 (1H, d, J=1.6 Hz), 10.03 (1H, s).

Example 372

3,4-Dichloro-N-(6-{2-[4-(4-ethoxybenzyl)piperazine-1-carbonyl]-1-methyl-1H-indol-5-yloxy}-2-methylpyridin-3-yl)-N-methylbenzamide maleate Melting point: 131-132° C.

Example 373

3,4-Dichloro-N-(6-{2-[4-(3-ethoxybenzyl)piperazine-1-carbonyl]-1-methyl-1H-indol-5-yloxy}pyridin-3-yl)benzamide hydrobromide Melting point: 225-227° C.

Example 374

3,4-Dichloro-N-(6-{2-[4-(3-ethoxybenzyl)piperazine-1-carbonyl]-1-methyl-1H-indol-5-yloxy}pyridin-3-yl)-N-methylbenzamide maleate Melting point: 99-100° C.

Example 375

3,4-Dichloro-N-(6-{2-[4-(4-methoxymethylbenzyl)piperazine-1-carbonyl]-1-methyl-1H-indol-5-yloxy}pyridin-3-yl)benzamide hydrobromide Melting point: 244-249° C. (decomposition)

Example 376

3,4-Dichloro-N-(6-{2-[4-(4-methoxymethylbenzyl)piperazine-1-carbonyl]-1-methyl-1H-indol-5-yloxy}pyridin-3-yl)-N-methyl-benzamide maleate Melting point: 100-101° C.

Example 377

N-{2-Methyl-6-[1-methyl-2-(4-pyridin-2-ylmethylpiperazine-1-carbonyl)-1H-indol-5-yloxy]pyridin-3-yl}-4-trifluoromethyl-benzamide dioxalate $^1$H NMR (CDCl$_3$) δ 2.26 (3H, s), 2.77 (4H, brs), 3.77 (4H, brs), 3.79 (3H, s), 3.93 (2H, s), 6.68 (1H, s), 6.76 (1H, d, J=8.6 Hz), 7.07 (1H, dd, J=2.4 Hz, 8.9 Hz), 7.32-7.36 (2H, m), 7.50 (1H, d, J=7.6 Hz), 7.57 (1H, d, J=9.2 Hz), 7.73 (1H, d, J=8.6 Hz), 7.83 (1H, dt, J=1.9 Hz, 7.6 Hz), 7.92 (2H, d, J=8.4 Hz), 8.17 (2H, d, J=8.1 Hz), 8.56 (1H, dd, J=0.8 Hz, 4.9 Hz), 10.22 (1H, s).

Example 378

3,4-Dichloro-N-(6-{2-[4-(5-ethoxypyridin-2-ylmethyl)piperazine-1-carbonyl]-1-methyl-1H-indol-5-yloxy}pyridin-3-yl)benzamide dihydrobromide Melting point: 218-220° C.

Example 379

3,4-Dichloro-N-(6-{2-[4-(5-ethoxypyridin-2-ylmethyl)piperazine-1-carbonyl]-1-methyl-M-indol-5-yloxy}pyridin-3-yl)-N-methyl-benzamide maleate Melting point: 98-99° C.

Example 380

N-(2-{2-[4-(4-Methoxybenzyl)piperazine-1-carbonyl]-1-methyl-1H-indol-5-yloxy}pyrimidin-5-yl)-4-trifluoromethylbenzamide Melting point: 179-180° C.

Example 381

N-(2-{2-[4-(4-Methoxybenzyl)piperazine-1-carbonyl]-1-methyl-1H-indol-5-yloxy}pyrimidin-5-yl)-N-methyl-4-trifluoromethylbenzamide maleate Melting point: 160-161° C.

Example 382

N-{2-[1-Methyl-2-(4-pyridin-2-ylmethylpiperazine-1-carbonyl)-1H-indol-5-yloxy]pyrimidin-5-yl}-4-trifluoromethylbenzamide Melting point: 181-182° C.

Example 383

N-(2-{2-[4-(4-Cyanobenzyl)piperazine-1-carbonyl]-1-methyl-1H-indol-5-yloxy}pyrimidin-5-yl)-N-methyl-4-trifluoromethylbenzamide maleate Melting point: 154-156° C.

Example 384

3,4-Dichloro-N-(2-{2-[4-(4-ethoxybenzyl)piperazine-1-carbonyl]-1-methyl-1H-indol-5-yloxy}pyrimidin-5-yl)benzamide Melting point: 156-157° C.

Example 385

3,4-Dichloro-N-{2-[1-methyl-2-(4-pyridin-2-ylmethylpiperazine-1-carbonyl)-1H-indol-5-yloxy]pyrimidin-5-yl}benzamide Melting point: 161-163° C.

Example 386

3,4-Dichloro-N-(6-{2-[4-(5-cyanopyridin-2-ylmethyl)piperazine-1-carbonyl]-1-methyl-1H-indol-5-yloxy}pyridin-3-yl)benzamide dihydrobromide Melting point: 216-219° C.

Example 387

N-(6-{2-[4-(5-Methoxypyridin-2-ylmethyl)piperazine-1-carbonyl]-1-methyl-1H-indol-5-yloxy}pyridin-3-yl)-N-methyl-4-trifluoromethyl-benzamide maleate Melting point: 143-144° C.

Example 388

3,4-Dichloro-N-(6-{2-[4-(5-methoxypyridin-2-ylmethyl)piperazine-1-carbonyl]-1-methyl-1H-indol-5-yloxy}pyridin-3-yl)benzamide dihydrobromide Melting point: 223-225° C.

Example 389

3,4-Dichloro-N-(6-{2-[4-(5-methoxypyridin-2-ylmethyl)piperazine-1-carbonyl]-1-methyl-1H-indol-5-yloxy}pyridin-3-yl)-N-methyl-benzamide maleate Melting point: 155-156° C.

Example 390

N-(6-{2-[4-(4-Ethylbenzyl)piperazine-1-carbonyl]-1-methyl-1H-indol-5-yloxy}pyridin-3-yl)-4-trifluoromethylbenzamide hydrobromide Melting point: 239-241° C.

Example 391

N-(6-{2-[4-(4-Ethylbenzyl)piperazine-1-carbonyl]-1-methyl-1H-indol-5-yloxy}pyridin-3-yl)-N-methyl-4-trifluoromethylbenzamide oxalate Melting point: 167-169° C.

Example 392

N-{6-[1-Methyl-2-((R)-2-methyl-4-pyridin-2-ylmethylpiperazine-1-carbonyl)-1H-indol-5-yloxy]pyridin-3-yl}-4-trifluoromethyl-benzamide dioxalate Melting point: 128-130° C.

Example 393

N-(6-{2-[(R)-4-(4-Methoxybenzyl)-2-methylpiperazine-1-carbonyl]-1-methyl-1H-indol-5-yloxy}pyridin-3-yl)-4-trifluoromethyl-benzamide oxalate Melting point: 161-163° C.

Example 394

N-(6-{2-[(R)-4-(4-Methoxybenzyl)-2-methylpiperazine-1-carbonyl]-1-methyl-1H-indol-5-yloxy}pyridin-3-yl)-N-methyl-4-trifluoro-methyl-benzamide oxalate Melting point: 126-130° C.

Example 395

N-Methyl-M-{6-[1-methyl-2-((R)-2-methyl-4-pyridin-2-ylmethyl-piperazine-1-carbonyl)-1H-indol-5-yloxy]pyridin-3-yl}-4-tri-fluoromethylbenzamide dioxalate $^1$H NMR (DMSO-d$_6$) δ 1.35 (3H, d, J=6.8 Hz), 2.26-2.44 (2H, m), 2.79 (1H, d, J=11.1 Hz), 2.96 (1H, d, J=11.1 Hz), 3.36 (4H, s), 3.68-3.84 (5H, m), 4.09 (1H, brs), 4.50 (1H, brs), 6.57 (1H, s), 6.91 (1H, d, J=8.4 Hz), 6.93 (1H, d, J=2.2 Hz, 8.9 Hz), 7.24 (1H, d, J=1.9 Hz), 7.31 (1H, dd, J=4.9 Hz, 6.2 Hz), 7.49 (2H, d, J=3.8 Hz), 7.52 (2H, d, J=2.4 Hz), 7.67 (2H, d, J=7.6 Hz), 7.77-7.85 (2H, m), 7.91 (1H, s), 8.52 (1H, dd, J=1.1 Hz, 4.6 Hz).

Example 396

N-(6-{2-[(S)-4-(4-Methoxybenzyl)-2-methylpiperazine-1-carbonyl]-1-methyl-1H-indol-5-yloxy}pyridin-3-yl)-4-trifluoromethyl-benzamide oxalate Melting point: 159-160° C.

Example 397

N-{6-[1-Methyl-2-((S)-2-methyl-4-pyridin-2-ylmethylpiperazine-1-carbonyl)-1H-indol-5-yloxy]pyridin-3-yl}-4-trifluoromethyl-benzamide dioxalate Melting point: 126-127° C.

Example 398

N-(6-{2-[(S)-4-(4-Methoxybenzyl)-2-methylpiperazine-1-carbonyl]-1-methyl-1H-indol-5-yloxy}pyridin-3-yl)-N-methyl-4-trifluoro-methyl-benzamide oxalate Melting point: 134-136° C.

Example 399

N-Methyl-N-{6-[1-methyl-2-((S)-2-methyl-4-pyridin-2-ylmethyl-piperazine-1-carbonyl)-1H-indol-5-yloxy]pyridin-3-yl}-4-tri-fluoramethylbenzamide dioxalate $^1$H NMR (DMSO-d$_6$) δ 1.35 (3H, d, J=6.8 Hz), 2.22-2.30 (1H, m), 2.38 (1H, d, J=8.9 Hz), 2.77 (1H, d, J=11.3 Hz), 2.94 (1H, d, J=11.3 Hz), 3.36 (4H, s), 3.66-3.81 (5H, m), 4.07 (1H, brs), 4.49 (1H, brs), 6.57 (1H, s), 6.92 (1H, d, J=8.9 Hz), 6.93 (1H, dd, J=2.2 Hz, 8.6 Hz), 7.24 (1H, d, J=2.2 Hz), 7.30 (1H, ddd, J=1.1 Hz, 5.1 Hz, 7.6 Hz), 7.49-7.52 (3H, m), 7.67 (2H, d, J=7.8 Hz), 7.77-7.85 (3H, m), 7.91 (1H, s), 8.52 (1H, dd, J=0.8 Hz, 4.9 Hz).

Example 400

N-(6-{2-[4-(4-Difluoromethoxybenzyl)piperazine-1-carbonyl]-1-methyl-1H-indol-5-yloxy}pyridin-3-yl)-4-trifluoromethylbenzamide hydrobromide Melting point: 229-231° C.

Example 401

N-(6-{2-[4-(4-Difluoromethoxybenzyl)piperazine-1-carbonyl]-1-methyl-1H-indol-5-yloxy}pyridin-3-yl)-N-methyl-4-trifluoromethyl-benzamide maleate Melting point: 146-147° C.

Example 402

N-[6-(1-Methyl-2-{4-[4-(1,1,2,2-tetrafluoroethoxy)benzyl]-piperazine-1-carbonyl}-1H-indol-5-yloxy)pyridin-3-yl]-4-tri-fluoromethylbenzamide hydrobromide Melting point: 255-257° C.

Example 403

N-Methyl-N-[6-(1-methyl-2-{4-[4-(1,1,2,2-tetrafluoroethoxy)-benzyl]piperazine-1-carbonyl}-1H-indol-5-yloxy)pyridin-3-yl]-4-trifluoromethylbenzamide maleate Melting point: 137-139° C.

Example 404

N-{4-Methyl-6-[1-methyl-2-(4-pyridin-3-ylmethylpiperazine-1-carbonyl)-1H-indol-5-yloxy]pyridin-3-yl}-4-trifluoromethyl-benzamide dihydrobromide Melting point: 215-217° C.

Example 405

N-{4-Methyl-6-[1-methyl-2-(4-pyridin-2-ylmethylpiperazine-1-carbonyl)-1H-indol-5-yloxy]pyridin-3-yl}-4-trifluoromethyl-benzamide dioxalate $^1$H NMR (DMSO-d$_6$) δ 2.24 (3H, s), 2.74 (4H, brs), 3.75 (4H, brs), 3.78 (3H, s), 3.90 (2H, s), 6.66 (1H, s), 6.91 (1H, s), 7.05 (1H, dd, J=2.2 Hz, 8.9 Hz), 7.31-7.35 (1H, m), 7.49 (1H, d, J=8.6 Hz), 7.56 (1H, d, J=8.9 Hz), 7.82 (1H, dt, J=1.9 Hz, 7.6 Hz), 7.92 (2H, d, J=8.4 Hz), 8.01 (1H, s), 8.17 (2H, d, J=8.1 Hz), 8.55 (1H, d, J=4.1 Hz), 10.20 (1H, s).

Example 406

N-[6-(2-{4-[4-(2,2-Difluoroethoxy)benzyl]piperazine-1-carbonyl}-1-methyl-1H-indol-5-yloxy)pyridin-3-yl]-N-methyl-4-trifluoro-methylbenzamide hydrobromide Melting point: 196-200° C.

Example 407

3,4-Dichloro-N-[6-(2-{4-[4-(2,2-difluoroethoxy)benzyl]piperazine-1-carbonyl}-1-methyl-1H-indol-5-yloxy)pyridin-3-yl]benzamide hydrobromide Melting point: 241-245° C.

Example 408

N-[6-(2-{4-[4-(2-Fluoroethoxy)benzyl]piperazine-1-carbonyl}-1-methyl-1H-indol-5-yloxy)pyridin-3-yl]-N-methyl-4-trifluoromethyl-benzamide maleate Melting point: 152-154° C.

Example 409

3,4-Dichloro-N-[6-(2-{4-[4-(2-fluoroethoxy)benzyl]piperazine-1-carbonyl}-1-methyl-1H-indol-5-yloxy)pyridin-3-yl]benzamide hydrobromide Melting point: 240-243° C.

Example 410

N-(6-{2-[4-(4-Isopropoxybenzyl)piperazine-1-carbonyl]-1-methyl-1H-indol-5-yloxy}pyridin-3-yl)-N-methyl-4-trifluoromethyl-benzamide maleate Melting point: 140-142° C.

Example 411

N-Methyl-N-(6-{1-methyl-2-[4-(4-propylbenzyl)piperazine-1-carbonyl]-1H-indol-5-yloxy}pyridin-3-yl)-4-trifluoromethyl-benzamide maleate Melting point: 132-134° C.

Example 412

N-(6-{2-[4-(4-Isopropylbenzyl)piperazine-1-carbonyl]-1-methyl-1H-indol-5-yloxy}pyridin-3-yl)-N-methyl-4-trifluoromethylbenzamide maleate Melting point: 129-131° C.

Example 413

N-Methyl-N-(6-{1-methyl-2-[4-(4-propoxybenzyl)piperazine-1-carbonyl]-1H-indol-5-yloxy}pyridin-3-yl)-4-trifluoromethyl-benzamide maleate Melting point: 144-147° C.

Example 414

N-Methyl-N-(6-{1-methyl-2-[4-(4-octyloxybenzyl)piperazine-1-carbonyl]-1H-indol-5-yloxy}pyridin-3-yl)-4-trifluoromethyl-benzamide maleate Melting point: 125-126° C.

Example 415

N-(6-{2-[4-(4-Methoxymethylbenzyl)piperazine-1-carbonyl]-1-methyl-1H-indol-5-yloxy}pyridin-3-yl)-N-methyl-4-trifluoromethyl-benzamide maleate Melting point: 137-139° C.

Example 416

N-(6-{2-[4-(4-Isobutylbenzyl)piperazine-1-carbonyl]-1-methyl-1H-indol-5-yloxy}pyridin-3-yl)-N-methyl-4-trifluoromethylbenzamide maleate Melting point: 147-149° C.

Example 417

N-(6-{2-[4-(5-Ethoxypyridin-2-ylmethyl)piperazine-1-carbonyl]-1-methyl-1H-indol-5-yloxy}pyridin-3-yl)-N-methyl-4-trifluoromethyl-benzamide maleate Melting point: 129-130° C.

Example 418

N-(6-{2-[4-(3-Ethoxybenzyl)piperazine-1-carbonyl]-1-methyl-1H-indol-6-yloxy}pyridin-3-yl)-N-methyl-4-trifluoromethylbenzamide hydrobromide Melting point: 234-236° C.

Example 419

N-(6-{2-[4-(4-Ethoxybenzyl)piperazine-1-carbonyl]-1-methyl-1H-indol-6-yloxy}pyridin-3-yl)-N-methyl-4-trifluoromethylbenzamide hydrobromide Melting point: 241-243° C.

Example 420

N-Methyl-N-(6-{1-methyl-2-[4-(4-propoxybenzyl)piperazine-1-carbonyl]-1H-indol-6-yloxy}pyridin-3-yl)-4-trifluoromethyl-benzamide hydrobromide Melting point: 246-248° C.

Example 421

N-(6-{2-[4-(4-Isopropoxybenzyl)piperazine-1-carbonyl]-1-methyl-1H-indol-6-yloxy}pyridin-3-yl)-N-methyl-4-trifluoromethyl-benzamide hydrobromide Melting point: 251-253° C.

Example 422

N-(6-{2-[4-(4-Difluoromethoxybenzyl)piperazine-1-carbonyl]-1-methyl-1H-indol-6-yloxy}pyridin-3-yl)-N-methyl-4-trifluoromethyl-benzamide hydrobromide Melting point: 229-230° C.

Example 423

N-(6-{2-[4-(6-Ethoxypyridin-3-ylmethyl)piperazine-1-carbonyl]-1-methyl-1H-indol-5-yloxy}pyridin-3-yl)-N-methyl-4-trifluoromethyl-benzamide maleate Melting point: 149-151° C.

Example 424

N-(6-{2-[4-(6-Isopropoxypyridin-3-ylmethyl)piperazine-1-carbonyl]-1-methyl-1H-indol-5-yloxy}pyridin-3-yl)-N-methyl-4-tri-fluoromethyl-benzamide maleate Melting point: 157-159° C.

Example 425

N-(6-{2-[4-(4-Cyanobenzyl)piperazine-1-carbonyl]-1,4-dimethyl-1H-indol-5-yloxy}pyridin-3-yl)-N-methyl-4-trifluoromethylbenzamide hydrobromide Melting point: 249-252° C.

Example 426

N-(6-{2-[4-(4-Methoxybenzyl)piperazine-1-carbonyl]-1,4-dimethyl-1H-indol-5-yloxy}pyridin-3-yl)-N-methyl-4-trifluoromethyl-benzamide Melting point: 184-186° C.

Example 427

N-(6-{2-[4-(4-Ethoxybenzyl)piperazine-1-carbonyl]-1,4-dimethyl-1H-indol-5-yloxy}pyridin-3-yl)-N-methyl-4-trifluoromethyl-benzamide hydrobromide Melting point: 224-226° C.

Example 428

N-(6-{2-[4-(4-Isopropylbenzyl)piperazine-1-carbonyl]-1,4-dimethyl-1H-indol-5-yloxy}pyridin-3-yl)-N-methyl-4-trifluoro-methylbenzamide hydrobromide Melting point: 225-229° C.

Example 429

N-(6-{2-[4-(4-Isopropylbenzyl)piperazine-1-carbonyl]-1-methyl-1H-indol-6-yloxy}pyridin-3-yl)-N-methyl-4-trifluoromethylbenzamide hydrobromide Melting point: 255-258° C.

Example 430

N-(6-{2-[4-(4-Isobutylbenzyl)piperazine-1-carbonyl]-1-methyl-1H-indol-6-yloxy}pyridin-3-yl)-N-methyl-4-trifluoromethylbenzamide hydrobromide Melting point: 262-265° C.

Example 431

N-Methyl-N-(6-{1-methyl-2-[4-(4-propylbenzyl)piperazine-1-carbonyl]-1H-indol-6-yloxy}pyridin-3-yl)-4-trifluoromethyl-benzamide hydrobromide Melting point: 255-257° C.

Example 432

N-Methyl-N-[6-(1-methyl-2-{4-[4-(2,2,2-trifluoroethoxy)benzyl]-piperazine-1-carbonyl}-1H-indol-5-yloxy)pyridin-3-yl]-4-tri-fluoromethylbenzamide dihydrobromide Melting point: 211-212° C.

Example 433

N-(6-{2-[4-(4-Methoxybenzyl)piperazine-1-carbonyl]-1-methyl-1H-indol-5-yloxy}-4-methylpyridin-3-yl)-4-trifluoromethylbenzamide oxalate Melting point: 144-147° C.

Example 434

N-(6-{1,4-Dimethyl-2-[4-(4-propoxybenzyl)piperazine-1-carbonyl]-1H-indol-5-yloxy}pyridin-3-yl)-N-methyl-4-trifluoromethyl-benzamide hydrobromide Melting point: 204-208° C.

Example 435

N-(6-{2-[4-(4-Isopropoxybenzyl)piperazine-1-carbonyl]-1,4-dimethyl-1H-indol-5-yloxy}pyridin-3-yl)-N-methyl-4-trifluoro-methylbenzamide hydrobromide Melting point: 224-226° C.

Example 436

N-Methyl-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzamide hydrobromide Melting point: 225.0-226.4° C.

Example 437

N-[6-(2-{4-[4-(2,2-Difluoroethoxy)benzyl]piperazine-1-carbonyl}-1-methyl-1H-indol-6-yloxy)pyridin-3-yl]-N-methyl-4-trifluoro-methylbenzamide hydrobromide Melting point: 218.4-219.9° C.

Example 438

N-[6-(2-{4-[4-(2-Fluoroethoxy)benzyl]piperazine-1-carbonyl}-1-methyl-1H-indol-6-yloxy)pyridin-3-yl]-N-methyl-4-trifluoromethyl-benzamide hydrobromide Melting point: 215.3-216.6° C.

Example 439

N-(6-{2-[4-(2,2-Difluorobenzo[1,3]dioxol-5-ylmethyl)piperazine-1-carbonyl]-1-methyl-1H-indol-5-yloxy}pyridin-3-yl)-N-methyl-4-tri-fluoromethylbenzamide oxalate Melting point: 155.7-156.9° C.

Example 440

N-(6-{2-[4-(2,2-Difluorobenzo[1,3]dioxol-5-ylmethyl)piperazine-1-carbonyl]-1-methyl-1H-indol-6-yloxy}pyridin-3-yl)-N-methyl-4-tri-fluoromethylbenzamide hydrobromide Melting point: 243.3-245.1° C.

Example 441

N-(6-{2-[4-(2,2-Difluorobenzo[1,3]dioxol-5-ylmethyl)piperazine-1-carbonyl]-1,4-dimethyl-1H-indol-5-yloxy}pyridin-3-yl)-N-methyl-4-trifluoromethylbenzamide Melting point: 97.9-99.5° C.

Example 442

N-(6-{2-[4-(4-Difluoromethoxybenzyl)piperazine-1-carbonyl]-1,4-dimethyl-1H-indol-5-yloxy}pyridin-3-yl)-N-methyl-4-trifluoro-methylbenzamide Melting point: 150.5-151.4° C.

Example 443

N-Methyl-N-[6-(1-methyl-2-{4-[4-(1,1,2,2-tetrafluoroethoxy)-benzyl]piperazine-1-carbonyl}-1H-indol-6-yloxy)pyridin-3-yl]-4-trifluoromethylbenzamide hydrobromide Melting point: 245.4-247.6° C.

Example 444

N-(6-{2-[4-(6-Isopropoxypyridin-3-ylmethyl)piperazine-1-carbonyl]-1-methyl-1H-indol-6-yloxy}pyridin-3-yl)-N-methyl-4-tri-fluoromethylbenzamide maleate Melting point: 156.8-157.4° C.

Example 445

N-[6-(2-{4-[4-(2-Fluoro-1-fluoromethylethoxy)benzyl]piperazine-1-carbonyl}-1-methyl-1H-indol-6-yloxy)pyridin-3-yl]-N-methyl-4-tri-fluoromethylbenzamide hydrobromide Melting point: 230.8-231.4° C.

Example 446

N-Methyl-N-(6-{1-methyl-2-[4-(4-trifluoromethoxybenzyl)-piperazine-1-carbonyl]-1H-indol-6-yloxy}pyridin-3-yl)-4-tri-fluoromethylbenzamide hydrobromide Melting point: 237-239° C.

Example 447

2-Chloro-N-[6-(2-{4-[4-(2-fluoroethoxy)benzyl]piperazine-1-carbonyl}-1-methyl-1H-indol-6-yloxy)pyridin-3-yl]-N-methyl-4-tri-fluoromethylbenzamide hydrobromide Melting point: 223.6-225.4° C.

Example 448

2-Chloro-N-[6-(2-{4-[4-(2,2-difluoroethoxy)benzyl]piperazine-1-carbonyl}-1-methyl-1H-indol-6-yloxy)pyridin-3-yl]-N-methyl-4-tri-fluoromethylbenzamide hydrobromide Melting point: 232.4-232.8° C.

Example 449

2-Chloro-N-methyl-N-[6-(1-methyl-2-{4-[4-(2,2,2-trifluoroethoxy)-benzyl]piperazine-1-carbonyl}-1H-indol-6-yloxy)pyridin-3-yl]-4-trifluoromethylbenzamide hydrobromide Melting point: 239.5-240.6° C.

Example 450

2-Chloro-N-methyl-N-(6-{1-methyl-2-[4-(4-propoxybenzyl)-piperazine-1-carbonyl]-1H-indol-6-yloxy}pyridin-3-yl)-4-tri-fluoromethylbenzamide hydrobromide Melting point: 238.6-240.1° C.

Example 451

2-Chloro-N-(6-{2-[4-(4-isopropoxybenzyl)piperazine-1-carbonyl]-1-methyl-1H-indol-6-yloxy}pyridin-3-yl)-N-methyl-4-trifluoromethyl-benzamide hydrobromide Melting point: 248.3-252.3° C.

Example 452

2-Chloro-N-(6-{2-[4-(4-difluoromethoxybenzyl)piperazine-1-carbonyl]-methyl-1H-indol-6-yloxy}pyridin-3-yl)-N-methyl-4-tri-fluoromethyl-benzamide hydrobromide Melting point: 238.6-243.9° C.

Example 453

N-(6-{2-[4-(6-Isopropoxypyridin-3-ylmethyl)piperazine-1-carbonyl]-1-methyl-1H-indol-6-yloxy}pyridin-3-yl)-4-trifluoro-methylbenzamide hydrobromide Melting point: 251.3-254.8° C.

Example 454

N-{6-[2-(4-Benzo[1,3]dioxol-5-ylmethylpiperazine-1-carbonyl)-1-methyl-1H-indol-6-yloxy]pyridin-3-yl}-4-trifluoromethylbenzamide hydrobromide Melting point: 264.0-265.6° C.

Example 455

N-(6-{2-[4-(2,2-Difluorobenzo[1,3]dioxol-5-ylmethyl)piperazine-1-carbonyl]-1-methyl-1H-indol-6-yloxy}pyridin-3-yl)-4-trifluoro-methylbenzamide hydrobromide Melting point: 273.6-275.9° C.

Example 456

N-Methyl-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethoxybenzamide hydrobromide Melting point: 227.4-229.2° C.

Example 457

N-[6-(2-{4-[4-(2,2-Difluoroethoxy)benzyl]piperazine-1-carbonyl}-1-methyl-1H-indol-6-yloxy)pyridin-3-yl]-N-methyl-4-trifluoro-methoxybenzamide hydrobromide Melting point: 222.8-226.8° C.

Example 458

N-[6-(2-{4-[4-(2-Fluoroethoxy)benzyl]piperazine-1-carbonyl}-1-methyl-1H-indol-6-yloxy)pyridin-3-yl]-N-methyl-4-trifluoro-methoxybenzamide hydrobromide Melting point: 220.8-221.6° C.

Example 459

N-(6-{2-[4-(4-Hydroxybenzyl)piperazine-1-carbonyl]-1-methyl-1H-indol-6-yloxy}pyridin-3-yl)-4-trifluoromethylbenzamide hydrobromide Melting point: 241.4-242.7° C.

Example 460

N-(6-{2-[4-(4-Isopropoxybenzyl)piperazine-1-carbonyl]-1-methyl-1H-indol-5-yloxy}pyridin-3-yl)-4-trifluoromethylbenzamide hydrobromide Melting point: 236.8-243.8° C.

Example 461

N-[6-(2-{4-[4-(2-Fluoroethoxy)benzyl]piperazine-1-carbonyl}-1-methyl-1H-indol-5-yloxy)pyridin-3-yl]-4-trifluoromethylbenzamide hydrobromide $^1$H NMR (DMSO-$d_6$) δ 3.18-3.45 (4H, m), 3.82 (3H, s), 3.91 (4H, brs), 4.23 (1H, d, J=4.0 Hz), 4.33 (1H, t, J=4.0 Hz), 4.46 (2H, brs), 4.67 (1H, t, J=3.8 Hz), 4.84 (1H, t, J=3.8 Hz), 6.76 (1H, s), 7.04 (2H, d, J=8.9 Hz), 7.08 (1H, dd, J=8.6 Hz, 2.2 Hz), 7.10 (1H, s), 7.37 (1H, d, J=2.1 Hz), 7.47 (2H, d, J=8.7 Hz), 7.59 (1H, d, J=8.9 Hz), 7.93 (2H, d, J=8.4 Hz), 8.16 (2H, d, J=8.4 Hz), 8.18 (1H, dd, J=8.6 Hz, 2.7 Hz), 8.47 (1H, d, J=2.6 Hz), 9.85 (1H, brs), 10.59 (1H, s).

Example 462

N-[6-(2-{4-[4-(2,2-Difluoroethoxy)benzyl]piperazine-1-carbonyl}-1-methyl-1H-indol-5-yloxy)pyridin-3-yl]-4-trifluoromethyl-benzamide hydrobromide Melting point: 229.1-230.8° C.

Example 463

N-[6-(1-Methyl-2-{4-[4-(2,2,2-trifluoroethoxy)benzyl]piperazine-1-carbonyl}-1H-indol-5-yloxy)pyridin-3-yl]-4-trifluoromethyl-benzamide hydrobromide Melting point: 236.8-237.5° C.

Example 464

3,4-Dichloro-N-[6-(2-{4-[4-(2-fluoroethoxy)benzyl]piperazine-1-carbonyl}-1-methyl-1H-indol-6-yloxy)pyridin-3-yl]benzamide hydrobromide Melting point: 232.4-234.2° C.

Example 465

3,4-Dichloro-N-[6-(1-methyl-2-{4-[4-(2,2,2-trifluoroethoxy)-benzyl]piperazine-1-carbonyl}-1H-indol-6-yloxy)pyridin-3-yl]-benzamide hydrobromide Melting point: 251.8-253.5° C.

Example 466

3,4-Dichloro-N-(6-{2-[4-(6-isopropoxypyridin-3-ylmethyl)-piperazine-1-carbonyl]-1-methyl-1H-indol-6-yloxy}pyridin-3-yl)-benzamide hydrobromide Melting point: 236.9-240.4° C.

Example 467

3,4-Dichloro-N-(6-{2-[4-(2,2-difluorobenzo[1,3]dioxol-5-yl-methyl)piperazine-1-carbonyl]-1-methyl-1H-indol-6-yloxy}pyridin-3-yl)benzamide hydrobromide Melting point: 253.0-254.8° C.

Example 468

N-[6-(2-{4-[4-(2-Fluoro-1-fluoromethylethoxy)benzyl]piperazine-1-carbonyl}-1-methyl-1H-indol-6-yloxy)pyridin-3-yl]-4-trifluoro-methylbenzamide hydrobromide Melting point: 262.9-264.7° C.

Example 469

N-[6-(2-{4-[4-(2-Fluoro-1-fluoromethylethoxy)benzyl]piperazine-1-carbonyl}-1-methyl-1H-indol-5-yloxy)pyridin-3-yl]-4-trifluoro-methylbenzamide hydrobromide $^1$H NMR (DMSO-d$_6$) δ 3.19 (4H, brs), 3.82 (3H, s), 4.35-4.47 (4H, s), 4.56-4.69 (2H, m), 4.73-4.86 (2H, m), 4.94-5.09 (1H, m), 6.76 (1H, s), 7.02 (1H, d, J=8.1 Hz), 7.08 (1H, dd, J=8.1 Hz, 2.7 Hz), 7.16 (2H, d, J=8.1 Hz), 7.37 (1H, d, J=2.7 Hz), 7.46 (2H, d, J=8.1 Hz), 7.58 (1H, d, J=8.1 Hz), 7.93 (2H, d, J=8.1 Hz), 8.17 (2H, d, J=8.1 Hz), 8.18 (1H, dd, J=8.1 Hz, 2.7 Hz), 8.47 (1H, d, J=2.7 Hz), 9.81 (1H, s), 10.58 (1H, s).

Example 470

3,4-Dichloro-N-[6-(2-{4-[4-(2-fluoro-1-fluoromethylethoxy)-benzyl]piperazine-1-carbonyl}-1-methyl-1H-indol-6-yloxy)pyridin-3-yl]benzamide hydrobromide Melting point: 242.8-243.9° C.

Example 471

N-Methyl-N-(6-{1-methyl-2-[4-(4-propoxybenzyl)piperazine-1-carbonyl]-1H-indol-6-yloxy}pyridin-3-yl)-4-trifluoromethoxy-benzamide hydrobromide Melting point: 240-242° C.

Example 472

N-(6-{2-[4-(4-Isopropoxybenzyl)piperazine-1-carbonyl]-1-methyl-1H-indol-6-yloxy}pyridin-3-yl)-N-methyl-4-trifluoromethoxy-benzamide hydrobromide Melting point: 237.2-238.5° C.

Example 473

N-(6-{2-[4-(4-Difluoromethoxybenzyl)piperazine-1-carbonyl]-1-methyl-1H-indol-6-yloxy}pyridin-3-yl)-N-methyl-4-trifluoro-methoxybenzamide hydrobromide Melting point: 226-229° C.

Example 474

N-[6-(1-Methyl-2-{4-[4-(2,2,2-trifluoroethoxy)benzyl]piperazine-1-carbonyl}-1H-indol-6-yloxy)pyridin-3-yl]-4-trifluoromethyl-benzamide hydrobromide Melting point: 269.0-270.3° C.

Example 475

N-(6-{1-Methyl-2-[4-(4-propoxybenzyl)piperazine-1-carbonyl]-1H-indol-6-yloxy}pyridin-3-yl)-4-trifluoromethylbenzamide hydrobromide Melting point: 254.0-255.7° C.

Example 476

N-(6-{2-[4-(4-Isopropoxybenzyl)piperazine-1-carbonyl]-1-methyl-1H-indol-6-yloxy}pyridin-3-yl)-4-trifluoromethylbenzamide hydrobromide Melting point: 258.7-259.6° C.

Example 477

N-(6-{2-[4-(4-Difluoromethoxybenzyl)piperazine-1-carbonyl]-1-methyl-1H-indol-6-yloxy}pyridin-3-yl)-4-trifluoromethylbenzamide hydrobromide Melting point: 265.6-268.3° C.

Example 478

N-(6-{1-Methyl-2-[4-(4-propylbenzyl)piperazine-1-carbonyl]-1H-indol-6-yloxy}pyridin-3-yl)-4-trifluoromethylbenzamide hydrobromide Melting point: 267.0-268.2° C.

Example 479

N-[6-(2-{4-[4-(2,2-Difluoroethoxy)benzyl]piperazine-1-carbonyl}-1-methyl-1H-indol-6-yloxy)pyridin-3-yl]-4-trifluoromethyl-benzamide hydrobromide Melting point: 260.7-261.2° C.

Example 480

N-(6-{2-[4-(2,2-Difluorobenzo[1,3]dioxol-5-ylmethyl)piperazine-1-carbonyl]-1-methyl-1,1-indol-5-yloxy}pyridin-3-yl)-4-trifluoro-methylbenzamide hydrobromide Melting point: 246.6-248.1° C.

Example 481

N-(6-{1-Methyl-2-[4-(4-propoxybenzyl)piperazine-1-carbonyl]-1H-indol-5-yloxy}pyridin-3-yl)-4-trifluoromethylbenzamide hydrobromide Melting point: 234.7-235.1° C.

Example 482

3,4-Dichloro-N-[6-(2-{4-[4-(2-fluoroethoxy)benzyl]piperazine-1-carbonyl}-1-methyl-1H-indol-6-yloxy)pyridin-3-yl]-N-methyl-benzamide hydrobromide Melting point: 186.9-188.8° C.

Example 483

3,4-Dichloro-N-[6-(2-{4-[4-(2,2-difluoroethoxy)benzyl]piperazine-1-carbonyl}-1-methyl-1H-indol-6-yloxy)pyridin-3-yl]-N-methyl-benzamide hydrobromide Melting point: 182.4-184.6° C.

Example 484

3,4-Dichloro-N-methyl-N-[6-(1-methyl-2-{4-[4-(2,2,2-trifluoro-ethoxy)benzyl]piperazine-1-carbonyl}-1H-indol-6-yloxy)pyridin-3-yl]benzamide hydrobromide Melting point: 197.1-201.5° C.

Example 485

3,4-Dichloro-N-[6-(2-{4-[4-(2-fluoro-1-fluoromethylethoxy)-benzyl]piperazine-1-carbonyl}-1-methyl-1H-indol-6-yloxy)pyridin-3-yl]-N-methylbenzamide hydrobromide Melting point: 188.2-191.8° C.

Example 486

3,4-Dichloro-N-(6-{2-[4-(4-isopropoxybenzyl)piperazine-1-carbonyl]-1-methyl-1H-indol-6-yloxy}pyridin-3-yl)-N-methyl-benzamide hydrobromide Melting point: 220.2-223.5° C.

Example 487

3,4-Dichloro-N-methyl-N-(6-{1-methyl-2-[4-(4-propoxybenzyl)-piperazine-1-carbonyl]-1H-indol-6-yloxy}pyridin-3-yl)benzamide hydrobromide Melting point: 204.9-208.5° C.

Example 488

3,4-Dichloro-N-(6-{2-[4-(4-difluoromethoxybenzyl)piperazine-1-carbonyl]-1-methyl-1H-indol-6-yloxy}pyridin-3-yl)-N-methyl-benzamide hydrobromide Melting point: 185.6-189.3° C.

Example 489

3,4-Dichloro-N-(6-{2-[4-(2,2-difluorobenzo[1,3]dioxol-5-yl-methyl)piperazine-1-carbonyl]-1-methyl-1H-indol-6-yloxy}pyridin-3-yl)-N-methylbenzamide hydrobromide Melting point: 225.4-227.1° C.

Example 490

N-{6-[2-(4-Isobutylpiperazine-1-carbonyl)-1-methyl-1H-indol-6-yl-oxy]pyridin-3-yl}-N-methyl-4-trifluoromethylbenzamide hydrochloride Melting point: 253.1-254.5° C.

Example 491

N-{6-[2-(4-Isobutylpiperazine-1-carbonyl)-1-methyl-1H-indol-6-yl-oxy]pyridin-3-yl}-4-trifluoromethylbenzamide hydrochloride Melting point: 270.2-272.2° C.

Example 492

2-Methyl-N-[6-(1-methyl-2-{4-[4-(2,2,2-trifluoroethoxy)benzyl]-piperazine-1-carbonyl}-1H-indol-6-yloxy)pyridin-3-yl]-4-tri-fluoromethylbenzamide hydrochloride Melting point: 217.4-218.3° C.

Example 493

N-[6-(2-{4-[4-(2-Fluoro-1-fluoromethylethoxy)benzyl]piperazine-1-carbonyl}-1-methyl-1H-indol-6-yloxy)pyridin-3-yl]-2-methyl-4-tri-fluoromethylbenzamide hydrochloride Melting point: 192.5-195.4° C.

Example 494

N-(6-{2-[4-(4-Isopropoxybenzyl)piperazine-1-carbonyl]-1-methyl-1H-indol-6-yloxy}pyridin-3-yl)-2-methyl-4-trifluoromethyl-benzamide hydrochloride Melting point: 197.7-199.3° C.

Example 495

N-(6-{2-[4-(2,2-Difluorobenzo[1,3]dioxol-5-ylmethyl)piperazine-1-carbonyl]-1-methyl-1H-indol-6-yloxy}pyridin-3-yl)-2-methyl-4-tri-fluoromethylbenzamide hydrochloride Melting point: 207.9-211.5° C.

Example 496

N-(6-{2-[4-(4-Difluoromethoxybenzyl)piperazine-1-carbonyl]-1-methyl-1H-indol-6-yloxy}pyridin-3-yl)-2-methyl-4-trifluoromethyl-benzamide hydrochloride Melting point: 204.9-205.7° C.

Example 497

N-[6-(2-{4-[4-(2,2-Difluoroethoxy)benzyl]piperazine-1-carbonyl}-1-methyl-1H-indol-6-yloxy)pyridin-3-yl]-2-methyl-4-trifluoro-methylbenzamide hydrochloride Melting point: 203.9-206.3° C.

Example 498

N-(6-{2-[4-(4-Hydroxybenzyl)piperazine-1-carbonyl]-1-methyl-1H-indol-6-yloxy}pyridin-3-yl)-hr-methyl-4-trifluoromethylbenzamide hydrochloride Melting point: 227.1-229.4° C.

Example 499

3,4-Dichloro-N-[6-(1-methyl-2-{4-[4-(2,2,2-trifluoroethoxy)-benzyl]piperazine-1-carbonyl}-1H-indol-6-yloxy)pyridin-3-yl]-benzenesulfonamide $^1$H NMR (CDCl$_3$) δ 2.48 (4H, brs), 3.51 (2H, s), 3.76 (7H, s), 4.35 (2H, q, J=8.1 Hz), 6.56 (1H, d, J=0.7 Hz), 6.84-6.90 (4H, m), 6.92-6.93 (1H, m), 7.08 (1H, d, J=2.0 Hz), 7.26-7.30 (2H, m), 7.50-7.60 (4H, m), 7.73 (1H, d, J=2.6 Hz), 7.82 (1H, t, J=1.2 Hz).

Example 500

3,4-Dichloro-N-[6-(2-{4-[4-(2,2-difluoroethoxy)benzyl]piperazine-1-carbonyl}-1-methyl-1H-indol-6-yloxy)pyridin-3-yl]benzene-sulfonamide $^1$H NMR (CDCl$_3$) δ 2.41 (4H, brs), 3.43 (2H, s), 3.68 (7H, s), 4.11 (2H, td, J=13.0 Hz, 4.2 Hz), 6.01 (1H, tt, J=55.2 Hz, 4.1 Hz), 6.49 (1H, s), 6.76-6.83 (4H, m), 7.01 (1H, d, J=1.6 Hz), 7.18-7.21 (3H, m), 7.43-7.52 (4H, m), 7.66 (1H, d, J=2.6 Hz), 7.75 (1H, s).

Example 501

3,4-Dichloro-N-(6-{2-[4-(4-difluoramethoxybenzyl)piperazine-1-carbonyl]-1-methyl-1H-indol-6-yloxy}pyridin-3-yl)-benzenesulfonamide $^1$H NMR (CDCl$_3$) δ 2.49 (4H, brs), 3.53 (2H, s), 3.74-3.79 (7H, m), 6.51 (1H, t, J=74.0 Hz), 6.56 (1H, d, J=1.0 Hz), 6.78-6.89 (3H, m), 7.09 (3H, d, J=8.6 Hz), 7.33 (2H, d, J=8.6 Hz), 7.47-7.60 (4H, m), 7.73-7.74 (1H, m), 7.82 (1H, d, J=1.3 Hz).

Example 502

3,4-Dichloro-N-(6-{1-methyl-2-[4-(4-propoxybenzyl)piperazine-1-carbonyl]-1H-indol-6-yloxy}pyridin-3-yl)benzenesulfonamide $^1$H NMR (CDCl$_3$) δ 1.04 (3H, t, J=7.4 Hz), 1.81 (2H, td, J=14.1 Hz, 7.1 Hz), 2.48 (4H, brs), 3.49 (2H, s), 3.75 (7H, s), 3.92 (2H, t, J=6.6 Hz), 6.56 (1H, s), 6.85-6.89 (4H, m), 7.08 (1H, d, J=1.6 Hz), 7.21-7.26 (3H, m), 7.50-7.60 (4H, m), 7.73 (1H, d, J=2.6 Hz), 7.82 (1H, s).

Example 503

N-[6-(2-{4-[4-(2,2-Difluoroethoxy)benzyl]piperazine-1-carbonyl}-1-methyl-1H-indol-6-yloxy)pyridin-3-yl]-2-fluoro-N-methyl-4-tri-fluoranethylbenzamide hydrochloride Melting point: 226.4-228.6° C.

Example 504

N-(6-{2-[4-(4-Difluoromethoxybenzyl)piperazine-1-carbonyl]-1-methyl-1H-indol-6-yloxy}pyridin-3-yl)-2-fluoro-N-methyl-4-tri-fluoromethylbenzamide hydrochloride Melting point: 228.7-230.4° C.

Example 505

2-Fluoro-N-methyl-N-(6-{1-methyl-2-[4-(4-propoxybenzyl)-piperazine-1-carbonyl]-1H-indol-6-yloxy}pyridin-3-yl)-4-tri-fluoromethylbenzamide hydrochloride Melting point: 247.1-249.2° C.

Example 506

3,4-Dichloro-N-[6-(2-{4-[4-(2-fluoro-1-fluoromethylethoxy)-benzyl]piperazine-1-carbonyl}-1-methyl-1H-indol-6-yloxy)pyridin-3-yl]-M-methylbenzenesulfonamide Melting point: 157.7-160.2° C.

Example 507

3,4-Dichloro-N-(6-{2-[4-(4-isopropoxybenzyl)piperazine-1-carbonyl]-1-methyl-1H-indol-6-yloxy}pyridin-3-yl)-N-methyl-benzenesulfonamide Melting point: 186.8-187° C.

Example 508

3,4-Dichloro-N-(6-{2-[4-(2,2-difluorobenzo[1,3]dioxol-5-yl-methyl)piperazine-1-carbonyl]-1-methyl-1H-indol-6-yloxy}pyridin-3-yl)-N-methylbenzenesulfonamide Melting point: 149.9-151.3° C.

Example 509

N-[6-(1-Methyl-2-{4-[4-(2,2,2-trifluoroethoxy)benzyl]piperazine-1-carbonyl}-1H-indol-6-yloxy)pyridin-3-yl]-4-trifluoromethyl-benzenesulfonamide $^1$H NMR (CDCl$_3$) δ 2.48 (4H, brs), 3.51 (2H, s), 3.76-3.79 (7H, m), 4.35 (2H, q, J=8.1 Hz), 6.56 (1H, s), 6.85-6.96 (5H, m), 7.09 (1H, d, J=1.6 Hz), 7.27-7.30 (2H, m), 7.54-7.60 (2H, m), 7.70-7.73 (3H, m), 7.85 (2H, d, J=8.2 Hz).

Example 510

N-(6-{2-[4-(4-Difluoromethoxybenzyl)piperazine-1-carbonyl]-1-methyl-1H-indol-6-yloxy}pyridin-3-yl)-4-trifluoromethylbenzene-sulfonamide $^1$H NMR (CDCl$_3$) δ 2.51 (4H, brs), 3.55 (2H, s), 3.74-3.79 (7H, m), 6.51 (1H, t, J=73.7 Hz), 6.56 (1H, s), 6.82-6.88 (2H, m), 7.09 (4H, d, J=8.6 Hz), 7.34 (2H, d, J=5.9 Hz), 7.52-7.59 (2H, m), 7.67-7.74 (3H, m), 7.84 (2H, d, J=8.2 Hz).

Example 511

N-(6-{1-Methyl-2-[4-(4-propoxybenzyl)piperazine-1-carbonyl]-1H-indol-6-yloxy}pyridin-3-yl)-4-trifluoromethylbenzenesulfonamide hydrobromide Melting point: 223.7-224.8° C.

Example 512

3,4-Dichloro-N-[6-(2-{4-[4-(2,2-difluoroethoxy)benzyl]piperazine-1-carbonyl}-1-methyl-1H-indol-6-yloxy)pyridin-3-yl]-N-methyl-benzenesulfonamide Melting point: 168.4-168.6° C.

Example 513

3,4-Dichloro-N-[6-(2-{4-[4-(2-fluoroethoxy)benzyl]piperazine-1-carbonyl}-1-methyl-1H-indol-6-yloxy)pyridin-3-yl]-N-methyl-benzenesulfonamide Melting point: 195.2-196.8° C.

Example 514

3,4-Dichloro-N-(6-{2-[4-(4-cyclopropylmethoxybenzyl)piperazine-1-carbonyl]-1-methyl-1H-indol-6-yloxy}pyridin-3-yl)-N-methyl-benzenesulfonamide Melting point: 194.1-195.8° C.

Example 515

3,4-Dichloro-N-(6-{2-[4-(4-difluoromethoxybenzyl)piperazine-1-carbonyl]-1-methyl-1H-indol-6-yloxy}pyridin-3-yl)-N-methyl-benzenesulfonamide Melting point: 143.4-147.2° C.

Example 516

3,4-Dichloro-N-methyl-N-[6-(1-methyl-2-{4-[4-(3-methylbutoxy)-benzyl]piperazine-1-carbonyl}-1H-indol-6-yloxy)pyridin-3-yl]-benzenesulfonamide Melting point: 145.9-147.1° C.

Example 517

3,4-Dichloro-N-(6-{2-[4-(6-isopropoxypyridin-3-ylmethyl)-piperazine-1-carbonyl]-1-methyl-1H-indol-6-yloxy}pyridin-3-yl)-N-methylbenzenesulfonamide Melting point: 179.1-179.7° C.

Example 518

N-{6-[2-(4-Benzo[1,3]dioxol-5-ylmethylpiperazine-1-carbonyl)-1-methyl-1H-indol-6-yloxy]pyridin-3-yl}-4,N-dimethylbenzene-sulfonamide hydrochloride Melting point: 242-249° C.

Example 519

N-Methyl-N-[2-(1-methyl-2-{4-[4-(2,2,2-trifluoroethoxy)benzyl]-piperazine-1-carbonyl}-1H-indol-6-yloxy)pyrimidin-5-yl]-4-tri-fluoromethylbenzamide hydrochloride $^1$H NMR (DMSO-$d_6$) δ 3.16 (2H, brs), 3.39 (3H, s), 3.35-3.45 (4H, m), 3.64 (2H, brs), 3.73 (3H, s), 4.34-4.44 (2H, m), 4.82 (2H, q, J=8.9 Hz), 6.80 (1H, s), 6.84 (1H, d, J=8.6 Hz), 7.17 (2H, d, J=8.6 Hz), 7.38 (1H, s), 7.52-7.63 (5H, m), 7.72-7.74 (2H, m), 8.58 (2H, brs), 10.56 (1H, brs).

Example 520

N-[2-(2-{4-[4-(2-Fluoro-1-fluoromethylethoxy)benzyl]piperazine-1-carbonyl}-1-methyl-1H-indol-6-yloxy)pyrimidin-5-yl]-N-methyl-4-trifluoromethyl-benzamide hydrochloride $^1$H NMR (DMSO-$d_6$) δ 3.16 (2H, brs), 3.39 (3H, s), 3.35-3.46 (4H, m), 3.64 (2H, brs), 3.73 (3H, s), 4.32-4.44 (2H, s), 4.56-4.69 (2H, m), 4.73-4.85 (2H, m), 4.95-5.09 (1H, m), 6.80 (1H, s), 6.86 (1H, d, J=7.0 Hz), 7.15 (2H, d, J=8.4 Hz), 7.38 (1H, s), 7.50-7.60 (5H, m), 7.72 (2H, brs), 8.58 (2H, brs), 10.55 (1H, brs).

Example 521

N-(2-{2-[4-(4-Isopropoxybenzyl)piperazine-1-carbonyl]-1-methyl-1H-indol-6-yloxy}pyrimidin-5-yl)-N-methyl-4-trifluoromethyl-benzamide hydrochloride $^1$H NMR (DMSO-$d_6$) δ 1.26 (3H, s), 1.28 (3H, s), 3.14 (2H, brs), 3.39 (3H, s), 3.35-3.49 (4H, m), 3.60-3.64 (2H, m), 3.72 (3H, s), 4.29-4.43 (2H, m), 4.62-4.70 (1H, m), 6.79 (1H, s), 6.85 (1H, d, J=7.6 Hz), 7.00 (1H, d, J=8.1 Hz), 7.20 (1H, brs), 7.37 (1H, s), 7.48 (2H, d, J=7.6 Hz), 7.57-7.63 (3H, m), 7.72-7.81 (2H, m), 8.58 (2H, brs), 10.80 (1H, brs).

Example 522

N-[2-(2-{4-[4-(2,2-Difluoroethoxy)benzyl]piperazine-1-carbonyl}-1-methyl-1H-indol-6-yloxy)pyrimidin-5-yl]-N-methyl-4-trifluoro-methylbenzamide hydrochloride $^1$H NMR (DMSO-$d_6$) δ 3.17 (2H, brs), 3.39 (3H, s), 3.36-3.47 (4H, m), 3.60-3.69 (2H, m), 3.73 (3H, s), 4.18-4.67 (4H, m), 6.40 (1H, t, J=57.0 Hz), 6.80 (1H, s), 6.82-6.98 (1H, m), 6.97 (1H, d, J=7.3 Hz), 7.12 (1H, d, J=7.8 Hz), 7.26 (1H, d, J=6.8 Hz), 7.35-7.38 (1H, m), 7.51 (1H, d, J=8.6 Hz), 7.57-7.63 (3H, m), 7.72-7.74 (2H, m), 8.58 (2H, s), 10.40 (1H, s).

Example 523

N-[6-(2-{4-[4-(2-Fluoro-1-fluoromethylethoxy)benzyl]piperazine-1-carbonyl}-1-methyl-1H-indol-6-yloxy)pyridin-3-yl]-4,N-dimethyl-benzenesulfonamide Melting point: 116.5-116.6° C.

Example 524

N-[6-(2-{4-[4-(2,2-Difluoroethoxy)benzyl]piperazine-1-carbonyl}-1-methyl-1H-indol-6-yloxy)pyridin-3-yl]-4,N-dimethylbenzene-sulfonamide Melting point: 121.9-122.5° C.

Example 525

N-(6-{2-[4-(4-Isopropoxybenzyl)piperazine-1-carbonyl]-1-methyl-1H-indol-6-yloxy}pyridin-3-yl)-4,N-dimethylbenzenesulfonamide Melting point: 140.9-145.8° C.

Example 526

N-(6-{2-[4-(2,2-Difluorobenzo[1,3]dioxol-5-ylmethyl)piperazine-1-carbonyl]-1-methyl-1H-indol-6-yloxy}pyridin-3-yl)-4,N-dimethyl-benzenesulfonamide hydrochloride Melting point: 240-243° C.

Example 527

N-Methyl-N-[6-(1-methyl-2-{4-[4-(2,2,2-trifluoroethoxy)benzyl]-piperazine-1-carbonyl}-1H-indol-5-yloxy)pyridin-3-yl]-4-tri-fluoromethylbenzene-sulfonamide Melting point: 191.8-194.4° C.

Example 528

3,4-Dichloro-N-methyl-N-[6-(1-methyl-2-{4-[4-(2,2,2-trifluoro-ethoxy)benzyl]piperazine-1-carbonyl}-1H-indol-5-yloxy)pyridin-3-yl]benzenesulfonamide Melting point: 174.8-175.8° C.

Example 529

4,N-Dimethyl-N-[6-(1-methyl-2-{4-[4-(2,2,2-trifluoroethoxy)-benzyl]piperazine-1-carbonyl}-1H-indol-5-yloxy)pyridin-3-yl]-benzenesulfonamide hydrochloride Melting point: 239.1-239.8° C.

Example 530

N-(6-{2-[4-(4-Cyclopropylmethoxybenzyl)piperazine-1-carbonyl]-1-methyl-1H-indol-6-yloxy}pyridin-3-yl)-4,N-dimethylbenzene-sulfonamide Melting point: 135.6-138.6° C.

Example 531

N-[6-(2-{4-[4-(2-Fluoroethoxy)benzyl]piperazine-1-carbonyl}-1-methyl-1H-indol-6-yloxy)pyridin-3-yl]-4,N-dimethylbenzene-sulfonamide Melting point: 138.7-139.8° C.

Example 532

N-(6-{2-[4-(4-Difluoromethoxybenzyl)piperazine-1-carbonyl]-1-methyl-1H-indol-6-yloxy}pyridin-3-yl)-4,N-dimethylbenzene-sulfonamide hydrobromide Melting point: 214.5-218.5° C. (decomposition)

Example 533

4,N-Dimethyl-N-[6-(1-methyl-2-{4-[4-(3-methylbutoxy)benzyl]-piperazine-1-carbonyl}-1H-indol-6-yloxy)pyridin-3-yl]benzene-sulfonamide hydrobromide Melting point: 236.5-238.3° C. (decomposition)

Example 534

N-(6-{2-[4-(6-Isopropoxypyridin-3-ylmethyl)piperazine-1-carbonyl]-1-methyl-1H-indol-6-yloxy}pyridin-3-yl)-4,N-dimethyl-benzenesulfonamide Melting point: 131.1-132.8° C.

Example 535

2-Chloro-N-(6-{1-methyl-2-[4-(4-propoxybenzyl)piperazine-1-carbonyl]-1H-indol-6-yloxy}pyridin-3-yl)-4-trifluoromethyl-benzamide $^1$H NMR (CDCl$_3$) δ 1.03 (3H, t, J=8.6 Hz), 1.73-1.86 (2H, m), 2.44 (4H, s), 3.47 (2H, s), 3.68 (7H, s), 3.91 (2H, t, J=6.5 Hz), 6.49 (1H, s), 6.83-6.90 (4H, m), 7.06 (1H, d, J=1.6 Hz), 7.21 (2H, d, J=8.4 Hz), 7.47 (1H, d, J=8.6 Hz), 7.58 (3H, dd, J=14.0 Hz, 8.4 Hz), 8.09 (1H, dd, J=8.9 Hz, 2.6 Hz), 8.30 (1H, d, J=2.6 Hz), 9.09 (1H, s).

Example 536

2-Chloro-N-(6-{2-[4-(4-difluoromethoxybenzyl)piperazine-1-carbonyl]-1-methyl-1H-indol-6-yloxy}pyridin-3-yl)-4-trifluoro-methylbenzamide hydrochloride Melting point: 235.5-236.1° C.

Example 537

2-Chloro-N-[6-(2-{4-[4-(2-fluoro-1-fluoromethyl-ethoxy)benzyl]-piperazine-1-carbonyl}-1-methyl-1H-indol-6-yloxy)pyridin-3-yl]-4-trifluoromethyl-benzamide hydrobromide Melting point: 239.8-240.8° C.

Example 538

2-Chloro-N-[6-(2-{4-[4-(2,2-difluoroethoxy)benzyl]piperazine-1-carbonyl}-1-methyl-1H-indol-6-yloxy)pyridin-3-yl]-4-trifluoro-methylbenzamide hydrochloride Melting point: 232.5-233.5° C.

Example 539

2-Fluoro-N-(6-{1-methyl-2-[4-(4-propoxybenzyl)piperazine-1-carbonyl]-1H-indol-6-yloxy}pyridin-3-yl)-4-trifluoromethyl-benzamide hydrochloride Melting point: 264.0-266.3° C.

Example 540

2-Fluoro-N-(6-{2-[4-(4-isopropoxybenzyl)piperazine-1-carbonyl]-1-methyl-1H-indol-6-yloxy}pyridin-3-yl)-4-trifluoromethylbenzamide hydrochloride Melting point: 267.6-268.2° C.

Example 541

N-(6-{2-[4-(4-Difluoromethoxybenzyl)piperazine-1-carbonyl]-1-methyl-1H-indol-6-yloxy}pyridin-3-yl)-2-fluoro-4-trifluoromethyl-benzamide hydrochloride Melting point: 265.3-265.8° C.

Example 542

N-[6-(2-{4-[4-(2,2-Difluoroethoxy)benzyl]piperazine-1-carbonyl}-1-methyl-1H-indol-6-yloxy)pyridin-3-yl]-2-fluoro-4-trifluoro-methylbenzamide hydrochloride Melting point: 272.3-275.0° C.

Example 543

2-Fluoro-N-[6-(2-{4-[4-(2-fluoro-1-fluoromethylethoxy)benzyl]-piperazine-1-carbonyl}-1-methyl-1H-indol-6-yloxy)pyridin-3-yl]-4-trifluoromethyl-benzamide hydrochloride Melting point: 267.3-267.7° C.

Example 544

2-Methyl-N-[2-(1-methyl-2-{4-[4-(2,2,2-trifluoroethoxy)benzyl]-piperazine-1-carbonyl}-1H-indol-6-yloxy)pyrimidin-5-yl]-4-tri-fluoromethylbenzamide hydrobromide $^1$H NMR (DMSO-$d_6$) δ 2.48 (3H, s), 3.12-3.44 (6H, m), 3.76 (3H, s), 4.37 (2H, s), 4.46-4.51 (2H, m), 4.82 (2H, q, J=8.8 Hz), 6.82 (1H, s), 6.96 (1H, dd, J=8.7 Hz, 2.1 Hz), 7.18 (2H, d, J=8.6 Hz), 7.44 (1H, d, J=1.6 Hz), 7.52 (2H, d, J=8.7 Hz), 7.66 (1H, d, J=8.6 Hz), 7.72-7.74 (3H, m), 8.91 (2H, s), 9.95 (1H, brs), 10.77 (1H, s).

Example 545

N-[2-(2-{4-[4-(2-Fluoro-1-fluoromethylethoxy)benzyl]piperazine-1-carbonyl}-1-methyl-1H-indol-6-yloxy)pyrimidin-5-yl]-2-methyl-4-trifluoromethyl-benzamide hydrobromide $^1$H NMR (DMSO-$d_6$) δ 2.47 (3H, s), 3.18-3.45 (6H, m), 3.76 (3H, s), 4.35 (2H, s), 4.45-4.50 (2H, m), 4.56-5.11 (5H, m), 6.82 (1H, s), 6.96 (1H, dd, J=8.6 Hz, 2.0 Hz), 7.16 (2H, d, J=8.7 Hz), 7.44 (1H, d, J=2.0 Hz), 7.48 (2H, d, J=8.7 Hz), 7.66 (1H, d, J=8.6 Hz), 7.72-7.75 (3H, m), 8.91 (2H, s), 9.89 (1H, brs), 10.77 (1H, s).

Example 546

N-(2-{2-[4-(4-Isopropoxybenzyl)piperazine-1-carbonyl]-1-methyl-1H-indol-6-yloxy}pyrimidin-5-yl)-2-methyl-4-trifluoromethyl-benzamide $^1$H NMR (CDCl$_3$) δ 1.32 (3H, s), 1.35 (3H, s), 2.47 (4H, brs), 2.53 (3H, s), 3.48 (2H, brs), 3.75 (4H, brs), 3.76 (3H, s), 4.47-4.60 (1H, m), 6.56 (1H, s), 6.85 (2H, dt, J=9.3 Hz, 2.5 Hz), 6.97 (1H, dd, J=8.6 Hz, 2.0 Hz), 7.18 (1H, d, J=2.0 Hz), 7.21 (2H, d, J=8.6 Hz), 7.51-7.64 (4H, m), 7.77 (1H, s), 8.86 (2H, s).

Example 547

Production of N-{6-[2-(4-isobutylpiperazine-1-carbonyl)-1-methyl-1H-indol-5-yloxy]pyridin-3-yl}-4-trifluoromethylbenzamide To a solution of N-{6-[1-methyl-2-(piperazine-1-carbonyl)-1H-indol-5-yloxy]pyridin-3-yl}-4-trifluoromethyl-benzamide (250 mg, 0.478 mmol) in acetonitrile (2 mL) were added 1-bromo-2-methylpropane (0.123 mL, 1.13 mmol), diisopropylethylamine (0.25 mL, 1.44 mmol) and sodium iodide (180 mg, 1.2 mmol). The reaction mixture was stirred under reflux for 14 hours. The solvent was removed under reduced pressure. Water was added to the residue and extracted with AcOEt. The organic layer was washed with saturated aqueous NaHCO$_3$ and brine, dried over anhydrous magnesium sulfate and evaporated in vacuo. The residue was purified by silica gel column chromatography (CH$_2$Cl$_2$:MeOH=40:1) and solidified with EtOH (2 mL). The precipitate was collected by filtration and dried to give 100 mg of the title compound as a white powder.

Melting point: 200-202° C.

The following compounds were produced in the same manner as in Example 547 using appropriate starting materials.

Example 548

N-Methyl-N-{6-[1-methyl-2-(4-pyridin-4-ylmethylpiperazine-1-carbonyl)-1H-indol-5-yloxy]pyridin-3-yl}-4-trifluoromethyl-benzamide dihydrobromide Melting point: 196-198° C.

Example 549

N-(6-{2-[4-(4-Fluorobenzyl)piperazine-1-carbonyl]-1-methyl-1H-indol-5-yloxy}pyridin-3-yl)-N-methyl-4-trifluoromethylbenzamide hydrobromide Melting point: 218-220° C.

Example 550

N-{6-[1-Methyl-2-(4-pyridin-4-ylmethylpiperazine-1-carbonyl)-1H-indol-5-yloxy]pyridin-3-yl}-4-trifluoromethylbenzamide dihydrobromide Melting point: 211-215° C. (decomposition)

Example 551

N-(6-{2-[4-(4-Fluorobenzyl)piperazine-1-carbonyl]-1-methyl-1H-indol-5-yloxy}pyridin-3-yl)-4-trifluoromethylbenzamide hydrobromide Melting point: 254-257° C.

Example 552

N-(6-{2-[4-(4-Cyanobenzyl)piperazine-1-carbonyl]-1-methyl-1H-indol-5-yloxy}pyridin-3-yl)-4-trifluoromethylbenzamide maleate Melting point: 149-152° C.

Example 553

N-Methyl-N-(6-{1-methyl-2-[4-(4-trifluoromethyl-benzyl)piperazine-1-carbonyl]-1H-indol-5-yloxy}pyridin-3-yl)-4-trifluoromethyl-benzamide hydrobromide Melting point: 254-260° C. (decomposition)

Example 554

3,4-Dichloro-N-methyl-N-{6-[1-methyl-2-(4-pyridin-4-ylmethyl-piperazine-1-carbonyl)-1H-indol-5-yloxy]pyridin-3-yl}benzamide dihydrobromide Melting point: 204-208° C. (decomposition)

Example 555

3,4-Dichloro-N-{6-[1-methyl-2-(4-pyridin-4-ylmethylpiperazine-1-carbonyl)-1H-indol-5-yloxy]pyridin-3-yl}benzamide dihydrobromide Melting point: 214-219° C. (decomposition)

Example 556

3,4-Dichloro-N-(6-{2-[4-(4-cyanobenzyl)piperazine-1-carbonyl]-1-methyl-1H-indol-5-yloxy}pyridin-3-yl)benzamide hydrobromide Melting point: 267-272° C. (decomposition)

Example 557

3,4-Dichloro-N-(6-{2-[4-(4-cyanobenzyl)piperazine-1-carbonyl]-1-methyl-1H-indol-5-yloxy}pyridin-3-ylmethylbenzamide hydrobromide Melting point: 238-240° C.

Example 558

N-{6-[1-Methyl-2-(4-pyridin-3-ylmethylpiperazine-1-carbonyl)-1H-indol-5-yloxy]pyridin-3-yl}-4-trifluoromethylbenzamide dihydrobromide Melting point: 201-204° C.

Example 559

N-Methyl-N-{6-[1-methyl-2-(4-pyridin-3-ylmethylpiperazine-1-carbonyl)-1H-indol-5-yloxy]pyridin-3-yl}-4-trifluoromethyl-benzamide dihydrobromide Melting point: 191-193° C.

Example 560

N-{6-[1-Methyl-2-(4-pyridin-2-ylmethylpiperazine-1-carbonyl)-1H-indol-5-yloxy]pyridin-3-yl}-4-trifluoromethylbenzamide bismethanesulfonate Melting point: 137-139° C.

Example 561

N-Methyl-N-{6-[1-methyl-2-(4-pyridin-2-ylmethylpiperazine-1-carbonyl)-1H-indol-5-yloxy]pyridin-3-yl}-4-trifluoromethyl-benzamide dioxalate Melting point: 114-117° C.

Example 562

N-{6-[2-(4-Isobutylpiperazine-1-carbonyl)-1-methyl-1H-indol-5-yl-oxy]pyridin-3-yl}-N-methyl-4-trifluoromethylbenzamide Melting point: 163-164° C.

Example 563

3,4-Dichloro-N-{6-[1-methyl-2-(4-pyridin-3-ylmethylpiperazine-1-carbonyl)-1H-indol-5-yloxy]pyridin-3-yl}benzamide dihydrobromide Melting point: 249-252° C. (decomposition)

Example 564

3,4-Dichloro-N-{6-[1-methyl-2-(4-pyridin-2-ylmethylpiperazine-1-carbonyl)-1H-indol-5-yloxy]pyridin-3-yl}benzamide dihydrobromide Melting point: 231-233° C. (decomposition)

Example 565

N-{2-Methyl-6-[1-methyl-2-(4-pyridin-4-ylmethylpiperazine-1-carbonyl)-1H-indol-5-yloxy]pyridin-3-yl}-4-trifluoromethyl-benzamide dihydrobromide Melting point: 223-225° C. (decomposition)

Example 566

N-Methyl-N-{2-methyl-6-[1-methyl-2-(4-pyridin-4-ylmethyl-piperazine-1-carbonyl)-1H-indol-5-yloxy]pyridin-3-yl}-4-tri-fluoromethylbenzamide dioxalate Melting point: 117-120° C.

Example 567

3,4-Dichloro-N-{6-[2-(4-isobutylpiperazine-1-carbonyl)-1-methyl-1H-indol-5-yloxy]pyridin-3-yl}benzamide hydrobromide Melting point: 251-254° C.

Example 568

N-Methyl-N-(6-{1-methyl-2-[4-(5-methylisoxazol-3-ylmethyl)-piperazine-1-carbonyl]-1H-indol-5-yloxy}pyridin-3-yl)-4-tri-fluoromethylbenzamide maleate Melting point: 112-115° C.

Example 569

N-(6-{1-Methyl-2-[4-(5-methylisoxazol-3-ylmethyl)piperazine-1-carbonyl]-1H-indol-5-yloxy}pyridin-3-yl)-4-trifluoromethyl-benzamide hydrobromide Melting point: 220-223° C.

Example 570

N-(6-{2-[4-(5-Cyanopyridin-2-ylmethyl)piperazine-1-carbonyl]-1-methyl-1H-indol-5-yloxy}pyridin-3-yl)-N-methyl-4-trifluoromethyl-benzamide dihydrobromide Melting point: 211-215° C.

Example 571

N-(6-{1-Methyl-2-[4-(4-[1,2,3]thiadiazol-4-ylbenzyl)piperazine-1-carbonyl]-1H-indol-6-yloxy}pyridin-3-yl)-4-trifluoromethyl-benzamide Melting point: 220.0-220.8° C.

Example 572

N-[6-(1-Methyl-2-{4-[2-(4-trifluoromethylphenyl)thiazol-5-yl-methyl]piperazine-1-carbonyl}-1H-indol-5-yloxy)pyridin-3-yl]-4-trifluoromethylbenzamide hydrobromide Melting point: 218.9-220.8° C.

Example 573

3,4-Dichloro-N-methyl-N-(6-{1-methyl-2-[4-(4-[1,2,3]thiadiazol-4-ylbenzyl)piperazine-1-carbonyl]-1H-indol-6-yloxy}pyridin-3-yl)-benzamide hydrobromide $^1$H NMR (DMSO-d$_6$) δ 3.27 (2H, s), 3.35 (3H, s), 3.45 (2H, s), 3.62 (4H, s), 3.74 (3H, s), 4.49 (2H, s), 6.81 (1H, s), 6.82 (1H, dd, J=8.4 Hz, 2.1 Hz), 7.01 (1H, d, J=8.6 Hz), 7.22-7.25 (1H, m), 7.29 (1H, d, J=1.4 Hz), 7.57 (1H, d, J=8.1 Hz), 7.62 (1H, d, J=8.6 Hz), 7.72 (1H, d, J=8.1 Hz), 7.85 (1H, dd, J=8.6 Hz, 2.7 Hz), 7.96 (1H, brs), 8.28 (1H, d, J=8.4 Hz), 9.73 (1H, s), 10.06 (1H, s).

Example 574

Production of N-{6-[2-(4-benzylpiperazine-1-carbonyl)-1-methyl-1H-indol-5-yloxy]pyridin-3-yl}-4,5-dichlorophthalamic acid To a solution of [5-(5-aminopyridin-2-yloxy)-1-methyl-1H-indol-2-yl](4-benzylpiperazin-1-yl)methanone (1.00 g, 2.26 mmol) in 1,2-dichloroethane (22 mL) was added 4,5-dichlorophthalic anhydride (0.57 g, 2.62 mmol), and the mixture was stirred at room temperature for 4 hours. The resulting precipitate was collected by filtration and dried to give 1.5 g of the title compound as a white powder.

$^1$H NMR (DMSO-d$_6$) δ 2.59 (4H, brs), 3.68 (4H, brs), 3.77 (3H, s), 3.90 (2H, s), 6.63 (1H, s), 6.98 (1H, d, J=8.7 Hz), 7.03 (1H, dd, J=8.7 Hz, 2.5 Hz), 7.25-7.45 (6H, m), 7.54 (1H, d, J=8.7 Hz), 7.94 (1H, s), 8.05 (1H, s), 8.07 (1H, dd, J=8.7 Hz, 2.6 Hz), 8.33 (1H, d, (7=2.4 Hz), 10.59 (1H, s).

The following compound was produced in the same manner as in Example 574 using appropriate starting materials.

Example 575

N-{6-[2-(4-Benzo[1,3]dioxol-5-ylmethylpiperazine-1-carbonyl)-1-methyl-1H-indol-5-yloxy]pyridin-3-yl}-4,5-dichlorophthalamic acid $^1$H NMR (DMSO-d$_6$) δ 2.56 (4H, brs), 3.68 (4H, brs), 3.77 (2H, s), 3.90 (3H, s), 6.00 (2H, s), 6.63 (1H, s), 6.80 (1H, dd, J=8.1 Hz, 1.5 Hz), 6.82-6.94 (2H, m), 6.98 (1H, d, J=8.9 Hz), 7.02 (1H, dd, J=8.9 Hz, 2.3 Hz), 7.32 (1H, d, J=2.3 Hz), 7.54 (1H, d, J=8.9 Hz), 7.94 (1H, s), 8.05 (1H, s), 8.07 (1H, dd, J=8.9 Hz, 2.7 Hz), 8.33 (1H, d, J=2.7 Hz), 10.61 (1H, s), 13.10 (1H, brs).

Example 576

Production of 1-(4-benzo[1,3]dioxol-5-ylmethylpiperazin-1-yl)-2-(4-{5-[(4-trifluoromethylphenylamino)methyl]pyridin-2-yloxy}-2,3-dihydroindol-1-yl)ethanone 1-(4-Benzo[1,3]dioxol-5-ylmethylpiperazin-1-yl)-2-[4-(5-hydroxymethylpyridin-2-yloxy)-2,3-dihydroindol-1-yl)ethanone (0.671 g, 1.34 mmol) was dissolved in dichloromethane (10 mL). To the solution were added triethylamine (0.205 mL, 1.47 mmol), then methanesulfonyl chloride (0.114 g, 1.47 mmol) under cooling with ice. The resulting solution was stirred for 1 hour at the same temperature. Dichloromethane was added to the reaction solution, and the organic layer was washed with brine, then dried over anhydrous sodium sulfate. The solvent was evaporated to yield a pale brown amorphous powder (0.778 g). Thus obtained powder (0.389 g) was mixed with 4-trifluoromethylaniline (0.252 mL, 2.01 mmol) and the mixture was stirred for 16 hours, followed by stirring for 2 hours at 80° C. After cooling with ice, saturated sodium bicarbonate solution (20 mL), ethyl acetate (30 mL) and THF (30 mL) were added, and the resulting mixture was stirred. After the organic layer was washed with brine, then dried over anhydrous sodium sulfate, the solvent was evaporated. The obtained residue was purified by silica gel column chromatography (CH$_2$Cl$_2$:MeOH=50:1) to yield 0.060 g of the title compound as a brownish yellow amorphous powder.

$^1$H NMR (CDCl$_3$) δ 2.41-2.44 (4H, m), 2.84 (2H, t, J=8.2 Hz), 3.40-3.52 (6H, m), 3.64 (2H, brs), 3.88 (2H, s), 4.27 (1H, brs), 4.32 (2H, s), 5.94 (2H, s), 6.29 (1H, d, J=7.8 Hz), 6.44

(1H, d, J=8.1 Hz), 6.63 (2H, d, J=8.4 Hz), 6.74-6.76 (2H, m), 6.83-6.87 (2H, m), 7.05-7.11 (1H, m), 7.40 (2H, d, J=8.4 Hz), 7.64 (1H, dd, J=8.4 Hz, 2.3 Hz), 8.17 (1H, d, J=2.1 Hz).

Example 577

Production of 2-(6-{1-[2-(4-benzo[1,3]dioxol-5-ylmethylpiperazin-1-yl)-2-oxoethyl]-1H-indol-5-yloxy}pyridin-3-yl)-1-(4-trifluoro-methylphenyl) ethanone fumarate To a solution of 1-(4-benzo[1,3]dioxol-5-ylmethyl-piperazin-1-yl)-2-[5-(5-bromopyridin-2-yloxy)indol-1-yl]ethanone (0.3 g, 0.55 mmol) in toluene (10 mL) were added tris(dibenzylideneacetone)dipalladium (25 mg, 0.03 mmol) and 4,5-bis(diphenylphospino)-9,9-dimethylxanthene (38 mg, 0.07 mmol), and the reaction mixture was stirred at room temperature for 5 minutes under a nitrogen atomoshere. To the reaction mixture were added 4'-(trifluoromethyl)acetophenone (0.15 g, 0.82 mmol) and potassium bis(trimethylsilyl)amide (0.16 g, 0.82 mmol), and the reaction mixture was stirred at 70-90° C. for 1.5 hours under a nitrogen atomoshere. After cooling water was added to the reaction mixture and the mixture was extracted with AcOEt. The organic layer was washed with brine, dried over anhydrous magnesium sulfate, and evaporated to dryness. The residue was purified by silica gel column chromatography (n-hexane:AcOEt=1:3 to 3:1), and an equimolar amount of fumaric acid was added to the purified substance. After azeotropic removal of residual solvent with EtOH the mixture was recrystallized from acetone and diethyl ether. The precipitate was collected by filtration and dried to afford 0.14 g of the title compound as a pale brown powder.

$^1$H NMR (DMSO-$d_6$) δ 2.18-2.54 (4H, m), 2.88-3.76 (6H, m), 4.48 (2H, s), 5.16 (2H, s), 5.98 (2H, s), 6.39 (1H, d, J=3.0 Hz), 6.76 (1H, dd, J=7.9 Hz, 1.4 Hz), 7.25 (1H, d, J=2.3 Hz), 7.29 (1H, d, J=3.0 Hz), 7.33 (1H, d, J=8.8 Hz), 7.67 (1H, dd, J=8.5 Hz, 2.3 Hz), 7.93 (2H, d, J=8.2 Hz), 7.99 (1H, d, J=2.1 Hz), 8.24 (2H, d, J=8.2 Hz).

The following compound was produced in the same manner as in Example 577 using appropriate starting materials.

Example 578

1-(4-Benzo[1,3]dioxol-5-ylmethylpiperazin-1-yl)-2-(5-{5-[2-(3,4-dichlorophenyl)-2-oxoethyl]pyridin-2-yloxy}indol-1-yl)ethanone fumarate $^1$H NMR (DMSO-$d_6$) δ 2.23-2.68 (4H, m), 3.08-3.61 (6H, m), 4.45 (2H, s), 5.18 (2H, s), 6.00 (2H, s), 6.42 (1H, d, J=3.1 Hz), 6.62 (2H, s), 6.73-6.81 (1H, m), 6.83-6.97 (4H, m), 7.26 (1H, d, J=2.3 Hz), 7.31 (1H, d, J=3.1 Hz), 7.35 (1H, d, J=8.7 Hz), 7.66 (1H, dd, J=8.4 Hz, 2.3 Hz), 7.85 (1H, d, J=8.4 Hz), 7.99 (1H, d, J=2.4 Hz), 8.01 (1H, dd, J=8.4 Hz, 1.9 Hz), 8.27 (1H, d, J=1.9 Hz).

Example 579

Production of 1-{6-[2-(4-benzylpiperazine-1-carbonyl)-1-methyl-1H-indol-5-yloxy]pyridin-3-yl}-3-(3,4-dichlorophenyl)-1-ethylurea hydrobromide To a solution of (4-benzylpiperazin-1-yl)[5-(5-ethyl-aminopyridin-2-yloxy)-1-methyl-1H-indol-2-yl]methanone (280 mg, 0.6 mmol) in THF (6 mL) was added 3,4-dichlorophenyl isocyanate (112 mg, 0.6 mmol) and the reaction mixture was stirred at room temperature for 2 hours. The solvent was evaporated under reduced pressure. The resulting residue was dissolved in AcOEt, and the organic layer was washed with water, saturated aqueous NaHCO$_3$ and brine. The organic layer was dried over anhydrous magnesium sulfate and evaporated to dryness. The residue was purified by silica gel column chromatography (CH$_2$Cl$_2$:MeOH=50:1) to afford a white powder (240 mg). This white powder was dissolved in EtOH and to the solution was added 47% hydrobromic acid (0.042 mL, 0.36 mmol). The reaction mixture was evaporated in vacuo and the residue was recrystallized from AcOEt to afford 155 mg of the title compound as a white powder.

Melting point: 172-177° C. (decomposition)

The following compounds were produced in the same manner as in Example 579 using appropriate starting materials.

Example 580

1-{6-[2-(4-Benzylpiperazine-1-carbonyl)-1-methyl-1H-indol-5-yl-oxy]pyridin-3-yl}-1-ethyl-3-(4-trifluoromethylphenyl)urea hydrobromide Melting point: 224-230° C.

Example 581

1-{6-[2-(4-Benzylpiperazine-1-carbonyl)-1-methyl-1H-indol-5-yl-oxy]pyridin-3-yl}-3-(3,4-dichlorophenyl)-1-ethylthiourea hydrobromide Melting point: 163-168° C.

Example 582

1-{6-[2-(4-Benzo[1,3]dioxol-5-ylmethylpiperazine-1-carbonyl)-1-methyl-1H-indol-5-yloxy]pyridin-3-yl}-1-ethyl-3-(4-trifluoro-methylphenyl)urea hydrobromide Melting point: 176-179° C.

Example 583

1-{6-[2-(4-Benzo[1,3]dioxol-5-ylmethylpiperazine-1-carbonyl)-1-methyl-1H-indol-5-yloxy]pyridin-3-yl}-3-(3,4-dichlorophenyl)-1-ethylurea hydrobromide Melting point: 224-228° C.

Example 584

1-{6-[2-(4-Benzo[1,3]dioxol-5-ylmethylpiperazine-1-carbonyl)-1-methyl-1H-indol-5-yloxy]pyridin-3-yl}-3-(3,4-dichlorophenyl)-1-ethylthiourea hydrochloride Melting point: 152-160° C.

Example 585

1-{6-[2-(4-Benzo[1,3]dioxol-5-ylmethylpiperazine-1-carbonyl)-1-methyl-1H-indol-5-yloxy]pyridin-3-yl}-3-(3,4-dichlorophenyl)-1-methylurea hydrochloride Melting point: 240-243° C.

Example 586

1-{6-[2-(4-Benzo[1,3]dioxol-5-ylmethylpiperazine-1-carbonyl)-1-methyl-1H-indol-5-yloxy]pyridin-3-yl}-1-methyl-3-(4-trifluoro-methylphenyl)urea hydrochloride Melting point: 230-233° C.

Example 587

1-{6-[2-(4-Benzo[1,3]dioxol-5-ylmethylpiperazine-1-carbonyl)-1-methyl-1H-indol-5-yloxy]pyridin-3-yl}-3-(3,4-dichlorophenyl)-1-methylthiourea hydrochloride $^1$H NMR (DMSO-d$_6$) δ 2.98-3.25 (2H, m), 3.24-3.65 (4H, m), 3.57 (3H, s), 3.80 (3H, s), 4.25 (2H, brs), 4.41 (2H, brs), 6.07 (2H, s), 6.75 (1H, s), 6.99 (1H, d, J=8.0 Hz), 6.96-7.08 (2H, m), 7.07 (1H, dd, J=9.1 Hz, 2.2 Hz), 7.24 (1H, s), 7.32 (1H, dd, J=8.8 Hz, 2.2 Hz), 7.37 (1H, d, J=2.2 Hz), 7.54 (1H, d, J=8.8 Hz), 7.57 (1H, d, J=8.8 Hz), 7.61 (1H, d, J=2.5 Hz), 7.83 (1H, dd, J=8.7 Hz, 2.8 Hz), 8.12 (1H, d, J=2.8 Hz), 9.20 (1H, s).

Example 588

1-{6-[2-(4-Benzo[1,3]dioxol-5-ylmethylpiperazine-1-carbonyl)-1-methyl-1H-indol-5-yloxy]pyridin-3-yl}-1-ethyl-3-(4-trifluoro-methylphenyl)thiourea hydrochloride $^1$H NMR (DMSO-d$_6$) δ 1.15 (3H, t, J=7.1 Hz), 3.00-3.22 (2H, m), 3.23-3.49 (2H, m), 3.54 (1H, brs), 3.80 (3H, s), 4.15 (2H, q, J=7.1 Hz), 4.27 (2H, s), 4.41 (1H, brs), 4.65 (2H, brs), 6.07 (2H, s), 6.74 (1H, s), 6.95-7.07 (2H, m), 7.04 (1H, d, J=8.7 Hz), 7.07 (1H, dd, J=8.9 Hz, 2.3 Hz), 7.24 (1H, s), 7.38 (1H, d, J=2.3 Hz), 7.51 (2H, d, J=8.6 Hz), 7.58 (1H, d, J=8.9 Hz), 7.62 (2H, d, J=8.6 Hz), 7.79 (1H, dd, J=8.7 Hz, 2.8 Hz), 8.08 (1H, d, J=2.8 Hz), 9.13 (1H, s).

Example 589

1-{6-[2-(4-Benzo[1,3]dioxol-5-ylmethylpiperazine-1-carbonyl)-1-methyl-1H-indol-5-yloxy]pyridin-3-yl}-1-methyl-3-(4-trifluoro-methylphenyl)thiourea hydrochloride Melting point: 202-207° C.

Example 590

Production of N-{6-[2-(4-benzo[1,3]dioxol-5-ylmethylpiperazine-1-carbonyl)-1-methyl-1H-indol-5-yloxy]pyridin-3-yl}-N-ethyl-4-tri-fluoromethylbenzamide hydrobromide To a solution of {6-[2-(4-benzo[1,3]dioxol-5-ylmethylpiperazine-1-carbonyl)-1-methyl-1H-indol-5-yloxy]pyridin-3-yl}-ethylcarbamic acid tert-butyl ester (290 mg, 0.47 mmol) in CH$_2$Cl$_2$ (2 mL) was added trifluoroacetic acid (2 mL) under ice cooling, and the reaction mixture was stirred at room temperature for 1 hour. The reaction mixture was evaporated under reduced pressure, and to the mixture was added water. The mixture was made alkaline with 5 M NaOH and extracted with AcOEt. The organic layer was washed with brine, dried over anhydrous magnesium sulfate, and evaporated to dryness. The residue was dissolved in CH$_2$Cl$_2$ (2 mL) and cooled with ice. To the solution was added triethylamine (0.1 mL, 0.72 mmol) and subsequently 4-(trifluoromethyl)benzoyl chloride (0.09 mL, 0.61 mmol) dropwise. The reaction mixture was stirred under ice cooling for 1 hour, quenched with water. The organic layer was washed with saturated aqueous NaHCO$_3$ and brine, dried over anhydrous magnesium sulfate, and evaporated to dryness. The residue was purified by silica gel column chromatography (CH$_2$Cl$_2$:MeOH=50:1) to afford a white amorphous powder (230 mg). This white amorphous powder was dissolved in EtOH (2 mL) and to the solution was added 47% hydrobromic acid (0.04 mL, 0.35 mmol) and the reaction mixture was stirred for 1 hour. The reaction mixture was evaporated in vacuo and the residue was recrystallized from EtOH and CH$_2$Cl$_2$ to give 190 mg of the title compound as a white powder.

Melting point: 192-195° C.

Example 591

Production of 2-hydroxy-N-(6-{2-[4-(4-methoxy-benzyl)piperazine-1-carbonyl]-1-methyl-1H-indol-5-yloxy}pyridin-3-yl)-4-trifluoro-methylbenzamide hydrobromide To a solution of 2-methoxymethoxy-4-trifluoromethylbenzoic acid (530 mg, 2.12 mmol) in dry CH$_2$Cl$_2$ (2 mL) were added oxalyl chloride (0.22 mL, 2.52 mmol) and dry DMF (2 drops), and the reaction mixture was stirred at room temperature for 1 hour. The reaction mixture was evaporated under reduced pressure and the residue was dissolved in AcOEt (4 mL). Half of this solution (2 mL) was added dropwise under ice cooling to a solution of [5-(5-aminopyridin-2-yloxy)-1-methyl-1H-indol-2-yl][4-(4-methoxy-benzyl)piperazin-1-yl]methanone (400 mg, 0.848 mmol) and triethylamine (0.15 mL, 1.076 mmol) in AcOEt (2 mL), and the reaction mixture was stirred at the same temperature for 1 hour. To the reaction mixture were added water and saturated aqueous NaHCO$_3$, and extracted with CH$_2$Cl$_2$ and AcOEt individually. The organic layers were washed with brine, dried over anhydrous magnesium sulfate, and evaporated to dryness. The residues were combined and purified by silica gel column chromatography (AcOEt:acetone=10:1). The purified substance was dissolved in CH$_2$Cl$_2$ (2 mL) and to the solution was added trifluoroacetic acid (2 mL) under ice cooling. The reaction mixture was stirred at room temperature for 1 hour. After removal of the solvent in vacuo, AcOEt and saturated aqueous NaHCO$_3$ were added to the residue. The organic layer was washed with brine, dried over anhydrous magnesium sulfate, and evaporated to dryness. The residue was purified by silica gel column chromatography (AcOEt:acetone=8:1) to give a white amorphous powder (120 mg). This amorphous powder was dissolved in EtOH (2 mL) and 47% hydrobromic acid (0.016 mL, 0.14 mmol) was added to the solution. The reaction mixture was stirred at room temperature for 1 hour. The reaction mixture was evaporated in vacuo and the residue was recrystallized from EtOH to give 80 mg of the title compound as a white powder.

Melting point: 218-221° C. (decomposition)

The following compounds were produced in the same manner as in Example 591 using appropriate starting materials.

Example 592

2-Hydroxy-N-(6-{2-[4-(4-methoxybenzyl)piperazine-1-carbonyl]-1-methyl-1H-indol-5-yloxy}pyridin-3-yl)-N-methyl-4-trifluoromethylbenzamide oxalate Melting point: 171-173° C.

Example 593

Production of N-[6-(2-{4-[(4-methoxybenzyl)methylamino]-piperidine-1-carbonyl}-1-methyl-1H-indol-5-yloxy)pyridin-3-yl]-N-methyl-4-trifluoromethylbenzamide oxalate To a solution of (4-methoxybenzyl)methyl(piridine-4-yl)amine dihydrochloride (390 mg, 1.27 mmol) in DMF (2 mL) was added trietylamine (0.45 mL, 3.23 mmol) and the reaction mixture was stirred at room temperature for 30 minutes. To the reaction mixture were added 1-methyl-5-[5-(4-trifluoromethylbenzoylamino)-pyridin-2-yloxy]-1H-indole-2-carboxylic acid (480 mg, 1.05 mmol), 1-ethyl-3-(3-dimethylaminopropyl)carbodiimide hydrochloride (310 mg, 1.62 mmol) and 1-hydroxybenzotiriazole monohydrate (210 mg, 1.39 mmol), and the reaction mixture was stirred at room temperature overnight. The solvent was removed in vacuo and to the residue were added AcOEt and saturated aqueous $NaHCO_3$. The organic layer was washed with water and brine, dried over anhydrous magnesium sulfate, and evaporated to dryness. The residue was purified by silica gel column chromatography ($CH_2Cl_2$:MeOH=40:1). The purified substance was dissolved in dry DMF (4 mL) under Ar and cooled with ice. To the solution were added iodomethane (0.05 mL, 0.803 mmol) and 60% sodium hydride in oil (50 mg, 1.25 mmol), and the mixture was stirred under ice cooling for 1 hour. The reaction mixture was quenched with water and extracted with AcOEt. The organic layer was washed with water and brine, dried over anhydrous magnesium sulfate, and evaporated to dryness. The residue was purified by silica gel column chromatography (AcOEt:acetone=10:1) to give a white amorphous powder (170 mg). This amorphous powder was dissolved in AcOEt (2 mL). Oxalic acid dihydrate (31 mg) was added to the solution and the reaction mixture was stirred at room temperature for 1 hour. To the reaction mixture were added diethyl ether and acetone. The resulting precipitate was collected and dried to give 140 mg of the title compound as a white powder.

Melting point: 121-123° C.

The following compounds were produced in the same manner as in Reference Example 255 using appropriate starting materials.

Example 594

N-(6-{2-[4-(4-Difluoromethoxybenzyl)piperazine-1-carbonyl]-1-methyl-1H-indol-5-yloxy}pyridin-3-yl)-2-hydroxy-N-methyl-4-tri-fluoromethylbenzamide oxalate Melting point: 155-160° C.

Example 595

Production of 2-hydroxy-N-methyl-N-[6-(1-methyl-2-{4-[4-(2,2,2-trifluoroethoxy)benzyl]piperazine-1-carbonyl}-1H-indol-6-yloxy)-pyridin-3-yl]-4-trifluoromethylbenzamide hydrobromide To a stirred solution of acetic acid 2-{methyl[6-(1-methyl-2-{4-[4-(2,2,2-trifluoroethoxy)benzyl]piperazine-1-carbonyl}-1H-indol-6-yloxy)pyridin-3-yl]carbamoyl}-5-trifluoro-methylphenyl ester (460 mg, 0.59 mmol) in MeOH (5 mL) was added potassium carbonate (65 mg, 0.47 mmol), and the mixture was stirred at room temperature for 1 hour. Water was added to the mixture, and the aqueous layer was extracted with AcOEt. The organic layer was washed with saturated aqueous $NaHCO_3$ and brine, dried over anhydrous magnesium sulfate, and evaporated to dryness. The residue was purified by silica gel column chromatography ($CH_2Cl_2$:MeOH=50:1). The purified substance was dissolved in diethyl ether, and an equimolar of 47% hydrobromic acid was added to the solution. The resulting precipitate was collected by filtration, and then dried in vacuo to give 0.36 g of the title compound as a white powder.

$^1$H NMR (DMSO-$d_6$) δ 3.17 (3H, s), 3.05-3.55 (6H, m), 3.71 (3H, s), 4.37 (2H, s), 4.30-4.60 (2H, m), 4.82 (2H, q, J=8.0 Hz), 6.73 (1H, d, J=8.3 Hz), 6.80 (1H, s), 6.87 (1H, d, J=8.9 Hz), 6.88 (1H, s), 7.05 (1H, d, J=7.6 Hz), 7.18 (2H, d, J=8.6 Hz), 7.24 (1H, s), 7.37 (1H, d, J=7.6 Hz), 7.53 (2H, d, J=8.6 Hz), 7.58 (1H, d, J=8.6 Hz), 7.75 (1H, d, J=8.9 Hz), 7.92 (1H, s), 9.98 (1H, brs).

Example 596

Production of N-(6-{2-[4-(4-difluoromethoxybenzyl)-4-oxy-piperazine-1-carbonyl]-1-methyl-1H-indol-5-yloxy}pyridin-3-yl)-N-methyl-4-trifluoromethylbenzamide To a solution of N-(6-{2-[4-(4-difluoromethoxybenzyl)-piperazine-1-carbonyl]-1-methyl-1H-indol-5-yloxy}pyridin-3-yl)-N-methyl-4-trifluoromethylbenzamide maleate (470 mg, 0.577 mmol) in AcOEt (10 ml) was added saturated aqueous $NaHCO_3$ (10 ml) and the mixture was stirred vigorously for 10 minutes. The organic layer was separated and washed with brine, dried over anhydrous magnesium sulfate and evaporated to dryness. To a solution of the residue in $CH_2Cl_2$ (12 ml) was added 3-chloroperbenzoic acid (75%, 139 mg, 0.604 mmol) under ice cooling and the mixture was stirred for 5 minutes under ice cooling. After the addition of saturated aqueous $NaHCO_3$, the reaction mixture was extracted with $CH_2Cl_2$. The organic layer was separated and washed with brine, dried over anhydrous magnesium sulfate and evaporated. The residue was purified by silica gel column chromatography ($CH_2Cl_2$:MeOH=20:1 to 1:3) to afford 170 mg of the title compound as a pale yellow amorphous powder.

$^1$H NMR (CDCl$_3$) δ 2.07 (2H, brs), 3.11 (2H, d, J=10.2 Hz), 3.23-3.27 (2H, m), 3.47 (3H, s), 3.83 (3H, s), 4.09 (1H, brs), 4.39 (3H, s), 6.54 (1H, t, J=72.9 Hz), 6.56 (1H, s), 6.84 (1H, d, J=8.9 Hz), 7.04 (1H, dd, J=8.9 Hz, 2.0 Hz), 7.18 (2H, d, J=8.2 Hz), 7.30 (1H, d, J=2.0 Hz), 7.36-7.39 (4H, m), 7.50 (2H, d, J=8.2 Hz), 7.58 (2H, d, J=8.6 Hz), 7.80 (1H, s).

The following compounds were produced in the same manner as in Example 596 using appropriate starting materials.

Example 597

N-(6-{2-[4-(4-Difluoramethoxybenzyl)-4-oxypiperazine-1-carbonyl]-1-methyl-1H-indol-6-yloxy}pyridin-3-yl)-2-fluoro-N-methyl-4-tri-fluoramethylbenzamide Melting point: 151.3-154.4° C.

Example 598

N-Methyl-N-[6-(1-methyl-2-{4-oxy-4-[4-(2,2,2-trifluoroethoxy)-benzyl]piperazine-1-carbonyl}-1H-indol-6-yloxy)pyridin-3-yl]-methanesulfonamide Melting point: 153.4-155.5° C.

Example 599

Production of N-methyl-N-[6-(2-{4-[4-(2,2,2-trifluoroethoxy)-benzyl]piperazine-1-carbonyl}-1H-indol-6-yloxy)pyridin-3-yl]-4-trifluoromethylbenzamide To a solution of M-methyl-N-[6-(1-methoxymethyl-2-{4-[4-(2,2,2-trifluoroethoxy)benzyl]piperazine-1-carbonyl}-1H-indol-6-yloxy)pyridin-3-yl]-4-trifluoromethylbenzamide (0.24 g, 0.31 mmol) in MeOH (12 mL) were added veratrole (0.43 g, 3.1 mmol) and 2 M HCl (6 mL), and the mixture was stirred under reflux for 7 hours. The solvent was evaporated in vacuo, and the residue was extracted with AcOEt. The organic layer was washed with saturated aqueous NaHCO$_3$ and brine, dried over anhydrous sodium sulfate and evaporated. The residue was purified by silica gel column chromatography (AcOEt) to give 0.34 g of the title compound as a colorless powder.

$^1$H NMR (CDCl$_3$) δ 2.54 (4H, s), 3.47 (3H, s), 3.51 (2H, s), 3.91 (4H, s), 4.35 (2H, q, J=8.1 Hz), 6.74 (1H, s), 6.84 (1H, d, J=8.6 Hz), 6.85 (1H, dd, J=8.6 Hz, 2.2 Hz), 6.92 (2H, d, J=8.6 Hz), 7.15 (1H, s), 7.29 (2H, d, J=8.6 Hz), 7.40 (3H, d, J=7.8 Hz), 7.50 (2H, d, J=7.9 Hz), 7.60 (1H, d, J=8.6 Hz), 7.80 (1H, s), 9.25 (1H, s).

Pharmacological Test 1
Inhibitory Effect on Collagen Synthesis (In Vitro)

LI90 cells, a human hepatic stellate cell line, were suspended in DMEM (Dulbecco's modified eagle medium) supplemented with 10% inactivated FBS (fetal bovine serum), seeded on a 12-well plate and cultured in a CO$_2$ incubator (preset temperature: 37° C., preset CO$_2$ concentration: 5%). After being cultured for 24 hours, the cells were washed with D-PBS (Dulbecco's phosphate buffered saline), placed in MEM (Eagle's minimum essential medium) supplemented with 0.1% inactivated FBS and then cultured in a CO$_2$ incubator. After being cultured for 3 days, the cells were again washed with D-PBS, placed in MEM (Eagle's minimum essential medium) supplemented with 0.1% inactivated FBS and treated with or without a test compound in the presence of 10 μM recombinant human TGF-β1 (transforming growth factor-β1) in a CO$_2$ incubator for 16 hours. After the incubation, the cells were washed with D-PBS and the medium was replaced with MEM containing 0.25 mM ascorbate. A radio-labeled compound, $^3$H-proline, was then added to the culture medium to radio-label the collagen proteins produced. After being cultured for 24 hours, the supernatant was collected and the collagen proteins were extracted from the supernatant as acid-soluble fractions. The amount of collagen produced was determined by measuring the radioactivity contained in the fractions. A concentration of test compound that produced 50% inhibition [IC$_{50}$ value (nM)] on collagen synthesis was calculated by comparing the radioactivity count in a supernatant of test-compound-treated cells with that of untreated cells (control).

The results are shown in Table 1.

TABLE 1

| Test compound | Collagen synthesis inhibitory activity IC$_{50}$ (nM) |
|---|---|
| Compound of Example 41 | <10 |
| Compound of Example 43 | <10 |
| Compound of Example 232 | <10 |
| Compound of Example 253 | <10 |
| Compound of Example 279 | <10 |
| Compound of Example 357 | <10 |
| Compound of Example 380 | <10 |
| Compound of Example 401 | <10 |
| Compound of Example 424 | <10 |
| Compound of Example 428 | <10 |
| Compound of Example 436 | <10 |
| Compound of Example 473 | <10 |
| Compound of Example 547 | <10 |
| Compound of Example 572 | <10 |

Pharmacological Test 2
Antiproliferative Effect on Cancer Cells (In Vitro)

Growth inhibition of human hepatic cancer cells (HuH-7) was determined by the sulforhodamine B method based on the method of Skehan P. et al. (J Natl Cancer Inst. 1990 Jul. 4; 82(13): 1107-12). In the study, HuH-7 cells were seeded in DMEM medium containing 10% fetal bovine serum in a 96-well microplate. After 24-hour incubation at 37° C. in the presence of 5% carbon dioxide, the test compound was added and the cells were incubated for another 5 days. After incubation, a trichloroacetic acid solution was added to yield the final concentration of 10% and the cells were left to stand at 4° C. for 1 hour to fix. Then, the cells were washed with water to remove the medium and trichloroacetic acid and dried in the air. The dried cells were stored at 4° C. until they were stained with sulforhodamine B. To each well, 1% acetic acid solution containing 0.4% sulforhodamine B was added and left to stand for 20 to 30 minutes at room temperature. After discarding the supernatant, each well was washed with 1% acetic acid solution, and 10 mM Tris (tris-hydroxyaminomethane) solution was added while stirring to elute the dye taken into the cells. Then, the optical density was determined at the measurement wavelength of 492 nm and the reference wavelength of 690 nm, and the difference was calculated. The cell growth activity in each well was defined as the value determined by subtracting the OD in the control well not containing cells (the difference in absorbance between 492 nm and 690 nm) from that in the test well.

The 50% inhibitory concentration (IC$_{50}$ (nM)) of the test compound was determined by comparing the cell growth activity in the well containing the test compound with that of the control not containing the test compound.

The growth inhibition on human pancreatic cancer cells (HPAC) was also determined by the above method using HPAC instead of HuH-7 and RPMI 1640 medium containing 10% fetal bovine serum instead of the DMEM medium containing 10% fetal bovine serum.

The growth inhibition on human chronic myelocytic leukemia cells (KU812) was determined by a WST-8 assay according to the method of Singh A K, et al. (Cancer Lett. 1996 Oct. 1; 107(1): 109-15.). In this method, KU812 cells were seeded in RPMI 1640 medium containing 10% fetal bovine serum in a 96-well microplate and incubated at 37° C. for 24 hours in the presence of 5% carbon dioxide. Then, the test compound was added and the cells were incubated for another 5 days. After incubation, 15 μL of 5 mM WST-8 (2-(2-methoxy-4-nitrophenyl)-3-(4-nitrophenyl)-5-(2,4-disulfenyl)-2H-tetrazolium, monosodium salt) was added and the cells were incubated for 2 hours. After the 2-hour incubation, 15 μL of 1% SDS (sodium dodecyl sulfate) was added and the optical density was determined at the measurement wavelength of 450 nm and the reference wavelength of 630 nm, and the difference was calculated. The cell growth activity in each well was defined as the value determined by subtracting the OD in the control well not containing cells (the difference in absorbance between 492 nm and 690 nm) from that in the test well.

The 50% inhibitory concentration ($IC_{50}$ (nM)) of the test compound was determined by comparing the cell growth activity in the well containing the test compound with that of the control not containing the test compound.

The results are shown in Table 2.

TABLE 2

| Test compound | HuH-7 $IC_{50}$(nM) | HPAC $IC_{50}$(nM) | KU812 $IC_{50}$(nM) |
|---|---|---|---|
| Compound of Example 73 | <10 | <70 | <2 |
| Compound of Example 253 | <10 | <70 | <2 |
| Compound of Example 338 | <10 | <70 | <2 |
| Compound of Example 368 | <10 | <70 | <2 |
| Compound of Example 391 | <10 | <70 | <2 |
| Compound of Example 401 | <10 | <70 | <2 |
| Compound of Example 424 | <10 | <70 | <2 |
| Compound of Example 428 | <10 | <70 | <2 |
| Compound of Example 436 | <10 | <70 | <2 |
| Compound of Example 473 | <10 | <70 | <2 |
| Compound of Example 521 | <10 | <70 | <2 |
| Compound of Example 571 | <10 | <70 | <2 |

Pharmacological Test 3
Antitumor Effect on Hepatic Cancer Cells, HuH-7 (In Vivo)

Human hepatic cancer cells (HuH-7) were transplanted in SCID mice (6 females/group) and the inhibitory effect of the invention on their growth was examined. In the study, 0.2 mL of a cell suspension adjusted to contain $2.5 \times 10^7$ cells/mL was injected subcutaneously in the right axilla to prepare tumor bearing mice. When the tumor diameter became 5 mm or more, the animals were allocated to groups based on the tumor volume. The test compound was administered orally as a suspension in 5% gum arabic, once daily, for 9 consecutive days. The control group received 5% gum arabic. Tumor volumes were measured on the following day of the last administration. The relative tumor volume was determined by calculating the ratio of the tumor volume on the following day of the last administration to that at group allocation. The ratio of the relative tumor volume in the treatment group to that in the control group (T/C %) was calculated as the index for the effect.

Relative tumor volume=Tumor volume on the following day of the last administration/Tumor volume at group allocation.

T/C %=(Mean relative tumor volume in the treatment group/Mean relative tumor volume in the control group)×100.

The results are shown in Table 3.

TABLE 3

| Test compound | dose (mg/kg/day) | T/C % |
|---|---|---|
| Compound of Example 401 | 10 | <50 |
| Compound of Example 445 | 10 | <50 |
| Compound of Example 473 | 10 | <50 |

TABLE 3-continued

| Test compound | dose (mg/kg/day) | T/C % |
|---|---|---|
| Compound of Example 493 | 10 | <50 |
| Compound of Example 521 | 10 | <50 |

Pharmacological Test 4
Inhibitory Effect on IL-6-induced STAT3 Phosphorylation in Human Myeloma Cells (In Vitro)

The inhibitory effect of the test compound on phosphorylation of STAT3 (signal transducer and activator of transcription-3) in human myeloma cells (U26631) induced by interleukin-6 (IL-6) was examined using the modified method of Tochizawa S. et al. (J Immunol Methods. 2006 Jun. 30; 313 (1-2): 29-37). In the study, U266B1 cells were seeded in an RPMI 1640 medium containing 10% fetal bovine serum (FBS) in a 12-well plate and incubated at 37° C. for 2 hours in the presence of carbon dioxide. After incubation, IL-6 was added to yield the concentration of 1 ng/mL and the cells were incubated at 37° C. for 15 minutes in the presence of 5% carbon dioxide. After fixation of the cells by the addition of a buffer containing formaldehyde (Lyse/Fix Buffer, BD Biosciences) at room temperature for 10 minutes, the suspension was centrifuged to remove the supernatant and the cells were treated with ice-cold methanol for 10 minutes to improve the permeability of the cell membrane. The cells were centrifuged to remove methanol and washed twice with Dulbecco's phosphate buffered saline (D-PBS) containing 2% fetal bovine serum (FBS). A fluorescence-labeled anti-phosphorylated STAT3 (pSTAT3) antibody (Alexa Fluor 488-labeled anti-pSTAT3 (Y705) antibody, BD Biosciences) was added for staining in an ice bath for 30 minutes.

The cells were washed once with 2% FBS-containing D-PBS and suspended in 2% FBS-containing D-PBS, and the fluorescence intensity was determined using a flow cytometer (FACS Sort, BD Biosciences). The ratio of fluorescence intensity in the test group to the control group (T/C) was determined from the difference in the geometric mean of pSTAT3 fluorescence intensity between the test compound group of each concentration and the non-stimulated control group according to the following equation by defining the difference in the geometric mean of pSTAT3 fluorescence intensity between the IL-6 induced control and the non-stimulated control as 100%.

T/C(%)=(Multiply mean of pSTAT3 fluorescence intensity in the cells treated with the test compound—geometric mean of pSTAT3 fluorescence intensity in non-stimulated control)/(geometric mean of fluorescence intensity of IL-6-induced pSTAT3 in the control–geometric mean of pSTAT3 fluorescence intensity in non-stimulated control)×100.

The concentration of the test compound inhibiting phosphorylation of STATS at 50% ($IC_{50}$; concentration of the test compound corresponding to 50% T/C(%)) was determined using T/C(%) values at the respective concentrations and defined as the index for the inhibitory activity.

The results are shown in Table 4.

TABLE 4

| Test compound | STAT3 phosphorylation inhibitory activity $IC_{50}$ (nM) |
|---|---|
| Compound of Example 321 | <10 |
| Compound of Example 338 | <10 |
| Compound of Example 342 | <10 |

TABLE 4-continued

| Test compound | STAT3 phosphorylation inhibitory activity IC$_{50}$ (nM) |
|---|---|
| Compound of Example 401 | <10 |
| Compound of Example 403 | <10 |
| Compound of Example 417 | <10 |
| Compound of Example 420 | <10 |
| Compound of Example 421 | <10 |
| Compound of Example 436 | <10 |
| Compound of Example 445 | <10 |
| Compound of Example 493 | <10 |
| Compound of Example 507 | <10 |
| Compound of Example 525 | <10 |
| Compound of Example 526 | <10 |

The invention claimed is:

1. A heterocyclic compound or a salt thereof represented by General Formula (1):

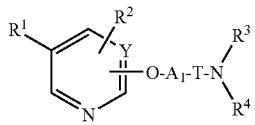

(1)

wherein $R^1$ is a group $R^5$—$Z_1$—, a group $R^5$—B—N($R^6$)—, a group $R^5$—N($R^6$)—B—, a group $R^5$—N($R^7$)—, a group $R^5$—N($R^8$)—CO—N($R^9$)—, a group $R^5$—N($R^{10}$)—CS—N($R^{11}$)—, a group $R^5$—SO$_2$—N($R^{12}$)—, a group $R^5$—CO—$B_1$—, a group $R^5$—$B_2$—CO—N($R^{12a}$)—, a group $R^5$—$B_9$—SO$_2$—N($R^{47}$)—, a group $R^5$—O—$B_{10}$—SO$_2$—N($R^{48}$)— or a group represented by General Formula:

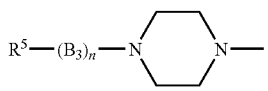

where $Z_1$ is a lower alkylene group or a lower alkenylene group;

$R^5$ is a heterocyclic group selected from the group consisting of pyrrolidinyl, piperidinyl, piperazinyl, morpholinyl, pyridyl, 1,2,5,6-tetrahydropyridyl, 1,2,4-triazolyl, 1,2,3-triazolyl, 1,2,5-triazolyl, thiazolidinyl, 1,2,3,4-tetrazolyl, thienyl, quinolyl, 1,4-dihydroquinolyl, benzothiazolyl, pyrazinyl, pyrimidyl, pyridazyl, 2H-pyrrolyl, pyrrolyl, 1,3,4-oxadiazolyl, tetrahydropyranyl, tetrahydrofuryl, furazanyl, carbostyril, 3,4-dihydrocarbostyril, 1,2,3,4-tetrahydroquinolyl, 1,2,3,4-tetrahydroisoquinolyl, indolyl, isoindolyl, indolinyl, benzimidazolyl, benzoxazolyl, imidazolidinyl, isoquinolyl, quinazolidinyl, quinoxalinyl, cinnolinyl, phthalazinyl, carbazoyl, acridinyl, chromanyl, isoindolinyl, isochromanyl, pyrazolyl, imidazolyl, pyrazolidinyl, phenothiazinyl, benzofuryl, 2,3-dihydrobenzo[b]furyl, benzothienyl, phenoxathiinyl, phenoxazinyl, 4H-chromenyl, 1H-indazolyl, phenazinyl, xanthenyl, thianthrenyl, 2-imidazolinyl, 2-pyrrolinyl, furyl, oxazolyl, isoxazolyl, isoxazolidinyl, thiazolyl, isothiazolyl, pyranyl, 2-thiazolinyl, 2-pyrazolinyl, quinuclidinyl, 1,4-benzoxadinyl, 3,4,-dihydro-2H-1,4-benzoxadinyl, 3,4-dihydro-2H-1,4-benzothiazinyl, 1,4-benzothiazinyl, 1,2,3,4-tetrahydroquinoxalinyl, 1,3-dithia-2,4-dihydronaphthalenyl, phenanthridinyl, 1,4-dithianaphthalenyl, dibenz[b,e]azepine, 6,11-dihydro-5H-dibenz[b,e]azepine, and imidazo[2,1-b]thiazolyl groups (wherein the heterocyclic ring may be substituted by 1 to 3 groups selected from the group consisting of oxo group; lower alkoxy groups optionally substituted by one or more halogen atoms; lower alkyl groups optionally substituted by one or more halogen atoms; halogen atoms; lower alkylsulfonyl groups; phenyl groups optionally substituted, on the phenyl ring, by one or more optionally halogenated lower alkyl groups; lower alkylthio groups; pyrrolyl groups; benzoyl group; lower alkanoyl groups; lower alkoxycarbonyl groups; lower alkylenedioxy groups; pyridyl groups; and amino groups that may have at least one substituent selected from the group consisting of lower alkyl groups and lower alkanoyl groups), optionally halogenated lower alkyl groups, cycloalkyl groups, naphthyl group that may have, on the naphthalene ring, 1 to 3 substituents selected from the group consisting of lower alkyl groups, halogen atoms, and amino groups optionally substituted by at least one substituent selected from the group consisting of lower alkyl groups and lower alkanoyl groups, or a group represented by General Formula:

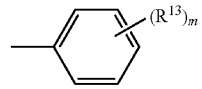

wherein $R^{13}$ is a hydrogen atom, a hydroxy group, a carboxy group, a halogen atom, a lower alkyl group optionally substituted by one or more halogen atoms, a lower alkoxy group optionally substituted by one or more halogen atoms or lower alkoxy groups; a lower alkanoyloxy group, a lower alkoxycarbonyl group, a lower alkoxycarbonyl group-substituted lower alkyl group, a cyano group, a phenyl group, a nitro group, a lower alkanoylamino group, a lower alkylenedioxy group, a phenoxy group, a pyrazolyl group optionally substituted by one or more lower alkyl groups, an oxazolyl group, or a pyrrolyl group;

m is an integer from 1 to 5, when m is any one of 2 to 5, the 2 to 5 of $R^{13}$s may be the same or different;

$R^{47}$ and $R^{48}$ are a hydrogen atom or a lower alkyl group;

$R^6$ is a hydrogen atom, a lower alkyl group optionally substituted by one or more lower alkoxy groups, a lower alkanoyl group, a lower alkylsulfonyl group, or a phenyl lower alkyl group;

B is a group —CO— or a lower alkylene group;

$R^7$ is a hydrogen atom or a lower alkyl group;

$R^8$, $R^9$, $R^{10}$ and $R^{11}$ are a hydrogen atom or a lower alkyl group;

$R^{12}$ and $R^{12a}$ are a hydrogen atom or a lower alkyl group;

$B_1$ and $B_3$ are a lower alkylene group;

n is 0 or 1;

$B_2$ is a lower alkenylene group;

$B_9$ is a lower alkylene group or a lower alkenylene group;

$B_{10}$ is a lower alkylene group;

$R^2$ is a hydrogen atom or a lower alkyl group;

Y is CH;

$A_1$ is a heterocyclic ring selected from the group consisting of indolediyl groups and indolinediyl groups, wherein the heterocyclic ring may have at least one substituent;

T is a group —N($R^{14}$)—$B_4$—CO—, a group —$B_5$—CO— or a group —CO—;

$R^{14}$ is a hydrogen atom, a lower alkyl group optionally substituted by one or more halogen atoms, a cycloalkyl group, a cycloalkylcarbonyl group, a lower alkanoyl group optionally substituted by one or more halogen atoms, a lower alkenyl group, an amino substituted lower alkanoyl group optionally substituted by one or more lower alkyl groups, or a lower alkylsulfonyl group;

$B_4$ is a lower alkylene group;

$B_5$ is a lower alkenylene group or a lower alkylene group optionally substituted by one or more hydroxy groups; and $R^3$ and $R^4$, together with the nitrogen atom to which they bind, bind to each other, via a nitrogen atom and form a piperidine ring that may have at least one substituent or a piperazine ring that may have at least one substituent.

2. The heterocyclic compound or a salt thereof according to claim 1, wherein $R^3$ and $R^4$, together with the nitrogen atom to which they bind, via a nitrogen atom, form a piperazine ring with one benzyl group that may have at least one substituent.

3. The heterocyclic compound or a salt thereof according to claim 1, wherein $R^1$ is a group $R^5$—$SO_2$—$N(R^{12})$— or a group $R^5$—B—$N(R^6)$—, wherein $R^5$ is a group represented by General Formula;

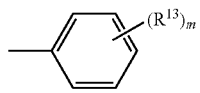

wherein m, B, $R^{13}$, $R^{12}$ and $R^6$ are the same as described above.

4. A pharmaceutical composition comprising the heterocyclic compound or a salt thereof represented by the General Formula (1) of claim 1, and a pharmacologically acceptable carrier.

5. The heterocyclic compound according to claim 1 or a salt thereof, which is selected from the group consisting of:

4,N-Dimethyl-N-[6-(2-{4-[4-(2,2,2-trifluoroethoxy)benzyl]piperazine-1-carbonyl}-1H-indol-6-yloxy)pyridin-3-yl]benzenesulfonamide, N-[6-(2-{4-[(4-Methoxybenzyl)methylamino]piperidine-1-carbonyl}-1-methyl-1H-indol-5-yloxy)pyridin-3-yl]-4-trifluoromethylbenzamide, 2-Chloro-N-(6-{2-[4-(4-isopropoxybenzyl)piperazine-1-carbonyl]-1-methyl-1H-indol-6-yloxy}pyridin-3-yl)-4-trifluoromethylbenzamide, N-[6-(2-{4-[4-(2-Fluoro-1-fluoromethylethoxy)benzyl]piperazine-1-carbonyl}-1-methyl-1H-indol-6-yloxy)pyridin-3-yl]-N-methyl-4-trifluoromethoxybenzamide, N-[6-(2-{4-[(E)-3-(4-Methoxyphenyl)allyl]piperazine-1-carbonyl}-1-methyl-1H-indol-5-yloxy)pyridin-3-yl]-4-trifluoromethylbenzamide, N-(6-{2-[4-(4-Difluoromethoxybenzyl)piperazine-1-carbonyl]-1-methyl-1H-indol-5-yloxy}pyridin-3-yl)-N-methyl-4-trifluoromethylbenzamide, N-(6-{2-[4-(6-Isopropoxypyridin-3-ylmethyl)piperazine-1-carbonyl]-1-methyl-1H-indol-5-yloxy}pyridin-3-yl)-N-methyl-4-trifluoromethylbenzamide, N-(6-{2-[4-(4-Isopropylbenzyl)piperazine-1-carbonyl]-1,4-dimethyl-1H-indol-5-yloxy}pyridin-3-yl)-N-methyl-4-trifluoromethylbenzamide, N-Methyl-N-[6-(1-methyl-2-{4-[4-(2,2,2-trifluoroethoxy)benzyl]piperazine-1-carbonyl}-1H-indol-6-yloxy)pyridin-3-yl]-4-trifluoromethylbenzamide, N-(6-{2-[4-(4-Difluoromethoxybenzyl)piperazine-1-carbonyl]-1-methyl-1H-indol-6-yloxy}pyridin-3-yl)-N-methyl-4-trifluoromethoxybenzamide, N-{6-[2-(4-Isobutylpiperazine-1-carbonyl)-1-methyl-1H-indol-5-yloxy]pyridin-3-yl}-4-trifluoromethylbenzamide, N-[6-(1-Methyl-2-{4-[2-(4-trifluoromethylphenyl)thiazol-5-ylmethyl]piperazine-1-carbonyl}-1H-indol-5-yloxy)pyridin-3-yl]-4-trifluoromethylbenzamide, 4-Methoxy-N-methyl-N-[6-(1-methyl-2-{4-[4-(2,2,2-trifluoroethoxy)benzyl]piperazine-1-carbonyl}-1H-indol-6-yloxy)pyridin-3-yl]benzenesulfonamide, N-(6-{2-[4-(4-Methoxybenzyl)piperazine-1-carbonyl]-1-methyl-1H-indol-5-yloxy}pyridin-3-yl)-N-methyl-4-trifluoromethylbenzamide, N-(6-{2-[4-(4-Ethoxybenzyl)piperazine-1-carbonyl]-1-methyl-1H-indol-5-yloxy}-2-methylpyridin-3-yl)-N-methyl-4-trifluoromethylbenzamide, N-(6-{2-[4-(4-Ethylbenzyl)piperazine-1-carbonyl]-1-methyl-1H-indol-5-yloxy}pyridin-3-yl)-N-methyl-4-trifluoromethylbenzamide, N-(6-{1-Methyl-2-[4-(4-[1,2,3]thiadiazol-4-ylbenzyl)piperazine-1-carbonyl]-1H-indol-6-yloxy}pyridin-3-yl)-4-trifluoromethylbenzamide, N-[6-(2-{4-[4-(2-Fluoro-1-fluoromethylethoxy)benzyl]piperazine-1-carbonyl}-1-methyl-1H-indol-6-yloxy)pyridin-3-yl]-N-methyl-4-trifluoromethylbenzamide, N-[6-(2-{4-[4-(2-Fluoro-1-fluoromethylethoxy)benzyl]piperazine-1-carbonyl}-1-methyl-1H-indol-6-yloxy)pyridin-3-yl]-2-methyl-4-trifluoromethylbenzamide, N-(6-{2-[4-(4-Cyanobenzyl)piperazine-1-carbonyl]-1-methyl-1H-indol-6-yloxy}pyridin-3-yl)-N-methyl-4-trifluoromethylbenzamide, N-(6-{2-[4-(4-Ethoxybenzyl)piperazine-1-carbonyl]-1-methyl-1H-indol-5-yloxy}pyridin-3-yl)-N-methyl-4-trifluoromethylbenzamide, N-Methyl-N-[6-(1-methyl-2-{4-[4-(1,1,2,2-tetrafluoroethoxy)benzyl]piperazine-1-carbonyl}-1H-indol-5-yloxy)pyridin-3-yl]-4-trifluoromethylbenzamide, N-(6-{2-[4-(5-Ethoxypyridin-2-ylmethyl)piperazine-1-carbonyl]-1-methyl-1H-indol-5-yloxy}pyridin-3-yl)-N-methyl-4-trifluoromethylbenzamide, N-Methyl-N-(6-{1-methyl-2-[4-(4-propoxybenzyl)piperazine-1-carbonyl]-1H-indol-6-yloxy}pyridin-3-yl)-4-trifluoromethylbenzamide, N-(6-{2-[4-(4-Isopropoxybenzyl)piperazine-1-carbonyl]-1-methyl-1H-indol-6-yloxy}pyridin-3-yl)-N-methyl-4-trifluoromethylbenzamide, 3,4-Dichloro-N-(6-{2-[4-(4-isopropoxybenzyl)piperazine-1-carbonyl]-1-methyl-1H-indol-6-yloxy}pyidin-3-yl)-N-methylbenzenesulfonamide, N-(6-{2-[4-(4-Isopropoxybenzyl)piperazine-1-carbonyl]-1-methyl-1H-indol-6-yloxy}pyridin-3-yl)-4,N-dimethylbenzenesulfonamide, N-(6-{2-[4-(2,2-Difluorobenzo[1,3]dioxol-5-ylmethyl)piperazine-1-carbonyl]-1-methyl-1H-indol-6-yloxy}pyridin-3-yl)-4,N-dimethylbenzenesulfonamide, N-{6-[2-(4-Benzo[1,3]dioxol-5-ylmethylpiperazine-1-carbonyl)-1-methyl-1H-indol-5-yloxy]pyridin-3-yl}-4-trifluoromethylbenzamide, N-{6-[2-(4-benzo[1,3]dioxol-5-ylmethylpiperazine-1-carbonyl)-1-methyl-1H-indol-5-yloxy]pyridin-3-yl}-N-methyl-4-trifluoromethylbenzamide, N-(6-{2-[4-(4-Methoxybenzyl)piperazine-1-carbonyl]-1-methyl-1H-indol-5-yloxy}pyridin-3-yl)-4-trifluoromethylbenzamide, N-(6-{2-[4-(4-Ethoxybenzyl)piperazine-1-carbonyl]-1-methyl-1H-indol-5-yloxy}pyridin-3-yl)-4-trifluoromethylbenzamide, N-(6-{2-[4-(4-Isopropoxybenzyl)piperazine-1-carbonyl]-1-methyl-1H-indol-5-yloxy}pyridin-3-yl)-N-methyl-4-trifluoromethylbenzamide, N-Methyl-N-(6-{1-methyl-2-[4-(4-propoxybenzyl)piperazine-1-carbonyl]-1H-indol-5-yloxy}pyridin-3-yl)-4-trifluoromethylbenzamide, N-(6-{2-[4-(4-Difluoromethoxybenzyl)piperazine-1-carbonyl]-1-methyl-1H-indol-6-yloxy}pyridin-3-yl)-N-methyl-4-trifluoromethylbenzamide, N-Methyl-N-[6-(1-methyl-2-{4-[4-(2,2,2-trifluoroethoxy)benzyl]piperazine-1-carbonyl}-1H-indol-5-yloxy)pyridin-3-yl]-4-trifluoromethylbenzamide, N-(6-{2-[4-(2,2-Difluorobenzo[1,3]dioxol-5-ylmethyl)piperazine-1-carbonyl]-1-methyl-1H-indol-5-yloxy}pyridin-3-yl)-N-methyl-4-trifluoromethylbenzamide, 2-Chloro-N-(6-{2-[4-(4-isopropoxybenzyl)piperazine-1-carbonyl]-1-methyl-1H-indol-6-yloxy}pyridin-3-yl)-N-methyl-4-trifluoromethylbenzamide, N-Methyl-N-[6-(1-methyl-2-{4-[4-(2,2,2-trifluoroethoxy)benzyl]piperazine-1-carbonyl}-1H-indol-6-yloxy)pyridin-3-yl]-4-trifluoromethoxybenzamide, N-[6-(2-{4-[4-(2,2-Difluoroethoxy)benzyl]piperazine-1-carbonyl}-1-methyl-1H-indol-6-yloxy)pyridin-3-yl]-N-methyl-4-trifluoromethoxybenzamide, N-(6-{2-[4-(4-Isopropoxybenzyl)piperazine-1-carbonyl]-1-methyl-1H-indol-5-yloxy}pyridin-3-yl)-4-trifluoromethylbenzamide, N-[6-(1-Methyl-2-{4-[4-(2,2,2-trifluoroethoxy)benzyl]piperazine-1-carbonyl}-1H-indol-5-yloxy)pyridin-3-yl]-4-trifluoromethylbenzamide, N-(6-{2-[4-(4-Isopropoxybenzyl)piperazine-1-carbonyl]-1-methyl-1H-indol-6-yloxy}pyridin-3-yl)-N-methyl-4-trifluoromethoxybenzamide, N-[6-(1-Methyl-2-{4-[4-(2,2,2-trifluoroethoxy)benzyl]piperazine-1-carbonyl}-1H-indol-6-yloxy)pyridin-3-yl]-4-trifluoromethylbenzamide, N-(6-{1-Methyl-2-[4-(4-propoxybenzyl)piperazine-1-carbonyl]-1H-indol-6-yloxy}pyridin-3-yl)-4-trifluoromethylbenzamide, N-(6-{2-[4-(4-Isopropoxybenzyl)piperazine-1-carbonyl]-1-methyl-1H-indol-6-yloxy}pyridin-3-yl)-4-trifluoromethylbenzamide, N-(6-{2-[4-(4-Difluoromethoxybenzyl)piperazine-1-carbonyl]-1-methyl-1H-indol-6-yloxy}pyridin-3-yl)-4-trifluoromethylbenzamide, N-[6-(2-{4-[4-(2,2-Difluoroethoxy)benzyl]piperazine-1-carbonyl}-1-methyl-1H-indol-6-yloxy)pyridin-3-yl]-4-trifluoromethylbenzamide, and N-(6-{1-Methyl-2-[4-(4-propoxybenzyl)piperazine-1-carbonyl]-1H-indol-5-yloxy}pyridin-3-yl)-4-trifluoromethylbenzamide.

6. The heterocyclic compound according to claim 1, which is selected from the group consisting of:

4,N-Dimethyl-N-[6-(2-{4-[4-(2,2,2-trifluoroethoxy)benzyl]piperazine-1-carbonyl}-1H-indol-6-yloxy)pyridin-3-yl]benzenesulfonamide, N-[6-(2-{4-[(4-Methoxybenzyl)methylamino]piperidine-1-carbonyl}-1-methyl-1H-indol-5-yloxy)pyridin-3-yl]-4-trifluoromethylbenzamide oxalate, 2-Chloro-N-(6-{2-[4-(4-Isopropoxybenzyl)piperazine-1-carbonyl]-1-methyl-1H-indol-6-yloxy}pyridin-3-yl)-4-trifluoromethylbenzamide hydrobromide, N-[6-(2-{4-[4-(2-Fluoro-1-fluoromethylethoxy)benzyl]piperazine-1-carbonyl}-1-methyl-1H-indol-6-yloxy)pyridin-3-yl]-N-methyl-4-trifluoromethoxybenzamide hydrobromide, N-[6-(2-{4-[(E)-3-(4-Methoxyphenyl)allyl]piperazine-1-carbonyl}-1-methyl-1H-indol-5-yloxy)pyridin-3-yl]-4-trifluoromethylbenzamide methanesulfonate, N-(6-{2-[4-(4-Difluoromethoxybenzyl)piperazine-1-carbonyl]-1-methyl-1H-indol-5-yloxy}pyridin-3-yl)-N-methyl-4-trifluoromethylbenzamide maleate, N-(6-{2-[4-(6-Isopropoxypyridin-3-ylmethyl)piperazine-1-carbonyl]-1-methyl-1H-indol-5-yloxy}pyridin-3-yl)-N-methyl-4-trifluoromethylbenzamide maleate, N-(6-{2-[4-(4-Isopropylbenzyl)piperazine-1-carbonyl]-1,4-dimethyl-1H-indol-5-yloxy}pyridin-3-yl)-N-methyl-4-trifluoromethylbenzamide hydrobromide, N-Methyl-N-[6-(1-methyl-2-{4-[4-(2,2,2-trifluoroethoxy)benzyl]piperazine-1-carbonyl}-1H-indol-6-yloxy)pyridin-3-yl]-4-trifluoromethylbenzamide hydrobromide, N-(6-{2-[4-(4-Difluoromethoxybenzyl)piperazine-1-carbonyl]-1-methyl-1H-indol-6-yloxy}pyridin-3-yl)-N-methyl-4-trifluoromethoxybenzamide hydrobromide, N-{6-[2-(4-isobutylpiperazine-1-carbonyl)-1-methyl-1H-indol-5-yloxy]pyridin-3-yl}-4-trifluoromethylbenzamide, N-[6-(1-Methyl-2-{4-[2-(4-trifluoromethylphenyl)thiazol-5-ylmethylpiperazine-1-carbonyl}-1H-indol-5-yloxy)pyridin-3-yl]-4-trifluoromethylbenzamide hydrobromide, 4-Methoxy-N-methyl-N-[6-(1-methyl-2-{4-[4-(2,2,2-trifluoroethoxy)benzyl]piperazine-1-carbonyl}-1H-indol-6-yloxy)pyridin-3-yl]benzenesulfonamide hydrochloride, N-(6-{2-[4-(4-Methoxybenzyl)piperazine-1-carbonyl]-1-methyl-1H-indol-5-yloxy}pyridin-3-yl)-N-methyl-4-trifluoromethylbenzamide maleate, N-(6-{2-[4-(4-Ethoxybenzyl)piperazine-1-carbonyl]-1-methyl-1H-indol-5-yloxy}-2-methylpyridin-3-yl)-N-methyl-4-trifluoromethylbenzamide hydrobromide, N-(6-{2-[4-(4-Ethylbenzyl)piperazine-1-carbonyl]-1-methyl-1H-indol-5-yloxy}pyridin-3-yl)-N-methyl-4-trifluoromethylbenzamide oxalate, N-(6-{1-Methyl-2-[4-(4-[1,2,3]thiadiazol-4-ylbenzyl)piperazine-1-carbonyl]-1H-indol-6-yloxy}pyridin-3-yl)-4-trifluoromethylbenzamide, N-[6-(2-{4-[4-(2-Fluoro-1-fluoromethylethoxy)benzyl]piperazine-1-carbonyl}-1-methyl-1H-indol-6-yloxy)pyridin-3-yl]-N-methyl-4-trifluoromethylbenzamide hydrobromide, N-[6-(2-{4-[4-(2-Fluoro-1-fluoromethylethoxy)benzyl]piperazine-1-carbonyl}-1-methyl-1H-indol-6-yloxy)pyridin-3-yl]-2-methyl-4-trifluoromethylbenzamide hydrochloride, N-(6-{2-[4-(4-Cyanobenzyl)piperazine-1-carbonyl]-1-methyl-1H-indol-6-yloxy}pyridin-3-yl)-N-methyl-4-trifluoromethylbenzamide hydrobromide, N-(6-{2-[4-(4-Ethoxybenzyl)piperazine-1-carbonyl]-1-methyl-1H-indol-5-yloxy}pyridin-3-yl)-N-methyl-4-trifluoromethylbenzamide maleate, N-Methyl-N-[6-(1-methyl-2-{4-[4-(1,1,2,2-tetrafluoroethoxy)benzyl]piperazine-1-carbonyl}-1H-indol-5-yloxy)pyridin-3-yl]-4-trifluoromethylbenzamide maleate, N-(6-{2-[4-(5-Ethoxypyridin-2-ylmethyl)piperazine-1-carbonyl]-1-methyl-1H-indol-5-yloxy}pyridin-3-yl)-N-methyl-4-trifluoromethylbenzamide maleate, N-Methyl-N-(6-{1-methyl-2-[4-(4-propoxybenzyl)piperazine-1-carbonyl]-1H-indol-6-yloxy}pyridin-3-yl)-4-trifluoromethylbenzamide hydrobromide, N-(6-{2-[4-(4-Isopropoxybenzyl)piperazine-1-carbonyl]-1-methyl-1H-indol-6-yloxy}pyridin-3-yl)-N-methyl-4-trifluoromethylbenzamide hydrobromide, 3,4-Dichloro-N-(6-{2-[4-(4-isopropoxybenzyl)piperazine-1-carbonyl]-1-methyl-1H-indol-6-yloxy}pyridin-3-yl)-N-methylbenzenesulfonamide, N-(6-{2-[4-(4-Isopropoxybenzyl)piperazine-1-carbonyl]-1-methyl-1H-indol-6-yloxy}pyridin-3-yl)-4,N-dimethylbenzenesulfonamide, N-(6-{2-[4-(2,2-Difluorobenzo[1,3]dioxol-5-ylmethyl)piperazine-1-carbonyl]-1-methyl-1H-indol-6-yloxy}pyridin-3-yl)-4,N-dimethylbenzenesulfonamide hydrochloride, N-{6-[2-(4-Benzo[1,3]dioxol-5-ylmethylpiperazine-1-carbonyl)-1-methyl-1H-indol-5-yloxy]pyridin-3-yl}-4-trifluoromethylbenzamide hydrobromide, N-{6-[2-(4-benzo[1,3]dioxol-5-ylmethylpiperazine-1-carbonyl)-1-methyl-1H-indol-5-yloxy]pyridin-3-yl}-N-methyl-4-trifluoromethylbenzamide hydrobromide, N-(6-{2-[4-(4-Methoxybenzyl)piperazine-1-carbonyl]-1-methyl-1H-indol-5-yloxy}pyridin-3-yl)-4-trifluoromethylbenzamide oxalate, N-(6-{2-[4-(4-Ethoxybenzyl)piperazine-1-carbonyl]-1-methyl-1H-indol-5-yloxy}pyridin-3-yl)-4-trifluoromethylbenzamide hydrobromide, N-(6-{2-[4-(4-Isopropoxybenzyl)piperazine-1-carbonyl]-1-methyl-1H-indol-5-yloxy}pyridin-3-yl)-N-methyl-4-trifluoromethylbenzamide maleate, N-Methyl-N-(6-{1-methyl-2-[4-(4-propoxybenzyl)piperazine-1-carbonyl]-1H-indol-5-yloxy}pyridin-3-yl)-4-trifluoromethylbenzamide maleate, N-(6-{2-[4-(4-Difluoromethoxybenzyl)piperazine-1-carbonyl]-1-methyl-1H-indol-6-yloxy}pyridin-3-yl)-N-methyl-4-trifluoromethylbenzamide hydrobromide, N-Methyl-N-[6-(1-methyl-2-{4-[4-(2,2,2-trifluoroethoxy)benzyl]piperazine-1-carbonyl}-1H-indol-5-yloxy)pyridin-3-yl]-4-trifluoromethylbenzamide dihydrobromide, N-(6-{2-[4-(2,2-Difluorobenzo[1,3]dioxol-5-ylmethyl)piperazine-1-carbonyl]-1-methyl-1H-indol-5-yloxy}pyridin-3-yl)-N-methyl-4-trifluoromethylbenzamide oxalate, 2-Chloro-N-(6-{2-[4-(4-isopropoxybenzyl)piperazine-1-carbonyl]-1-methyl-1H-indol-6-yloxy}pyridin-3-yl)-N-methyl-4-trifluoromethylbenzamide hydrobromide, N-Methyl-N-[6-(1-methyl-2-{4-[4-(2,2,2-trifluoroethoxy)benzyl]piperazine-1-carbonyl}-1H-indol-6-yloxy)pyridin-3-yl]-4-trifluoromethoxybenzamide hydrobromide, N-[6-(2-{4-[4-(2,2-Difluoroethoxy)benzyl]piperazine-1-carbonyl}-1-methyl-1H-indol-6-yloxy)pyridin-3-yl]-N-methyl-4-trifluoromethoxybenzamide hydrobromide, N-(6-{2-[4-(4-Isopropoxybenzyl)piperazine-1-carbonyl]-1-methyl-1H-indol-5-yloxy}pyridin-3-yl)-4-trifluoromethylbenzamide hydrobromide, N-[6-(1-Methyl-2-{4-[4-(2,2,2-trifluoroethoxy)benzyl]piperazine-1-carbonyl}-1H-indol-5-yloxy)pyridin-3-yl]-4-trifluoromethylbenzamide hydrobromide, N-(6-{2-[4-(4-Isopropoxybenzyl)piperazine-1-carbonyl]-1-methyl-1H-indol-6-yloxy}pyridin-3-yl)-N-methyl-4-trifluoromethoxybenzamide hydrobromide, N-[6-(1-Methyl-2-{4-[4-(2,2,2-trifluoroethoxy)benzyl]piperazine-1-carbonyl}-1H-indol-6-yloxy)pyridin-3-yl]-4-trifluoromethylbenzamide hydrobromide, N-(6-{1-Methyl-2-[4-(4-propoxybenzyl)piperazine-1-carbonyl]-1H-indol-6-yloxy}pyridin-3-yl)-4-trifluoromethylbenzamide hydrobromide, N-(6-{2-[4-(4-Isopropoxybenzyl)piperazine-1-carbonyl]-1-methyl-1H-indol-6-yloxy}pyridin-3-yl)-4-trifluoromethylbenzamide hydrobromide, N-(6-{2-[4-(4-Difluoromethoxybenzyl)piperazine-1-carbonyl]-1-methyl-1H-indol-6-yloxy}pyridin-3-yl)-4-trifluoromethylbenzamide hydrobromide, N-[6-(2-{4-[4-(2,2-Difluoroethoxy)benzyl]piperazine-1-carbonyl}-1-methyl-1H-indol-6-yloxy)pyridin-3-yl]-4-trifluoromethylbenzamide hydrobromide, and N-(6-{1-Methyl-2-[4-(4-propoxybenzyl)piperazine-1-carbonyl]-1H-indol-5-yloxy}pyridin-3-yl)-4-trifluoromethylbenzamide hydrobromide.

* * * * *